United States Patent
Ozaki

(10) Patent No.: US 11,732,247 B2
(45) Date of Patent: Aug. 22, 2023

(54) METHOD OF PRODUCING LIPID

(71) Applicant: Kao Corporation, Tokyo (JP)

(72) Inventor: Tatsuro Ozaki, Wakayama (JP)

(73) Assignee: Kao Corporation, Tokyo (JP)

( * ) Notice: Subject to any disclaimer, the term of this patent is extended or adjusted under 35 U.S.C. 154(b) by 73 days.

(21) Appl. No.: 17/271,685

(22) PCT Filed: Aug. 23, 2019

(86) PCT No.: PCT/JP2019/033053
§ 371 (c)(1),
(2) Date: Feb. 26, 2021

(87) PCT Pub. No.: WO2020/045283
PCT Pub. Date: Mar. 5, 2020

(65) Prior Publication Data
US 2021/0254027 A1    Aug. 19, 2021

(30) Foreign Application Priority Data
Aug. 28, 2018 (JP) .................. 2018-159659

(51) Int. Cl.
| | |
|---|---|
| *C12N 9/10* | (2006.01) |
| *C12N 9/16* | (2006.01) |
| *C12N 9/88* | (2006.01) |
| *C12N 9/90* | (2006.01) |
| *C12N 9/00* | (2006.01) |
| *C12P 7/64* | (2022.01) |
| *C12P 7/6409* | (2022.01) |

(52) U.S. Cl.
CPC ............. *C12N 9/1022* (2013.01); *C12N 9/16* (2013.01); *C12N 9/88* (2013.01); *C12N 9/90* (2013.01); *C12N 9/93* (2013.01); *C12P 7/64* (2013.01); *C12P 7/6409* (2013.01); *C12Y 202/01001* (2013.01); *C12Y 301/02014* (2013.01); *C12Y 401/02013* (2013.01); *C12Y 503/01006* (2013.01); *C12Y 602/01003* (2013.01)

(58) Field of Classification Search
None
See application file for complete search history.

(56) References Cited

U.S. PATENT DOCUMENTS

| | | |
|---|---|---|
| 2018/0245110 A1 | 8/2018 | Sugihara |
| 2019/0071698 A1 | 3/2019 | Sugihara |

FOREIGN PATENT DOCUMENTS

| | | | |
|---|---|---|---|
| WO | WO 2017/043419 A1 | 3/2017 | |
| WO | WO 2017/183421 A1 | 10/2017 | |

OTHER PUBLICATIONS

Chica et al. Curr Opin Biotechnol. Aug. 2005;16(4):378-84. (Year: 2005).*
Singh et al. Curr Protein Pept Sci. 2017, 18, 1-11. (Year: 2017).*
WO2017043419. Mar. 16, 2017, English language machine translation. (Year: 2017).*
WO2017183421. Oct. 26, 2017, English language machine translation. (Year: 2017).*
Accession W7TKJ5. Apr. 16, 2014 (Year: 2014).*
Accession W7TFC8. Apr. 16, 2014 (Year: 2014).*
Accession K8Z9G7. Feb. 6, 2013 (Year: 2013).*
Uniprot accession No. K8Z9G7, SubName: Full= Ribose-5-phosphate isomerase A, sequence version 1 (Feb. 6, 2013), entry version 19 (Nov. 22, 2017); retrieved May 20, 2022 from https://www.uniprot.org/uniprot/K8Z9G7.txt?version=19.
International Search Report for PCT/JP2019/033053; I.A. fd Aug. 23, 2019, dated Nov. 19, 2019 from the Japan Patent Office, Tokyo, Japan.
International Preliminary Report on Patentability (IPRP), Chapter I of the Patent Cooperation Treaty, including the Written Opinion, for PCT/JP2019/033053; I.A. fd Aug. 23, 2019, dated Mar. 2, 2021, by the International Bureau of WIPO, Geneva, Switzerland.
Liang, F, et al., "Engineered cyanobacteria with enhanced growth show increased ethanol production and higher biofuel to biomass ratio." Metab Eng. Mar. 2018;46:51-59. doi: 10.1016/j.ymben.2018.02.006. Epub Feb. 23, 2018, PMID: 29477858.
Liang, F, et al., "Effects of overexpressing photosynthetic carbon flux control enzymes in the cyanobacterium *Synechocystis* PCC 6803." Metab Eng. Nov. 2016;38:56-64. doi: 10.1016/j.ymben.2016.06.005. Epub Jun. 18, 2016, PMID: 27328433.
EWM26607 transketolase [Nannochloropsis gaditana] [online], 2014, retrieved on Nov. 6, 2019 https://www.ncbi.nlm.nih.gov/protein/585108695?sat=37&satkey=176326898>.
EWM25715 fructose-bisphosphate aldolase [Nannochloropsis gaditana] [online], 2014, retrieved on Nov. 6, 2019 https://www.ncbi.nlm.nih.gov/protein/585107575?sat=37&satkey=176326670>.
Tamoi, M et al., "Chapter 3. Purification, activity measurement and quantification of enzymes and electron transfer components, a. Calvin Cycle Enzymes," Low Temperature Science 67:209-214 (2009).
EWM26793 ribose-5-phosphate isomerase [Nannochloropsis gaditana] [online], 2014, retrieved on Nov. 6, 2019 https://www.ncbi.nlm.nih.gov/protein/EMW26793.1.
Driever, SM et al., "Increased SBPase activity improves photosynthesis and grain yield in wheat grown in greenhouse conditions." Philos Trans R Soc Lond B Biol Sci. Sep. 26, 2017;372(1730):20160384. doi: 10.1098/rstb.2016.0384. PMID: 28808101; PMCID: PMC5566882.
EWM26793 ribose-5-phosphate isomerase [Nannochloropsis gaditana] [online], 2014, retrieved on Nov. 6, 2019 https://www.ncbi.nlm.nih.gov/protein/EWM26793.1.

* cited by examiner

*Primary Examiner* — Christian L Fronda
(74) *Attorney, Agent, or Firm* — Sterne, Kessler, Goldstein & Fox P.L.L.C.

(57) ABSTRACT

A method of improving photosynthetic ability of an alga, containing enhancing expression of a transketolase and a fructose-1,6-bisphosphate aldolase.

6 Claims, No Drawings
Specification includes a Sequence Listing.

METHOD OF PRODUCING LIPID

TECHNICAL FIELD

The present invention relates to a method of producing lipids. Further, the present invention also relates to a transformant for use in this method.

BACKGROUND ART

A Fatty acid is one kind of the principal component of a lipid. In vivo, fatty acids are bonded to glycerin via an ester bond to form lipids such as triacylglycerol (hereinafter, also merely referred to as "TAG"). Further, many animals and plants also store and utilize fatty acids as an energy source. These fatty acids and lipids stored in animals and plants are widely utilized for food or industrial use.

For example, higher alcohol derivatives that are obtained by reducing higher fatty acids having approximately 12 to 18 carbon atoms are used as surfactants. Alkyl sulfuric acid ester salts, alkyl benzene sulfonic acid salts and the like are utilized as anionic surfactants. Further, polyoxyalkylene alkyl ethers, alkyl polyglycosides and the like are utilized as nonionic surfactants. These surfactants are used for detergents or disinfectants. Cationic surfactants such as alkylamine salts and mono- or dialkyl-quaternary amine salts, as other higher alcohol derivatives, are commonly used for fiber treatment agents, hair conditioning agents or disinfectants. Further, benzalkonium type quaternary ammonium salts are commonly used for disinfectants, antiseptics, or the like. Furthermore, fats and oils derived from plants are also used as raw materials of biodiesel fuels.

As mentioned above, fatty acids or lipids are widely used in various applications. Therefore, attempts have been made on improving productivity of the fatty acids or the lipids in vivo by using plants and the like. Furthermore, applications and usefulness of the fatty acids depend on the number of carbon atoms thereof. Therefore attempts have been made also on controlling the number of carbon atoms of the fatty acids, namely chain length.

To date, researches on renewable energy have been promoted toward realization of a sustainable society. Especially in recent years, algae such as photosynthetic microorganisms attract attention due to its usefulness in biofuel production. The algae can produce lipids that can be used as the biodiesel fuels through photosynthesis, and do not compete with foods. Therefore, the algae attract attention as next-generation biomass resources. Moreover, it is also reported that the algae have higher lipid productivity and lipid accumulation ability in comparison with plants.

Plants, and algae such as photosynthetic microorganisms are known to fix carbon by carrying out photosynthesis through the Calvin-Benson-Bassham cycle (hereinafter also referred to as "CBB cycle"). The CBB cycle consists of 13 reactions and one carbon dioxide molecule is fixed per reaction cycle. The resulting photosynthetic product is utilized not only as a biological component but also as an energy source. It has therefore been attempted to control produced biomass by reinforcing the CBB cycle so as to increase the photosynthetic ability of plants, algae, or the like.

For example, it is known that photosynthetic ability and biomass are increased in a transformant wherein, among enzymes involved in the CBB cycle, expression of ribulose-1,5-bisphosphate carboxylase/oxygenase (hereinafter, also referred to as "RuBisCO"), sedoheptulose 1,7-bisphosphatase (hereinafter, also referred to as "SBP"), fructose 1,6-bisphosphate aldolase (hereinafter, also referred to as "FBA"), or transketolase (hereinafter, also referred to as "TK") is solely enhanced respectively in plants or cyanobacteria (see Non-Patent Literatures 1 and 2). Further, it is known that an ability of producing alcohol is improved, and biomass is increased by enhancing expression of RuBisCO, fructose 1,6/sedoheptulose-1,7-bisphosphatase (FBP/SBP), FBA or TK, and expression of pyruvate decarboxylase (PDC) and alcohol dehydrogenase (ADH) in a cell of cyanobacteria (Non-Patent Literature 3).

CITATION LIST

Non-Patent Literatures

Non-Patent Literature 1: Liang F. and Lindblad P., Metab Eng. 2016 November; 38: 56-64
Non-Patent Literature 2: Driever S. M. et al., Philos Trans R Soc Lond B Biol Sci. 2017 Sep. 26; 372 (1730)
Non-Patent Literature 3: Liang F. et al., Metab Eng. 2018 March; 46: 51-59

SUMMARY OF INVENTION

The present invention relates to a method of producing lipids, containing the steps of:
culturing an alga in which expression of a TK and expression of a FBA are enhanced, and
producing fatty acids or lipids containing the same as components:
Further, the present invention relates to a transformant of an alga, in which expression of a TK and expression of a FBA are enhanced.

MODE FOR CARRYING OUT THE INVENTION

Although plants and algae have been studied, little is known about the relationship between fatty acid synthesis and control of photosynthetic ability by CBB cycle reinforcement. The present inventors therefore conducted intensive research in this regard.

The present inventors first used sequence information on all genes of *Nannochloropsis oceanica* to identify the CBB cycle genes (genes encoding proteins involved in the CBB cycle) presumed to function in chloroplasts. This led to the discovery that when TK and FBA among the CBB cycle genes are co-expressed in the algae cells, productivity of produced fatty acids and lipids containing the same as components can be significantly improved.

The present invention was completed based on these findings.

The present invention relates to providing a method of producing lipids, which improves productivity of fatty acids or lipids containing the same as components.

Further, the present invention relates to providing a transformant in which productivity of fatty acids or lipids containing the same as components is improved.

In the transformant of the present invention, expression of several CBB cycle genes are enhanced, and as a result, production amount of the lipids can be increased. Therefore, according to the method of producing the lipids of the present invention, productivity of fatty acids or lipids containing the same as components can be improved.

Moreover, expression of several CBB cycle genes are enhanced in the transformant of the present invention, and thereby the transformant of the present invention is excellent in the productivity of fatty acids or lipids containing the same as components.

Other and further features and advantages of the invention will appear more fully from the following description.

The term "lipid(s)" in the present specification, covers a simple lipid such as a neutral lipid (TAG, or the like), wax, and a ceramide; a complex lipid such as a phospholipid, a glycolipid, and a sulfolipid; and a derived lipid obtained from the lipid such as a fatty acid (free fatty acid), alcohols, and hydrocarbons.

The fatty acids categorized into the derived lipid generally refer to the fatty acids per se and mean "free fatty acids". In the present invention, the fatty acid group in molecules of a simple lipid and a complex lipid is expressed as "fatty acid residue". Then, unless otherwise specified, a term "fatty acid" is used as a generic term for "free fatty acid" and "fatty acid residue" contained in a salt or an ester compound, or the like.

Moreover, a term "fatty acids or lipids containing the same as components" in the present specification is generically used as including "free fatty acids" and "lipids having the fatty acid residues". Further, a term "fatty acid composition" in the present specification means a weight proportion of each fatty acid relative to the weight of whole fatty acids (total fatty acids) obtained by totaling the free fatty acids and the fatty acid residues described above. The weight (production amount) of the fatty acids or the fatty acid composition can be measured according to the method used in Examples.

Further in the present specification, the description of "Cx:y" for the fatty acid or the acyl group constituting the fatty acid means that the number of carbon atoms is "x" and the number of double bonds is "y". The description of "Cx" means a fatty acid or an acyl group having "x" as the number of carbon atoms.

In the present specification, the identity of the nucleotide sequence and the amino acid sequence is calculated through the Lipman-Pearson method (Science, 1985, vol. 227, p. 1435-1441). Specifically, the identity can be determined through use of a homology analysis (search homology) program of genetic information processing software Genetyx-Win with Unit size to compare (ktup) being set to 2.

It should be noted that, in the present specification, the "stringent conditions" includes, for example, the method described in Molecular Cloning—A LABORATORY MANUAL THIRD EDITION [Joseph Sambrook and David W. Russell, Cold Spring Harbor Laboratory Press], and examples thereof include conditions where hybridization is performed by incubating a solution containing 6×SSC (composition of 1×SSC: 0.15 M sodium chloride, 0.015 M sodium citrate, pH 7.0), 0.5% SDS, 5×Denhardt's solution and 100 mg/mL herring sperm DNA together with a probe at 65° C. for 8 to 16 hours.

Furthermore, in the present specification, the term "upstream" of a gene means a region subsequent to a 5' side of a targeted gene or region, and not a position from a translational initiation site. On the other hand, the term "downstream" of the gene means a region subsequent to a 3' side of the targeted gene or region.

As demonstrated in Examples below, a transformant into which each gene encoding the TK or the FBA is introduced alone, which is defined in the present invention that is the CBB cycle gene, fails to exhibit a marked increase in productivity of fatty acids relative to that of the wild-type strain. By contrast, a transformant into which both the genes encoding the TK and the FBA defined in the present invention are introduced exhibits a marked increase in productivity of fatty acids compared to that of the wild-type strain. And the proportion of palmitic acid among the fatty acids is particularly pronounced. Moreover, an increase in culture fluid turbidity is observed. In microalgae, culture fluid turbidity is correlated with the dry algal body weight. Accordingly, the transformant into which both the genes encoding the TK and the FBA are introduced should have an increased dry weight compared to that of the wild-type strain. In addition, since both the TK and the FBA are enzymes involved in the CBB cycle, the above results can be construed to indicate that co-introduction of the genes encoding the TK and the FBA causes the photosynthetic ability to increase in the transformant.

In the present specification, the term "TK" means a protein (enzyme) that catalyzes a reaction of producing an erythrose-4-phosphate and a xylulose-5-phosphate from a fructose-6-phosphate and a glyceraldehyde-3-phosphate, and a reaction of producing a xylulose-5-phosphate and a ribose-5-phosphate from a sedoheptulose-7-phosphate and a glyceraldehyde-3-phosphate. In the present specification, the term "transketolase activity" (hereinafter, also referred to as "TK activity") means activity of transferring the ketol group of ketose to the aldehyde group of aldose.

It can be confirmed that the protein to be used for the present invention has TK activity by, for example, a method described in Plant Physiol. (1989) 90, 814-819 and the like. Specifically, it can be confirmed by preparing solution containing objective proteins by an ordinary method, and analyzing a formation of an erythrose-4-phosphate and a xylulose-5-phosphate from mixture of a fructose-6-phosphate and a glyceraldehyde-3-phosphate, or a formation of a xylulose-5-phosphate and a ribose-5-phosphate from mixture of a sedoheptulose-7-phosphate and a glyceraldehyde-3-phosphate.

The TK used for the present invention is not particularly limited, as long as which is a protein (enzyme) having TK activity. Preferred examples of the TK in the present invention include the following proteins (A) and (B):
(A) a protein consisting of the amino acid sequence set forth in SEQ ID NO: 1; and
(B) a protein consisting of an amino acid sequence having 60% or more identity with the amino acid sequence of the protein (A), and having TK activity.

The protein (A) consisting of the amino acid sequence set forth in SEQ ID NO: 1 is a TK derived from *Nannochloropsis oceanica* strain NIES-2145 being algae belonging to the genus *Nannochloropsis*. The protein consisting of the amino acid sequence set forth in SEQ ID NO: 1 of the present invention (the protein (A)) has TK activity.

In general, it is known that an amino acid sequence encoding an enzyme protein does not necessarily exhibit enzyme activity unless the sequence in the whole region is conserved, and there exists a region in which the enzyme activity is not influenced even if the amino acid sequence is changed. In such a region which is not essential to the enzyme activity, even if the mutation of the amino acid, such as deletion, substitution, insertion and addition thereof is introduced thereinto, the activity inherent to the enzyme can be maintained. Also in the present invention, such a protein can be used in which the TK activity is kept and a part of the amino acid sequence of the protein (A) is subjected to mutation.

A method of introducing the mutation into an amino acid sequence includes a method of, for example, introducing a mutation into a nucleotide sequence encoding the amino acid sequence. A method of introducing the mutation includes a method of introducing a site-specific mutation. Specific examples of the method of introducing the site-specific mutation include a method of utilizing the splicing overlap extension (SOE)-PCR reaction (Horton et al., Gene 77, 61-68, 1989), the ODA method (Hashimoto-Gotoh et al., Gene, 152, 271-276, 1995), and the Kunkel method (Kunkel, T. A., Proc. Natl. Acad. Sci. USA, 1985, 82, 488). Further, commercially available kits such as Site-Directed Mutagenesis System Mutan-Super Express Km kit (Takara Bio), Transformer™ Site-Directed Mutagenesis kit (Clontech Laboratories), and KOD-Plus-Mutagenesis Kit (TOYOBO) can also be utilized. Furthermore, an objective gene can also be obtained by introducing a genetic mutation at random, and then performing an evaluation of the enzyme activities and a gene analysis thereof by an appropriate method.

In the protein (B), the identity with the amino acid sequence of the protein (A) is 60% or more, preferably 65% or more, more preferably 70% or more, further preferably 75% or more, further preferably 80% or more, further preferably 85% or more, further preferably 90% or more, further preferably 91% or more, further preferably 92% or more, further preferably 93% or more, further preferably 95% or more, further preferably 97% or more, further preferably 98% or more, and furthermore preferably 99% or more, in view of TK activity.

Further, specific examples of the protein (B) include a protein in which 1 or several (for example 1 or more and 289 or less, preferably 1 or more and 253 or less, more preferably 1 or more and 216 or less, further preferably 1 or more and 180 or less, furthermore preferably 1 or more and 144 or less, furthermore preferably 1 or more and 108 or less, furthermore preferably 1 or more and 72 or less, furthermore preferably 1 or more and 65 or less, furthermore preferably 1 or more and 57 or less, furthermore preferably 1 or more and 50 or less, furthermore preferably 1 or more and 36 or less, furthermore preferably 1 or more and 21 or less, furthermore preferably 1 or more and 14 or less, and furthermore preferably 1 or more and 7 or less) amino acids are deleted, substituted, inserted or added to the amino acid sequence of the protein (A), and having TK activity.

In addition, the TK used in the present invention may be a protein consisting of an amino acid sequence obtained by addition of a signal peptide involved in protein transport or an amino acid sequence that increases protein stability to the amino acid sequence of the protein (A) or (B). Further, the TK used in the present invention may be a protein consisting of an amino acid sequence wherein a putative chloroplast transit signal sequence present on a region on the N-terminal side of the amino acid sequence of the protein (A) or (B) is changed to another chloroplast transit signal sequence that functions in the host. In prediction of localization using ChloroP (www.cbs.dtu.dk/services/ChloroP/), the amino acid sequence at positions 1 to 63 of the amino acid sequence set forth in SEQ ID NO: 1 is predicted to be a chloroplast transit signal sequence. In fact, the present inventors verified that addition of the amino acid sequence at positions 1 to 100 of the amino acid sequence set forth in SEQ ID NO: 1 to the N-terminal end of a reporter protein can cause the reporter protein to localize to chloroplasts.

The proteins (A) and (B) can be obtained by chemical techniques, genetic engineering techniques or the like that are ordinarily carried out. For example, a natural product-derived protein can be obtained through isolation, purification and the like from an alga having the TK gene on a genome, such as an alga belonging to the genus *Nannochloropsis*. In addition, the proteins (A) and (B) can be obtained by artificial chemical synthesis based on the amino acid sequence set forth in SEQ ID NO: 1. Alternatively, as recombinant proteins, proteins (A) and (B) may also be prepared by gene recombination technologies.

The TK used for the present invention may be used alone or in combination with two or more kinds thereof.

Note that the algae such as *Nannochloropsis oceanica* can be obtained from culture collection such as private or public research institutes or the like. For example, *Nannochloropsis oceanica* strain NIES-2145 can be obtained from National Institute for Environmental Studies (NIES).

In the present invention, it is preferred that expression of the TK is enhanced by using a gene encoding the TK, according to the method described below.

A specific example of the gene encoding the TK that can be used for the present invention (preferably, a gene encoding the protein (A) or (B) (hereinafter, also referred to as "TK gene")) includes a gene consisted of the following DNA (a) or (b):

(a) a DNA consisting of the nucleotide sequence set forth in SEQ ID NO: 2; and
(b) a DNA consisting of a nucleotide sequence having 60% or more identity with the nucleotide sequence of the DNA (a), and encoding a protein having TK activity.

The DNA (a) consisting of the nucleotide sequence set forth in SEQ ID NO: 2 is a gene encoding the protein consisting of the amino acid sequence set forth in SEQ ID NO: 1, and which is a TK gene derived from *Nannochloropsis oceanica* strain NIES-2145.

In the DNA (b), the identity with the nucleotide sequence of the DNA (a) is 60% or more, preferably 65% or more, more preferably 70% or more, further preferably 75% or more, further preferably 80% or more, further preferably 85% or more, further preferably 90% or more, further preferably 91% or more, further preferably 92% or more, further preferably 93% or more, further preferably 95% or more, further preferably 97% or more, further preferably 98% or more, and furthermore preferably 99% or more, in view of TK activity.

Further, the DNA (b) is also preferably a DNA in which 1 or several (for example 1 or more and 868 or less, preferably 1 or more and 760 or less, more preferably 1 or more and 651 or less, further preferably 1 or more and 543 or less, further preferably 1 or more and 434 or less, further preferably 1 or more and 325 or less, further preferably 1 or more and 217 or less, further preferably 1 or more and 195 or less, further preferably 1 or more and 173 or less, further preferably 1 or more and 152 or less, further preferably 1 or more and 108 or less, further preferably 1 or more and 65 or less, further preferably 1 or more and 43 or less, and furthermore preferably 1 or more and 21 or less) nucleotides are deleted, substituted, inserted or added to the nucleotide sequence set forth in SEQ ID NO: 2, and encoding a protein having TK activity.

Furthermore, the DNA (b) is also preferably a DNA capable of hybridizing with a DNA consisting of the nucleotide sequence complementary with the DNA (a) under a stringent condition, and encoding a protein having TK activity.

Examples of a mutation include deletion, substitution, insertion and addition of nucleotides. A method of introducing the mutation into a nucleotide sequence includes a method of introducing a site-specific mutation. Specific examples of the method of introducing the site-specific mutation include a method of utilizing the SOE-PCR, the ODA method, and the Kunkel method. Further, commercially available kits such as Site-Directed Mutagenesis System Mutan-Super Express Km kit (Takara Bio), Transformer™ Site-Directed Mutagenesis kit (Clontech Laboratories), and KOD-Plus-Mutagenesis Kit (TOYOBO) can also be utilized. Furthermore, a gene containing a desired mutation can also be obtained by introducing a genetic mutation at random, and then performing an evaluation of the enzyme activities and a gene analysis thereof by an appropriate method.

In addition, the TK gene used in the present invention may be a gene consisted of a nucleotide sequence obtained by addition of a DNA encoding a signal peptide involved in protein transport, an amino acid sequence that increases protein stability, or the like, to the nucleotide sequence of the DNA (a) or (b). Further, the TK gene used in the present invention may be a DNA consisting of a nucleotide sequence, wherein a nucleotide sequence encoding a putative chloroplast transit signal sequence present on a region on the 5' side in the nucleotide sequence of the DNA (a) or (b) is changed to another nucleotide sequence encoding a chloroplast transit signal sequence that functions in the host. In prediction of localization using ChloroP (www.cbs.dtu.dk/services/ChloroP/), the nucleotide sequence at positions 1 to 189 of the nucleotide sequence set forth in SEQ ID NO: 2 is predicted to encode a chloroplast transit signal sequence. In fact, the present inventors verified that addition of the nucleotide sequence at positions 1 to 300 of the nucleotide sequence set forth in SEQ ID NO: 2 to the 5' end of a nucleotide sequence encoding a reporter protein can cause the reporter protein to localize to chloroplasts.

The DNA (a) or (b) can be obtained by genetic engineering techniques that are ordinarily carried out. For example, the TK gene can be artificially synthesized based on the amino acid sequence set forth in SEQ ID NO: 1, or the nucleotide sequence set forth in SEQ ID NO: 2. The synthesis of the TK gene can be achieved by utilizing, for example, the services of Invitrogen. Further, the gene can also be obtained by cloning from an alga having the TK gene on a genome, such as an alga belonging to the genus *Nannochloropsis*. The cloning can be carried out by, for example, the methods described in Molecular Cloning: A LABORATORY MANUAL THIRD EDITION [Joseph Sambrook, David W. Russell, Cold Spring Harbor Laboratory Press (2001)], or the like. In addition, depending on the type of the host to be used, a part of the nucleotide sequence set forth in SEQ ID NO: 2 may be optimized. For example, GeneArt Gene Synthesis service from Thermo Fisher Scientific can be used therefor.

The TK gene used for the present invention may be used alone or in combination with two or more kinds thereof.

In the present specification, the term "FBA" means a protein (enzyme) that catalyzes, in the CBB cycle, a reaction of producing a fructose-1,6-bisphosphate from a glyceraldehyde-3-phosphate and dihydroxyacetone phosphate, and a reaction of producing a sedoheptulose-1,7-bisphosphate from an erythrose-4-phosphate and dihydroxyacetone phosphate. In the present specification, the term "fructose-1,6-bisphosphate aldolase activity" (hereinafter, also referred to as "FBA activity") means activity of condensing glyceraldehyde-3-phosphate and dihydroxyacetone phosphate or condensing erythrose-4-phosphate and dihydroxyacetone phosphate.

It can be confirmed that the protein to be used in the present invention has the FBA activity by, for example, a method described in Plant Physiol. (1989) 90, 814-819 and the like. Specifically, it can be confirmed by preparing solution containing objective proteins by an ordinary method, and analyzing a formation of a fructose-1,6-bisphosphate from mixture of a glyceraldehyde-3-phosphate and a dihydroxyacetone phosphate, or a formation of a sedoheptulose-1,7-bisphosphate from mixture of an erythrose-4-phosphate and a dihydroxyacetone phosphate.

The FBA used for the present invention is not particularly limited, as long as which is a protein (enzyme) having FBA activity. Preferred examples of the FBA in the present invention include the following proteins (C) and (D):

(C) a protein consisting of the amino acid sequence set forth in SEQ ID NO: 3; and (D) a protein consisting of an amino acid sequence having 60% or more identity with the amino acid sequence of the protein (C), and having FBA activity.

The protein (C) consisting of the amino acid sequence set forth in SEQ ID NO: 3 is a FBA derived from *Nannochloropsis oceanica* strain NIES-2145 being algae belonging to the genus *Nannochloropsis*. The protein consisting of the amino acid sequence set forth in SEQ ID NO: 3 of the present invention (the protein (C)) has FBA activity.

As for the FBA utilized in the present invention, as similar to the TK, a protein can be used in which FBA activity is kept and a part of the amino acid sequence of the protein (C) is subjected to mutation. A method of introducing the mutation into an amino acid sequence of the FBA includes the methods described above.

In the protein (D), the identity with the amino acid sequence of the protein (C) is 60% or more, preferably 65% or more, more preferably 70% or more, further preferably 75% or more, further preferably 80% or more, further preferably 85% or more, further preferably 90% or more, further preferably 91% or more, further preferably 92% or more, further preferably 93% or more, further preferably 95% or more, further preferably 97% or more, further preferably 98% or more, and furthermore preferably 99% or more, in view of FBA activity.

Further, specific examples of the protein (D) include a protein in which 1 or several (for example 1 or more and 152 or less, preferably 1 or more and 133 or less, more preferably 1 or more and 114 or less, further preferably 1 or more and 95 or less, furthermore preferably 1 or more and 76 or less, furthermore preferably 1 or more and 57 or less, furthermore preferably 1 or more and 38 or less, furthermore preferably 1 or more and 34 or less, furthermore preferably 1 or more and 30 or less, furthermore preferably 1 or more and 26 or less, furthermore preferably 1 or more and 19 or less, furthermore preferably 1 or more and 11 or less, furthermore preferably 1 or more and 7 or less, and furthermore preferably 1 or more and 3 or less) amino acids are deleted, substituted, inserted or added to the amino acid sequence of the protein (C), and having FBA activity.

In addition, the FBA used in the present invention may be a protein consisting of an amino acid sequence obtained by addition of a signal peptide involved in protein transport, or an amino acid sequence that increases protein stability, to the amino acid sequence of the protein (C) or (D). Further, the FBA used in the present invention may be a protein consisting of an amino acid sequence wherein a putative chloroplast transit signal sequence present on a region on the N-terminal side of the amino acid sequence of the protein (C) or (D) is changed to another chloroplast transit signal sequence that functions in the host. In prediction of localization using ChloroP (www.cbs.dtu.dk/services/ChloroP/), the amino acid sequence at positions 1 to 20, or at positions 1 to 26 of the amino acid sequence set forth in SEQ ID NO: 3 is predicted to be chloroplast transit signal sequences. In fact, the present inventors verified that addition of the amino acid sequence at positions 1 to 100 of the amino sequence set forth in SEQ ID NO: 3 to the N-terminal end of a reporter protein can cause the reporter protein to localize to chloroplasts.

The proteins (C) and (D) can be obtained by chemical techniques, genetic engineering techniques or the like that are ordinarily carried out. For example, a natural product-derived protein can be obtained through isolation, purification and the like from an alga having the FBA gene on a genome, such as an alga belonging to the genus *Nannochloropsis*. In addition, the proteins (C) and (D) can be obtained by artificial chemical synthesis based on the amino acid sequence set forth in SEQ ID NO: 3. Alternatively, as recombinant proteins, proteins (C) and (D) may also be prepared by gene recombination technologies.

The FBA used for the present invention may be used alone or in combination with two or more kinds thereof.

In the present invention, it is preferred that expression of the FBA is enhanced by using a gene encoding the FBA, according to a method described below.

A specific example of the gene encoding the FBA that can be used for the present invention (preferably, a gene encoding the protein (C) or (D) (hereinafter, also referred to as "FBA gene")) includes a gene consisted of the following DNA (c) or (d):
(c) a DNA consisting of the nucleotide sequence set forth in SEQ ID NO: 4; and
(d) a DNA consisting of a nucleotide sequence having 60% or more identity with the nucleotide sequence of the DNA (c), and encoding a protein having FBA activity.

The DNA (c) consisting of the nucleotide sequence set forth in SEQ ID NO: 4 is a gene encoding the protein consisting of the amino acid sequence set forth in SEQ ID NO: 3, and which is a FBA gene derived from *Nannochloropsis oceanica* strain NIES-2145.

In the DNA (d), the identity with the nucleotide sequence of the DNA (c) is 60% or more, preferably 65% or more, more preferably 70% or more, further preferably 75% or more, further preferably 80% or more, further preferably 85% or more, further preferably 90% or more, further preferably 91% or more, further preferably 92% or more, further preferably 93% or more, further preferably 95% or more, further preferably 97% or more, further preferably 98% or more, and furthermore preferably 99% or more, in view of FBA activity.

Further, the DNA (d) is also preferably a DNA in which 1 or several (for example 1 or more and 459 or less, preferably 1 or more and 402 or less, more preferably 1 or more and 344 or less, further preferably 1 or more and 287 or less, further preferably 1 or more and 229 or less, further preferably 1 or more and 172 or less, further preferably 1 or more and 114 or less, further preferably 1 or more and 103 or less, further preferably 1 or more and 91 or less, further preferably 1 or more and 80 or less, further preferably 1 or more and 57 or less, further preferably 1 or more and 34 or less, further preferably 1 or more and 22 or less, and furthermore preferably 1 or more and 11 or less) nucleotides are deleted, substituted, inserted or added to the nucleotide sequence set forth in SEQ ID NO: 4, and encoding a protein having FBA activity.

Furthermore, the DNA (d) is also preferably a DNA capable of hybridizing with a DNA consisting of the nucleotide sequence complementary with the DNA (c) under a stringent condition, and encoding a protein having FBA activity.

A method of introducing the mutation into a nucleotide sequence of the FBA includes the methods described above.

In addition, the FBA gene used in the present invention may be a gene consisted of a nucleotide sequence obtained by addition of a DNA encoding a signal peptide involved in protein transport, an amino acid sequence that increases protein stability, or the like, to the nucleotide sequence of the DNA (c) or (d). Further, the FBA gene used in the present invention may be a DNA consisting of a nucleotide sequence, wherein a nucleotide sequence encoding a putative chloroplast transit signal sequence present on a region on the 5' side in the nucleotide sequence of the DNA (c) or (d) is changed to another nucleotide sequence encoding a chloroplast transit signal sequence that functions in the host. In prediction of localization using ChloroP (www.cbs.dtu.dk/services/ChloroP/), the nucleotide sequence at positions 1 to 60, or at positions 1 to 78 of the nucleotide sequence set forth in SEQ ID NO: 4 is predicted to encode chloroplast transit signal sequences. In fact, the present inventors verified that addition of the nucleotide sequence at positions 1 to 300 of the nucleotide sequence set forth in SEQ ID NO: 4 to the 5' end of a nucleotide sequence encoding a reporter protein can cause the reporter protein to localize to chloroplasts.

The DNA (c) or (d) can be obtained by genetic engineering techniques that are ordinarily carried out. For example, the FBA gene can be artificially synthesized based on the amino acid sequence set forth in SEQ ID NO: 3, or the nucleotide sequence set forth in SEQ ID NO: 4. The synthesis of the FBA gene can be achieved by utilizing, for example, the services of Invitrogen. Further, the gene can also be obtained by cloning from an alga having the FBA gene on a genome, such as an alga belonging to the genus *Nannochloropsis*. The cloning can be carried out by, for example, the methods described in Molecular Cloning: A LABORATORY MANUAL THIRD EDITION [Joseph Sambrook, David W. Russell, Cold Spring Harbor Laboratory Press (2001)], or the like. In addition, depending on the type of the host to be used, a part of the nucleotide sequence set forth in SEQ ID NO: 4 may be optimized. For example, GeneArt Gene Synthesis service from Thermo Fisher Scientific can be used therefor.

The FBA gene used for the present invention may be used alone or in combination with two or more kinds thereof.

In algae used for the present invention, expression of a ribose-5-phosphate isomerase (hereinafter, also referred to as "RPI") is preferably enhanced, in addition to expression of the proteins TK and FBA. In the present specification, the term "RPI" means a protein (enzyme) which catalyzes a reaction of conversion of a ribulose-5-phosphate from a ribose-5-phosphate. As used herein, the term "ribose-5-phosphate isomerase activity" (hereinafter, also referred to as "RPI activity") means activity of converting an aldehyde group of an aldose to a keto group.

Photosynthetic ability of the transformant used for lipid production, and especially, productivity of lipids (preferably, fatty acids) can be further improved by enhancing expression of the RPI, in addition to the proteins TK and FBA.

The RPI that can be used for the present invention is not particularly limited, as long as which is a protein (enzyme) having RPI activity. Preferred examples of the RPI in the present invention include the following proteins (E) and (F):
(E) a protein consisting of the amino acid sequence set forth in SEQ ID NO: 7; and
(F) a protein consisting of an amino acid sequence having 60% or more identity with the amino acid sequence of the protein (E), and having RPI activity.

It can be confirmed that the protein to be used for the present invention has RPI activity by, for example, a method described in The Plant Journal (2006) 48, 606-618 or the like. Specifically, it can be confirmed by preparing solution containing target proteins, and analyzing a formation of a ribulose-5-phosphate from mixture of a ribose-5-phosphate.

The protein (E) consisting of the amino acid sequence set forth in SEQ ID NO: 7 is a RPI derived from *Nannochloropsis oceanica* strain NIES-2145 being algae belonging to the genus *Nannochloropsis*. The protein consisting of the amino acid sequence set forth in SEQ ID NO: 7 of the present invention (the protein (E)) has RPI activity.

As for the RPI utilized in the present invention, as similar to the TK and the FBA, a protein can be used in which RPI activity is kept and a part of the amino acid sequence of the protein (E) is subjected to mutation.

A method of introducing the mutation into an amino acid sequence of the RPI includes the method described above.

In the protein (F), the identity with the amino acid sequence of the protein (E) is 60% or more, preferably 65% or more, more preferably 70% or more, further preferably 75% or more, further preferably 80% or more, further preferably 85% or more, further preferably 90% or more, further preferably 91% or more, further preferably 92% or more, further preferably 93% or more, further preferably 95% or more, further preferably 97% or more, further preferably 98% or more, and furthermore preferably 99% or more, in view of RPI activity.

Further, specific examples of the protein (F) include a protein in which 1 or several (for example 1 or more and 112 or less, preferably 1 or more and 98 or less, more preferably 1 or more and 84 or less, further preferably 1 or more and 70 or less, furthermore preferably 1 or more and 56 or less, furthermore preferably 1 or more and 42 or less, furthermore preferably 1 or more and 28 or less, furthermore preferably 1 or more and 25 or less, furthermore preferably 1 or more and 22 or less, furthermore preferably 1 or more and 19 or less, furthermore preferably 1 or more and 14 or less, furthermore preferably 1 or more and 8 or less, furthermore preferably 1 or more and 5 or less, and furthermore preferably 1 or 2) amino acids are deleted, substituted, inserted or added to the amino acid sequence of the protein (E), and having RPI activity.

In addition, the RPI used in the present invention may be a protein consisting of an amino acid sequence obtained by addition of a signal peptide involved in protein transport, or an amino acid sequence that increases protein stability, to the amino acid sequence of the protein (E) or (F). Further, the RPI used in the present invention may be a protein consisting of an amino acid sequence wherein a putative chloroplast transit signal sequence present on a region on the N-terminal side of the amino acid sequence of the protein (E) or (F) is changed to another chloroplast transit signal sequence that functions in the host. In prediction of localization using ChloroP (www.cbs.dtu.dk/services/ChloroP/), the amino acid sequence at positions 1 to 49 of the amino acid sequence set forth in SEQ ID NO: 7 is predicted to be a chloroplast transit signal sequence. In fact, the present inventors verified that addition of the amino acid sequence at positions 1 to 100 of the amino acid sequence set forth in SEQ ID NO: 7 to the N-terminal end of a reporter protein can cause the reporter protein to localize to chloroplasts.

The proteins (E) and (F) can be obtained by chemical techniques, genetic engineering techniques or the like that are ordinarily carried out. For example, a natural product-derived protein can be obtained through isolation, purification and the like from an alga having the RPI gene on a genome, such as an alga belonging to the genus *Nannochloropsis*. In addition, the proteins (E) and (F) can be obtained by artificial chemical synthesis based on the amino acid sequence set forth in SEQ ID NO: 7. Alternatively, as recombinant proteins, proteins (E) and (F) may also be prepared by gene recombination technologies.

The RPI used for the present invention may be used alone or in combination with two or more kinds thereof.

In the present invention, by using a gene encoding the RPI, expression of the RPI is preferably enhanced according to the method described below.

A specific example of the gene encoding the RPI that can be used for the present invention (preferably, a gene encoding the protein (E) or (F) (hereinafter, also referred to as "RPI gene")) includes a gene consisting of the following DNA (e) or (f):

(e) a DNA consisting of the nucleotide sequence set forth in SEQ ID NO: 8; or (f) a DNA consisting of a nucleotide sequence having 60% or more identity with the nucleotide sequence of the DNA (e), and encoding a protein having RPI activity.

The DNA (e) consisting of the nucleotide sequence set forth in SEQ ID NO: 8 is a gene encoding the protein consisting of the amino acid sequence set forth in SEQ ID NO: 7, and which is a RPI gene derived from *Nannochloropsis oceanica* strain NIES-2145.

In the DNA (f), the identity with the nucleotide sequence of the DNA (e) is 60% or more, preferably 65% or more, more preferably 70% or more, further preferably 75% or more, further preferably 80% or more, further preferably 85% or more, further preferably 90% or more, further preferably 91% or more, further preferably 92% or more, further preferably 93% or more, further preferably 95% or more, further preferably 97% or more, further preferably 98% or more, and furthermore preferably 99% or more, in view of RPI activity.

Further, the DNA (f) is also preferably a DNA in which 1 or several (for example 1 or more and 339 or less, preferably 1 or more and 297 or less, more preferably 1 or more and 254 or less, further preferably 1 or more and 212 or less, further preferably 1 or more and 169 or less, further preferably 1 or more and 127 or less, further preferably 1 or more and 84 or less, further preferably 1 or more and 76 or less, further preferably 1 or more and 67 or less, further preferably 1 or more and 59 or less, further preferably 1 or more and 42 or less, further preferably 1 or more and 25 or less, further preferably 1 or more and 16 or less, and furthermore preferably 1 or more and 8 or less) nucleotides are deleted, substituted, inserted or added to the nucleotide sequence set forth in SEQ ID NO: 8, and encoding a protein having RPI activity.

Furthermore, the DNA (f) is also preferably a DNA capable of hybridizing with a DNA consisting of the nucleotide sequence complementary with the DNA (e) under a stringent condition, and encoding a protein having RPI activity.

A method of introducing the mutation into a nucleotide sequence of the RPI includes the method described above.

In addition, the RPI gene used in the present invention may be a gene consisted of a nucleotide sequence obtained by addition of a DNA encoding a signal peptide involved in protein transport, an amino acid sequence that increases protein stability, or the like, to the nucleotide sequence of the DNA (e) or (f). Further, the RPI gene used in the present invention may be a DNA consisting of a nucleotide sequence, wherein a nucleotide sequence encoding a putative chloroplast transit signal sequence present on a region on the 5' side in the nucleotide sequence of the DNA (e) or (f) is changed to another nucleotide sequence encoding a chloroplast transit signal sequence that functions in the host. In prediction of localization using ChloroP (www.cbs.dtu.dk/services/ChloroP/), the nucleotide sequence at positions 1 to 147 of the nucleotide sequence set forth in SEQ ID NO: 8 is predicted to encode a chloroplast transit signal sequence. In fact, the present inventors verified that addition of the nucleotide sequence at positions 1 to 300 of the nucleotide sequence set forth in SEQ ID NO: 8 to the 5' end of a nucleotide sequence encoding a reporter protein can cause the reporter protein to localize to chloroplasts.

The DNA (e) or (f) can be obtained by genetic engineering techniques that are ordinarily carried out. For example, the RPI gene can be artificially synthesized based on the amino acid sequence set forth in SEQ ID NO: 7, or the nucleotide sequence set forth in SEQ ID NO: 8. The synthesis of the RPI gene can be achieved by utilizing, for example, the services of Invitrogen. Further, the gene can also be obtained by cloning from an alga having the RPI gene on a genome, such as an alga belonging to the genus *Nannochloropsis*. The cloning can be carried out by, for example, the methods described in Molecular Cloning: A LABORATORY MANUAL THIRD EDITION [Joseph Sambrook, David W. Russell, Cold Spring Harbor Laboratory Press (2001)], or the like. In addition, depending on the type of the host to be used, a part of the nucleotide sequence set forth in SEQ ID NO: 8 may be optimized. For example, GeneArt Gene Synthesis service from Thermo Fisher Scientific can be used therefor.

The RPI gene used for the present invention may be used alone or in combination with two or more kinds thereof.

The transformant of the present invention can be obtained by introducing the genes into the host according to an ordinarily method, respectively. Specifically, the transformant can be produced by preparing a recombinant vector or a gene expression cassette which is capable of expressing the genes in a host cell, introducing this vector or cassette into the host cell, and thereby transforming the host cell. In the transformant of the present invention, it is preferred that expression of the gene is enhanced.

Further, the transformant of the present invention can be obtained by, in a host having the above-described gene on a genome, modifying expression regulation region of the gene by an ordinary method, thereby enhancing expression of the gene. Specifically, it can be prepared by interchanging a promoter sited upstream of the gene present on a genome of the host with that having higher promoter activity, or the like.

In the transformant of the present invention, from viewpoints of improving photosynthetic ability and improving productivity of lipids, it is also preferred that expression of at least one kind or two or more kinds of proteins involved in the fatty acid synthetic pathway and the TAG synthetic pathway is enhanced, in addition to the TK and the FBA. Specific examples of the proteins involved in the fatty acids synthetic pathway and the TAG synthetic pathway include an acetyl-CoA carboxylase (hereinafter, also referred to as "ACC"), an acyl-carrier protein (hereinafter, also referred to as "ACP"), a holo-ACP synthase (phosphopantetheinyl transferases), an ACP-malonyltransferase (hereinafter, also referred to as "MAT"), a β-ketoacyl-ACP synthase (hereinafter, also referred to as "KAS"), a β-ketoacyl-ACP reductase (hereinafter, also referred to as "KAR"), a hydroxyacyl-ACP dehydratase (hereinafter, also referred to as "HD"), an enoyl-ACP reductase (hereinafter, also referred to as "KAR"), an acyl-ACP thioesterase (hereinafter, also referred to as "TE"), an acyl-CoA synthetase (hereinafter, also referred to as "ACS"), a glycerol-3-phosphate dehydrogenase (hereinafter, also referred to as "G3PDH"), an acyltransferase (hereinafter, also referred to as "AT") such as a glycerol-3-phosphate acyltransferase (hereinafter, also referred to as "GPAT"), a lysophosphatidic acid acyltransferase (hereinafter, also referred to as "LPAAT"), and diacylglycerol acyltransferase (hereinafter, also referred to as "DGAT"), and a phosphatidate phosphatase (hereinafter, also referred to as "PAP").

From viewpoints of improving photosynthetic ability and improving productivity of lipids, it is preferred that expression of at least one kind or two or more kinds of proteins selected from the ACC, the ACP, the KAS, the TE, the ACS, and the AT, in addition to the TK and the FBA, is enhanced, more preferred that expression of at least one kind or two or more kinds of proteins selected from the TE, the ACS, and the AT is enhanced, further preferred that expression of at least one kind or two or more kinds of proteins selected from the TE, the ACS, and the DGAT is enhanced. Further, from viewpoints of improving photosynthetic ability and improving productivity of lipids, it is preferred that expression of the DGAT is enhanced, more preferred that expression of the ACS and the DGAT is enhanced, and further preferred that expression of the TE, the ACS and the DGAT is enhanced.

The TE that can be used in the present invention is not particularly limited, and needs to be the protein having acyl-ACP thioesterase activity (hereinafter, also referred to as "TE activity"). Herein, the term "TE activity" means an activity of hydrolyzing the thioester bond of the acyl-ACP.

A TE is an enzyme that hydrolyzes the thioester bond of the acyl-ACP synthesized by a fatty acid synthase such as the KAS to produce a free fatty acid. The function of the TE terminates the fatty acid synthesis on the ACP, and then the thus-hydrolyzed fatty acid is supplied to the synthesis of polyunsaturated fatty acids or TAG or the like.

Therefore, lipid productivity of the transformant to be used for the lipid production, particularly productivity of the fatty acids can be further improved by enhancing expression of the TE, in addition to the TK and the FBA.

To date, it is known that a TE shows different reaction specificities depending on the number of carbon atoms and the number of unsaturated bonds of the acyl group (fatty acid residue) constituting an acyl-ACP being a substrate. Therefore, TE is considered to be an important factor in determining the fatty acid composition of an organism. In particular, when a host originally having no gene encoding a TE is used, enhancing expression of a gene encoding the TE (hereinafter, also referred to as "TE gene") is preferable. Further, productivity of fatty acids is improved by enhancing expression of the TE gene having substrate specificity to a medium-chain acyl-ACP. The productivity of fatty acids is further improved by introducing such a gene.

The TE that can be used in the present invention can be appropriately selected from ordinary TEs and proteins functionally equivalent to the TEs, according to a kind of host or the like. Specific examples thereof include a TE derived from *Nannochloropsis oceanica* (SEQ ID NO: 13, the nucleotide sequence of a gene encoding the same: SEQ ID NO: 14). Moreover, as the proteins functionally equivalent to them, a protein consisting of an amino acid sequence having 50% or more (preferably 70% or more, more preferably 80% or more, and further preferably 90% or more) identity with the amino acid sequence of the TE described above, and having TE activity, can be also used.

The TE activity of the protein can be confirmed by, for example, introducing a DNA produced by linking the TE gene to the downstream of a promoter which functions in a host cell such as *Escherichia coli*, into a host cell which lacks a fatty acid degradation system, culturing the thus-obtained cell under the conditions suitable for the expression of the introduced TE gene, and analyzing any change caused thereby in the fatty acid composition of the host cell or the cultured liquid by using a gas chromatographic analysis or the like.

Alternatively, the TE activity can be measured by introducing a DNA produced by linking the TE gene to the downstream of a promoter which functions in a host cell such as *Escherichia coli*, into a host cell, culturing the thus-obtained cell under the conditions suitable for the expression of the introduced TE gene, and subjecting a disruption liquid of the cell to a reaction which uses several acyl-ACPs, as substrates, prepared according to the method of Yuan et al. (Yuan L. et al., Proc. Natl. Acad. Sci. U.S.A., 1995, vol. 92 (23), p. 10639-10643).

The AT that can be used in the present invention is not particularly limited, and needs to be the protein having acyltransferase activity (hereinafter, also referred to as "AT activity"). Herein, the term "AT activity" means the activity to catalyze the acylation of a glycerol compound such as a glycerol-3-phosphate, a lysophosphatidic acid, and a diacylglycerol.

An AT is a protein catalyzing the acylation of a glycerol compound such as a glycerol-3-phosphate, a lysophosphatidic acid and a diacylglycerol. Fatty acid acyl CoA, in which a free fatty acid is bonded to CoA, or acyl ACP is catalyzed by each AT to be incorporated into a glycerol backbone. Then, the three fatty acid molecules are ester-bonded to one glycerol molecule to produce and accumulate TAG.

Therefore, lipid productivity of the transformant to be used for the lipid production, particularly productivity of the fatty acids can be further improved by enhancing expression of the AT, in addition to the TK and the FBA.

To date, it is known that there are several ATs showing different reaction specificities depending on the number of carbon atoms and the number of unsaturated bonds of the acyl group (fatty acid residue) constituting a fatty acyl-CoA or a fatty acyl-ACP being a substrate. Therefore, AT is considered to be an important factor in determining the fatty acid composition of an organism. In particular, when a host originally having no gene encoding an AT is used, enhancing expression of an AT gene is preferable. Further, productivity of medium-chain fatty acids is improved by enhancing expression of the AT gene having substrate specificity to a medium-chain fatty acyl-CoA or a medium-chain fatty acyl-ACP. The productivity of fatty acids is further improved by introducing such a gene.

The AT that can be used in the present invention can be appropriately selected from ordinary ATs and proteins functionally equivalent to the ATs, according to a kind of host or the like. Specific examples thereof include a DGAT derived from *Nannochloropsis oceanica* (SEQ ID NO: 9, the nucleotide sequence of a gene encoding the same: SEQ ID NO: 10; or SEQ ID NO: 138, the nucleotide sequence of a gene encoding the same: SEQ ID NO: 139). Moreover, as the proteins functionally equivalent to them, a protein consisting of an amino acid sequence having 50% or more (preferably 70% or more, more preferably 80% or more, and further preferably 90% or more) identity with the amino acid sequence of the DGAT described above, and having AT activity, can be also used.

The ACS that can be used in the present invention is not particularly limited, and needs to be the protein having acyl-CoA synthetase activity (hereinafter, also referred to as "ACS activity"). Here, the term "ACS activity" means activity of bonding a free fatty acid and a CoA to produce an acyl-CoA.

The ACS is a protein involved synthesis of acyl-CoA by adding CoA to a biosynthesized fatty acid (free fatty acid).

Therefore, lipid productivity of the transformant to be used for the lipid production, particularly productivity of the fatty acids can be further improved by enhancing expression of the ACS, in addition to the TK and the FBA.

The ACS that can be used in the present invention can be appropriately selected from ordinary ACSs and proteins functionally equivalent to the ACSs, according to a kind of host or the like. Specific examples thereof include a long chain acyl-CoA synthetase (hereinafter, also merely referred to as "LACS") derived from *Nannochloropsis oceanica* (SEQ ID NO: 11, the nucleotide sequence of a gene encoding the same: SEQ ID NO: 12) and the like. Moreover, as the proteins functionally equivalent to them, a protein consisting of an amino acid sequence having 50% or more (preferably 70% or more, more preferably 80% or more, and further preferably 90% or more) identity with the amino acid sequence of the LACS derived from *Nannochloropsis oceanica*, and having ACS activity, can be also used.

The amino acid sequence information of the TE, the DGAT and the LACS, the nucleotide sequence information of the genes encoding the same, and the like can be obtained from, for example, National Center for Biotechnology Information (NCBI), or the like.

Further, the transformant in which expression of the RPI gene, the TE gene, the AT gene, or the ACS gene is enhanced can be prepared by an ordinary method. For example, the transformant can be prepared by a method similar to the later-described method for enhancing expression of the TK gene and the FBA gene, such as a method for introducing the each gene into a host, a method for modifying expression regulation regions of the gene in the host having the each gene on a genome, or the like.

The gene to be introduced into each of hosts is preferably optimized in codon in accordance with use frequency of codon in the host to be used. Information of codons used in each of organisms is available from Codon Usage Database (www.kazusa.or.jp/codon/).

In the present specification, a cell in which expression of an objective protein or a gene encoding the same is enhanced is also referred to as the "transformant", and a cell in which expression of the objective protein or the gene encoding the same is not enhanced is also referred to as the "host" or "wild type strain".

The transformant used in the present invention is excellent in photosynthetic ability as compared to a host itself, and productivity of fatty acids and lipids containing the same as components is significantly increased therein. Moreover, as a result, in the transformant, the fatty acid composition in the lipid is modified. Therefore, the present invention using the transformant can be preferably applied to production of fatty acids or lipids having specific number of carbon atoms, particularly fatty acids or lipids containing the same as components, preferably fatty acids having 12 or more and 20 or less carbon atoms or lipids containing the same as components, more preferably fatty acids having 14 or more and 18 or less carbon atoms or lipids containing the same as components, further preferably fatty acids having 16 carbon atoms or lipids containing the same as components, or furthermore preferably saturated fatty acids (palmitic acids) or lipids containing the same as components. Further, as demonstrated in Examples below, a transformant used in the present invention has an increased total amount of each fatty acid (total fatty acid amount).

Note that as used herein, the term "photosynthetic ability" indicates production efficiency of photosynthetic products and can be confirmed by measuring production amount (e.g., dry weight, turbidity, organic carbon weight, oxygen generation) of photosynthetic products or consumption amount of carbon dioxide. Further, the productivity of fatty acids and lipids of the host and the transformant can be measured by the method used in Examples described below.

A method of preparing the transformant of the present invention is explained. However, the present invention is not limited thereto.

The host for the transformant can be appropriately selected from ordinarily used hosts. For example, microorganisms (including photosynthetic bacteria, and algae including microalgae), plants or plant cells can be used as the host in the present invention. Among these, microorganisms are preferable, algae are more preferable, and microalgae are further preferable as a host, from the viewpoints of production efficiency and the usability of lipids to be obtained.

Examples of the microalgae include prokaryote (cyanobacteria) and eukaryote (eukaryotic algae), and from a viewpoint of lipid productivity, eukaryotic algae are preferable. In a case where eukaryotic alga is used as a host, it is preferable that the TK, the FBA and the RPI are localized in the chloroplast. Examples of methods of making the proteins localize in the chloroplast include a method of introducing a gene encoding the protein containing a chloroplast transit signal which functions in a host into a nuclear genome, a method of introducing a gene encoding the protein without a chloroplast transit signal into a chloroplast genome, and the like.

For eukaryotic algae, from a viewpoint of establishment of a gene recombinant technique, algae belonging to the genus *Chlamydomonas*, algae belonging to the genus *Chlorella*, algae belonging to the genus *Phaeodactylum*, and algae belonging to the class Eustiqmatophyceae are preferable, and algae belonging to the class Eustiqmatophyceae are more preferable. Specific examples of algae belonging to the class Eustiqmatophyceae include algae belonging to the genus *Nannochloropsis*, algae belonging to the genus *Monodopsis*, algae belonging to the genus *Vischeria*, algae belonging to the genus *Chlorobotrys*, and algae belonging to the genus *Goniochloris*. Among them, from a viewpoint of lipid productivity, algae belonging to the genus *Nannochloropsis* is preferable. Specific examples of the algae belonging to the genus *Nannochloropsis* include *Nannochloropsis oceanica, Nannochloropsis oculata, Nannochloropsis qaditana, Nannochloropsis salina, Nannochloropsis limnetica, Nannochloropsis granulata, Nannochloropsis* sp., and the like. Among these, from a viewpoint of the lipid productivity, *Nannochloropsis oceanica* or *Nannochloropsis gaditana* is preferable, and *Nannochloropsis oceanica* is more preferable.

A vector for use as the plasmid vector for gene expression or a vector containing the gene expression cassette (plasmid) may be any vector capable of introducing the gene encoding the objective protein into a host, and expressing the objective gene in the host cell. For example, a vector which has expression regulation regions such as a promoter and a terminator in accordance with the type of the host to be used, and has a replication initiation point, a selection marker or the like, can be used. Furthermore, the vector may also be a vector such as a plasmid capable of self-proliferation and self-replication outside the chromosome, or may also be a vector which is incorporated into the chromosome.

Specific examples of the vector that can be used preferably in the present invention include, in the case of using a microorganism as the host, pBluescript (pBS) II SK(−) (manufactured by Stratagene), a pSTV-based vector (manufactured by Takara Bio), a pUC-based vector (manufactured by Takara Shuzo), a pET-based vector (manufactured by Takara Bio), a pGEX-based vector (manufactured by GE Healthcare), a pCold-based vector (manufactured by Takara Bio), pHY300PLK (manufactured by Takara Bio), pUB110 (1986, Plasmid 15(2), p. 93-103), pBR322 (manufactured by Takara Bio), pRS403 (manufactured by Stratagene), and pMW218/219 (manufactured by Nippon Gene).

When the algae or the microalgae are used as the host, specific examples of the vector include pUC18 (manufactured by Takara Bio), pUC19 (manufactured by Takara Bio), P66 (*Chlamydomonas* Center), P-322 (*Chlamydomonas* Center), pPha-T1 (see Journal of Basic Microbiology, 2011, vol. 51, p. 666-672) and pJET1 (manufactured by COSMO BIO). In particular, in the case of using the algae belonging to the genus *Nannochloropsis* as the host, pUC18, pPha-T1 or pJET1 is preferably used. Moreover, when the host is the algae belonging to the genus *Nannochloropsis*, the host can be transformed, with referring to the method described in Proceedings of the National Academy of Sciences of the United States of America, 2011, vol. 108(52), by using the DNA fragment (gene expression cassette) consisting of the objective gene, a promoter and a terminator.

Moreover, a kind of promoter regulating the expression of the gene encoding an objective protein introduced into the expression vector can also be appropriately selected according to a kind of the host to be used. Specific examples of the promoter that can be preferably used in the present invention include lac promoter, trp promoter, tac promoter, trc promoter, T7 promoter, SpoVG promoter, a promoter that relates to a substance that can be induced by addition of isopropyl β-D-1-thiogalactopyranoside (IPTG), a promoter of Rubisco operon (rbc), operon encoding PSI reaction center protein (psaA and psaB), operon encoding D1 protein of PSII (psbA), operon encoding c-phycocyanin (β subunit (cpcB), rrnA operon encoding ribosomal RNA and the like, cauliflower mosaic virus 35S RNA promoter, promoters for housekeeping genes (e.g., tubulin promoter, actin promoter and ubiquitin promoter), *Brassica napus* or *Brassica rapa*-derived Napin gene promoter, a promoter of a violaxanthin/(chlorophyll a)-binding protein gene derived from the genus *Nannochloropsis* (VCP1 promoter, VCP2 promoter) (Proceedings of the National Academy of Sciences of the United States of America, 2011, vol. 108(52)), a promoter of an oleosin-like protein LDSP (lipid droplet surface protein) gene derived from the genus *Nannochloropsis* (Astrid Vieler, et al., PLOS Genetics, 2012; 8(11): e1003064. doi: 10.1371) (LDSP promoter), a promoter of a glutamine synthetase gene derived from the genus *Nannochloropsis* (GS promoter), and a promoter of an ammonium transporter gene derived from the genus *Nannochloropsis* (AMT promoter). In a case where algae belonging to the genus *Nannochloropsis* are used as a host in the present invention, a tubulin promoter, a heat shock protein promoter, a promoter of a violaxanthin/chlorophyll a-binding protein gene (VCP1 promoter, VCP2 promoter), and a promoter of an oleosin-like protein LDSP gene derived from the genus *Nannochloropsis*, a promoter of an ACP gene (ACP promoter), a promoter of a desaturase gene, a promoter of an AT gene (AT promoter), a GS promoter and an AMT promoter can be preferably used. In addition, algae belonging to the genus *Nannochloropsis* have been generally known to efficiently produce lipids under nutrient (in particular, nitrogen)-depleted conditions and/or high light conditions. Thus, it is more preferable to use a promoter that can be strongly expressed under such conditions. From a viewpoint of expressing under the nitrogen-depleted conditions or the high light conditions, a promoter of a gene involved in the fatty acid synthetic pathway or the TAG synthetic pathway, or a promoter of a gene involved in nitrogen assimilation is preferred, the promoter of the LDSP gene, the ACP promoter, the promoter of the desaturase gene, the AT promoter, the GS promoter, and the AMT promoter are more preferred, and the promoter of the LDSP gene, the GS promoter and the AMT promoter are further preferred.

Moreover, a kind of selection marker for confirming introduction of the gene encoding an objective protein can also be appropriately selected according to a kind of the host to be used. Examples of the selection marker that can be preferably used in the present invention include drug resistance genes such as an ampicillin resistance gene, a chloramphenicol resistance gene, an erythromycin resistance gene, a neomycin resistance gene, a kanamycin resistance gene, a spectinomycin resistance gene, a tetracycline resistance gene, a blasticidin S resistance gene, a bialaphos resistance gene, a zeocin resistance gene, a paromomycin resistance gene, a gentamicin resistance gene, and a hygromycin resistance gene. Further, it is also possible to use a deletion of an auxotrophy-related gene or the like as the selection marker gene.

Introduction of the gene encoding an objective protein to the vector can be conducted by an ordinary technique such as restriction enzyme treatment and ligation.

The method for transformation can be appropriately selected from ordinary techniques according to a kind of the host to be used. Examples of the method for transformation include a transformation method of using calcium ion, a general competent cell transformation method, a protoplast transformation method, an electroporation method, an LP transformation method, a method of using *Agrobacterium*, a particle gun method, and the like. In a case where an alga belonging to the genus *Nannochloropsis* is used as a host, transformation can also be performed by using the electroporation method described in Randor Radakovits, et al., Nature Communications, DOI: 10.1038/ncomms1688, 2012, or the like. Further, in a case where an eukaryotic alga, especially an alga belonging to the genus *Nannochloropsis* is used as a host, a gene can be introduced into a chloroplast genome, according to the method described in WO 103834640 A, Qinhua Gan, et al., Frontiers in Plant Science, DOI: 10.3389/fpls.2018.00439, or the like.

The selection of a transformant having an objective gene fragment introduced therein can be carried out by utilizing the selection marker or the like. For example, the selection can be carried out by using an indicator whether a transformant acquires the drug resistance as a result of introducing a drug resistance gene into a host cell together with an objective DNA fragment upon the transformation. Further, the introduction of an objective DNA fragment can also be confirmed by PCR method using a genome as a template or the like.

In a host having the gene on a genome, a method of modifying expression regulation regions of the genes and enhancing the expression of the genes is described.

The term "expression regulation region" indicates the promoter, the terminator and untranslated region, in which these sequences are generally involved in regulation of the expression amount (transcription amount, translation amount) of the gene adjacent thereto. In a host having the TK gene on a genome, productivity of fatty acids can be improved by modifying expression regulation regions of the genes and enhancing expression of the genes.

Specific examples of the method of modifying the expression regulation regions include interchange of promoters. In the host having the gene on the genome, expression of the gene can be enhanced by interchanging the promoter of the gene with a promoter having higher transcriptional activity.

As the host, it is possible to preferably use an organism having the genes on the genome, among the above-described organisms.

The promoter used for promoter interchanging is not particularly limited, and can be appropriately selected from promoters that are higher in the transcriptional activity than the promoter of the gene, and suitable for production of fatty acids.

In a case where a *Nannochloropsis* is used as a host, a tubulin promoter, a heat shock protein promoter, a promoter of the violaxanthin/(chlorophyll a)-binding protein gene (VCP1 promoter, VCP2 promoter), a promoter of an oleosin-like protein LDSP gene derived from the genus *Nannochloropsis*, an ACP promoter, a promoter of a desaturase gene, an AT promoter, a GS promoter, and an AMT promoter can preferably be used. From a viewpoint of improvement in the productivity of fatty acids or lipids containing the same as components, a promoter of a gene which is involved in the pathway of fatty acid biosynthesis or TAG biosynthesis, and a promoter of a gene which is involved in the pathway of nitrogen assimilation is preferable, and the promoter of the LDSP gene, the ACP promoter, the promoter of a desaturase gene, the AT promoter, the GS promoter, and the AMT promoter are more preferable, and the promoter of the LDSP gene, the GS promoter and the AMT promoter are further preferable.

The above-described modification of a promoter can employ according to an ordinarily method such as homologous recombination. Specifically, a linear DNA fragment containing upstream and downstream regions of a target promoter and containing other promoter instead of the target promoter is constructed, and the resultant DNA fragment is incorporated into a host cell to cause double crossover homologous recombination on the side upstream and downstream of the target promoter of the host genome. As a result, the target promoter on the genome is substituted with other promoter fragment, and the promoter can be modified.

The method of modifying a target promoter according to such homologous recombination can be conducted with, for example, referring to literature such as Methods in molecular biology, 1995, vol. 47, p. 291-302. In particular, in the case where the host is the algae belonging to the genus *Nannochloropsis*, specific region in a genome can be modified, with referring to literature such as Proceedings of the National Academy of Sciences of the United States of America, 2011, vol. 108(52), by homologous recombination method.

In the transformant of the present invention, photosynthetic ability, and productivity of fatty acids or lipids containing the same as components are improved in comparison with that in the host in which expression of the TK, the FBA, and the like is not enhanced. Accordingly, if the transformant of the present invention is cultured under suitable conditions and then the fatty acids or the lipids containing the same as components are collected from an obtained cultured product, the fatty acids or the lipids containing the same as components can be efficiently produced.

Herein, the term "cultured product" means liquid medium and a transformant subjected to cultivation.

The culture conditions of the transformant of the present invention can be appropriately selected in accordance with the type of the host to be used for a transformation, and any ordinary used culture conditions for the host can be employed. Further, from a viewpoint of the production efficiency of fatty acids, for example, precursor substances involved in the fatty acid biosynthesis system, such as glycerol, acetic acid, or glucose, may be added to the medium.

In a case where an alga is used as the host, a medium based on natural seawater or artificial seawater, or a commercially available culture medium may be used. Specific examples of the culture medium include f/2 medium, ESM medium, Daigo's IMK medium, L1 medium and MNK medium. Above all, from viewpoints of an improvement in the lipid productivity and a nutritional ingredient concentration, f/2 medium, ESM medium or Daigo's IMK medium is preferred, f/2 medium or Daigo's IMK medium is more preferred, and f/2 medium is further preferred. For growth promotion of the algae and an improvement in productivity of fatty acids, a nitrogen source, a phosphorus source, metal salts, vitamins, trace metals or the like can be appropriately added to the culture medium.

An amount of the transformant to be seeded to the culture medium is appropriately selected. In view of viability, the range of an amount of the transformant to be seeded is preferably 1 to 50% (vol/vol), and more preferably 1 to 10% (vol/vol), per culture medium. Culture temperature is not particularly limited within the range in which the temperature does not adversely affect growth of the algae, and is ordinarily in the range of 5 to 40° C. From viewpoints of the growth promotion of the algae, the improvement in productivity of fatty acids, and reduction of production cost, the range of the culture temperature is preferably 10 to 35° C., and more preferably 15 to 30° C.

Moreover, the algae are preferably cultured under irradiation with light so that photosynthesis can be made. The light irradiation only needs to be made under conditions in which the photosynthesis can be made, and artificial light or sunlight may be applied. From viewpoints of the growth promotion of the algae and the improvement in the productivity of fatty acids, the range of light intensity during the light irradiation is preferably 1 to 4,000 $\mu mol/m^2/s$, more preferably 10 to 2,500 $\mu mol/m^2/s$, further preferably 100 to 2,500 $\mu mol/m^2/s$, further preferably 200 to 2,500 $\mu mol/m^2/s$, and further preferably 250 to 2,500 $\mu mol/m^2/s$, and furthermore preferably 300 to 2,500 $\mu mol/m^2/s$. Moreover, an interval of the light irradiation is not particularly limited. From the viewpoints similar to that described above, the irradiation is preferably performed under a light and dark cycle. In 24 hours, the range of the light period is preferably from 8 to 24 hours, more preferably from 10 to 18 hours, and further preferably 12 hours.

Moreover, the algae are preferably cultured in the presence of a carbon dioxide-containing gas or in a culture medium containing carbonate such as sodium hydrogen carbonate so that the photosynthesis can be made. A concentration of carbon dioxide in the gas is not particularly limited. From viewpoints of the growth promotion and the improvement in the productivity of fatty acids, the range of the concentration thereof is preferably 0.03 (which is the same degree as the concentration under atmospheric conditions) to 10%, more preferably from 0.05 to 5%, further preferably from 0.1 to 3%, and furthermore preferably from 0.3 to 1%. A concentration of carbonate is not particularly limited. When sodium hydrogen carbonate is used, for example, from viewpoints of the growth promotion and the improvement in the productivity of fatty acids, the range of the concentration of sodium hydrogen carbonate is preferably from 0.01 to 5% by mass, more preferably from 0.05 to 2% by mass, and further preferably from 0.1 to 1% by mass.

A culture time is not particularly limited, and the culture may be performed for a long time (for example, about 150 days) so that an alga body in which the lipids are accumulated at a high concentration can grow at a high concentration. From viewpoints of the algal growth promotion, the improvement in the productivity of fatty acids, and reduction of production cost, the range of the culture time is preferably from 3 to 90 days, more preferably from 7 to 30 days, and further preferably from 14 to 21 days. The culture may be performed in any of aerated and agitated culture, shaking culture or static culture. From a viewpoint of improving air-permeability, aerated and agitated culture is preferred.

A method of collecting the lipids from the cultured product is appropriately selected from an ordinary method. For example, lipid components can be isolated and collected from the above-described cultured product by means of filtration, centrifugation, cell disruption, gel filtration chromatography, ion exchange chromatography, chloroform/methanol extraction, hexane extraction, ethanol extraction, or the like. In the case of carrying out the larger scales culturing, lipids can be obtained by collecting oil components from the cultured product through pressing or extraction, and then performing general purification processes such as degumming, deacidification, decoloration, dewaxing, and deodorization. After lipid components are isolated as such, the isolated lipids are hydrolyzed, and thereby fatty acids can be obtained. Specific examples of the method of isolating fatty acids from lipid components include a method of treating the lipid components at a high temperature of about 70° C. in an alkaline solution, a method of performing a lipase treatment, and a method of degrading the lipid components using high-pressure hot water.

The lipids produced in the production method of the present invention preferably contain fatty acids or fatty acid compounds, and more preferably contain fatty acids or fatty acid ester compounds, in view of usability thereof.

In view of usability for a surfactant or the like, the fatty acid or the ester compound thereof contained in the lipid is preferably a fatty acid or an ester compound thereof, more preferably a fatty acid having 12 or more and 20 or less carbon atoms or an ester compound thereof, further preferably a fatty acid having 14 or more and 18 or less carbon atoms or an ester compound thereof, further preferably a fatty acid having 16 carbon atoms or an ester compound thereof, furthermore preferably a saturated fatty acid having 16 carbon atoms (palmitic acid) or an ester compound thereof.

From a viewpoint of the productivity, the fatty acid ester compound is preferably a simple lipid or a complex lipid, more preferably a simple lipid, and further preferably a TAG.

The fatty acid obtained by the production method of the present invention can be utilized for food, as well as a plasticizer, an emulsifier incorporated into cosmetic products or the like, a cleansing agent such as a soap or a detergent, a fiber treatment agent, a hair conditioning agent, a disinfectant or an antiseptic.

With regard to the embodiments described above, the present invention also discloses proteins, genes, transformants and methods, described below.

<1> A method of improving photosynthetic ability of an alga, containing enhancing expression of a TK and a FBA, or a TK gene and a FBA gene.

<2> A method of producing lipids, containing the steps of:
culturing an alga in which expression of a TK and expression of a FBA, or a TK gene and a FBA gene are enhanced, and
producing fatty acids or lipids containing the same as components, preferably fatty acids having 12 or more and 20 or less carbon atoms or lipids containing the same as components, more preferably fatty acids having 14 or more and 18 or less carbon atoms or lipids containing the same as components, further preferably fatty acids having 16 carbon atoms or lipids containing the same as components, or further preferably saturated fatty acids having 16 carbon atoms (palmitic acids) or lipids containing the same as components.

<3> A method of improving lipid productivity, containing
enhancing expression of a TK and a FBA, or a TK gene and a FBA gene in an alga to improve productivity of fatty acids or lipids containing the same as components produced in an algal cell.

<4> A method of modifying fatty acid composition, containing the steps of:
enhancing expression of a TK and a FBA, or a TK gene and a FBA gene in an alga, and
modifying the composition of fatty acids or fatty acids in lipids containing the same as components produced in an algal cell.

<5> The method described in the above item <4>, which increases the proportion of fatty acids having 12 or more and 20 or less carbon atoms, preferably fatty acids having 14 or more and 18 or less carbon atoms, more preferably fatty acids having 16 carbon atoms, or further preferably saturated fatty acids having 16 carbon atoms (palmitic acids) in the total fatty acids to be produced.

<6> The method described in any one of the above items <1> to <5>, wherein expression of the TK and expression of the FBA are enhanced by enhancing expression of the TK gene and the FBA gene in the algal cell.

<7> The method described in any one of the above items <1> to <6>, wherein the TK gene and the FBA gene are introduced into the alga to enhance expression of the introduced TK gene and FBA gene.

<8> The method described in any one of the above items <1> to <7>, wherein the TK is the following protein (A) or (B):
(A) a protein consisting of the amino acid sequence set forth in SEQ ID NO: 1; or
(B) a protein consisting of an amino acid sequence having 60% or more, preferably 65% or more, more preferably 70% or more, more preferably 75% or more, more preferably 80% or more, more preferably 85% or more, more preferably 90% or more, more preferably 91% or more, more preferably 92% or more, more preferably 93% or more, more preferably 95% or more, more preferably 97% or more, more preferably 98% or more, and further preferably 99% or more identity with the amino acid sequence of the protein (A), and having TK activity.

<9> The method described in the above item <8>, wherein the protein (B) is a protein which consists of an amino acid sequence in which 1 or several, preferably 1 or more and 289 or less, more preferably 1 or more and 253 or less, further preferably 1 or more and 216 or less, furthermore preferably 1 or more and 180 or less, furthermore preferably 1 or more and 144 or less, furthermore preferably 1 or more and 108 or less, furthermore preferably 1 or more and 72 or less, furthermore preferably 1 or more and 65 or less, furthermore preferably 1 or more and 57 or less, furthermore preferably 1 or more and 50 or less, furthermore preferably 1 or more and 36 or less, furthermore preferably 1 or more and 21 or less, furthermore preferably 1 or more and 14 or less, and furthermore preferably 1 or more and 7 or less amino acids are deleted, substituted, inserted or added to the amino acid sequence of the protein (A), and has TK activity.

<10> The method described in any one of the above items <1> to <9>, wherein the TK gene is a gene consisting of the following DNA (a) or (b):
(a) a DNA consisting of the nucleotide sequence set forth in SEQ ID NO: 2; or
(b) a DNA consisting of a nucleotide sequence having 60% or more, preferably 65% or more, more preferably 70% or more, further preferably 75% or more, furthermore preferably 80% or more, furthermore preferably 85% or more, furthermore preferably 90% or more, furthermore preferably 91% or more, furthermore preferably 92% or more, furthermore preferably 93% or more, furthermore preferably 95% or more, furthermore preferably 97% or more, furthermore preferably 98% or more, and furthermore preferably 99% or more identity with the nucleotide sequence of the DNA (a), and encoding a protein having TK activity.

<11> The method described in the above item <10>, wherein the DNA (b) is a DNA consisting of a nucleotide sequence in which 1 or several, preferably 1 or more and 868 or less, more preferably 1 or more and 760 or less, further preferably 1 or more and 651 or less, furthermore preferably 1 or more and 543 or less, furthermore preferably 1 or more and 434 or less, furthermore preferably 1 or more and 325 or less, furthermore preferably 1 or more and 217 or less, furthermore preferably 1 or more and 195 or less, furthermore preferably 1 or more and 173 or less, furthermore preferably 1 or more and 152 or less, furthermore preferably 1 or more and 108 or less, furthermore preferably 1 or more and 65 or less, furthermore preferably 1 or more and 43 or less, and furthermore preferably 1 or more and 21 or less nucleotides, are deleted, substituted, inserted or added to the nucleotide sequence of the DNA (a), and encoding a protein having TK activity.

<12> The method described in any one of the above items <1> to <11>, wherein the FBA is the following protein (C) or (D):
(C) a protein consisting of the amino acid sequence set forth in SEQ ID NO: 3; or
(D) a protein consisting of an amino acid sequence having 60% or more, preferably 65% or more, more preferably 70% or more, more preferably 75% or more, more preferably 80% or more, more preferably 85% or more, more preferably 90% or more, more preferably 91% or more, more preferably 92% or more, more preferably 93% or more, more preferably 95% or more, more preferably 97% or more, more preferably 98% or more, and further preferably 99% or more identity with the amino acid sequence of the protein (C), and having FBA activity.

<13> The method described in the above item <12>, wherein the protein (D) is a protein which consists of an amino acid sequence in which 1 or several, preferably 1 or more and 152 or less, more preferably 1 or more and 133 or less, further preferably 1 or more and 114 or less, furthermore preferably 1 or more and 95 or less, furthermore preferably 1 or more and 76 or less, furthermore preferably 1 or more and 57 or less, furthermore preferably 1 or more and 38 or less, furthermore preferably 1 or more and 34 or less, furthermore preferably 1 or more and 30 or less, furthermore preferably 1 or more and 26 or less, furthermore preferably 1 or more and 19 or less, furthermore preferably 1 or more and 11 or less, furthermore preferably 1 or more and 7 or less, and furthermore preferably 1 or more and 3 or less amino acids are deleted, substituted, inserted or added to the amino acid sequence of the protein (C), and has FBA activity.

<14> The method described in any one of the above items <1> to <13>, wherein the FBA gene is a gene consisting of the following DNA (c) or (d):

(c) a DNA consisting of the nucleotide sequence set forth in SEQ ID NO: 4; or (d) a DNA consisting of a nucleotide sequence having 60% or more, preferably 65% or more, more preferably 70% or more, further preferably 75% or more, furthermore preferably 80% or more, furthermore preferably 85% or more, furthermore preferably 90% or more, furthermore preferably 91% or more, furthermore preferably 92% or more, furthermore preferably 93% or more, furthermore preferably 95% or more, furthermore preferably 97% or more, furthermore preferably 98% or more, and furthermore preferably 99% or more identity with the nucleotide sequence of the DNA (c), and encoding a protein having FBA activity.

<15> The method described in the above item <14>, wherein the DNA (d) is a DNA consisting of a nucleotide sequence in which 1 or several, preferably 1 or more and 459 or less, more preferably 1 or more and 402 or less, further preferably 1 or more and 344 or less, furthermore preferably 1 or more and 287 or less, furthermore preferably 1 or more and 229 or less, furthermore preferably 1 or more and 172 or less, furthermore preferably 1 or more and 114 or less, furthermore preferably 1 or more and 103 or less, furthermore preferably 1 or more and 91 or less, furthermore preferably 1 or more and 80 or less, furthermore preferably 1 or more and 57 or less, furthermore preferably 1 or more and 34 or less, furthermore preferably 1 or more and 22 or less, and furthermore preferably 1 or more and 11 or less nucleotides, are deleted, substituted, inserted or added to the nucleotide sequence of the DNA (c), and encoding a protein having FBA activity.

<16> The method described in any one of the above items <1> to <15>, wherein expression of a RPI is enhanced by enhancing expression of a RPI gene in the algal cell.

<17> The method described in any one of the above items <1> to <16>, wherein the RPI gene is introduced into the alga to enhance expression of the introduced RPI gene.

<18> The method described in the above item <16> or <17>, wherein the RPI is the following protein (E) or (F):

(E) a protein consisting of the amino acid sequence set forth in SEQ ID NO: 7; or (F) a protein consisting of an amino acid sequence having 60% or more, preferably 65% or more, more preferably 70% or more, more preferably 75% or more, more preferably 80% or more, more preferably 85% or more, more preferably 90% or more, more preferably 91% or more, more preferably 92% or more, more preferably 93% or more, more preferably 95% or more, more preferably 97% or more, more preferably 98% or more, and further preferably 99% or more identity with the amino acid sequence of the protein (E), and having RPI activity.

<19> The method described in the above item <18>, wherein the protein (F) is a protein which consists of an amino acid sequence in which 1 or several, preferably 1 or more and 112 or less, more preferably 1 or more and 98 or less, further preferably 1 or more and 84 or less, furthermore preferably 1 or more and 70 or less, furthermore preferably 1 or more and 56 or less, furthermore preferably 1 or more and 42 or less, furthermore preferably 1 or more and 28 or less, furthermore preferably 1 or more and 25 or less, furthermore preferably 1 or more and 22 or less, furthermore preferably 1 or more and 19 or less, furthermore preferably 1 or more and 14 or less, and furthermore preferably 1 or more and 8 or less amino acids are deleted, substituted, inserted or added to the amino acid sequence of the protein (E), and has RPI activity.

<20> The method described in any one of the above items <16> to <19>, wherein the RPI gene is the following DNA (e) or (f):

(e) a DNA consisting of the nucleotide sequence set forth in SEQ ID NO: 8; or (f) a DNA consisting of a nucleotide sequence having 60% or more, preferably 65% or more, more preferably 70% or more, further preferably 75% or more, furthermore preferably 80% or more, furthermore preferably 85% or more, furthermore preferably 90% or more, furthermore preferably 91% or more, furthermore preferably 92% or more, furthermore preferably 93% or more, furthermore preferably 95% or more, furthermore preferably 97% or more, furthermore preferably 98% or more, and furthermore preferably 99% or more identity with the nucleotide sequence of the DNA (e), and encoding a protein having RPI activity.

<21> The method described in the above item <20>, wherein the DNA (f) is a DNA consisting of a nucleotide sequence in which 1 or several, preferably 1 or more and 339 or less, more preferably 1 or more and 297 or less, further preferably 1 or more and 254 or less, furthermore preferably 1 or more and 212 or less, furthermore preferably 1 or more and 169 or less, furthermore preferably 1 or more and 127 or less, furthermore preferably 1 or more and 84 or less, furthermore preferably 1 or more and 76 or less, furthermore preferably 1 or more and 67 or less, furthermore preferably 1 or more and 59 or less, furthermore preferably 1 or more and 42 or less, furthermore preferably 1 or more and 25 or less, furthermore preferably 1 or more and 16 or less, and furthermore preferably 1 or more and 8 or less nucleotides, are deleted, substituted, inserted or added to the nucleotide sequence of the DNA (e), and encoding a protein having RPI activity.

<22> The method described in any one of the above items <1> to <21>, wherein expression of at least one kind or two or more kinds of proteins involved in fatty acid synthetic pathway or TAG synthetic pathway is enhanced in the alga.

<23> The method described in the above item <22>, wherein at least one kind or two or more kinds of the proteins involved in fatty acid synthetic pathway or TAG synthetic pathway are at least one kind or two or more kinds of proteins selected from the group consisting of an ACC, an ACP, a holo-ACP synthase (phosphopantetheinyl transferases), a MAT, a KAS, a KAR, a HD, a KAR, a TE, an ACS, a G3PDH, an AT (GPAT, LPAAT, DGAT or the like), and a PAP, preferably are at least one kind or two or more kinds of proteins selected from the group consisting of an ACC, an ACP, a KAS, a TE, an ACS, and an AT (GPAT, LPAAT, DGAT or the like), more preferably are at least one kind or two or more kinds of proteins selected from the group consisting of a TE, an ACS and an AT (GPAT, LPAAT, DGAT or the like), and further more preferably are at least one kind or two or more kinds of proteins selected from the group consisting of a TE, an ACS and a DGAT.

<24> The method described in any one of the above items <1> to <23>, wherein expression of the DGAT, preferably the ACS and the DGAT, and more preferably the TE, the ACS and the DGAT is enhanced in the alga.

<25> The method described in the above item <23> or <24>, wherein the TE is the following protein (G) or (H):
(G) a protein consisting of the amino acid sequence set forth in SEQ ID NO: 13; or
(H) a protein consisting of an amino acid sequence having 50% or more, preferably 70% or more, more preferably 80% or more, and further preferably 90% or more identity with the amino acid sequence of the protein (G), and having TE activity.
<26> The method described in any one of the above items <23> to <25>, wherein the ACS is the following protein (I) or (J):
(I) a protein consisting of the amino acid sequence set forth in SEQ ID NO: 11; or
(J) a protein consisting of an amino acid sequence having 50% or more, preferably 70% or more, more preferably 80% or more, and further preferably 90% or more identity with the amino acid sequence of the protein (I), and having ACS activity.
<27> The method described in any one of the above items <23> to <26>, wherein the AT is any one of the AT selected form the group consisting of the following (K) to (N):
(K) a protein consisting of the amino acid sequence set forth in SEQ ID NO: 9;
(L) a protein consisting of an amino acid sequence having 50% or more, preferably 70% or more, more preferably 80% or more, and further preferably 90% or more identity with the amino acid sequence of the protein (K), and having AT activity;
(M) a protein consisting of the amino acid sequence set forth in SEQ ID NO: 138; and
(N) a protein consisting of an amino acid sequence having 50% or more, preferably 70% or more, more preferably 80% or more, and further preferably 90% or more identity with the amino acid sequence of the protein (M), and having AT activity
<28> The method described in any one of the above items <1> to <27>, wherein the alga is an eukaryotic alga, and preferably an alga belonging to the class Eustigmatophyceae.
<29> The method described in the above item <28>, wherein the alga belonging to the class Eustigmatophyceae is an alga belonging to the genus *Nannochloropsis*.
<30> The method described in the above item <29>, wherein the alga belonging to the genus *Nannochloropsis* is at least an alga selected from the group consisting of *Nannochloropsis oceanica*, *Nannochloropsis oculata*, *Nannochloropsis qaditana*, *Nannochloropsis salina*, *Nannochloropsis limnetica*, *Nannochloropsis granulata*, and *Nannochloropsis* sp.
<31> The method described in any one of the above items <2> to <30>, wherein the lipids contain a fatty acid or an ester compound thereof, preferably a fatty acid having 12 or more and 20 or less carbon atoms or an ester compound thereof, more preferably a fatty acid having 14 or more and 18 or less carbon atoms or an ester compound thereof, further preferably a fatty acid having 16 carbon atoms or an ester compound thereof, and specifically preferably a saturated fatty acid having 16 carbon atoms (palmitic acid) or an ester compound thereof.
<32> The method described in any one of the above items <1> to <31>, wherein expression of the gene is enhanced by a promoter which strongly expresses under nutrient-depleted conditions or high light conditions, preferably a promoter of a gene involved in fatty acid synthetic pathway or TAG synthetic pathway, or a promoter of a gene involved in nitrogen assimilation, more preferably a promoter of a LDSP gene, an ACP promoter, a promoter of a desaturase gene, an AT promoter, a GS promoter or an AMT promoter, or further preferably a promoter of a LDSP gene, a GS promoter, or an AMT promoter.
<33> The method described in any one of the above items <1> to <32>, wherein the alga is cultured under the conditions in which light intensity is in a range of 1 to 4,000 µmol/m$^2$/s, preferably 10 to 2,500 µmol/m$^2$/s, more preferably 100 to 2,500 µmol/m$^2$/s, more preferably 200 to 2,500 µmol/m$^2$/s, more preferably 250 to 2,500 µmol/m$^2$/s, and more preferably 300 to 2,500 µmol/m$^2$/s.
<34> The method described in any one of the above items <1> to <33>, wherein the alga is cultured by using a f/2 medium wherein concentrations of a nitrogen source and a phosphorus source are reinforced.
<35> A transformant of an alga, wherein expression of a TK and expression of a FBA, or expression of a TK gene and expression of a FBA gene are enhanced.
<36> The transformant described in the above item <35>, wherein the TK gene and the FBA gene are introduced into the algal cell, and thereby expression of the TK and expression of the FBA are enhanced.
<37> The transformant described in the above item <35> or <36>, which contains a recombinant vector containing the TK gene and the FBA gene, or a recombinant cassette containing the TK gene and the FBA gene.
<38> A method of preparing a transformant, containing introducing a recombinant vector containing a TK gene and a FBA gene, or a recombinant cassette containing a TK gene and a FBA gene, into an alga.
<39> The transformant described in the above item <35> or <36>, wherein the TK is a protein specified in the above item <8> or <9>.
<40> The transformant, or the method of preparing the same described in any one of the above items <35> to <38>, wherein the TK gene is a DNA specified in the above item <10> or <11>.
<41> The transformant, or the method of preparing the same described in any one of the above items <35> to <40>, wherein the FBA is a protein specified in the above item <12> or <13>.
<42> The transformant, or the method of preparing the same described in any one of the above items <35> to <40>, wherein the FBA gene is a DNA specified in the above item <14> or <15>.
<43> The transformant described in any one of the above items <35> to <37> and <39> to <42>, wherein expression of a RPI, or expression of a RPI gene is enhanced.
<44> The transformant described in any one of the above items <35> to <37> and <39> to <43>, wherein expression of the RPI gene is enhanced in the algal cell, thereby expression of the RPI is enhanced.
<45> The transformant described in any one of the above items <35> to <37> and <39> to <44>, containing a recombinant vector containing the RPI gene, or a recombinant cassette containing the RPI gene.
<46> The method of preparing a transformant described in any one of the above items <38> to <42>, containing introducing a recombinant vector containing a RPI gene, or a recombinant cassette containing a RPI gene, into an alga.
<47> The transformant, or the method of preparing the same described in any one of the above items <43> to <46>, wherein the RPI is a protein specified in the above item <18> or <19>.

<48> The transformant, or the method of preparing the same described in any one of the above items <43> to <46>, wherein the RPI gene is a DNA specified in the above item <20> or <21>.

<49> The transformant described in any one of the above items <35> to <37>, <39> to <45>, <47>, and <48>, wherein expression of at least one kind or two or more kinds of proteins involved in fatty acid synthetic pathway or TAG synthetic pathway is enhanced in the alga.

<50> The transformant described in the above item <49>, wherein at least one kind or two or more kinds of the proteins involved in fatty acid synthetic pathway or TAG synthetic pathway are at least one kind or two or more kinds of proteins selected from the group consisting of an ACC, an ACP, a holo-ACP synthase (phosphopantetheinyl transferases), a MAT, a KAS, a KAR, a HD, a KAR, a TE, an ACS, a G3PDH, an AT (GPAT, LPAAT, DGAT or the like), and a PAP, preferably are at least one kind or two or more kinds of proteins selected from the group consisting of an ACC, an ACP, a KAS, a TE, an ACS, and an AT (GPAT, LPAAT, DGAT or the like), more preferably are at least one kind or two or more kinds of proteins selected from the group consisting of a TE, an ACS and an AT (GPAT, LPAAT, DGAT or the like), and further more preferably are at least one kind or two or more kinds of proteins selected from the group consisting of a TE, an ACS and a DGAT.

<51> The transformant described in any one of the above items <35> to <37>, <39> to <45>, and <47> to <50>, wherein expression of the DGAT, preferably the ACS and the DGAT, and more preferably the TE, the ACS and the DGAT is enhanced in the alga.

<52> The transformant described in any one of the above items <35> to <37>, <39> to <45>, and <47> to <51>, containing a recombinant vector containing a gene encoding a protein specified in the above item <49> or <50>, or a recombinant cassette containing a gene encoding a protein specified in the above item <49> or <50>.

<53> A method of preparing a transformant, containing introducing a recombinant vector or a recombinant cassette specified in the above item <52> into an alga.

<54> The transformant, or the method of preparing the same described in any one of the above items <50> to <53>, wherein the DGAT is a protein specified in the above item <27>.

<55> The transformant, or the method of preparing the same described in any one of the above items <50> to <54>, wherein the ACS is a protein specified in the above item <26>.

<56> The transformant, or the method of preparing the same described in any one of the above items <50> to <55>, wherein the TE is a protein specified in the above item <25>.

<57> The transformant, or the method of preparing the same described in any one of the above items <35> to <56>, wherein expression of the gene is enhanced by a promoter which expresses under nutrient-depleted conditions or high light conditions, preferably a promoter of a gene involved in fatty acid synthetic pathway or TAG synthetic pathway, or a promoter of a gene involved in nitrogen assimilation, more preferably a promoter of a LDSP gene, an ACP promoter, a promoter of a desaturase gene, an AT promoter, a GS promoter or an AMT promoter, or further preferably a promoter of a LDSP gene, a GS promoter, or an AMT promoter.

<58> The transformant, or the method of preparing the same described in any one of the above items <35> to <57>, wherein the alga is an eukaryotic alga, and preferably an alga belonging to the class Eustigmatophyceae.

<59> The transformant, or the method of preparing the same described in the above item <58>, wherein the alga belonging to the class Eustigmatophyceae is an alga belonging to the genus *Nannochloropsis*.

<60> The transformant, or the method of preparing the same described in the above item <59>, wherein the alga belonging to the genus *Nannochloropsis* is at least an alga selected from the group consisting of *Nannochloropsis oceanica*, *Nannochloropsis oculata*, *Nannochloropsis gaditana*, *Nannochloropsis salina*, *Nannochloropsis limnetica*, *Nannochloropsis granulata*, and *Nannochloropsis* sp.

<61> Use of the transformant, the transformant prepared by the method of preparing the same, the protein, the gene or the recombinant vector described in any one of the above items <35> to <60>, for producing lipids.

<62> The use described in the above item <61>, wherein the lipids contain a fatty acid or an ester compound thereof, preferably a fatty acid having 12 or more and 20 or less carbon atoms or an ester compound thereof, more preferably a fatty acid having 14 or more and 18 or less carbon atoms or an ester compound thereof, further preferably a fatty acid having 16 carbon atoms or an ester compound thereof, and specifically preferably a saturated fatty acid having 16 carbon atoms (palmitic acid) or an ester compound thereof.

<63> A method of improving photosynthetic ability, containing enhancing expression of proteins involved in CBB cycle, or a gene encoding the same.

<64> The method described in the above item <63>, wherein the proteins involved in CBB cycle are a TK and a FBA, preferably a TK, a FBA and a RPI, more preferably the TK specified in the above item <8> or <9>, the FBA specified in the above item <12> or <13>, and the RPI specified in the above item <18> or <19>.

<65> The method described in the above item <63> or <64>, containing enhancing expression of at least one kind or two or more kinds of proteins involved in fatty acid synthetic pathway and TAG synthetic pathway, or a gene encoding the same.

<66> The method described in the above item <65>, wherein at least one kind or two or more kinds of the proteins involved in fatty acid synthetic pathway or TAG synthetic pathway are at least one kind or two or more kinds of proteins selected from the group consisting of an ACC, an ACP, a holo-ACP synthase (phosphopantetheinyl transferases), a MAT, a KAS, a KAR, a HD, a KAR, a TE, an ACS, a G3PDH, an AT (GPAT, LPAAT, DGAT or the like), and a PAP, preferably are at least one kind or two or more kinds of proteins selected from the group consisting of an ACC, an ACP, a KAS, a TE, an ACS, and an AT (GPAT, LPAAT, DGAT or the like), more preferably are at least one kind or two or more kinds of proteins selected from the group consisting of a TE, an ACS and an AT (GPAT, LPAAT, DGAT or the like), further more preferably are at least one kind or two or more kinds of proteins selected from the group consisting of a TE, an ACS and a DGAT, further preferably a DGAT, further preferably an ACS and a DGAT, further preferably a TE, an ACS and a DGAT, and furthermore preferably the TE specified in the above item <25>, the ACS specified in the above item <26> and the DGAT specified in the above item <27>.

<67> The method described in any one of the above items <1> to <34> and <63> to <66>, containing culturing the alga for 3 to 90 days, preferably for 7 to 30 days, and more preferably 14 to 21 days.

EXAMPLES

Hereinafter, the present invention will be described more in detail with reference to Examples, but the present invention is not limited thereto. Herein, the nucleotide sequences of the primers used in Examples are shown in Tables 1 and 2.

TABLE 1

| SEQ ID NO: | Nucleotide sequence (5' -> 3') |
|---|---|
| SEQ ID NO: 26 | CTTTTTTGTGAAGCAATGGCCAAGCTGACCAGCGC |
| SEQ ID NO: 27 | TTTCCCCCATCCCGATTAGTCCTGCTCCTCGGCCAC |
| SEQ ID NO: 28 | CTTTTTTGTGAAGCAATGGTCGAGATTCGAAGCAT |
| SEQ ID NO: 29 | TTTCCCCCATCCCGATCAGAAGAACTCGTCCAACA |
| SEQ ID NO: 30 | CTTTTTTGTGAAGCAATGACACAAGAATCCCTGTTAC |
| SEQ ID NO: 31 | TTTCCCCCATCCCGATCAGGCGCCGGGGCGGTGTC |
| SEQ ID NO: 32 | CGAGCTCGGTACCCGACTGCGCATGGATTGACCGA |
| SEQ ID NO: 33 | TGCTTCACAAAAAAGACAGCTTCTTGAT |
| SEQ ID NO: 34 | TCGGGATGGGGGAAAAAAACCTCTG |
| SEQ ID NO: 35 | ACTCTAGAGGATCCCCTTTCGTAAATAAATCAGCTC |
| SEQ ID NO: 36 | GGGATCCTCTAGAGTCGACC |
| SEQ ID NO: 37 | CGGGTACCGAGCTCGAATTC |
| SEQ ID NO: 38 | CGAGCTCGGTACCCGTTCTTCCGCTTGTTGCTGCC |
| SEQ ID NO: 39 | TGTTGATGCGGGCTGAGATTGGTGG |
| SEQ ID NO: 40 | GCTTCTGTGGAAGAGCCAGTG |
| SEQ ID NO: 41 | GGCAAGAAAGCTGGGGAAAAGACAGG |
| SEQ ID NO: 42 | CCAGCTTTTCTTGCCACTGCGCATGGATTGACCGA |
| SEQ ID NO: 43 | CGAGCTCGGTACCCGGTGTGTCCTGCGTGTTGATCAGTAG |
| SEQ ID NO: 44 | TTTTAGGGGTGGTCGAGTTGCTGTGGTG |
| SEQ ID NO: 45 | GAAAGATCCAAGAGAGACGAGTAG |
| SEQ ID NO: 46 | AGGACCGAATCGAGGCTCTGATAAATGAGG |
| SEQ ID NO: 47 | CCTCGATTCGGTCCTTTCTTCCGCTTGTTGCTGCCGATG |
| SEQ ID NO: 48 | CGAGCTCGGTACCCGCGCAAAAAACAGACAAACTT |
| SEQ ID NO: 49 | TTTTGAAGTGTTCGGCGAGGAAAGGTTTCCTGTG |
| SEQ ID NO: 50 | TTTGGAAGAGAGTTTGCTGTTTGTAAG |
| SEQ ID NO: 51 | TGTTACATCGGCGCTTGCTTGACTTGG |
| SEQ ID NO: 52 | AGCGCCGATGTAACAGTGTGTCCTGCGTGTTGATCAG |
| SEQ ID NO: 53 | TTCTTCCGCTTGTTGCTGCCGATGGCGGCCATGGTCTC |

TABLE 1-continued

| SEQ ID NO: | Nucleotide sequence (5' -> 3') |
|---|---|
| SEQ ID NO: 54 | GTGTGTCCTGCGTGTTGATCAGTAGATGCGCAAG |
| SEQ ID NO: 55 | CGCAAAAAACAGACAAACTTCGTCACTCAC |
| SEQ ID NO: 56 | CTTTCGTAAATAAATCAGCTCCTCCTCGGAGAAGCGAAAG |
| SEQ ID NO: 57 | CAGCCCGCATCAACAATGGTTGCTAAAGCTGCTTTTGC |
| SEQ ID NO: 58 | CTCTTCCACAGAAGCTTACAGATAGGCCTTGGCCTCC |
| SEQ ID NO: 59 | CAGCCCGCATCAACAATGGCTCGCCTCTTCGTCACCG |
| SEQ ID NO: 60 | CTCTTCCACAGAAGCTTAGTACTTATACCCCTTCACG |

TABLE 2

| SEQ ID NO: | Nucleotide sequence (5' -> 3') |
|---|---|
| SEQ ID NO: 61 | CAGCCCGCATCAACAATGAGCCGCCAAAAGACTCTC |
| SEQ ID NO: 62 | CTCTTCCACAGAAGCCTACTTCTTATTGATGACGTC |
| SEQ ID NO: 63 | GACCACCCCTAAAAATGGTTGCTAAAGCTGCTTTTGCC |
| SEQ ID NO: 64 | TCTCTTGGATCTTTCTTACAGATAGGCCTTGGCCTCCTTG |
| SEQ ID NO: 65 | CCGAACACTTCAAAAATGAGCCGCCAAAAGACTCTCTTTT |
| SEQ ID NO: 66 | AAACTCTCTTCCAAACTACTTCTTATTGATGACGTCGATG |
| SEQ ID NO: 67 | GACCACCCCTAAAAATGACGCCGCAAGCCGACATCAC |
| SEQ ID NO: 68 | TCTCTTGGATCTTTCTTACTCAATGGACAACGGGC |
| SEQ ID NO: 69 | CAGCCCGCATCAACAATGCCCGCCTACACGACGACATC |
| SEQ ID NO: 70 | CTCTTCCACAGAAGCCTACTTGTAGAGATTGGCGATG |
| SEQ ID NO: 71 | CAGCCCGCATCAACAATGAGAATACCTTCCCTTATCC |
| SEQ ID NO: 72 | CTCTTCCACAGAAGCCTACGTCGTGCCCATGTTCA |
| SEQ ID NO: 124 | CAGCCCGCATCAACAATGAAGACCGCCGCTCTCCTC |
| SEQ ID NO: 125 | GCGCGCAACACCGCGGGTGCGGGAGAAC |
| SEQ ID NO: 126 | CAGCCCGCATCAACAATGAAGTTCACCGGCCTCGTC |
| SEQ ID NO: 127 | CTCTTCCACAGAAGCTTAAGACTCGTTGAGGGCCG |

TABLE 2-continued

| SEQ ID NO: | Nucleotide sequence (5' -> 3') |
|---|---|
| SEQ ID NO: 128 | CAGCCCGCATCAACAATGCGAAGCTACGCGGTG CTTTCC |
| SEQ ID NO: 129 | CTCTTCCACAGAAGCTTATGAAGACGCCGAATT CAAACG |
| SEQ ID NO: 130 | CAGCCCGCATCAACAATGGCCCGTCTCTCTGCT TTGAG |
| SEQ ID NO: 131 | CTCTTCCACAGAAGCTTACTTGAGCATGGCCAC GAGC |
| SEQ ID NO: 132 | CAGCCCGCATCAACAATGAAGGGTGCTATCCTC CTCGC |
| SEQ ID NO: 133 | CTCTTCCACAGAAGCTTACGCGTGCGCCGCATT CTGG |
| SEQ ID NO: 134 | CAGCCCGCATCAACAATGGTCAAGACTGCTGCC GTC |
| SEQ ID NO: 135 | CTCTTCCACAGAAGCTTAAGCCGCCACCGGCGC CTTC |
| SEQ ID NO: 136 | CGCGGTGTTGCGCGCGAGAAGACGATCGGTCTC GAG |
| SEQ ID NO: 137 | CTCTTCCACAGAAGCCTACCGCTCCGGCCGCCA TTTG |

Test Example Searching for Putative CBB Cycle Gene Derived from *Nannochloropsis oceanica*, and Localization Analysis Based on RNA sequence data of *Nannochloropsis oceanica* strain NIES-2145, searching for CBB cycle genes except for RubisCO was conducted. As a result, total 28 genes were selected as candidates. The amino acid sequence and the nucleotide sequence of each of the genes are shown as SEQ ID NOs: 1 to 8, and 73 to 120. Among them, a transketolase 1 (TK1; amino acid SEQ ID NO: 1, nucleotide sequence: 2, hereinafter shown in a similar manner), a fructose-1,6-bisphosphate aldolase 2 (FBA2; SEQ ID NO: 3, 4), a fructose-1,6-bisphosphate aldolase 4 (FBA4; SEQ ID NO: 5, 6), a RPI (SEQ ID NO: 7, 8), a phosphoglycerate kinase 1 (PGK1; SEQ ID NO: 73, 74), a glyceraldehyde-3-phosphate dehydrogenase 1 (GAPDH1; SEQ ID NO: 79, 80), a triosephosphate isomerase 2 (TPI2; SEQ ID NO: 91, 92), a fructose-1,6-bisphosphatase 2 (FBP2; SEQ ID NO: 99, 100), a fructose-1,6-bisphosphatase 3 (FBP3; SEQ ID NO: 101, 102), a fructose-1,6-bisphosphatase 4 (FBP4; SEQ ID NO: 103, 104), a fructose-1,6-bisphosphatase 5 (FBP5; SEQ ID NO: 105, 106), a sedoheptulose-1,7-bisphosphatase 1 (SBP1; SEQ ID NO: 107, 108), a ribulose-5-phosphate epimerase (RPE1; SEQ ID NO: 113, 114), a phosphoribulokinase (PRK; SEQ ID NO: 119, 120), were suggested as chloroplast localized proteins, and considered as enzymes constituting CBB cycle present in chloroplast.

Comparative Example 1 Preparation of a Plasmid for Expression of CBB Cycle Gene Derived from *Nannochloropsis oceanica* or FBP/SBP Gene Derived from *Synechococcus elongatus*, Transformation of *Nannochloropsis*, and Production of Lipids by the Transformant (1) Construction of Plasmid for Zeocin Resistance Gene Expression A zeocin resistance gene (SEQ ID NO: 15), and a tubulin promoter sequence (SEQ ID NO: 18) derived from *Nannochloropsis gaditana* strain CCMP 526 described in a literature (Randor Radakovits, et al., Nature Communications, DOI:10.1038/ncomms1688, 2012) were artificially synthesized. Using the thus-synthesized DNA fragments as templates, and a pair of the primers set forth in SEQ ID NO: 26 and SEQ ID NO: 27, and a pair of the primers set forth in SEQ ID NO: 32 and SEQ ID NO: 33 shown in Table 1, PCRs were carried out to amplify the zeocin resistance gene and the tubulin promoter sequence, respectively. Further, using a genome of *Nannochloropsis oceanica* strain NIES-2145 as a template, and a pair of the primers set forth in SEQ ID SEQ ID NO: 34 and SEQ ID NO: 35 shown in Table 1, PCR was carried out to amplify the heat shock protein terminator sequence (SEQ ID NO: 19). Furthermore, using a plasmid vector pUC19 (manufactured by Takara Bio) as a template, and a pair of the primers set forth in SEQ ID NO: 36 and SEQ ID NO: 37 shown in Table 1, PCR was carried out to amplify the plasmid vector pUC19.

These four amplified fragments were treated by restriction enzyme DpnI (manufactured by TOYOBO) respectively, and were purified using a High Pure PCR Product Purification Kit (manufactured by Roche Applied Science). Then, obtained four fragments were fused using an In-Fusion HD Cloning Kit (manufactured by Clontech) to construct a plasmid for zeocin resistance gene expression. Herein, the expression plasmid consists of the pUC19 vector sequence and an insert sequence in which the tubulin promoter sequence, the zeocin resistance gene and the heat shock protein terminator sequence were linked in this order.

(2) Obtaining CBB Cycle Genes Derived from *Nannochloropsis oceanica*, and Construction of Plasmid for CBB Cycle Genes Expression Total RNA of *Nannochloropsis oceanica* strain NIES-2145 was extracted. The cDNA was obtained by reverse transcription using the total RNA, and SuperScript (trademark) III First-Strand Synthesis SuperMix for qRT-PCR (manufactured by Invitrogen). Using the above cDNA as a template, and a pair of the primers set forth in SEQ ID NO: 57 and SEQ ID NO: 58, a pair of the primers set forth in SEQ ID NO: 59 and SEQ ID NO: 60, a pair of the primers set forth in SEQ ID NO: 61 and SEQ ID NO:62, a pair of the primers set forth in SEQ ID NO: 126 and SEQ ID NO: 127, a pair of the primers set forth in SEQ ID NO: 128 and SEQ ID NO: 129, a pair of the primers set forth in SEQ ID NO: 130 and SEQ ID NO: 131, a pair of the primers set forth in SEQ ID NO: 132 and SEQ ID NO: 133, and a pair of the primers set forth in SEQ ID NO: 134 and SEQ ID NO: 135 shown in Tables 1 and 2 respectively, PCRs were carried out to obtain the TK1 gene fragment consisting of the nucleotide sequence set forth in SEQ ID NO: 2, the FBA2 gene fragment consisting of the nucleotide sequence set forth in SEQ ID NO: 4, the RPI gene fragment consisting of the nucleotide sequence set forth in SEQ ID NO: 8, the phosphoglycerate kinase 1 gene (hereinafter, also referred to as "PGK1 gene") fragment consisting of the nucleotide sequence set forth in SEQ ID NO: 74, the fructose 1,6- bisphosphatase 2 gene (hereinafter, also referred to as "FBP2 gene") fragment consisting of the nucleotide sequence set forth in SEQ ID NO: 100, the fructose 1,6-bisphosphatase 5 gene (hereinafter, also referred to as "FBP5 gene") fragment consisting of the nucleotide sequence set forth in SEQ ID NO: 106, the sedoheptulose-1,7-bisphosphatase 1 gene (hereinafter, also referred to as "SBP1 gene") fragment consisting of the nucleotide sequence set forth in SEQ ID NO: 108, and the phosphoribulokinase gene (hereinafter, also referred to as "PRK gene") fragment consisting of the nucleotide sequence set forth in SEQ ID NO: 120, respectively.

Further, using a genome of *Nannochloropsis oceanica* strain NIES-2145 as a template, and a pair of the primers set forth in SEQ ID NO: 38 and SEQ ID NO: 39, and a pair of the primers set forth in SEQ ID NO: 40 and SEQ ID NO: 41 shown in Table 1, PCRs were carried out to obtain the LDSP promoter fragment (SEQ ID NO: 20), and the VCP1 terminator fragment (SEQ ID NO: 21).

Furthermore, using the plasmid for zeocin resistance gene expression prepared in the above (1) as a template, and a pair of the primers set forth in SEQ ID NO: 42 and SEQ ID NO: 37 shown in Table 1, PCR was carried out to amplify a fragment containing the cassette for zeocin resistance gene expression (the tubulin promoter sequence, the zeocin resistance gene, and the heat shock protein terminator sequence) and the pUC19 sequence.

The fragment of each of the CBB cycle genes, the LDSP promoter fragment, the VCP1 terminator fragment, and the fragment containing the zeocin resistance gene expression cassette and pUC19 sequence, were fused by a method in a manner similar to the above (1), to construct a plasmid for TK1 gene expression, a plasmid for FBA2 gene expression, a plasmid for RPI gene expression, a plasmid for PGK1 gene expression, a plasmid for FBP2 gene expression, a plasmid for FBP5 gene expression, a plasmid for SBP1 gene expression, and a plasmid for PRK gene expression respectively. Herein, the expression plasmid consists of the pUC19 vector sequence and an insert sequence in which the LDSP promoter sequence, the each CBB cycle gene, the VCP1 terminator sequence, the tubulin promoter sequence, the zeocin resistance gene and the heat shock protein terminator sequence were linked in this order.

(3) Obtaining Bifunctional Fructose-1,6-Bisphosphatase/Sedoheptulose-1,7-Bisphosphatase Gene (Hereinafter, Also Referred to as "SeFBP/SBP Gene") Derived from *Synechococcus elongatus*, and Construction of Plasmid for SeFBP/SBP Gene Expression Using a genome DNA of *Synechococcus elongatus* strain PCC7942 as a template, and a pair of the primers set forth in SEQ ID NO: 136 and SEQ ID NO: 137 shown in Table 2, PCR was carried out to amplify a DNA fragment containing SeFBP/SBP gene (SEQ ID NO: 122, the amino acid sequence corresponding thereto: SEQ ID NO: 121; wherein valine was substituted for the first methionine). In the present Example, the SeFBP/SBP gene is also regarded as a "CBB cycle gene". Further, using a genome DNA of *Nannochloropsis oceanica* strain NIES-2145 as a template, and a pair of the primers set forth in SEQ ID NO: 124 and SEQ ID NO: 125 shown in Table 2, PCR was carried out to obtain a fragment of chloroplast transit signal of a VCP1 (SEQ ID NO: 123). Furthermore, using the plasmid for the TK1 gene expression as a template, and a pair of the primers set forth in SEQ ID NO: 40 and SEQ ID NO: 39 shown in Table 1, PCR was carried out to amplify a fragment consisting of the VCP1 terminator sequence, the tubulin promoter sequence, the zeocin resistance gene, the heat shock protein terminator sequence, the pUC19 vector, and the LDSP promoter sequence.

These three fragments were fused by a method in a manner similar to the above (1), thereby a plasmid for the SeFBP/SBP gene expression was constructed. Herein, the expression plasmid consists of the pUC19 vector sequence and an insert sequence in which the LDSP promoter sequence, a VCP1 chloroplast transit signal, the SeFBP/SBP gene, the VCP1 terminator sequence, the tubulin promoter sequence, the zeocin resistance gene and the heat shock protein terminator sequence were linked in this order.

(4) Introduction of a Cassette for CBB Cycle Gene Expression into *Nannochloropsis*, Culturing the Transformant, Extraction of Lipid from Culture Fluid, and Analysis of Fatty Acids Contained Therein Using each of the plasmids for CBB cycle gene expression prepared in the above (2) and (3) as a template respectively, and a pair of the primers set forth in SEQ ID NO: 53 and SEQ ID NO: 56 shown in Table 1, PCRs were carried out to amplify the cassette for each CBB cycle gene expression (a DNA fragment containing the LDSP promoter sequence, the each CBB cycle gene, the VCP1 terminator sequence, the tubulin promoter sequence, the zeocin resistance gene, and the heat shock protein terminator sequence) respectively.

The amplified fragment was purified using High Pure PCR Product Purification Kit (manufactured by Roche Applied Science). Herein, sterilized water was used for elution upon purification without using an elution buffer included in the kit.

About $1\times10^9$ cells of *Nannochloropsis oceanica* strain NIES-2145 were washed with 384 mM sorbitol solution to remove a salt, and the resultant was used as a host cell for transformation. The cassette for each CBB cycle gene expression as amplified above was mixed by about 500 ng with the host cell respectively, and electroporation was carried out under the conditions of 50 μF, 500Ω and 2,200 v/2 mm. After twenty four hours recovery cultivation in f/2 liquid medium (75 mg of $NaNO_3$, 6 mg of $NaH_2PO_4.2H_2O$, 0.5 μg of vitamin B12, 0.5 μg of biotin, 100 μg of thiamine, 10 mg of $Na_2SiO_3.9H_2O$, 4.4 mg of $Na_2EDTA.2H_2O$, 3.16 mg of $FeCl_3.6H_2$), 12 μg of $CoSO_4.7H_2O$, 21 μg of $ZnSO_4.7H_2O$, 180 μg of $MnCl_2.4H_2O$, 7 μg of $CuSO_4.5H_2O$, 7 μg of $Na_2MoO_4.2H_2O$/artificial sea water 1 L), the resultant was inoculated in a f/2 agar medium containing 2 μg/mL of zeocin, and cultured for two to three weeks under 12 h/12 h light-dark conditions at 25° C. under an atmosphere of 0.3% $CO_2$. Each strain containing the cassette for each CBB cycle gene expression was selected from the resultant colonies by a PCR method. The selected strain was inoculated to 20 mL of medium in which a nitrogen concentration in the f/2 medium was reinforced 15 times, and a phosphorus concentration therein was reinforced 5 times (hereinafter, also referred to as "N15P5 medium"), and subjected to shaking culture for two weeks under the 12 h/12 h light-dark conditions at 25° C. under the atmosphere of 0.3% $CO_2$.

Then, 2 mL of the culture fluid was inoculated to 18 mL of medium in which a nitrogen concentration in the f/2 medium was reinforced 5 times, and a phosphorus concentration therein was reinforced 5 times (hereinafter, also referred to as "N5P5 medium"), and subjected to shaking culture for two weeks under the 12 h/12 h light-dark conditions, and about 100 μmol/m²/s light intensity, at 25° C. under the atmosphere of 0.3% $CO_2$, to prepare preceding culture fluid. A 96-well plate and an Infinite M200 PRO (TECAN, Inc.) were used to measure turbidity at 750 nm (hereinafter, also referred to as "$OD_{750}$"). The last preceding culture fluid was inoculated to 18 mL of N5P5 medium so that the final concentration of $OD_{750}$ is 0.1, and was cultured for 5 days under the same conditions to prepare a pre-culture fluid. The pre-culture fluid was likewise inoculated to 18 mL of N5P5 medium so that the final concentration of $OD_{750}$ is 0.1, and was subjected to main culture under the same conditions. In addition, as a negative control, an experiment was also conducted on the wild type strain, *Nannochloropsis oceanica* strain NIES-2145. The wild-type strain was cultured (N=2 to 4), and 3 to 4 independent lines for each CBB cycle transgenic strain were cultured.

(5) Extraction of Lipid from Culture Fluid of *Nannochloropsis*, and Analysis of Fatty Acids Contained Therein After the start, the main culture was sampled over time to extract lipids by the method below.

To 0.25 mL of the culture fluid, 50 µL of 1 mg/mL glyceryl triheptadecanoate (manufacture by SIGMA) solution in chloroform as an internal standard was added, and then 0.5 mL of chloroform and 1 mL of methanol were further added thereto. The mixture was vigorously stirred and then was left for 10 minutes. Further, 0.5 mL of chloroform and 0.5 mL of 1.5% KCl were added thereto. The mixture was stirred and centrifuged for 5 minutes at 3,000 rpm, and then the chloroform layer (lower layer) was collected with Pasteur pipette. A nitrogen gas was blown onto the resultant chloroform layer to be dried into solid, then 50 µL of chloroform was added thereto to be resuspended. Then, 0.5 mL of 14% boron trifluoride solution (manufactured by SIGMA) was added thereto, and the mixture was stirred and kept warm at 80° C. for 30 minutes. Thereafter, 0.5 mL of hexane and 0.5 mL of saturated saline were added thereto, and the mixture was vigorously stirred and then was left for 10 minutes at room temperature. Then, the hexane layer being upper layer was collected to obtain fatty acid esters.

The obtained fatty acid esters were provided for gas chromatographic analysis. The measuring conditions are described below.

<Gas Chromatography Conditions>
Analysis apparatus: 7890A (Agilent Technologies)
Capillary column: DB-1 MS 30 m×200 µm×0.25 µm (J&W Scientific)
Mobile phase: high purity helium
Oven temperature: maintained for 0.5 minutes at 150° C.→150 to 220° C. (temperature increase at 40° C./minute)→220 to 320° C. (temperature increase at 20° C./minute)→maintained for 2 minutes at 320° C. (post run: 2 minutes)
Injection port temperature: 300° C.
Injection method: split injection (split ratio: 75:1)
Amount of injection: 1 µL
Cleaning vial: methanol/chloroform
Detection method: FID
Detector temperature: 300° C.

In addition, each fatty acid methyl ester was identified by subjecting each fatty acid methyl ester standard to gas chromatography under the same conditions and comparing their retention times. Further, gas chromatography-mass spectroscopy was optionally used for the identification.

Amounts of the fatty acid methyl esters of each of the fatty acids were quantitatively determined based on the peak areas of waveform data obtained by the above gas chromatographic analysis. The peak area corresponding to each of the fatty acid methyl esters was compared with that of fatty acid methyl esters having 17 carbon atoms derived from the internal standard, and carried out corrections between the samples, and then the amount of each of the fatty acids per liter of the culture fluid was calculated. Further, the amount of total fatty acids was calculated by summing the amounts of each of the fatty acids thus obtained, and weight proportion of each of the fatty acids in the amount of total fatty acids were calculated. Herein, the term "total fatty acid" in the present Example means the sum of the amount of C12:0, the amount of C14:0, the amount of 16:1, the amount of C16:0, the amount of C18:n and the amount of C20:n, and the term "Cx:n" means the sum of fatty acids wherein that the number of carbon atoms is "x" and the number of double bonds is "0 to 5".

Tables 3 to 7 show the results. Note that in the Table below, the wild-type strain is designated as "WT". Each transformant was named as each CBB cycle gene introduced. The total fatty acid yield ("TFA yield" in the Table) is represented in the mean±standard deviation of each independent line. In addition, the days designated in the Table indicate culturing days.

TABLE 3

| | TFA yield (mg/L) | | | | | |
|---|---|---|---|---|---|---|
| | 3 days | 7 days | 10 days | 14 days | 17 days | 21 days |
| WT (Comparative example) | 77.3 ± 4.4 | 444.6 ± 29.2 | 824.8 ± 44.2 | 1324.1 ± 73.6 | 1654.5 ± 85.7 | 2123.2 ± 87.3 |
| FBA2 (Comparative example) | 83.2 ± 2.4 | 462.8 ± 44.7 | 846.9 ± 87.8 | 1358.8 ± 175.6 | 1682.6 ± 254.0 | 2142.4 ± 339.5 |
| TK1 (Comparative example) | 80.8 ± 4.3 | 489.3 ± 41.8 | 882.9 ± 80.8 | 1436.8 ± 179.1 | 1830.7 ± 239.0 | 2356.8 ± 334.9 |

TABLE 4

| | TFA yield (mg/L) | | | | |
|---|---|---|---|---|---|
| | 3 days | 7 days | 10 days | 14 days | 27 days |
| WT (Comparative example) | 68.5 ± 3.2 | 466.3 ± 28.9 | 894.7 ± 16.4 | 1319.6 ± 40.7 | 2336.6 ± 4.4 |
| RPI (Comparative example) | 73.9 ± 3.0 | 426.8 ± 22.6 | 873.9 ± 32.8 | 1350.6 ± 61.5 | 2398.5 ± 148.2 |

TABLE 5

| | TFA yield (mg/L) | | | | |
| --- | --- | --- | --- | --- | --- |
| | 3 days | 6 days | 9 days | 12 days | 20 days |
| WT (Comparative example) | 54.6 ± 8.3 | 246.0 ± 43.6 | 705.2 ± 47.8 | 1040.1 ± 57.0 | 1921.7 ± 116.9 |
| FBP2 (Comparative example) | 72.4 ± 2.3 | 277.2 ± 3.1 | 684.6 ± 22.8 | 988.5 ± 36.5 | 1972.2 ± 26.8 |
| FBP5 (Comparative example) | 61.8 ± 10.7 | 232.5 ± 61.9 | 619.1 ± 114.4 | 935.8 ± 113.0 | 1925.1 ± 151.6 |

TABLE 6

| | TFA yield (mg/L) | | | | | |
| --- | --- | --- | --- | --- | --- | --- |
| | 3 days | 7 days | 10 days | 14 days | 17 days | 21 days |
| WT (Comparative example) | 60.1 ± 2.4 | 443.7 ± 24.2 | 865.9 ± 58.0 | 1413.5 ± 62.6 | 1800.0 ± 44.9 | 2316.9 ± 54.1 |
| SBP1 (Comparative example) | 58.5 ± 4.1 | 327.7 ± 18.5 | 460.9 ± 41.1 | 552.3 ± 64.1 | 591.9 ± 68.2 | 667.6 ± 84.3 |

TABLE 7

| | TFA yield (mg/L) | | | | |
| --- | --- | --- | --- | --- | --- |
| | 4 days | 9 days | 14 days | 18 days | 21 days |
| WT (Comparative example) | 101.9 ± 5.2 | 735.5 ± 24.9 | 1370.9 ± 34.2 | 1771.5 ± 69.5 | 2207.1 ± 106.6 |
| SeFBP/SBP (Comparative example) | 128.8 ± 5.5 | 746.5 ± 61.5 | 1357.0 ± 111.4 | 1740.7 ± 136.6 | 2029.2 ± 144.8 |
| PGK1 (Comparative example) | 117.2 ± 13.7 | 777.9 ± 85.4 | 1497.1 ± 260.6 | 1913.8 ± 369.4 | 2274.9 ± 440.3 |
| PRK (Comparative example) | 108.9 ± 7.4 | 706.8 ± 46.5 | 1336.7 ± 101.4 | 1700.2 ± 140.5 | 2059.4 ± 189.3 |

As is apparent from the Tables 3 to 7, it was not shown a large improvement of fatty acid productivity in the transformant wherein expression of one kind of CBB cycle gene was enhanced in *Nannochloropsis*, in comparison with that in the wild type strain. Although a tendency of a slight improvement of fatty acid productivity was shown in the transformant wherein expression of the TK1 gene was enhanced, a large improvement was not accomplished.

It has been known in some plants and algae that expression of SBP gene can be enhanced to increase photosynthetic ability, growth, and the like (Non-Patent Literatures 1 and 2). In *Nannochloropsis*, a transformant ("SBP1" in Table 6), in which expression of *Nannochloropsis*-derived SBP was enhanced, had a marked decrease in productivity of fatty acids. This transformant also had decreased growth (cell count and turbidity). Meanwhile, there has been a finding that a cyanobacterium-derived bifunctional FBP/SBP gene is introduced to increase photosynthetic ability, growth, and the like, of some plants or cyanobacteria (Non-Patent Literature 3). In *Nannochloropsis*, no increase in productivity of fatty acids was found even when the SeFBP/SBP gene (linked to a chloroplast transit signal sequence that functions in *Nannochloropsis*) was introduced ("SeFBP/SBP" in Table 7).

Example 1 Preparation of Transformant Wherein Several Kinds of CBB Cycle Genes are Introduced into *Nannochloropsis*, and Production of Lipids by the Transformant (1) Construction of Plasmid for Several CBB Cycle Genes Expression Using the each plasmid for FBA2 gene expression and plasmid for TK1 gene expression constructed in Comparative Example 1 as a template respectively, and a pair of the primers set forth in SEQ ID NO: 47 and SEQ ID NO: 37 shown in Table 1, and a pair of the primers set forth in SEQ ID NO: 63 and SEQ ID NO: 64 shown in Table 2, PCRs were carried out. Further, using a genome DNA of *Nannochloropsis oceanica* strain NIES-2145 as a template, and a pair of the primers set forth in SEQ ID NO: 43 and SEQ ID NO: 44, and a pair of the primers set forth in SEQ ID NO: 45 and SEQ ID NO: 46 shown in Table 1, PCRs were carried out to obtain a GS promoter fragment (SEQ ID NO: 22) and a LDSP terminator fragment (SEQ ID NO: 23). These four fragments were fused by a method in a manner similar to that in Comparative Example 1, thereby a plasmid for the TK1 gene and the FBA2 gene expression was constructed. Herein, the expression plasmid consists of the pUC19 vector sequence and an insert sequence in which the GS promoter sequence, the TK1 gene, the LDSP terminator sequence, the LDSP promoter sequence, the FBA2 gene, the VCP1 terminator sequence, the tubulin promoter sequence, the zeocin resistance gene and the heat shock protein terminator sequence were linked in this order.

Using thus-obtained the plasmid for the TK1 gene and the FBA2 gene expression, and the plasmid for RPI gene expression constructed in Comparative Example 1 as a template respectively, and a pair of the primers set forth in SEQ ID NO: 52 and SEQ ID NO: 37 shown in Table 1, and a pair of the primers set forth in SEQ ID NO: 65 and SEQ ID NO: 66 shown in Table 2, PCRs were carried out. Further, using a genome DNA of *Nannochloropsis oceanica* strain NIES-2145 as a template, and a pair of the primers set forth in SEQ ID NO: 48 and SEQ ID NO: 49, and a pair of the primers set forth in SEQ ID NO: 50 and SEQ ID NO: 51 shown in Table 1, PCRs were carried out to obtain an AMT promoter fragment (SEQ ID NO: 24) and a Δ9 desaturase (Δ9DES) terminator fragment (SEQ ID NO: 25).

These four fragments were fused by a method in a manner similar to that in Comparative Example 1, thereby a plasmid for the RPI gene, the TK1 gene and the FBA 2 gene expression was constructed. Herein, the expression plasmid consists of the pUC19 vector sequence and an insert sequence in which the AMT promoter sequence, the RPI gene, the Δ9DES terminator sequence, the GS promoter sequence, the TK1 gene, the LDSP terminator sequence, the LDSP promoter sequence, the FBA2 gene, the VCP1 terminator sequence, the tubulin promoter sequence, the zeocin resistance gene and the heat shock protein terminator sequence were linked in this order.

Using thus-obtained plasmid for the RPI gene, the TK1 gene and the FBA2 gene expression as a template, and a pair of the primers set forth in SEQ ID NO: 54 and SEQ ID NO: 56, and a pair of the primers set forth in SEQ ID NO: 55 and SEQ ID NO: 56 shown in Table 1, PCRs were carried out respectively to obtain "a cassette for the TK1 gene and the FBA2 gene expression" and "a cassette for the RPI gene, the TK1 gene and the FBA2 gene expression" respectively.

Thus-obtained amplified fragments were purified by a method in a manner similar to that in Comparative Example 1, then the resultant fragments were introduced into *Nannochloropsis oceanica* strain NIES-2145 by electroporation. Selection of transformants were performed by a method in a manner similar to that in Comparative Example 1.

(2) Production of Fatty Acids by Transformant, Extraction of Lipid and Analysis of Fatty Acids Contained Therein Each selected strain was subjected to preceding culture, pre-culture, and main culture by a method in a manner similar to that in Comparative Example 1. In addition, the culturing was likewise carried out under high light conditions in which the light intensity was set to about 300 µmol/m$^2$/s. In addition, as a negative control, a similar experiment was also conducted on the wild type strain, the TK1 transgenic strain and the FBA2 transgenic strain prepared in Comparative Example 1. The wild-type strain was cultured (N=2), and 4 independent lines for transformants were cultured.

The obtained culture fluid was used to extract lipids and analyze fatty acid compositions by a method in a manner similar to that in Comparative Example 1. Table 8 shows the total fatty acid yield under normal light conditions and Table 9 shows the total fatty acid yield under high light conditions. Table 10 shows each fatty acid composition at culture day 21 under normal light conditions. Table 11 shows each fatty acid composition at culture day 21 under high light conditions. Each fatty acid composition ("FA composition" in the Tables) is represented in the weight ratio of each fatty acid yield with respect to the total fatty acid weight. The term "Cx:y" means that the number of carbon atoms is "x" and the number of double bonds is "y". Further, the term "Cx:n" indicates the sum of fatty acids wherein the number of carbon atoms is "x", and the number of double bounds is "0 to 5". Furthermore, OD$_{750}$ in the normal light conditions is shown in Table 12, and that in the high light conditions is shown in Table 13.

TABLE 8

Light intensity: about 100 µmol/m$^2$/s

| | TFA yield (mg/L) | | | | | |
|---|---|---|---|---|---|---|
| | 3 days | 7 days | 10 days | 14 days | 17 days | 21 days |
| WT (Comparative example) | 77.3 ± 4.4 | 444.6 ± 29.2 | 824.8 ± 44.2 | 1324.1 ± 73.6 | 1654.5 ± 85.7 | 2123.2 ± 87.3 |
| FBA2 (Comparative example) | 83.2 ± 2.4 | 462.8 ± 44.7 | 846.9 ± 87.8 | 1358.8 ± 175.6 | 1682.6 ± 254.0 | 2142.4 ± 339.5 |
| TK1 (Comparative example) | 80.8 ± 4.3 | 489.3 ± 41.8 | 882.9 ± 80.8 | 1436.8 ± 179.1 | 1830.7 ± 239.0 | 2356.8 ± 334.9 |
| TK1-FBA2 (Present invention) | 79.4 ± 4.6 | 487.0 ± 22.3 | 928.8 ± 23.6 | 1632.5 ± 46.6 | 2124.2 ± 82.3 | 2743.2 ± 96.9 |
| RPI-TK1-FBA2 (Present invention) | 69.8 ± 3.1 | 491.3 ± 18.8 | 935.3 ± 29.1 | 1599.1 ± 44.5 | 2039.3 ± 57.4 | 2590.2 ± 80.2 |

TABLE 9

Light intensity: about 300 µmol/m$^2$/s

| | TFA yield (mg/L) | | | | | |
|---|---|---|---|---|---|---|
| | 3 days | 7 days | 10 days | 14 days | 17 days | 21 days |
| WT (Comparative example) | 191.8 ± 17.6 | 1030.2 ± 240.5 | 1447.0 ± 299.3 | 1960.2 ± 456.0 | 2261.3 ± 561.8 | 2555.7 ± 604.8 |
| FBA2 (Comparative example) | 198.7 ± 13.2 | 911.6 ± 159.6 | 1275.1 ± 293.4 | 1658.1 ± 402.2 | 1915.8 ± 471.2 | 2229.6 ± 551.1 |
| TK1 (Comparative example) | 212.1 ± 22.9 | 935.1 ± 132.8 | 1392.3 ± 229.1 | 1878.9 ± 366.1 | 2104.8 ± 427.8 | 2398.0 ± 555.2 |
| TK1-FBA2 (Present invention) | 188.0 ± 19.9 | 1085.6 ± 244.3 | 1631.1 ± 296.0 | 2355.3 ± 456.1 | 2652.8 ± 412.7 | 2908.2 ± 340.0 |
| RPI-TK1-FBA2 (Present invention) | 194.9 ± 18.6 | 1230.8 ± 128.7 | 1864.8 ± 211.8 | 2608.5 ± 301.1 | 2955.9 ± 321.5 | 3301.3 ± 339.7 |

TABLE 10

| | Light intensity: about 100 μmol/m$^2$/s | | | | | |
|---|---|---|---|---|---|---|
| | FA composition (wt %) | | | | | |
| | C12:0 | C14:0 | C16:1 | C16:0 | C18:n | C20:n |
| WT (Comparative example) | 0.2 ± 0.0 | 3.6 ± 0.2 | 30.0 ± 0.5 | 39.8 ± 0.4 | 18.0 ± 0.3 | 8.4 ± 0.3 |
| FBA2 (Comparative example) | 0.2 ± 0.0 | 3.6 ± 0.1 | 30.2 ± 0.3 | 40.8 ± 0.6 | 17.1 ± 0.7 | 8.1 ± 0.9 |
| TK1 (Comparative example) | 0.2 ± 0.0 | 3.5 ± 0.2 | 30.1 ± 0.3 | 40.4 ± 0.5 | 18.2 ± 0.7 | 7.6 ± 0.8 |
| TK1-FBA2 (Present invention) | 0.1 ± 0.0 | 2.9 ± 0.1 | 29.2 ± 0.2 | 43.6 ± 0.8 | 18.2 ± 0.7 | 6.1 ± 0.3 |
| RPI-TK1-FBA2 (Present invention) | 0.2 ± 0.0 | 3.2 ± 0.1 | 29.6 ± 0.2 | 42.2 ± 0.4 | 18.3 ± 0.2 | 6.6 ± 0.2 |

TABLE 11

| | Light intensity: about 300 μmol/m$^2$/s | | | | | |
|---|---|---|---|---|---|---|
| | FA composition (wt %) | | | | | |
| | C12:0 | C14:0 | C16:1 | C16:0 | C18:n | C20:n |
| WT (Comparative example) | 0.2 ± 0.0 | 5.4 ± 0.1 | 31.4 ± 0.5 | 39.4 ± 0.1 | 17.3 ± 1.2 | 6.2 ± 0.5 |
| FBA2 (Comparative example) | 0.2 ± 0.0 | 4.5 ± 0.4 | 33.0 ± 1.2 | 40.3 ± 0.2 | 15.0 ± 1.7 | 7.0 ± 1.0 |
| TK1 (Comparative example) | 0.2 ± 0.0 | 5.9 ± 0.1 | 31.1 ± 0.2 | 40.3 ± 1.4 | 16.8 ± 0.8 | 5.6 ± 0.9 |
| TK1-FBA2 (Present invention) | 0.2 ± 0.0 | 3.6 ± 0.4 | 30.3 ± 0.5 | 44.9 ± 1.3 | 15.9 ± 1.7 | 5.1 ± 0.5 |
| RPI-TK1-FBA2 (Present invention) | 0.2 ± 0.0 | 4.0 ± 0.3 | 30.3 ± 0.4 | 43.1 ± 0.5 | 16.8 ± 0.9 | 5.6 ± 0.5 |

TABLE 12

| | Light intensity: about 100 μmol/m$^2$/s | | | | | |
|---|---|---|---|---|---|---|
| | OD$_{750}$ | | | | | |
| | 3 days | 7 days | 10 days | 14 days | 17 days | 21 days |
| WT (Comparative example) | 0.100 ± 0.001 | 1.402 ± 0.077 | 2.042 ± 0.064 | 2.608 ± 0.123 | 3.025 ± 0.126 | 3.522 ± 0.170 |
| FBA2 (Comparative example) | 0.101 ± 0.000 | 1.449 ± 0.056 | 2.031 ± 0.140 | 2.701 ± 0.192 | 3.027 ± 0.288 | 3.513 ± 0.368 |
| TK1 (Comparative example) | 0.101 ± 0.000 | 1.456 ± 0.071 | 2.087 ± 0.117 | 2.773 ± 0.202 | 3.129 ± 0.225 | 3.642 ± 0.393 |
| TK1-FBA2 (Present invention) | 0.101 ± 0.000 | 1.448 ± 0.031 | 2.140 ± 0.035 | 2.957 ± 0.045 | 3.384 ± 0.048 | 3.986 ± 0.036 |
| RPI-TK1-FBA2 (Present invention) | 0.101 ± 0.001 | 1.500 ± 0.041 | 2.177 ± 0.047 | 2.903 ± 0.065 | 3.342 ± 0.079 | 3.866 ± 0.083 |

TABLE 13

| | Light intensity: about 300 μmol/m$^2$/s | | | | | |
|---|---|---|---|---|---|---|
| | OD$_{750}$ | | | | | |
| | 3 days | 7 days | 10 days | 14 days | 17 days | 21 days |
| WT (Comparative example) | 0.105 ± 0.001 | 1.887 ± 0.281 | 2.469 ± 0.373 | 3.023 ± 0.599 | 3.308 ± 0.648 | 3.545 ± 0.687 |
| FBA2 (Comparative example) | 0.104 ± 0.000 | 1.722 ± 0.254 | 2.235 ± 0.407 | 2.647 ± 0.520 | 2.894 ± 0.565 | 3.228 ± 0.638 |
| TK1 (Comparative example) | 0.105 ± 0.000 | 1.721 ± 0.177 | 2.316 ± 0.338 | 2.799 ± 0.442 | 2.982 ± 0.539 | 3.253 ± 0.658 |
| TK1-FBA2 (Present invention) | 0.104 ± 0.001 | 1.942 ± 0.287 | 2.634 ± 0.446 | 3.279 ± 0.501 | 3.527 ± 0.393 | 3.626 ± 0.217 |
| RPI-TK1-FBA2 (Present invention) | 0.105 ± 0.000 | 2.135 ± 0.159 | 2.883 ± 0.269 | 3.649 ± 0.316 | 3.890 ± 0.328 | 4.069 ± 0.256 |

As is apparent from the Table 8, in the transformant into which the TK1 gene and the FBA2 gene were introduced ("TK1-FBA2" in Table 8) (hereinafter, also referred to as "TK1-FBA2 strain"), fatty acid productivity was largely improved, in comparison with that in the wild type strain, the FBA2 transgenic strain ("FBA2" in the Table), and the TK1 transgenic strain ("TK1" in the Table). Further as is apparent from the Table 9, even though the FBA 2 transgenic strain and the TK1 transgenic strain showed lower productivity than the wild type strain under the high light conditions, TK1-FBA2 strain showed extremely higher productivity than the wild type strain. Furthermore, under the high light conditions, the transformant into which the RPI gene, the TK1 gene, and the FBA2 gene were introduced ("RPI-TK1-FBA2" in Table 9) (hereinafter, also referred to as "RPI-TK1-FBA2 strain") showed further improved productivity.

As is apparent from the Table 10 and the Table 11, in the TK1-FBA2 strain and the RPI-TK1-FBA2 strain, the proportion of C16:0 fatty acid was significantly improved in comparison with that in the wild type strain, the FBA2 transgenic strain and the TK1 transgenic strain.

Tables 12 and 13 show a tendency that the $OD_{750}$ of TK1-FBA2 strain or RPI-TK1-FBA2 strain increased more than that of the wild-type strain, FBA2 transgenic strain, or TK1 transgenic strain. In microalgae, the culture fluid turbidity ($OD_{750}$) is known to be correlated with the dry alga body weight. Thus, the TK1-FBA2 strain and RPI-TK1-FBA2 strain seemed to have an increased dry weight when compared to the wild-type strain, FBA2 transgenic strain, or TK1 transgenic strain. This indicates an increase in their photosynthetic ability.

From these results, it was shown that, by enhancing expression of the TK1 and the FBA2 in *Nannochloropsis*, photosynthetic activity can be improved and the amount of fatty acid production can also be improved. Further, by enhancing expression of the RPI, it was shown that productivity of fatty acids was significantly increased (especially, under the high light conditions).

Example 2 Preparation of Transformant of *Nannochloropsis* into which CBB Cycle Gene and TAG Synthetic Gene were Introduced, Production of Lipids by Transformant, Extraction of Lipids and Analysis of Fatty Acids Contained Therein (1) Preparation of TAG Synthetic Pathway Gene Transgenic Strain, and Analysis of Lipids Using the cDNA of *Nannochloropsis oceanica* strain NIES-2145 prepared in Comparative Example 1 as a template, and a pair of the primers set forth in SEQ ID NO: 67 and SEQ ID NO: 68, a pair of the primers set forth in SEQ ID NO: 69 and SEQ ID NO: 70, and a pair of the primers set forth in SEQ ID NO: 71 and SEQ ID NO: 72 shown in Table 2, PCRs were carried out to amplify a DGAT gene (SEQ ID NO: 10) fragment, a LACS gene (SEQ ID NO: 12) fragment, and a TE gene (SEQ ID NO: 14) fragment, respectively. By methods in a manner similar to that in Comparative Example 1 and Example 1, a plasmid for the DGAT gene and the LACS gene expression and a plasmid for the TE gene expression were constructed respectively. Herein, the plasmid for the DGAT gene and the LACS gene expression consists of the pUC19 vector sequence and an insert sequence in which the GS promoter sequence, the DGAT gene, the LDSP terminator sequence, the LDSP promoter sequence, the LACS gene, the VCP1 terminator sequence, the tubulin promoter sequence, the zeocin resistance gene and the heat shock protein terminator sequence were linked in this order. The plasmid for the TE gene expression consists of the pUC19 vector sequence and an insert sequence in which the LDSP promoter sequence, the TE gene, the VCP1 terminator sequence, the tubulin promoter sequence, the zeocin resistance gene and the heat shock protein terminator sequence were linked in this order.

Using thus-constructed plasmid for TE gene expression as a template, and a pair of the primers set forth in SEQ ID NO: 33 and SEQ ID NO: 34 shown in Table 1, PCR was carried out. Further, a paromomycin resistance gene (SEQ ID NO: 16) was artificially synthesized. Using thus-synthesized DNA fragment of the paromomycin resistance gene as a template, and a pair of the primers set forth in SEQ ID NO: 28 and SEQ ID NO: 29 shown in Table 1, PCR was carried out. These two fragments were fused by a method in a manner similar to that in Comparative Example 1, thereby a plasmid for TE gene expression (paromomycin resistance) was constructed. Herein, the expression plasmid consists of the pUC19 vector sequence and an insert sequence in which the LDSP promoter sequence, the TE gene, the VCP1 terminator sequence, the tubulin promoter sequence, the paromomycin resistance gene and the heat shock protein terminator sequence were linked in this order.

Using the plasmid for DGAT gene and LACS gene expression as a template, and a pair of the primers SEQ ID NO: 54 and SEQ ID NO: 56, PCR was carried out to obtain a "cassette for DGAT gene and LACS gene expression.

Thus-obtained amplified fragments were purified by a method in a manner similar to that in Comparative Example 1, then the resultant fragments were introduced into *Nannochloropsis oceanica* strain NIES-2145 by electroporation. Selection of transformants were performed by a method in a manner similar to that in Comparative Example 1.

Using the plasmid for TE gene expression (paromomycin resistance) as a template, and a pair of the primers set forth in SEQ ID NO: 53 and SEQ ID NO: 56 shown in Table 1, PCR was carried out to obtain a "cassette for TE gene and LACS gene expression".

Thus-obtained amplified fragment was purified by a method in a manner similar to that in Comparative Example 1, then the resultant fragment was introduced into the DGAT gene and the LACS2 gene transgenic strain (hereinafter, also referred to as "DGAT-LACS strain") by electroporation. Substantially the same method as in Comparative Example 1 was used to carry out recovery culture. Then, the culture was applied on an f/2 agar medium containing 2 µg/mL zeocin and 100 µg/mL paromomycin, and was cultured for 2 to 3 weeks under an atmosphere at 25° C. and 0.3% $CO_2$ and in a 12-h/12-h light/dark condition. Substantially the same method as in Comparative Example 1 was used to select transformants, which were then cultured and analyzed for lipids. Note that the culturing was performed at a normal light intensity of about 100 µmol/m$^2$/s.

Tables 14 and 15 show the results. Evaluation was conducted for the wild-type strain (N=1), the DGAT-LACS strain (N=2), and 6 independent lines of the TE gene, the DGAT gene and the LASC gene transgenic strain (hereinafter, also referred to as "TE on DGAT-LACS strain").

TABLE 14

| | TFA yield (mg/L) | | | | |
|---|---|---|---|---|---|
| | 3 days | 7 days | 10 days | 17 days | 21 days |
| WT (Comparative example) | 59.6 | 438.3 | 846.3 | 1826.1 | 2304.1 |

TABLE 14-continued

| | TFA yield (mg/L) | | | | |
|---|---|---|---|---|---|
| | 3 days | 7 days | 10 days | 17 days | 21 days |
| DGAT-LACS (Comparative example) | 75.1 | 510.8 | 1016.4 | 1954.7 | 2392.5 |
| DGAT-LACS (Comparative example) | 83.0 | 500.9 | 976.0 | 2128.2 | 2491.2 |
| TE on DGAT2-LACS (Comparative example) | 77.9 | 565.5 | 961.7 | 2047.7 | 2554.5 |
| | 79.0 | 540.2 | 977.3 | 1950.8 | 2420.0 |
| | 81.7 | 525.6 | 969.8 | 1967.3 | 2460.5 |
| | 83.0 | 475.2 | 914.8 | 1996.5 | 2496.1 |
| | 85.3 | 513.4 | 1014.1 | 2019.0 | 2450.0 |
| | 80.4 | 489.7 | 955.8 | 1982.4 | 2409.7 |

TABLE 15

| | FA composition (wt %) | | | | | |
|---|---|---|---|---|---|---|
| | C12:0 | C14:0 | C16:1 | C16:0 | C18:n | C20:n |
| WT (Comparative example) | 0.0 | 4.2 | 27.8 | 42.2 | 18.1 | 7.7 |
| DGAT-LACS (Comparative example) | 0.0 | 4.4 | 28.0 | 46.1 | 14.3 | 7.2 |
| DGAT-LACS (Comparative example) | 0.0 | 4.7 | 28.3 | 45.9 | 14.1 | 7.0 |
| TE on DGAT2-LACS (Comparative example) | 0.3 | 4.7 | 28.1 | 45.2 | 14.7 | 7.0 |
| | 0.3 | 4.6 | 28.2 | 45.3 | 14.4 | 7.2 |
| | 0.0 | 4.4 | 28.2 | 45.3 | 15.1 | 7.0 |
| | 0.3 | 4.6 | 28.1 | 45.3 | 14.5 | 7.2 |
| | 0.0 | 4.6 | 28.1 | 46.0 | 14.3 | 7.0 |
| | 0.4 | 4.7 | 28.3 | 44.6 | 14.8 | 7.3 |

As is apparent from the Table 14, productivity of fatty acids in the DGAT-LACS strain and the TE on DGAT-LACS strain was improved in comparison with that in the wild type strain. Further, as is apparent from the Table 15, the proportion of C16:0 fatty acid was increased in the DGAT-LACS strain and the TE on DGAT-LACS strain in comparison with that in the wild type strain.

(2) Preparation of CBB Cycle Gene and TAG Synthetic Pathway Gene Transgenic Strain, and Analysis of Lipids Using the plasmid for RPI gene, TK1 gene and FBA2 gene expression constructed in Example 1 as a template, and a pair of the primers set forth in SEQ ID NO: 33 and SEQ ID NO: 34 shown in Table 1, PCR was carried out. Further, a hygromycin resistance gene (SEQ ID NO: 17) was artificially synthesized. Using thus-synthesized DNA fragment of the hygromycin resistance gene as a template, and a pair of the primers set forth in SEQ ID NO: 30 and SEQ ID NO: 31 shown in Table 1, PCR was carried out. These two fragments were fused by a method in a manner similar to that in Comparative Example 1, thereby a plasmid for RPI gene, TK1 gene and FBA2 gene expression (hygromycin resistance) was constructed. Herein, the expression plasmid consists of the pUC19 vector sequence and an insert sequence in which the AMT promoter sequence, the RPI gene, the Δ9DES terminator sequence, the GS promoter sequence, the TK1 gene, the LDSP terminator sequence, the LDSP promoter sequence, the FBA2 gene, the VCP1 terminator sequence, the tubulin promoter sequence, the hygromycin resistance gene and the heat shock protein terminator sequence were linked in this order.

Using the plasmid for RPI gene, TK1 gene and FBA2 gene expression (hygromycin resistance) as a template, and a pair of the primers set forth in SEQ ID NO: 53 and SEQ ID NO: 56, a pair of the primers set forth in SEQ ID NO: 54 and SEQ ID NO: 56, and a pair of the primers set forth in SEQ ID NO: 55 and SEQ ID NO: 56 shown in Table 1, PCRs were carried out respectively to obtain a "cassette for FBA2 gene expression (hygromycin resistance)", a "cassette for TK1 gene and FBA2 gene expression (hygromycin resistance)", and a "cassette for RPI gene, TK1 gene, and FBA2 gene expression (hygromycin resistance)", respectively.

Thus-obtained amplified fragments were purified by a method in a manner similar to that in Comparative Example 1, then the purified fragments were introduced into the TE on DGAT-LACS strain by electroporation. Substantially the same method as in Comparative Example 1 was used to carry out recovery culture. Then, the culture was applied on an f/2 agar medium containing 500 μg/mL hygromycin, and was cultured for 2 to 3 weeks under an atmosphere at 25° C. and 0.3% $CO_2$ and in a 12-h/12-h light/dark condition. Selection of the transformants was performed by a method in a manner similar to that in Comparative Example 1.

Each selected strain was cultured by substantially the same method as in Example 1 (under normal light conditions or high light conditions). The culture fluid was sampled over time to extract and analyze lipids by a method in a manner similar to that in Comparative Example 1. Table 16 shows the results of the total fatty acid amount under normal light conditions (at about 100 μmol/m²/s). Table 17 shows the results of the total fatty acid amount under high light conditions (at about 300 μmol/m²/s). Table 18 shows the results of fatty acid composition under the normal light conditions. Table 19 shows the results of fatty acid composition under the high light conditions. The wild-type strain and the TE on DGAT-LACS strain were cultured (N=2), and 4 independent lines for the CBB cycle gene and the TAG synthetic pathway gene transgenic strain were cultured.

TABLE 16

| | Light intensity: about 100 μmol/m²/s | | | | | |
|---|---|---|---|---|---|---|
| | TFA yield (mg/L) | | | | | |
| | 3 days | 7 days | 10 days | 14 days | 17 days | 21 days |
| WT (Comparative example) | 80.3 ± 5.8 | 433.6 ± 45.3 | 826.2 ± 54.3 | 1248.1 ± 40.3 | 1544.6 ± 16.4 | 1906.4 ± 11.9 |
| TE on DGAT-LACS (Comparative example) | 93.8 ± 8.4 | 501.6 ± 31.2 | 973.3 ± 39.8 | 1525.0 ± 38.3 | 1911.3 ± 10.6 | 2390.9 ± 33.7 |
| FBA2 on TE on DGAT-LACS (Comparative example) | 101.6 ± 6.7 | 535.3 ± 16.8 | 1016.6 ± 24.4 | 1584.3 ± 30.1 | 1962.2 ± 23.2 | 2353.4 ± 41.9 |
| TK1-FBA2 on TE on DGAT-LACS (Present invention) | 111.3 ± 6.0 | 538.5 ± 30.4 | 1016.8 ± 34.0 | 1638.0 ± 28.1 | 2096.0 ± 65.3 | 2546.3 ± 92.7 |
| RPI-TK1-FBA2 on TE on DGAT-LACS (Present invention) | 91.9 ± 2.7 | 503.1 ± 26.6 | 1020.5 ± 39.2 | 1679.3 ± 66.6 | 2096.3 ± 48.1 | 2559.7 ± 131.3 |

TABLE 17

Light intensity: about 300 μmol/m²/s

| | TFA yield (mg/L) | | | | | |
|---|---|---|---|---|---|---|
| | 3 days | 7 days | 10 days | 14 days | 17 days | 21 days |
| WT (Comparative example) | 188.5 ± 5.7 | 991.2 ± 109.3 | 1488.3 ± 216.7 | 1879.4 ± 391.2 | 2089.3 ± 386.8 | 2322.8 ± 390.0 |
| TE on DGAT-LACS (Comparative example) | 182.4 ± 17.0 | 1029.5 ± 64.1 | 1548.7 ± 80.2 | 2044.8 ± 50.8 | 2295.4 ± 84.7 | 2541.7 ± 80.4 |
| FBA2 on TE on DGAT-LACS (Comparative example) | 176.9 ± 13.4 | 974.0 ± 72.4 | 1334.4 ± 169.4 | 1648.8 ± 248.8 | 1848.3 ± 255.9 | 2087.4 ± 233.5 |
| TK1-FBA2 on TE on DGAT-LACS (Present invention) | 170.2 ± 12.2 | 1025.7 ± 51.0 | 1645.9 ± 84.0 | 2240.8 ± 76.0 | 2538.1 ± 81.3 | 2919.3 ± 111.5 |
| RPI-TK1-FBA2 on TE on DGAT-LACS (Present invention) | 172.0 ± 9.9 | 1104.3 ± 46.6 | 1783.7 ± 63.5 | 2434.3 ± 95.7 | 2654.0 ± 97.9 | 3055.6 ± 89.8 |

TABLE 18

Light intensity: about 100 μmol/m²/s

| | FA composition (wt %) | | | | | |
|---|---|---|---|---|---|---|
| | C12:0 | C14:0 | C16:1 | C16:0 | C18:n | C20:n |
| WT (Comparative example) | 0.2 ± 0.0 | 4.1 ± 0.0 | 28.8 ± 0.0 | 40.3 ± 0.3 | 17.7 ± 0.1 | 8.9 ± 0.3 |
| TE on DGAT-LACS (Comparative example) | 0.3 ± 0.0 | 4.3 ± 0.1 | 27.4 ± 0.2 | 45.6 ± 0.0 | 15.3 ± 0.3 | 7.0 ± 0.0 |
| FBA2 on TE on DGAT-LACS (Comparative example) | 0.3 ± 0.0 | 3.8 ± 0.0 | 26.7 ± 0.1 | 47.1 ± 0.2 | 15.7 ± 0.1 | 6.5 ± 0.1 |
| TK1-FBA2 on TE on DGAT-LACS (Present invention) | 0.3 ± 0.0 | 3.4 ± 0.1 | 26.5 ± 0.2 | 48.4 ± 0.3 | 15.8 ± 0.3 | 5.8 ± 0.1 |
| RPI-TK1-FBA2 on TE on DGAT-LACS (Present invention) | 0.3 ± 0.0 | 3.5 ± 0.3 | 26.7 ± 0.7 | 48.3 ± 0.5 | 15.4 ± 0.5 | 5.7 ± 0.1 |

TABLE 19

Light intensity: about 300 μmol/m²/s

| | FA composition (wt %) | | | | | |
|---|---|---|---|---|---|---|
| | C12:0 | C14:0 | C16:1 | C16:0 | C18:n | C20:n |
| WT (Comparative example) | 0.2 ± 0.0 | 5.4 ± 0.1 | 32.5 ± 0.4 | 38.5 ± 0.6 | 17.0 ± 0.7 | 6.3 ± 0.8 |
| TE on DGAT-LACS (Comparative example) | 0.4 ± 0.0 | 5.8 ± 0.2 | 31.4 ± 0.1 | 42.7 ± 0.7 | 13.9 ± 0.3 | 5.9 ± 0.1 |
| FBA2 on TE on DGAT-LACS (Comparative example) | 0.3 ± 0.0 | 4.0 ± 0.2 | 33.4 ± 0.9 | 42.8 ± 1.3 | 12.7 ± 0.8 | 6.8 ± 0.9 |
| TK1-FBA2 on TE on DGAT-LACS (Present invention) | 0.3 ± 0.0 | 3.7 ± 0.3 | 29.8 ± 0.3 | 48.2 ± 0.4 | 13.7 ± 0.1 | 4.4 ± 0.3 |
| RPI-TK1-FBA2 on TE on DGAT-LACS (Present invention) | 0.3 ± 0.0 | 3.8 ± 0.4 | 29.8 ± 0.4 | 47.9 ± 0.9 | 13.6 ± 0.2 | 4.6 ± 0.3 |

As is apparent from the Tables 16 and 17, it was not shown the improvement of fatty acid productivity in the strain into which only the FBA2 gene in addition to the TAG synthetic pathway gene were introduced ("FBA2 on TE on DGAT-LACS" in the tables), and fatty acid productivity was rather decreased in the high light conditions. However, in the strain into which the FBA2 gene and the TK1 gene in addition to the TAG synthetic pathway gene were introduced ("TK1-FBA2 on TE on DGAT-LACS" in the tables), fatty acid productivity was largely improved in comparison with that in the wild type strain, and TE on DGAT-LACS strain. In the strain into which further the RPI gene in addition to the TK1 gene and the FBA2 gene were introduced ("RPI-TK1-FBA2 on TE on DGAT-LACS" in the tables), productivity under the high light conditions was further improved.

Further, as is apparent from the Tables 18 and 19, in the TK1-FBA2 on TE on DGAT-LACS strain and the RPI-TK1-FBA2 on TE on DGAT-LACS strain, the proportion of C16:0 fatty acid was significantly increased in comparison with that in the wild type strain and the TE on DGAT-LACS strain.

From these results, it was shown that by enhancing expression of the TK1 gene and the FBA2 gene in addition to the TAG synthetic pathway gene, photosynthetic activity was further improved, and the production amount of fatty acids was furthermore improved. Further, it was shown that by also enhancing expression of the RPI gene, the improvement effect was further increased (especially, under the high light conditions).

As described above, it can be obtained a transformant wherein photosynthetic ability is improved and lipid productivity is improved, by enhancing expression of both the TK and the FBA. Therefore, by using the transformant, a method of producing lipids which improve productivity of fatty acids or lipids containing the same can be provided.

Having described our invention as related to the present embodiments, it is our intention that the invention not be limited by any of the details of the description, unless otherwise specified, but rather be construed broadly within its spirit and scope as set out in the accompanying claims.

This application claims priority on Patent Application No. 2018-159659 filed in Japan on Aug. 28, 2018, which is entirely herein incorporated by reference.

What is claimed is:

1. A method of improving productivity of fatty acids or lipids containing the same as components in a *Nannochloropsis* cell, the method comprising:
   culturing, in culture medium, a *Nannochloropsis* cell that has been transformed with, and expresses, a gene encoding transketolase and a gene encoding fructose-1,6-bisphosphate aldolase; and
   isolating fatty acids or lipids containing the same as components from the cultured product;
   wherein the productivity of the fatty acids or lipids containing the same as components that are isolated from the cultured product is improved as compared to that of a *Nannochloropsis* host cell that has not been transformed with either gene; and,
   wherein the amino acid sequence of the transketolase is that of the following protein (A) or (B), and the amino acid sequence of the fructose-1,6-bisphosphate aldolase is that of the following protein (C) or (D):
   (A) a protein consisting of the amino acid sequence set forth in SEQ ID NO: 1;
   (B) a protein consisting of an amino acid sequence having 90% or more identity with the amino acid sequence of protein (A), and having transketolase activity;
   (C) a protein consisting of the amino acid sequence set forth in SEQ ID NO: 3; and
   (D) a protein consisting of an amino acid sequence having 90% or more identity with the amino acid sequence of protein (C), and having fructose-1,6-bisphosphate aldolase activity.

2. The method according to claim 1, wherein the fatty acids or lipids containing the same as components that are produced comprise palmitic acids or lipids containing the palmitic acids as components.

3. The method according to claim 1, wherein the amino acid sequence of the transketolase is that of the following protein (A) or (B), and the amino acid sequence of the fructose-1,6-bisphosphate aldolase is that of the following protein (C) or (D):
   (A) a protein consisting of the amino acid sequence set forth in SEQ ID NO: 1;
   (B) a protein consisting of an amino acid sequence having 95% or more identity with the amino acid sequence of protein (A), and having transketolase activity;
   (C) a protein consisting of the amino acid sequence set forth in SEQ ID NO: 3; and
   (D) a protein consisting of an amino acid sequence having 95% or more identity with the amino acid sequence of protein (C), and having fructose-1,6-bisphosphate aldolase activity.

4. The method according to claim 1, wherein the *Nannochloropsis* has been transformed with, and expresses, a gene encoding a protein having the amino acid sequence of the following protein (E) or (F):
   (E) a protein consisting of the amino acid sequence set forth in SEQ ID NO: 7; or
   (F) a protein consisting of an amino acid sequence having 90% or more identity with the amino acid sequence of protein (E), and having ribose-5-phosphate isomerase activity.

5. The method according to claim 1, wherein the *Nannochloropsis* has been transformed with, and expresses, one or more genes encoding proteins selected from the group consisting of an acyl-ACP thioesterase, an acyl-CoA synthetase and an acyltransferase.

6. The method according to claim 1, wherein the *Nannochloropsis* belongs to the species *Nannochloropsis oceanica*.

* * * * *

SEQUENCE LISTING

```
<160> NUMBER OF SEQ ID NOS: 139

<210> SEQ ID NO 1
<211> LENGTH: 723
<212> TYPE: PRT
<213> ORGANISM: Nannochloropsis oceanica

<400> SEQUENCE: 1

Met Val Ala Lys Ala Ala Phe Ala Gly Val Ala Ala Met Gly Val Leu
1               5                   10                  15

Gly Ala Gln Ala Phe Ile Pro Thr Pro Val Ser Leu Ser Ser Val Phe
                20                  25                  30

Gly Gln Arg Thr Ser Ala Ala Arg Ser Gly Pro Val Met Met Ala Thr
            35                  40                  45

Val Ala Pro Ala Lys Ala Val Ala Thr Pro Ala Asp Leu Thr Arg Ala
    50                  55                  60

Ala Asn Glu Ala Arg Gly Leu Ala Leu Asp Ser Ile Thr Ala Ala His
65                  70                  75                  80

Ser Gly His Leu Gly Leu Pro Leu Gly Ala Ala Asp Ile Gly Ala Val
                85                  90                  95

Leu Trp Gly Lys Leu Leu Gln His Asn Pro Glu Asp Pro Gln Trp Ile
                100                 105                 110

Asn Arg Asp Arg Phe Ile Leu Ser Ala Gly His Gly Ser Met Phe Ile
            115                 120                 125

Tyr Ser Trp Leu His Leu Ser Gly Tyr Ala Leu Pro Leu Glu Glu Val
    130                 135                 140

Lys Lys Phe Arg Gln His His Ser Met Thr Pro Gly His Pro Glu Phe
145                 150                 155                 160

Pro Ser Ser Glu His Asn Thr Pro Gly Ile Glu Cys Thr Thr Gly Pro
                165                 170                 175

Leu Gly Gln Gly Val Ser Asn Ala Val Gly Met Ala Ala Ala Gln Lys
            180                 185                 190

His Ala Ala Ala Ser Tyr Asn Thr Pro Lys His Thr Ile Phe Asn Gly
        195                 200                 205

His Ile Ile Ala Leu Gly Gly Asp Gly Cys Ile Gln Glu Gly Val Ala
    210                 215                 220

Ala Glu Ser Ala Ala Phe Ala Ala His Glu Lys Leu Asp Asn Leu Ile
225                 230                 235                 240

Ile Leu Tyr Asp Ala Asn Asp Val Thr Leu Asp Ala Met Ala Asp Arg
                245                 250                 255

Thr Gln Ser Glu Asp Val Ala Met Arg Tyr Lys Ala Tyr Gly Trp Asp
            260                 265                 270

Val Val Thr Ile Asp Gly His Asp Leu Thr Ala Ile Glu Lys Ser Ile
        275                 280                 285

Ser Asp Ala Lys Ala Asn Asp Asn Gly Lys Pro Lys Met Ile Ile Cys
    290                 295                 300

Lys Thr Ile Ile Gly Lys Gly Ile Asp Glu Ile Ala Gly Thr Asn Ala
305                 310                 315                 320

Ala His Gly Glu Ala Gly Val Lys Phe Cys Asp Glu Ser Arg Lys Arg
```

```
                      325                 330                 335
Leu Gly Leu Pro Ala Glu Lys Trp Phe Val Ser Pro Glu Thr Arg Ala
                340                 345                 350

Phe Met Ala Ser Arg Gln Ala Thr Leu Lys Ala Glu Tyr Asp Ala Trp
            355                 360                 365

Gln Lys Thr Phe Ala Glu Trp Lys Ser Ala Asn Pro Asp Lys Ala Lys
        370                 375                 380

Leu Leu Gln Asp Ala Ile Asp Lys Lys Val Pro Ser Ser Glu Asp Leu
385                 390                 395                 400

Met Lys Ala Ile Pro Glu Phe Asp Ala Ser Lys Asp Ile Ala Thr Arg
                405                 410                 415

Glu Ala Gly Ala Val Val Leu Gln Pro Val Ala Ala Val Pro Asn
            420                 425                 430

Tyr Leu Thr Gly Ser Ala Asp Leu Phe Gly Ser Thr Lys Asn Tyr Ile
        435                 440                 445

Lys Asn Gly Gly Asp Phe Gly Ser Gly Glu Gly Lys Thr Tyr Thr Gly
    450                 455                 460

Arg Asn Val Leu Tyr Gly Ile Arg Glu His Ala Met Gly Ser Ile Leu
465                 470                 475                 480

Asn Gly Phe Ala Tyr Phe Gly Leu His Arg Val Ser Gly Ala Thr Phe
                485                 490                 495

Leu Val Phe Ala Asp Tyr Met Arg Ala Pro Val Arg Val Ala Ala Leu
            500                 505                 510

Ser Glu Leu Pro Ile Gly Tyr Ile Trp Thr His Asp Ser Ile Gly Val
        515                 520                 525

Gly Glu Asp Gly Pro Thr His Gln Pro Val Glu Thr Val Ser Gly Leu
    530                 535                 540

Arg Val Phe Pro Asn Leu Asp Val Ile Arg Pro Ala Asp Ser Glu Glu
545                 550                 555                 560

Thr Ala Gly Ala Phe Val Ser Ser Ile Val Arg Lys Asp Gly Pro Thr
                565                 570                 575

Ala Leu Ile Leu Thr Arg Gln Asn Val Lys Gln Leu Pro Gly Thr Pro
            580                 585                 590

Ala Glu Lys Arg Ala Gly Val Leu Lys Gly Ala Tyr Ile Val Lys Lys
        595                 600                 605

Glu Ser Gly Pro Leu Lys Ala Ile Ile Met Ala Ser Gly Ser Glu Val
    610                 615                 620

Gln His Ala Val Glu Ala Ala Ala Leu Gly Glu Gly Ile Arg Val
625                 630                 635                 640

Val Ser Met Pro Cys Met Glu Ile Phe Glu Arg Gln Ser Ala Glu Tyr
                645                 650                 655

Lys Glu Ser Ile Leu Pro Ala Asp Cys Arg Lys Arg Ile Ala Met Glu
            660                 665                 670

Ala Gly Val Thr Gly Leu Trp Tyr Lys Tyr Val Gly Leu Asp Gly Lys
        675                 680                 685

Val Ile Gly Val Asp Arg Phe Gly Phe Ser Ala Pro Gly Pro Thr Val
    690                 695                 700

Met Lys Glu Leu Gly Met Thr Ala Asp Asn Leu Val Lys Glu Ala Lys
705                 710                 715                 720

Ala Tyr Leu

<210> SEQ ID NO 2
<211> LENGTH: 2172
```

-continued

```
<212> TYPE: DNA
<213> ORGANISM: Nannochloropsis oceanica

<400> SEQUENCE: 2
atggttgcta aagctgcttt tgccggcgtt gccgccatgg gtgtgctggg cgcccaagcg      60
ttcatcccca cgcccgtgag cttgagcagc gtgttcggcc agcgtacgtc cgcggcccgc     120
agcggccctg taatgatggc caccgtggca cctgccaagg ccgtcgccac tccggcagac     180
ctcacccgtg cggccaacga agctcgtggt cttgccctgg actccatcac cgctgctcat     240
tctggtcact gggtcttcc ccttggggcc gccgacatcg cgctgtgct ttggggcaaa      300 ctccttcagc acaaccccga ggaccccag tggatcaacc gtgaccgatt catcctctca      360
gccggtcacg gttctatgtt catttactcc tggctgcact tgtccgggta cgcgctgccc     420
ctggaggagg tgaagaagtt ccgccagcac cactccatga cccccggcca cccagagttc     480
ccctcctccg agcacaacac gcccggcatt gagtgtacta cgggtcccct gggccagggt     540
gtttccaacg ccgtcgggat ggccgcagcc cagaagcacg ccgcagccag ctacaacacg     600
cccaagcaca cgatattcaa tggccacatc atcgccctcg gcggtgacgg ctgcattcag     660
gagggtgtcg ccgcagagtc ggccgccttt gcagcccacg agaaactgga caacctgatc     720
attctgtacg acgcgaatga cgtgaccctg gacgctatgg ctgaccgcac ccagtccgag     780
gacgtggcta tgcgctacaa ggcctacggg tgggacgttg tgaccatcga cgggcacgac     840
ctgaccgcca tcgagaagtc tatctccgat gccaaggcta acgataacgg caagcccaag     900
atgattattt gcaaaaccat catcggtaag ggcattgacg agatcgccgg caccaacgcc     960
gcccacggtg aagccggggt caaattctgt gacgagtccc gcaagcgcct cggcctcccc    1020
gctgagaagt ggtttgtatc tcccgagacc cgtgcttta tggcttcccg ccaggccacc     1080
ctcaaggccg agtacgatgc ctggcagaaa accttcgccg agtggaagtc cgccaacccc    1140
gacaaggcca agctgctcca ggacgcgatc gacaagaagg tgccctcctc ggaggatctg    1200
atgaaggcca tccccgaatt cgacgcctct aaggacatcg ctacccgtga ggccggcgcc    1260
gtcgtcctcc agcccgtggc cgccgctgtg ccgaattacc tgaccggctc ggctgatctc    1320
ttcggctcca ccaagaacta catcaagaac ggtggcgact cggcagcgg cgagggtaag    1380 acctacacgg gccgcaacgt cctctatggc atccgcgagc acgcaatggg ctccatcctc    1440
aacggttttg cctatttcgg cttgcaccgg gtctccgggg ccactttctt ggtcttcgcc    1500
gactacatgc gcgcgcccgt ccgtgtcgcc gccctctccg agctccccat cgggtacatc    1560
tggacgcacg actcaatcgg tgtcggtgag atggaccta cccaccagcc ggtggagacg     1620
gtatctggtc ttcgtgtctt tcccaacctt gacgtcatcc gccccgccga ctccgaggaa    1680
accgccggtg ccttcgtctc ctccatcgtg cgcaaggacg gtcccaccgc gcttatcctt    1740
acccgccaga acgtgaaaca gctccccggc actcccgccg agaagcgtgc cggcgttctc    1800
aagggcgctt acatcgtgaa gaaagagtct gggcccctca aggccatcat catggcttcc    1860
ggctctgagg tgcagcacgc cgtcgaggcc gctgctgccc tgggcgaggg aatccgtgtc    1920
gtctctatgc catgcatgga gatcttcgag cgccagtcgg ctgaatacaa ggagtccatc    1980
ctccctgcga actgtcgtaa gcgtatcgcc atggaggcgg cgtgacgggg cttgtggtac    2040
aagtacgttg gcttggacgg gaaggtcatc ggtgtggacc gctttgggtt ctcggccccg    2100 ggcccccaccg tcatgaagga gttgggcatg acggccgaca atctcgtcaa ggaggccaag    2160
gcctatctgt aa                                                       2172
```

<210> SEQ ID NO 3
<211> LENGTH: 382
<212> TYPE: PRT
<213> ORGANISM: Nannochloropsis oceanica

<400> SEQUENCE: 3

```
Met Ala Arg Leu Phe Val Thr Val Ala Ser Phe Val Ala Ala Cys Ala
1               5                   10                  15

Thr Val Asn Ala Phe Gln Val Pro Arg Met Ser Leu Asp Lys Tyr Arg
            20                  25                  30

Ser Glu Leu Ala Glu Thr Ala Lys Lys Ile Ala Ala Pro Gly Lys Gly
        35                  40                  45

Ile Leu Ala Val Asp Glu Ser Thr Lys Thr Ile Gly Lys Arg Leu Glu
    50                  55                  60

Gly Ile Ser Val Glu Asn Thr Glu Ala Asn Arg Gln Ala Tyr Arg Gly
65                  70                  75                  80

Leu Leu Phe Thr Thr Pro Asn Ile Gly Asn Tyr Ile Ser Gly Ala Ile
                85                  90                  95

Leu Tyr Glu Glu Thr Leu Phe Gln Asn Asn Val Asp Gly Thr Pro Phe
            100                 105                 110

Val Lys Asn Leu Asn Thr Ala Gly Val Ile Pro Gly Ile Lys Val Asp
        115                 120                 125

Met Gly Leu Ser Pro Leu Pro Gly Gly His Pro Val Glu Thr Trp Cys
130                 135                 140

Thr Gly Leu Asp Gly Leu Val Glu Arg Ala Gln Lys Tyr Tyr Ala Gln
145                 150                 155                 160

Gly Ala Arg Phe Ala Lys Trp Arg Ala Val Leu Gln Ile Thr Ser Asp
                165                 170                 175

Gly Ala Pro Ser Glu Leu Ser Ile Gln Glu Asn Ala Trp Gly Leu Ala
            180                 185                 190

Arg Tyr Ala Arg Ala Val Gln Glu Gly Gly Leu Val Pro Ile Val Glu
        195                 200                 205

Pro Glu Ile Leu Met Asp Gly Asp His Asn Ile Glu Thr Thr Ala Arg
    210                 215                 220

Val Gln Glu Arg Val Leu Ala Ala Val Tyr Lys Ala Leu Ser Asp Asn
225                 230                 235                 240

Gly Val Tyr Leu Glu Gly Ser Leu Leu Lys Pro Ser Met Thr Leu Pro
                245                 250                 255

Gly Ala Asp Cys Gly Glu Thr Val Thr Ser Glu Lys Ile Ala Glu Tyr
            260                 265                 270

Thr Val Arg Thr Leu Glu Arg His Val Pro Ser Ser Val Pro Gly Val
        275                 280                 285

Met Phe Leu Ser Gly Gly Met Ser Glu Glu Glu Ala Ser Ile Asn Leu
    290                 295                 300

Asn Ala Leu Asn Lys Arg Ala Arg Lys Gly Pro Trp Ser Leu Ser Phe
305                 310                 315                 320

Ser Tyr Gly Arg Ala Leu Gln Gln Ser Cys Leu Lys Ala Trp Gln Gly
                325                 330                 335

Lys Gln Glu Asn Val Pro Ala Ala Arg Ala Ala Leu Leu Ala Arg Ala
            340                 345                 350

Gln Ala Asn Ser Glu Ala Asn Leu Gly Lys Tyr Val Ala Gly Ser Gln
        355                 360                 365

Pro Ser Ala Asp Glu Thr Leu Phe Val Lys Gly Tyr Lys Tyr
    370                 375                 380
```

<210> SEQ ID NO 4
<211> LENGTH: 1149
<212> TYPE: DNA
<213> ORGANISM: Nannochloropsis oceanica

<400> SEQUENCE: 4

```
atggctcgcc tcttcgtcac cgttgcctcc ttcgtggccg cctgtgccac cgtcaacgcc      60
ttccaggtgc cccgtatgtc tttggacaag tacaggagcg agctggccga gaccgctaag     120
aagattgccg cccccggcaa gggtattttg gccgtagatg agtcgaccaa gaccatcggc     180
aagcgtttgg aagggatcag cgtggagaac acggaggcca accgtcaggc gtaccgtggt     240
ctcctcttca ccaccccccaa catcggcaac tacatctccg cgccatcct ctacgaggag      300
actctcttcc agaacaacgt ggacggtacc cccttcgtca agaacctgaa cactgctggc     360
gtcattccgg gtatcaaggt cgacatgggt ctgtcgcccc ttcccggggg acaccccgtc     420
gagacctggt gcacgggctt ggacggactc gtcgagcgcg ctcagaagta ctacgctcaa     480
ggcgcgcgtt cgcgaagtg gcgtgccgtg ctccagatca cctccgacgg tgcccccctct     540
gagctctcca tccaagagaa cgcgtggggc ctggcccgtt acgcgcgtgc cgtgcaagag     600
ggtggcctgg ttcccattgt cgagcccgag atcctgatgg acggcgacca caatatcgag     660
acgactgcgc gtgtgcagga gcgtgtcttg gccgcggtct acaaggctct gtctgacaac     720
ggcgtgtatc tcgagggctc cctgctcaag ccctctatga ctctccccgg agccgactgc     780
ggggaaaccg tcacgtccga gaagatcgct gagtatacgg ttcgcaccct cgagcgccac     840
gtcccttcgt ccgtacctgg tgtgatgttc ctctccggcg gcatgtccga ggaggaggcc     900
tccatcaacc tgaacgccct gaacaagcgc gctcgtaagg gcccgtggtc cttgtccttt     960
tcctacggcc gtgctctgca gcagtcttgc ctcaaggcgt ggcaggggaa gcaggagaac    1020
gtccccgccg cccgcgcggc tttgttggcc cgtgcccagg ctaacagcga ggccaacctg    1080
ggaaagtacg tcgcgggctc ccagccgtcg gcggacgaga ccctgttcgt gaaggggtat    1140
aagtactaa                                                           1149
```

<210> SEQ ID NO 5
<211> LENGTH: 407
<212> TYPE: PRT
<213> ORGANISM: Nannochloropsis oceanica

<400> SEQUENCE: 5

Met Lys Val Leu Ser Ser Leu Ile Leu Thr Ser Val Val Ser Cys
1               5                   10                  15

Ser Ala Phe Val Ser Leu Asn Pro Lys Leu Asn Ser Ile Pro Leu Lys
                20                  25                  30

Thr Arg Ala Arg His Ala Ala Leu Asn Met Val Ser Arg Ala Glu Lys
            35                  40                  45

Glu Asn Pro Tyr Met Glu Glu Leu Lys Ala Asn Ala Lys Lys Ile Gly
        50                  55                  60

Gly Arg Gly Arg Gly Ile Leu Ala Ser Asp Glu Ser Asn Ala Thr Thr
65                  70                  75                  80

Gly Ile Arg Leu Gly Ser Ile Gly Val Glu Asn Thr Glu Glu Asn Arg
                85                  90                  95

Arg Lys Trp Arg Glu Leu Leu Tyr Thr Ala Pro Gly Leu Gly Glu Tyr
            100                 105                 110

Ile Ser Gly Ala Ile Met Phe Asp Glu Thr Leu Tyr Gln Lys Thr Ser

```
            115                 120                 125
Glu Gly Lys Pro Phe Val Asp Val Leu Arg Glu Gln Asn Ile Leu Pro
        130                 135                 140
Gly Ile Lys Val Asp Thr Gly Leu Gln Asn Met Phe Gly Thr Asp Gly
145                 150                 155                 160
Glu Thr Ala Thr Gln Gly Leu Asp Gly Leu Gly Asp Arg Cys Lys Ala
                165                 170                 175
Tyr Tyr Lys Gln Gly Ala Arg Phe Ala Lys Trp Arg Ala Val Leu Lys
            180                 185                 190
Cys Asp Glu Lys Asp Leu Pro Ser Glu Lys Ala Ile Trp Glu Asn Ala
        195                 200                 205
His Ala Leu Ala Arg Tyr Ala Ala Ile Ala Gln Glu Asn Gly Leu Val
    210                 215                 220
Pro Ile Val Glu Pro Glu Val Thr Leu Gly Pro Gly Thr Tyr Ser Ile
225                 230                 235                 240
Glu Arg Thr Ala Phe Ile Ser Glu Arg Val Asn Ser Ile Thr Met Asn
                245                 250                 255
Trp Leu Asn Arg Tyr Asp Val Val Leu Asp Ala Ile Leu Leu Lys Pro
            260                 265                 270
Asn Met Ile Leu Pro Gly Leu Asp Ala Pro Met Ala Ser Lys Glu Glu
        275                 280                 285
Val Ala Lys Tyr Thr Val Gln Val Met Lys Arg Thr Ile Pro Pro Ala
    290                 295                 300
Val Pro Ser Ile His Phe Leu Ser Gly Gly Met Gly Glu Gly Glu Ala
305                 310                 315                 320
Thr Leu Asn Leu Gln Gln Leu Gln Lys Glu Tyr Pro Asp Ala Pro Trp
                325                 330                 335
Ser Leu Thr Phe Ser Tyr Gly Arg Ala Leu Gln Ser Ser Thr Leu Lys
            340                 345                 350
Thr Trp Gly Gly Lys Pro Glu Asn Trp Lys Ala Ala Gln Asp Ile Leu
        355                 360                 365
Val Lys Leu Ala Gln Ala Asn Ser Gln Ala Gln Leu Gly Lys Phe Val
    370                 375                 380
Glu Gly Thr His Pro Ala Pro Gly Gly Gly Arg Ile Leu Gln Ala Leu
385                 390                 395                 400
Arg Leu Gly Gly Ala Gly Lys
                405

<210> SEQ ID NO 6
<211> LENGTH: 1224
<212> TYPE: DNA
<213> ORGANISM: Nannochloropsis oceanica

<400> SEQUENCE: 6
atgaaggtct tgtcttcttt aattctgacc tccgtggtcg tctcctgctc cgcttttgtc     60
tccctgaacc ccaagctcaa cagcatcccc ctcaagaccc gcgctcgtca tgcggccttg    120
aacatggtca gccgtgcgga gaaggagaac ccatatatgg aggagctaaa ggccaatgcc    180
aagaagatcg gggggcgagg ccgaggtatt ctggccagtg acgagagtaa cgccactacg    240
ggcatccgtt tggggtccat ggcgtggag aacacggaag agaatcgccg caagtggcgt    300
gagcttttgt acacggcccc cggtttgggt gaatatattt cggggcaat catgtttgac    360 gagacactct accaaaaaac ctcggagggc aagccgttcg tggacgtgct ccgcgagcag    420
aacatccttc cgggcatcaa ggtagatacg ggcctgcaaa atatgtttgg cacggatggg    480
```

```
gagacggcga cgcagggatt agatggtctt ggtgatcgat gcaaggccta ctacaagcag    540
ggcgctcgtt tcgccaagtg gcgtgccgtc ctcaagtgcg acgagaagga cttacccagc    600
gagaaggcca tctgggagaa tgcccatgcc ttggccaggt acgccgccat cgcacaagaa    660
aacggcctgg tccccattgt cgagcccgag gtcaccttgg ccccggcac ttactccatt     720 gagcgcactg cctttatctc cgagcgtgtc aactccatca ccatgaactg gctcaaccgt    780
tacgacgtgt tcttggatgc gatccttctg aaaccgaaca tgattctgcc tggtcttgat    840
gccccgatgg caagcaagga ggaagttgca agtacaccg tgcaggtaat gaagcgcacc     900
attccccccg ccgtccccct catccatttc ctctccggag catgggcga ggaagaggcc     960 accctgaatc tgcagcaact gcagaaggag taccctgacg cgccttggag cttgaccttt   1020
tcctatggcc gtgctttgca gtcaagcacg ctcaagacct ggggtggaaa gccggagaac   1080
tggaaggcgg cacaggatat tcttgtgaag ctcgcgcagg ccaacagcca ggctcagctt   1140
ggaaagtttg tcgaggggac tcaccctgcc cctggtgggg gcgtattct gcaggcccta    1200 cgtttgggag gggcagggaa gtaa                                          1224

<210> SEQ ID NO 7
<211> LENGTH: 282
<212> TYPE: PRT
<213> ORGANISM: Nannochloropsis oceanica

<400> SEQUENCE: 7

Met Ser Arg Gln Lys Thr Leu Phe Ser Val Met Ala Met Val Thr Val
1               5                   10                  15

Gly Ala Ser Ala Phe Ile Leu Pro Val Arg Gln Pro Leu His Gly Pro
                20                  25                  30

Ala Leu Cys Thr Arg Arg Ala Ser Thr Thr Ala Arg Phe Ala Val
            35                  40                  45

Ser Gln Asp Glu Leu Lys Lys Gln Val Gly Tyr Lys Ser Val Asp Asp
        50                  55                  60

Tyr Val Thr Ser Gly Met Val Gly Leu Gly Thr Gly Ser Thr Ala
65                  70                  75                  80

Ala Phe Ala Val Glu Arg Leu Gly Gln Lys Leu Lys Ala Gly Glu Leu
                85                  90                  95

Lys Asp Ile Val Ala Ile Pro Thr Ser Ile Arg Thr Lys Glu Gln Ala
            100                 105                 110

Glu Gly Leu Gly Ile Pro Leu Val Thr Leu Asp Thr His Ser Val Leu
        115                 120                 125

Asp Val Ala Ile Asp Gly Ala Asp Glu Val Asp Pro Ala Leu Asn Leu
    130                 135                 140

Val Lys Gly Arg Gly Gly Ala Leu Leu Arg Glu Lys Met Val Glu Val
145                 150                 155                 160

Cys Ala Lys Lys Phe Ile Val Ile Val Asp Asp Ser Lys Met Val Pro
                165                 170                 175

Gly Leu Gly Val Thr Gly Ala Met Pro Val Glu Ile Thr Pro Phe Cys
            180                 185                 190

His Glu His Thr Gln Arg Thr Ile Leu Gly Leu Pro Gly Val Lys Gly
        195                 200                 205

Ala Ala Thr Gly Lys Leu Arg Met Asp Gly Asp Lys Pro Tyr Val Thr
    210                 215                 220

Asp Asn Asp Asn Tyr Ile Val Asp Leu Tyr Tyr Thr Ala Pro Ile Ala
225                 230                 235                 240
```

Asp Val Met Ala Val Ala Gly Ala Leu Glu Lys Val Gly Val Val
                245                 250                 255

Glu His Gly Phe Phe Leu Asp Met Thr Thr Ala Val Ile Val Ala Gly
            260                 265                 270

Lys Thr Gly Ile Asp Val Ile Asn Lys Lys
        275                 280

<210> SEQ ID NO 8
<211> LENGTH: 849
<212> TYPE: DNA
<213> ORGANISM: Nannochloropsis oceanica

<400> SEQUENCE: 8

```
atgagccgcc aaaagactct cttttctgtc atggccatgg tcaccgtggg tgcctctgcg      60
tttatccttc ctgtccgcca gccctgcac ggcccggctc tgtgcactcg ccgtgcctcg     120
accaccaccg cgcgcttcgc cgtgagccaa gacgagctca agaagcaagt gggctacaag     180
tccgtggatg actacgtgac cagcggcatg gtcgtgggcc tgggcaccgg ttccactgcc     240
gcctttgctg tggagcgcct cgggcagaag ctcaaggctg gcgagcttaa ggacatcgtt     300
gccatcccta cttccatccg caccaaggag caagcggaag gctgggaat cccctggtg      360
acgcttgaca ctcactctgt gttggatgtg gccattgacg gtgccgatga ggtggacccg     420
gctctgaact tggtgaaggg acgagggggt gctttgctgc gtgagaagat ggtggaggtg     480
tgcgctaaga agttcatcgt cattgtggac gacagcaaga tggtgcctgg cctgggagtc     540
actggtgcga tgcccgtgga gatcaccccc ttctgccatg agcacactca acggacgatc     600
ctaggcttgc caggggtgaa gggcgcggcg acggggaagc ttcgcatgga tggagacaag     660
ccctacgtga ctgacaatga caactacatc gtggatttgt actacaccgc gccaattgcg     720
gacgtgatgg ccgttgcggg ggcgctggag aaggtggtag gtgtggtgga gcacggttt       780
ttcttagaca tgaccacggc ggtgatcgtg gctgggaaga cgggcatcga cgtcatcaat     840
aagaagtag                                                            849
```

<210> SEQ ID NO 9
<211> LENGTH: 363
<212> TYPE: PRT
<213> ORGANISM: Nannochloropsis oceanica

<400> SEQUENCE: 9

Met Thr Pro Gln Ala Asp Ile Thr Ser Lys Thr Thr Pro Asn Leu Lys
1               5                  10                  15

Thr Ala Ala Ser Ser Pro Ser Lys Thr Ser Pro Ala Pro Ser Val Gln
            20                  25                  30

Tyr Lys Ala Ala Asn Gly Lys Val Ile Thr Val Ala Met Ala Glu Gln
        35                  40                  45

Asp Asp Gly Asn Met Gly Ile Phe Arg Glu Cys Phe Ala Met Val Thr
    50                  55                  60

Met Gly Ile Ile Met Ser Trp Tyr Tyr Ile Val Val Ile Leu Ser Leu
65                  70                  75                  80

Leu Cys Leu Val Gly Ile Cys Ile Phe Pro Ala Trp Arg Ala Val Ala
                85                  90                  95

Ala Thr Val Phe Val Leu Met Trp Ser Ala Ala Leu Leu Pro Leu Asp
            100                 105                 110

Tyr Gln Gly Trp Asp Ala Phe Cys Asn Ser Phe Ile Phe Arg Leu Trp
        115                 120                 125

```
Arg Asp Tyr Phe His Tyr Glu Tyr Val Leu Glu Glu Met Ile Asp Pro
        130                 135                 140

Asn Lys Arg Tyr Leu Phe Ala Glu Met Pro His Gly Ile Phe Pro Trp
145                 150                 155                 160

Gly Glu Val Ile Ser Ile Ser Ile Thr Lys Gln Leu Phe Pro Gly Ser
                165                 170                 175

Arg Val Gly Ser Ile Gly Ala Ser Val Ile Phe Leu Leu Pro Gly Leu
            180                 185                 190

Arg His Phe Phe Ala Trp Ile Gly Cys Arg Pro Ala Ser Pro Glu Asn
        195                 200                 205

Ile Lys Lys Ile Phe Glu Asp Gly Gln Asp Cys Ala Val Thr Val Gly
210                 215                 220

Gly Val Ala Glu Met Phe Leu Val Gly Gly Asp Lys Glu Arg Leu Tyr
225                 230                 235                 240

Leu Lys Lys His Lys Gly Phe Val Arg Glu Ala Met Lys Asn Gly Ala
                245                 250                 255

Asp Leu Val Pro Val Phe Cys Phe Gly Asn Ser Lys Leu Phe Asn Val
            260                 265                 270

Val Gly Glu Ser Ser Arg Val Ser Met Gly Leu Met Lys Arg Leu Ser
        275                 280                 285

Arg Arg Ile Lys Ala Ser Val Leu Ile Phe Tyr Gly Arg Leu Phe Leu
290                 295                 300

Pro Ile Pro Ile Arg His Pro Leu Leu Phe Val Val Gly Lys Pro Leu
305                 310                 315                 320

Pro Val Val His Lys Ala Glu Pro Thr Lys Glu Ile Ala Ala Thr
                325                 330                 335

His Ala Leu Phe Cys Glu Lys Val Glu Glu Leu Tyr Tyr Lys Tyr Arg
            340                 345                 350

Pro Glu Trp Glu Thr Arg Pro Leu Ser Ile Glu
        355                 360

<210> SEQ ID NO 10
<211> LENGTH: 1092
<212> TYPE: DNA
<213> ORGANISM: Nannochloropsis oceanica

<400> SEQUENCE: 10
atgacgccgc aagccgacat caccagcaag acgacaccca acctcaagac ggctgcgtca       60 tcccctcca agacctcgcc cgccccctcc gttcaataca aggcggcgaa tggcaaggtg      120
atcacggtgg ccatggccga gcaagacgac gggaacatgg gcattttccg cgagtgtttt      180
gcaatggtga caatgggcat aattatgtcg tggtattaca tcgtcgtcat tctctccctc      240
ctctgcttgg tggggatctg catcttccct gcctggcggg cggtagcggc cacggttttt      300
gtgcttatgt ggagtgcggc gctattgccg cttgactacc agggatggga tgctttctgc      360 aactcccttta tcttcaggct gtggcgggac tacttccact atgaatacgt cctgaggag      420 atgatcgacc caaacaagcg ctacctctttt gctgagatgc ctcacggtat cttcccctgg      480
ggagaggtga tttccatttc gatcaccaaa cagcttttc ccgggagccg cgtaggctcc      540
atcggtgcga gtgtcatctt cctccttccc ggtctcaggc acttcttcgc ttggatcggg      600
tgtcggcccg cgagcccaga gaacatcaaa aagattttg aggatgggca ggactgtgcc      660
gtgacggtgg gggggtcgc cgagatgttt ctagtcggag agacaagga acgactgtac      720 ctgaagaagc acaagggttt cgttcgagaa gccatgaaga tggggcgga cctggttcct      780
```

```
gtcttctgct tcggcaacag caagctgttc aatgtggtgg gggagagcag tcgggtttct    840
atgggcctga tgaagcgcct ctcaaggagg attaaggcca gcgtcctcat cttttacggc    900
cgtctcttcc tgcccattcc gattcgacac ccgctcttgt tcgtggtggg gaagcccctg    960
ccggtcgtgc acaaggcaga gccgaccaag gaggagatcg cggcaacgca cgcactcttt   1020
tgcgagaagg tcgaggagct ttactacaaa tacaggccgg agtgggagac gcgcccgttg   1080
tccattgagt aa                                                       1092

<210> SEQ ID NO 11
<211> LENGTH: 648
<212> TYPE: PRT
<213> ORGANISM: Nannochloropsis oceanica

<400> SEQUENCE: 11
```

Met Pro Ala Tyr Thr Thr Ser Ala Ser Gly Glu Val Asp Leu Arg
1               5                   10                  15

Met Glu Lys Glu Gly Pro Gly Ala Trp Glu Pro Arg Thr Val Tyr Gln
            20                  25                  30

Val Phe Glu Glu Thr Val Gln Arg Tyr Gly Asp Arg Pro Ala Leu His
        35                  40                  45

Phe Lys Lys Val Pro His Gly Gly Ser Pro Glu Thr Thr Glu Trp Ser
    50                  55                  60

Val Tyr Thr Trp Arg Glu Tyr Tyr Asp Leu Thr Leu Thr Phe Ala Lys
65                  70                  75                  80

Ser Leu Leu Ala Leu Asp Phe Pro Ala His Gly Ala Ile Asn Ile Ile
                85                  90                  95

Gly Phe Asn Ser Pro Glu Trp Leu Ile Ala Asn Cys Gly Ala Ile Ala
            100                 105                 110

Ala Gly Gly Val Gly Val Gly Ile Tyr Thr Ser Asn Asn Ala Glu Ala
        115                 120                 125

Cys Asn Tyr Ile Ser Glu His Ser Glu Ala Glu Val Val Val Val Glu
    130                 135                 140

Asn Ala Lys Gln Leu Glu Lys Tyr Val Lys Ile Ala Lys Asn Leu Pro
145                 150                 155                 160

Arg Leu Lys Ala Leu Val Val Tyr Asp Gly Thr Gly Glu Gly Phe Thr
                165                 170                 175

Cys Asp Thr Pro Ile Tyr Ser Trp Lys Ala Phe Met Ala Leu Gly Lys
            180                 185                 190

Asp Lys Ser Glu Ala Ala Val Arg Ala Arg Ile Glu Ala Gln Arg Pro
        195                 200                 205

Gly His Cys Cys Thr Leu Ile Tyr Thr Ser Gly Thr Thr Gly Pro Pro
    210                 215                 220

Lys Ala Val Met Ile Ser His Asp Asn Leu Thr Trp Thr Val Lys Asn
225                 230                 235                 240

Phe Val Ala Ala Leu Pro Phe Thr Leu Thr Cys Glu Asp Arg Ser Val
                245                 250                 255

Ser Ser Leu Pro Leu Ser His Val Ala Ala Gln Met Leu Asp Val His
            260                 265                 270

Cys Pro Ile Ala Ser Gly Ala Lys Ile Tyr Phe Ala Gln Ala Asp Ala
        275                 280                 285

Leu Arg Gly Ser Leu Pro Asn Thr Leu Lys Asp Val Cys Pro Thr Tyr
    290                 295                 300

Phe Phe Gly Val Pro Arg Val Trp Glu Lys Ile Tyr Glu Lys Met Gln

```
             305                 310                 315                 320
        Glu Val Ala Arg Ser Thr Thr Gly Val Lys Arg Ala Leu Ala Gln Trp
                        325                 330                 335
        Ala Lys Ala Lys Gly Leu Glu Lys Asn Arg Arg Gln Gln Tyr Gly Gly
                        340                 345                 350
        Gly Gly Gly Ala Pro Val Gly Phe Gly Cys Ala Tyr Ala Leu Val Leu
                        355                 360                 365
        Ser Lys Val Lys Ala Ala Leu Gly Leu His Gln Thr Lys Ile Cys Ile
                        370                 375                 380
        Thr Ser Ala Ala Pro Ile Ser Val Glu Val Leu Glu Tyr Phe Ala Ser
        385                 390                 395                 400
        Leu Asp Ile Pro Val Leu Glu Leu Phe Gly Gln Ser Glu Cys Thr Gly
                        405                 410                 415
        Pro His Thr Ser Asn Phe Ser Tyr Ala Trp Lys Ile Gly Ser Ile Gly
                        420                 425                 430
        Arg Asp Ile Pro Gly Val Lys Thr Lys Gln Glu Ala Ala Ala Lys Glu
                        435                 440                 445
        Phe Cys Met Phe Gly Arg His Ile Met Met Gly Tyr Met Lys Met Glu
                        450                 455                 460
        Glu Lys Thr Lys Glu Ala Val Asp Glu Gly Trp Leu His Ser Gly
        465                 470                 475                 480
        Asp Val Ala Asp Val Asp Ala Asp Gly Phe Trp Thr Ile Thr Gly Arg
                        485                 490                 495
        Ile Lys Glu Leu Ile Ile Thr Ala Gly Gly Glu Asn Ile Pro Pro Val
                        500                 505                 510
        Leu Ile Glu Thr Glu Val Lys Ala Ala Leu His Ala Val Ala Asn Cys
                        515                 520                 525
        Met Val Val Gly Asp Lys Lys Phe Leu Thr Val Leu Leu Thr Met
                        530                 535                 540
        Lys Thr Lys Leu Asp Glu Gln Gly Asn Pro Thr Asn Ala Leu Asn Arg
        545                 550                 555                 560
        Glu Ala Leu Asp Ile Gly Lys Glu Leu Gly Ser Glu Ala Thr Thr Thr
                        565                 570                 575
        Glu Gln Val Gly Lys Asp Pro Ala Trp Lys Lys Tyr Phe Asp Glu Gly
                        580                 585                 590
        Leu Lys Lys Ala Asn Ala Ala Thr Ser Asn Ala Gln Phe Val Gln
                        595                 600                 605
        Lys Trp Ala Val Leu Pro Leu Asp Phe Ser Glu Lys Gly Gly Glu Leu
                        610                 615                 620
        Thr Pro Thr Leu Lys Leu Lys Arg Ser Val Val Ala Glu Lys Tyr Ala
        625                 630                 635                 640
        Asp Val Ile Ala Asn Leu Tyr Lys
                        645

<210> SEQ ID NO 12
<211> LENGTH: 1947
<212> TYPE: DNA
<213> ORGANISM: Nannochloropsis oceanica

<400> SEQUENCE: 12
atgcccgcct acacgacgac atcggcgtcc ggggaggtgg acttgcgcat ggagaaggag    60
ggccctggag cttgggagcc ccgaactgtt taccaggtct tcgaggagac tgtccaacgt   120
tacggggacc ggcccgcgct ccacttcaag aaagttccgc acggcggtag ccccgagacg   180
```

```
actgagtgga gcgtttacac atggcgcgaa tactatgacc tgaccctcac cttcgccaag      240
agcctcctgg ccctcgactt cccggcccac ggggccatca acatcatcgg tttcaactcg      300
cctgagtggc tcatcgccaa ctgcggtgcc attgccgcgg gtggcgtggg tgtgggtatc      360
tatacgagca acaacgcgga ggcctgcaat tacatctcgg agcactcgga ggctgaagtg      420
gttgtggtgg agaacgctaa gcagctggag aagtacgtaa aaatcgccaa gaacctgccc      480
cgccttaagg cgctggtggt gtacgatggc acgggcgagg gattcacgtg tgacacgcct      540
atatactcct ggaaggcctt catggcactg ggaaaggaca aaagcgaggc agcggtccgt      600
gcgcgcattg aggcccagcg gcccggacat tgttgcacgc tcatctacac gtccggcacc      660
acgggcccgc ccaaggccgt catgatatcg cacgataacc tgacctggac cgtcaaaaac      720
tttgtggctg ccctgccttt cacgcttact tgcgaggacc ggtcggtgtc ctccctgccg      780
ctgtcccacg tggcggcaca gatgctggac gtgcactgcc ccatcgcctc gggcgctaag      840
atttatttcg cgcaggccga cgcactccgg ggctcgctac ccaacacgct gaaggatgtc      900
tgtcccacct acttttttgg cgtaccgcgt gtctgggaga gatctacga gaaaatgcag       960
gaggtggcgc gctccaccac aggggtcaag cgggcgctgg cccagtgggc caaagccaag     1020
ggattggaga agaaccggcg ccagcaatat ggggcggtg gtggggcgcc cgtgggattc      1080
ggttgcgctt acgccctcgt cctgtccaaa gtgaaggcgg cgctagggct gcaccagacc     1140
aagatctgca tcacctcggc agcgcccata tccgtcgagg tgctcgaata cttcgcctcc     1200
ctggacatcc ctgtgctaga gctgttcggg cagtccgagt gcacaggccc acacacctcc     1260
aacttctcct acgcctggaa gatcggctcc attggccgcg acataccggg ggttaagacc     1320
aaacaggaag cggccgccaa ggaattctgc atgttcgggc ggcacattat gatgggctac     1380
atgaagatgg aggagaagac caaggaggca gtggacgagg agggttggct gcattcagga     1440
gacgtggccg acgtggatgc ggacgggttc tggaccatca cgggccgtat caaggagctc     1500
atcatcacgg ccggcgggga gaacatcccg cccgtgctaa ttgagaccga ggtcaaggcc     1560
gcccttcacg ccgtggctaa ttgcatggtg gtgggcgata agaagaaatt tttgactgtg     1620
ctgctgacga tgaagaccaa gctggacgag caggcaacc ccacgaacgc cttgaaccgc      1680
gaggccctgg atatcgggaa agagctgggc tcggaagcca caaccacgga gcaggtcggc     1740
aaggaccctg cctggaagaa gtatttcgac gaggggctca gaaggccaa tgccgccgcc      1800
acctctaatg cgcagttcgt acagaagtgg gccgtgctgc ccttggactt ctccgagaag     1860
ggcggcgagc tcacgcccac gctcaagctc aaacgctctg tggtggccga gaaatacgcc     1920
gacgtcatcg ccaatctcta caagtag                                        1947
```

<210> SEQ ID NO 13
<211> LENGTH: 348
<212> TYPE: PRT
<213> ORGANISM: Nannochloropsis oceanica

<400> SEQUENCE: 13

Met Arg Ile Pro Ser Leu Ile Leu Cys Phe Ala Phe Leu Ala Ser Ala
1               5                   10                  15

Pro Ala Val Ala Phe Leu Leu Pro Pro Leu Pro Cys Phe Ser Ser
            20                  25                  30

Leu Gln Thr Val Thr Asn Thr Ile Thr Thr Ser Ser Arg Phe Ser Ser
        35                  40                  45

Ser Ser Ser Ser Ser Ser Ser Ser Ser Ser Ser Arg Pro Arg
    50                  55                  60

Cys Ser Pro Leu Leu Ser Val Thr Thr Ala Ala Thr Ala Ser Ser Ala
 65                  70                  75                  80

Thr Glu Glu Ala Glu Asn Pro Ser Leu Thr Gln Gly Val Phe Ile Glu
                 85                  90                  95

His Thr Asp Arg Tyr Gly Met Val Tyr His Ser Asn Tyr Leu Leu Phe
            100                 105                 110

Leu Cys Arg Ala Leu His Leu Thr Leu Gly Arg His Val Val Thr Arg
        115                 120                 125

Leu Asp Asn Phe Arg Phe Lys Ala Ser Ala Arg Leu Gly His Asp Ile
130                 135                 140

Ala Ile Asp Val Arg Pro Lys Ala Gly Lys Asp Asn Thr Phe Val Thr
145                 150                 155                 160

Ser Ile Lys Glu Ser Glu Thr Pro His Thr Thr Phe Ile Thr Ala Asp
                165                 170                 175

Val Ser Ala Phe Pro Leu Pro Glu Arg Gly Arg Glu Gly Gly Arg Glu
            180                 185                 190

Asp Trp Ala Ala Tyr Thr Ile Ser Glu Glu Ala Leu Arg Lys Val
        195                 200                 205

Val Ala Ser Pro Asp Lys Val Met Glu Ala Val Leu Trp Thr Asp Glu
210                 215                 220

Leu Gly Val His Gly Leu Leu Thr Pro His Ala Val Leu Ser Leu Phe
225                 230                 235                 240

Glu Arg Gly Arg Ser Asp Ser Leu Gly Gly Pro Asp Arg Leu Glu Glu
                245                 250                 255

Leu Met Asp Asp Gly Tyr Met Phe Val Ala Arg Ile Asp Gly Tyr
        260                 265                 270

Arg Phe Asp Pro Ser Leu Arg Leu Glu Glu Gly Glu Ala Leu Gln Val
        275                 280                 285

Leu Gly Arg Phe Lys Pro Lys Ser Asp Ala Ile Val Val Cys Glu Gln
290                 295                 300

Val Leu Ile Val Lys Ala Thr Gln Gln Ile Val Ala Gln Ala Leu Val
305                 310                 315                 320

Thr Leu Ala Cys Ile Gly Ala Val Asp Gly Leu Arg Gly Val Pro
                325                 330                 335

Ser Lys Ala Leu Glu Ser Met Asn Met Gly Thr Thr
            340                 345

<210> SEQ ID NO 14
<211> LENGTH: 1047
<212> TYPE: DNA
<213> ORGANISM: Nannochloropsis oceanica

<400> SEQUENCE: 14

```
atgagaatac cttcccttat cctttgcttc gcattctag cgagcgctcc cgctgttgcc    60
ttcctgctgc cgccgctgcc ttgcttctct tcttcgcttc agacagtcac caacacaatc   120
acgacaagca gtcgcttcag cagcagcagc agcagcagca gcagcagcag cagcagcagc   180
agcagaccaa gatgcagccc cttgttatcc gtcacgactg ccgctactgc ttcatctgcg   240
acagaggaag cggaaaaccc gagcttgact caaggagtat tcatcgagca taccgacagg   300
tacgggatgg tctaccactc caactacctg ctcttcctct gtcgcgctct ccacctcacc   360
ctgggccggc acgtggtgac acgcctagat aactttcggt tcaaagcatc ggctcgcctg   420
ggccacgata tcgccatcga cgtgaggccc aaggcgggga agacaacac tttcgtcacc   480
```

| | |
|---|---|
| agcatcaagg aaagcgaaac tcctcacact acctttatca ccgcggacgt atcggccttc | 540 |
| cccctcctg agcgaggaag ggagggagga agggaggatt gggctgcata tacgatctcg | 600 |
| gaggaagagg cattgaggaa ggtggtggcc tcccccgaca aggtcatgga ggccgttttg | 660 |
| tggaccgacg agctgggagt gcacggcctg ctcacaccgc atgccgtcct ttccctgttt | 720 |
| gagcggggaa ggagtgattc cctgggtggt ccggaccgcc tggaggagct catggatgac | 780 |
| ggctacatgt tcgtcgtcgc ccgcatcgac ggctaccgct tcgacccctc cctccgtctc | 840 |
| gaggagggag aggcccttca agtgctcggc cgatttaagc ccaagtccga cgccatcgtt | 900 |
| gtatgcgagc aggtcctcat cgtcaaggcc acccaacaga tcgtggctca ggccctcgtg | 960 |
| acgcttgcct gcatcggcgc cgtggatggc aaattgcgag gcgtgccttc caaggcccctt | 1020 |
| gagagtatga acatgggcac gacgtag | 1047 |

```
<210> SEQ ID NO 15
<211> LENGTH: 375
<212> TYPE: DNA
<213> ORGANISM: Artificial sequence
<220> FEATURE:
<223> OTHER INFORMATION: Zeocin resistance gene

<400> SEQUENCE: 15
```

| | |
|---|---|
| atggccaagc tgaccagcgc cgttccggtg ctcaccgcgc gcgacgtcgc cggagcggtc | 60 |
| gagttctgga ccgaccggct cgggttctcc cggacttcg tggaggacga cttcgccggt | 120 |
| gtggtccggg acgacgtgac cctgttcatc agcgcggtcc aggaccaggt ggtgccggac | 180 |
| aacaccctgg cctgggtgtg ggtgcgcggc ctggacgagc tgtacgccga gtggtcggag | 240 |
| gtcgtgtcca cgaacttccg ggacgcctcc gggccggcca tgaccgagat cggcgagcag | 300 |
| ccgtgggggc gggagttcgc cctgcgcgac ccggccggca actgcgtgca cttcgtggcc | 360 |
| gaggagcagg actaa | 375 |

```
<210> SEQ ID NO 16
<211> LENGTH: 822
<212> TYPE: DNA
<213> ORGANISM: Artificial sequence
<220> FEATURE:
<223> OTHER INFORMATION: Paromomycin resistance gene

<400> SEQUENCE: 16
```

| | |
|---|---|
| atggtcgaga ttcgaagcat ggacgatgcg ttgcgtgcac tgcggggtcg gtatcccggt | 60 |
| tgtgagtggt tgttgtgga ggatgggggcc tcggggggctg gtgtttatcg gcttcggggt | 120 |
| ggtgggcggg agttgtttgt caaggtggca gctctggggg ccggggtggg cttgttgggt | 180 |
| gaggctgaac ggctggtgtg gttggcgag gtgggattc ccgtacctcg tgttgtggag | 240 |
| ggtggtgggg acgagagggt cgcctggttg gtcaccgaag cggttccggg gcgtccggcc | 300 |
| agtgcgcggt ggccgcggga gcagcggctg acgtggcgg tggcgctcgc ggggctcgct | 360 |
| cgttcgctgc acgcgctgga ctgggagcgg tgtccgttcg atcgcagtct cgcggtgacg | 420 |
| gtgccgcagg cggcccgtgc tgtcgctgaa gggagcgtcg acttggagga tctggacgag | 480 |
| gagcggaagg ggtggtcggg ggagcggctt ctcgccgagc tggagcggac tcggcctgcg | 540 |
| gacgaggatc tggcggtttg ccacggtgac ctgtgcccgg acaacgtgct gctcgaccct | 600 |
| cgtacctgcg aggtgaccgg gctgatcgac gtggggcggg tcggccgtgc ggaccggcac | 660 |
| tccgatctcg cgctggtgct gcgcgagctg gcccacgagg aggacccgtg gttcgggccg | 720 |
| gagtgttccg cggcgttcct gcgggagtac gggcgcgggt gggatggggc ggtatcggag | 780 |

```
gaaaagctgg cgttttaccg gctgttggac gagttcttct ga                        822
```

<210> SEQ ID NO 17
<211> LENGTH: 999
<212> TYPE: DNA
<213> ORGANISM: Artificial sequence
<220> FEATURE:
<223> OTHER INFORMATION: Hygromycin resistance gene

<400> SEQUENCE: 17

```
atgacacaag aatccctgtt acttctcgac cgtattgatt cggatgattc ctacgcgagc     60
ctgcggaacg accaggaatt ctgggagccg ctggcccgcc gagccctgga ggagctcggg    120
ctgccggtgc cgccggtgct gcgggtgccc ggcgagagca ccaaccccgt actggtcggc    180
gagcccggcc cggtgatcaa gctgttcggc gagcactggt gcggtccgga gagcctcgcg    240
tcggagtcgg aggcgtacgc ggtcctggcg gacgccccgg tgccggtgcc ccgcctcctc    300
ggccgcggcg agctgcggcc cggcaccgga gcctggccgt ggccctacct ggtgatgagc    360
cggatgaccg gcaccacctg gcggtccgcg atggacggca cgaccgaccg gaacgcgctg    420
ctcgccctgg cccgcgaact cggccgggtg ctcggccggc tgcacagggt gccgctgacc    480
gggaacaccg tgctcacccc ccattccgag gtcttcccgg aactgctgcg ggaacgccgc    540
gcggcgaccg tcgaggacca ccgcgggtgg ggctacctct cgccccggct gctggaccgc    600
ctggaggact ggctgccgga cgtggacacg ctgctggccg gccgcgaacc ccggttcgtc    660
cacggcgacc tgcacgggac caacatcttc gtggacctgg ccgcgaccga ggtcaccggg    720
atcgtcgact tcaccgacgt ctatgcggga gactcccgct acagcctggt gcaactgcat    780
ctcaacgcct ccggggcgac cgcgagatc ctggccgcgc tgctcgacgg ggcgcagtgg     840
aagcggaccg aggacttcgc ccgcgaactg ctcgccttca ccttcctgca cgacttcgag    900
gtgttcgagg agaccccgct ggatctctcc ggcttcaccg atccggagga actggcgcag    960
ttcctctggg ggccgccgga caccgccccc ggcgcctga                          999
```

<210> SEQ ID NO 18
<211> LENGTH: 500
<212> TYPE: DNA
<213> ORGANISM: Artificial sequence
<220> FEATURE:
<223> OTHER INFORMATION: Tubulin Promoter

<400> SEQUENCE: 18

```
actgcgcatg gattgaccga cggccggttg ccaactttg gggtcggccc cccttttcta     60
gcccttgccc gtccagcaat taaaaattat caacggcata ccggcactgg aagcttcggg   120
tttacaattt tggcttgcct tcctaatact gtaccgcgga gaacgtatga tattacagaa   180
aaatgccttg cacagttagc gcaaagggaa aacgtttctc cgccattgta cttttggaa    240
gagggaaagc gattgtaaaa tatgctctc cgctacgaga gtttgggctg ttgatacatg   300
tgaaaataag tgtggacgac tttgaatgac ttgatcaggc tgtttgcaca tataaccagc   360
gcgcatgcac ttctgacatg tcaatgacga aatttcacac ttcaccaata aattgtatcc   420
ttacgttttg tctttctcac acgcacatat atgatcatag ataaaagcca atatcaagaa   480
gctgtctttt ttgtgaagca                                                500
```

<210> SEQ ID NO 19
<211> LENGTH: 1000
<212> TYPE: DNA

<213> ORGANISM: Artificial sequence
<220> FEATURE:
<223> OTHER INFORMATION: Heat shock protein terminator

<400> SEQUENCE: 19

```
tcgggatggg ggaaaaaaac ctctgtgtgg gctgtcagtt gatactatta gaggtctttt      60
gttttgtttg tggctgcgtg tgtgtgtttg catgagaaat agacttgaga atatcggaag     120
gaactttgac atggtaaacg aggaaaagaa aatcttcaaa aaggaataat gggtaaaaac     180
aaggagcacc gggtctcttt agaaatgctt ctcggcggaa aaccagaaaa aaaggtagaa     240
tatgtcgact ttttcgctta tcattataga atgaaagatc gaatggccaa gggatttata     300
aattcttcct ttatgttgtc gtagaactta cttcccatcc cgagggaggt gtatgcaggc     360
caaaccctct gacatgggcg caatatctct atgaaaggtt gttggaatac attgtccgac     420
ctccttcgag gcggagccgc atagttgaag tataggtgct tgcttcatcc atctcatgac     480
gctttgccag tgactcactc atgcatgtga cacatttagt tctgctcgct caagcctggc     540
ccctcctgac atgcacacat tgcacttgta ggtgggccac gtttagtata gacgccaccc     600
ctgtcgcacc atcggtccca gagcaggagc acgcttccct actcctgtac gctcccctg     660
cttccccccc tgctcgtcaa cgatggcgac gccagcggct gcgaattaca gtgacggcgc     720
ggccgctcag gatgacagct cctctccttc aacatctccc aatcttccac ccccgcccat     780
gtcgtcgttc gtacggccta tgctgaccga tatgtaccaa attacaatgg tcttcgcgta     840
ctggaagcaa aagcggcacc aggacagggc catctttgag ctcttttcc ggaagacacc     900
ctttaaggga gagtttgcca ttatggccgg cattgacgaa gtactcaagt acttggccca     960
ctttcgcttc tccgaggagg agctgattta tttacgaaag                          1000
```

<210> SEQ ID NO 20
<211> LENGTH: 800
<212> TYPE: DNA
<213> ORGANISM: Nannochloropsis oceanica

<400> SEQUENCE: 20

```
ttcttccgct tgttgctgcc gatggcggcc atggtctcta agatggagtg gatggaggag      60
gaggcgagcg tagcagcaag cgtgagttat acagccaggc acatgtcgca atccttcggt     120
ctcgggctta aaatccacgc actaatcacg ctgggccatg caaagagcaa tgccgaggcc     180
caccacacaa aacgctgtgt cgcgcgttgc ggcctgaagc ttcatacttc ttagtcgccg     240
ccaaaagggc tcgagagacg agacccgttg gcatgaccga tgttgttcga cgcggttttgc     300
ttcgtcacag tcgacgtgat tcaggaatct ggagcctgca gatcatttt ttcagcctga     360
tatcgttctt ttccactgag aaccatcaga ccaccttttc ttccattgtg tgaaggagta     420
ggagttgccg tgctgctttg tgggagacat ctgcgatggt gaccagcctc ccgtcgtctg     480
gtcgacgtga cgagcctctt cactgttctt cgacggagag acgcaagcga acggctcta     540
gaccttttgg acacgcattc tgtgtgtgaa ctagtggaca gtgataccac gtctgaaagc     600
tcaccactgc ccatggtgca gctacttgtc acaaagtttt gactccgtcg gtatcaccat     660
tcgcgctcgt gtgcctggtt gttccgccac gccggcctgc cccggggcgg ggcaatattc     720
taaaatctca cgcaaaacac cgcacttacc cctcacacat attcgtgata gaccaccacc     780
aatctcagcc cgcatcaaca                                                  800
```

<210> SEQ ID NO 21
<211> LENGTH: 613

<212> TYPE: DNA
<213> ORGANISM: Nannochloropsis oceanica

<400> SEQUENCE: 21

```
gcttctgtgg aagagccagt ggtagtagca gtagcagcag cagtagcagc cgcagcactc    60
agtgttggcg cgagagattg tccatccctt cttaacctac cggaagagaa ataaggcctt   120
tctcccgtag ctgtcttcgt ttgtttgtgc tgattgcttg atatgagagt gttgaattcc   180
tgcatcatgt ttttctctgt agtccttcc taccccgtc attttctttt ctccctggtt   240
cttcttttgt caccttatt ttacataaaa ttttctttgt ttatagtgag aggaaggtag   300
agaggggaaa acaagaacaa cgaacgcaag cgtgtgaaag gagggcgagt agaagagaaa   360
cagatctgtt gagcattgag agtggagccg ggggaaaggc ttgtgtgttg tctttgaaaa   420
agttgtttaa atcacgaatc cgttagttct catgtgtacc tctttcacta catgtgatgg   480
agaaaacaaa agtgtgagga ttaattgaag aaaaagaaga gttcgacacg tcaaaccgcc   540
caaaagacgt cacaaagaga acttgattct ctttgccgtg ttgatcctgt cttttccccc   600
agcttttctt gcc                                                     613
```

<210> SEQ ID NO 22
<211> LENGTH: 1000
<212> TYPE: DNA
<213> ORGANISM: Nannochloropsis oceanica

<400> SEQUENCE: 22

```
gtgtgtcctg cgtgttgatc agtagatgcg caagataccg tcagttagcc agtcgcgtgt    60
gatacactca tcacgaattg aaaaaaaagg gggagggagg aaacgaaggg ccaattgctt   120
acctggccgt gtgcttcatg tgtaaaacaa aatacagtat ggcttcttgt caacctgtcc   180
cccggcactt ccagcttgcc tgccaaggta ctaggcatat ttggtttcgt agaagtagag   240
tcttcatata tgaatgctgt cccggaccctt ctcaagggct gcagctcgtt ggcgattggt   300
gaatctatgc ccaattcatc cgactctttg tcgggttccg agaggaggac ttgtcatgaa   360
agagataggg gctttggtct tgcacacgcc cgcgttccag cttccccccc gcaacctcgc   420
gcgtcgacca tgcgttgttg cctttgcatg acgcgcggtc ataatctact gtagatgctg   480
gcgacctttt ccttttttt catctttgaa cacaacagat atacgctgag gcgtcgggaa   540
agcgcaaaat accgcgcgct gttgacgtcc gcttattttg ttggcccgcc ccgcgctctt   600
ccttgtgcct tcgcaggtcc atctgtggat tcgcgtccca agaccaagca ccattgtctt   660
tcatagctgc catgcatggt tgtggcacgc caggggaggc gaatcccata gccaccaaac   720
ctcgtggctg tgccgagtgc cgtgcacccc aaggagtatc cttgcactca tgcggcctgc   780
gttgccttcg tgctcatgcc cccatgagac gcgcaaaggc agcaaagacc tgagctagcg   840
gaatctttga tttcacaagg catgtaaaat gtatcaaggt cctgggcgca gggcttttgc   900
ctcacgcagc aacacattcc aatcctatct cacatgtcca atccttcatt catcacctcc   960
ggccctccgc acaccacagc aactcgacca cccccctaaaa                      1000
```

<210> SEQ ID NO 23
<211> LENGTH: 938
<212> TYPE: DNA
<213> ORGANISM: Nannochloropsis oceanica

<400> SEQUENCE: 23

```
gaaagatcca agagagacga gtagagattt ttttttggg attgatgttt gtcgttcttt    60
```

| | |
|---|---|
| gagttgtcgt cgagttacgc cttttgtaag aatgttccgc aggagaggag gaggatgggc | 120 |
| atgagtgagg gtgagagggc ttgcccgctt tttttttaa aaacgctgaa gacgtggttg | 180 |
| tcaaacaaac cccccataga aacgattttg ttacggtgcg gtccagacgt cacttgaatg | 240 |
| gctccgcgga aaggccaggg agggaagggg ggagggagga aacatgaaac atgttgaacg | 300 |
| gctcaacagg gtttggggga caagagaggt agcgccctga tggactgctc cctcccctcc | 360 |
| tttccctcaa tgtctcattc atccatgctt ccccttctc tctctcccct ccgttccatc | 420 |
| ccccgcgggc gtggtagtgg cgtgatggga tccactaaaa tgtacgtgta agaaaagccg | 480 |
| gtgagcttac gcttttgtga aagtgggagt acgagtgttg tgtgtgtgtg tagtggtttc | 540 |
| agaccccaga cagaggcgaa gcagaaaaag cagacgatga agacgacgaa gaaatgagca | 600 |
| gtctatttt atcgtggaaa cagaagaggt gatatcgtct cgttctttgt tatcacctac | 660 |
| cccgcgtgca tgtacatgca gcctttttat tttgtaatct ttcccgaaaa atcaaccgcc | 720 |
| acctccccc cgccttctct cacccatcat cttctcctgt ttatcttcta ctttacacta | 780 |
| gatcgcatgg cacatctccc tcgcaatcca tcggtgcaac catcatcgat cccactcctc | 840 |
| cctccctccc tccctccctc ctcccctctc ttctaagaaa tccgctagct gcgaacccag | 900 |
| ctcacctacc tcatttatca gagcctcgat tcggtcct | 938 |

<210> SEQ ID NO 24
<211> LENGTH: 1000
<212> TYPE: DNA
<213> ORGANISM: Nannochloropsis oceanica

<400> SEQUENCE: 24

| | |
|---|---|
| cgcaaaaaac agacaaactt cgtcactcac cgtcgggagg gcttttgctg ctccagtagt | 60 |
| ggttggtcga cttcggccca cttttcctcc agaacaagcc cccaatactc tcgaagagct | 120 |
| gccgttgcgg gggcgagcga ccttgacgtc gcggtattta cgaagcctca tctcggctct | 180 |
| tttacaattg tttgtgttgt tactcttgtt gtgactccac accactttgg tcgggatggt | 240 |
| gtcgactaga tttcgtcgtc gttgtgtgct ggcattcttt cgagcgacaa tgccttcatc | 300 |
| aattcagagg acaggcattg tttcttcttg tgtgtgctgg ttgggcggtg aggcgctgat | 360 |
| ttgtgcctac tttgtggctt tgatacgccg cctttccgcc cttttcaccc tgtacaacca | 420 |
| cgcacagctc gagacggcta attatgcctg tatatctgcg cccctgtgt aaggggtgtg | 480 |
| tgtttgccgc tcggatgcgt gtgtcctgac gatgtcgacg ctgcatcacc tcgcttcccg | 540 |
| ccagcaggag gtggtcgcat gggttgggc cgcacatcca cacgacaagc aacaagcccc | 600 |
| gcttcctcgg tgctcaaggc attgatgaca taccctgtat cgcgtgcctg ggtggcacga | 660 |
| ttgccatacc gtgtgcattg tgctgcctct tgtgcaggcg ggcgagggtg tggcaatacg | 720 |
| ctccttacta agatagtggc ggggctttgt tgcccgagcg gtggcacttg tcggcaacag | 780 |
| actctctggg cacgcttcac ttgccaccag caacacaagg ccaggcggcg gacattacgg | 840 |
| tgccctaaga acagaggcag cacgtgtgca cgccctaaga aatgaccgcg gtacatcagg | 900 |
| attaattccc gtcacgccgc atcctcaact ccctcccctt tccacccaca accccgcta | 960 |
| ctctatcaca ggaaacctttt cctcgccgaa cacttcaaaa | 1000 |

<210> SEQ ID NO 25
<211> LENGTH: 1000
<212> TYPE: DNA
<213> ORGANISM: Nannochloropsis oceanica

<400> SEQUENCE: 25
tttggaagag agtttgctgt ttgtaagaga aaagggaaag gggaaaacta atcgtcagga    60
ggtatgatat ggatatgaag agtgcgccgc ggaaagaaaa ctagagttgt ttcattcctt   120
tgattccatt taagcaagca acagcaacgc caacagcaac cgcatttaga aaaagataga   180
gggaacagtc tgagtagaga gaatacaagt agagcggaag tgatagagtg aggcaagagg   240
gaagtatctg cggggcagga gatggggac agattgcgca tcataaaagg agtagaaatg    300
ccattggtta gcgtcgcttt cctctgccct ctctgtcctc aaattcctat gcacccacac   360
ttctcggtcc cgtgttccac gcatgccttc ccccgtgtct ccctctccgc cttaccctct   420 ccccatctt tatccattat tagaaatagt tgtgtcgagt cgatcggatc gcagaagtat   480
gtgtacagag tgagggggga gggagaagaa gacgacggaa gttaagagga cggacatgat   540
gacggagtag aaaagaaac gcaagcacac cagcagcggg agaaactttt aaaaaaagac    600
caaggactgg aaatctgtaa tcttggcgaa gacaaaaaaa tccacctact taatctctga   660
atcaagaaaa taacacactc actcccctcg gttttaattc tacacgtctt tcttttcttt   720
gctttgttgt atgctcgatg aagccttcca catttctgtc tcgatacttt ctggtatcct   780
tcattttggg ctagtttact ctcacggctg tcttaatggt gccaatgtac aaagcgagaa   840
atacaaaccc ttgtgcgcct cctttttctttt cgcgacaaca tctcaagatg atgataccgc   900
agacgccgct gctacgggtg ctgctacttc tgttgctgct ccacctgctc ctcctacctt    960
tcctcctttg cagccaagtc aagcaagcgc cgatgtaaca                          1000

<210> SEQ ID NO 26
<211> LENGTH: 35
<212> TYPE: DNA
<213> ORGANISM: Artificial sequence
<220> FEATURE:
<223> OTHER INFORMATION: Primer No. 26

<400> SEQUENCE: 26
cttttttgtg aagcaatggc caagctgacc agcgc                               35

<210> SEQ ID NO 27
<211> LENGTH: 36
<212> TYPE: DNA
<213> ORGANISM: Artificial sequence
<220> FEATURE:
<223> OTHER INFORMATION: Primer No. 27

<400> SEQUENCE: 27
tttcccccat cccgattagt cctgctcctc ggccac                              36

<210> SEQ ID NO 28
<211> LENGTH: 35
<212> TYPE: DNA
<213> ORGANISM: Artificial sequence
<220> FEATURE:
<223> OTHER INFORMATION: Primer No. 28

<400> SEQUENCE: 28
cttttttgtg aagcaatggt cgagattcga agcat                               35

<210> SEQ ID NO 29
<211> LENGTH: 35
<212> TYPE: DNA
<213> ORGANISM: Artificial sequence
<220> FEATURE:
<223> OTHER INFORMATION: Primer No. 29

<400> SEQUENCE: 29
tttcccccat cccgatcaga agaactcgtc caaca                                    35

<210> SEQ ID NO 30
<211> LENGTH: 37
<212> TYPE: DNA
<213> ORGANISM: Artificial sequence
<220> FEATURE:
<223> OTHER INFORMATION: Primer No. 30

<400> SEQUENCE: 30 ctttttttgtg aagcaatgac acaagaatcc ctgttac                                 37

<210> SEQ ID NO 31
<211> LENGTH: 36
<212> TYPE: DNA
<213> ORGANISM: Artificial sequence
<220> FEATURE:
<223> OTHER INFORMATION: Primer No. 31

<400> SEQUENCE: 31
tttcccccat cccgatcagg cgccgggggc ggtgtc                                   36

<210> SEQ ID NO 32
<211> LENGTH: 35
<212> TYPE: DNA
<213> ORGANISM: Artificial sequence
<220> FEATURE:
<223> OTHER INFORMATION: Primer No. 32

<400> SEQUENCE: 32
cgagctcggt acccgactgc gcatggattg accga                                    35

<210> SEQ ID NO 33
<211> LENGTH: 28
<212> TYPE: DNA
<213> ORGANISM: Artificial sequence
<220> FEATURE:
<223> OTHER INFORMATION: Primer No. 33

<400> SEQUENCE: 33
tgcttcacaa aaaagacagc ttcttgat                                            28

<210> SEQ ID NO 34
<211> LENGTH: 25
<212> TYPE: DNA
<213> ORGANISM: Artificial sequence
<220> FEATURE:
<223> OTHER INFORMATION: Primer No. 34

<400> SEQUENCE: 34
tcgggatggg ggaaaaaaac ctctg                                               25

<210> SEQ ID NO 35
<211> LENGTH: 36
<212> TYPE: DNA
<213> ORGANISM: Artificial sequence
<220> FEATURE:
<223> OTHER INFORMATION: Primer No. 35

<400> SEQUENCE: 35
actctagagg atccccttc gtaaataaat cagctc                                    36

<210> SEQ ID NO 36
<211> LENGTH: 20

```
<212> TYPE: DNA
<213> ORGANISM: Artificial sequence
<220> FEATURE:
<223> OTHER INFORMATION: Primer No. 36

<400> SEQUENCE: 36
gggatcctct agagtcgacc                                              20

<210> SEQ ID NO 37
<211> LENGTH: 20
<212> TYPE: DNA
<213> ORGANISM: Artificial sequence
<220> FEATURE:
<223> OTHER INFORMATION: Primer No. 37

<400> SEQUENCE: 37
cgggtaccga gctcgaattc                                              20

<210> SEQ ID NO 38
<211> LENGTH: 35
<212> TYPE: DNA
<213> ORGANISM: Artificial sequence
<220> FEATURE:
<223> OTHER INFORMATION: Primer No. 38

<400> SEQUENCE: 38
cgagctcggt acccgttctt ccgcttgttg ctgcc                             35

<210> SEQ ID NO 39
<211> LENGTH: 25
<212> TYPE: DNA
<213> ORGANISM: Artificial sequence
<220> FEATURE:
<223> OTHER INFORMATION: Primer No. 39

<400> SEQUENCE: 39
tgttgatgcg ggctgagatt ggtgg                                        25

<210> SEQ ID NO 40
<211> LENGTH: 21
<212> TYPE: DNA
<213> ORGANISM: Artificial sequence
<220> FEATURE:
<223> OTHER INFORMATION: Primer No. 40

<400> SEQUENCE: 40
gcttctgtgg aagagccagt g                                            21

<210> SEQ ID NO 41
<211> LENGTH: 28
<212> TYPE: DNA
<213> ORGANISM: Artificial sequence
<220> FEATURE:
<223> OTHER INFORMATION: Primer No. 41

<400> SEQUENCE: 41
ggcaagaaaa gctgggggaa aagacagg                                     28

<210> SEQ ID NO 42
<211> LENGTH: 35
<212> TYPE: DNA
<213> ORGANISM: Artificial sequence
<220> FEATURE:
<223> OTHER INFORMATION: Primer No. 42

<400> SEQUENCE: 42
```
ccagcttttc ttgccactgc gcatggattg accga                35

<210> SEQ ID NO 43
<211> LENGTH: 40
<212> TYPE: DNA
<213> ORGANISM: Artificial sequence
<220> FEATURE:
<223> OTHER INFORMATION: Primer No. 43

<400> SEQUENCE: 43
cgagctcggt acccggtgtg tcctgcgtgt tgatcagtag        40

<210> SEQ ID NO 44
<211> LENGTH: 29
<212> TYPE: DNA
<213> ORGANISM: Artificial sequence
<220> FEATURE:
<223> OTHER INFORMATION: Primer No. 44

<400> SEQUENCE: 44
ttttaggggg tggtcgagtt gctgtggtg        29

<210> SEQ ID NO 45
<211> LENGTH: 24
<212> TYPE: DNA
<213> ORGANISM: Artificial sequence
<220> FEATURE:
<223> OTHER INFORMATION: Primer No. 45

<400> SEQUENCE: 45
gaaagatcca agagagacga gtag        24

<210> SEQ ID NO 46
<211> LENGTH: 30
<212> TYPE: DNA
<213> ORGANISM: Artificial sequence
<220> FEATURE:
<223> OTHER INFORMATION: Primer No. 46

<400> SEQUENCE: 46
aggaccgaat cgaggctctg ataaatgagg        30

<210> SEQ ID NO 47
<211> LENGTH: 39
<212> TYPE: DNA
<213> ORGANISM: Artificial sequence
<220> FEATURE:
<223> OTHER INFORMATION: Primer No. 47

<400> SEQUENCE: 47
cctcgattcg gtcctttctt ccgcttgttg ctgccgatg        39

<210> SEQ ID NO 48
<211> LENGTH: 35
<212> TYPE: DNA
<213> ORGANISM: Artificial sequence
<220> FEATURE:
<223> OTHER INFORMATION: Primer No. 48

<400> SEQUENCE: 48
cgagctcggt acccgcgcaa aaaacagaca aactt        35

<210> SEQ ID NO 49
<211> LENGTH: 34
<212> TYPE: DNA
<213> ORGANISM: Artificial sequence

```
<220> FEATURE:
<223> OTHER INFORMATION: Primer No. 49

<400> SEQUENCE: 49
ttttgaagtg ttcggcgagg aaaggtttcc tgtg                            34

<210> SEQ ID NO 50
<211> LENGTH: 27
<212> TYPE: DNA
<213> ORGANISM: Artificial sequence
<220> FEATURE:
<223> OTHER INFORMATION: Primer No. 50

<400> SEQUENCE: 50
tttggaagag agtttgctgt ttgtaag                                    27

<210> SEQ ID NO 51
<211> LENGTH: 27
<212> TYPE: DNA
<213> ORGANISM: Artificial sequence
<220> FEATURE:
<223> OTHER INFORMATION: Primer No. 51

<400> SEQUENCE: 51
tgttacatcg gcgcttgctt gacttgg                                    27

<210> SEQ ID NO 52
<211> LENGTH: 37
<212> TYPE: DNA
<213> ORGANISM: Artificial sequence
<220> FEATURE:
<223> OTHER INFORMATION: Primer No. 52

<400> SEQUENCE: 52
agcgccgatg taacagtgtg tcctgcgtgt tgatcag                         37

<210> SEQ ID NO 53
<211> LENGTH: 38
<212> TYPE: DNA
<213> ORGANISM: Artificial sequence
<220> FEATURE:
<223> OTHER INFORMATION: Primer No. 53

<400> SEQUENCE: 53
ttcttccgct tgttgctgcc gatggcggcc atggtctc                        38

<210> SEQ ID NO 54
<211> LENGTH: 34
<212> TYPE: DNA
<213> ORGANISM: Artificial sequence
<220> FEATURE:
<223> OTHER INFORMATION: Primer No. 54

<400> SEQUENCE: 54
gtgtgtcctg cgtgttgatc agtagatgcg caag                            34

<210> SEQ ID NO 55
<211> LENGTH: 30
<212> TYPE: DNA
<213> ORGANISM: Artificial sequence
<220> FEATURE:
<223> OTHER INFORMATION: Primer No. 55

<400> SEQUENCE: 55
cgcaaaaaac agacaaactt cgtcactcac                                 30
```

<210> SEQ ID NO 56
<211> LENGTH: 40
<212> TYPE: DNA
<213> ORGANISM: Artificial sequence
<220> FEATURE:
<223> OTHER INFORMATION: Primer No. 56

<400> SEQUENCE: 56
ctttcgtaaa taaatcagct cctcctcgga gaagcgaaag                          40

<210> SEQ ID NO 57
<211> LENGTH: 38
<212> TYPE: DNA
<213> ORGANISM: Artificial sequence
<220> FEATURE:
<223> OTHER INFORMATION: Primer No. 57

<400> SEQUENCE: 57
cagcccgcat caacaatggt tgctaaagct gcttttgc                            38

<210> SEQ ID NO 58
<211> LENGTH: 37
<212> TYPE: DNA
<213> ORGANISM: Artificial sequence
<220> FEATURE:
<223> OTHER INFORMATION: Primer No. 58

<400> SEQUENCE: 58
ctcttccaca gaagcttaca gataggcctt ggcctcc                             37

<210> SEQ ID NO 59
<211> LENGTH: 37
<212> TYPE: DNA
<213> ORGANISM: Artificial sequence
<220> FEATURE:
<223> OTHER INFORMATION: Primer No. 59

<400> SEQUENCE: 59
cagcccgcat caacaatggc tcgcctcttc gtcaccg                             37

<210> SEQ ID NO 60
<211> LENGTH: 37
<212> TYPE: DNA
<213> ORGANISM: Artificial sequence
<220> FEATURE:
<223> OTHER INFORMATION: Primer No. 60

<400> SEQUENCE: 60
ctcttccaca gaagcttagt acttataccc cttcacg                             37

<210> SEQ ID NO 61
<211> LENGTH: 36
<212> TYPE: DNA
<213> ORGANISM: Artificial sequence
<220> FEATURE:
<223> OTHER INFORMATION: Primer No. 61

<400> SEQUENCE: 61
cagcccgcat caacaatgag ccgccaaaag actctc                              36

<210> SEQ ID NO 62
<211> LENGTH: 36
<212> TYPE: DNA
<213> ORGANISM: Artificial sequence
<220> FEATURE:
<223> OTHER INFORMATION: Primer No. 62

<400> SEQUENCE: 62
ctcttccaca gaagcctact tcttattgat gacgtc						36

<210> SEQ ID NO 63
<211> LENGTH: 39
<212> TYPE: DNA
<213> ORGANISM: Artificial sequence
<220> FEATURE:
<223> OTHER INFORMATION: Primer No. 63

<400> SEQUENCE: 63
gaccaccccc taaaaatggt tgctaaagct gcttttgcc					39

<210> SEQ ID NO 64
<211> LENGTH: 40
<212> TYPE: DNA
<213> ORGANISM: Artificial sequence
<220> FEATURE:
<223> OTHER INFORMATION: Primer No. 64

<400> SEQUENCE: 64
tctcttggat ctttcttaca gataggcctt ggcctccttg					40

<210> SEQ ID NO 65
<211> LENGTH: 40
<212> TYPE: DNA
<213> ORGANISM: Artificial sequence
<220> FEATURE:
<223> OTHER INFORMATION: Primer No. 65

<400> SEQUENCE: 65
ccgaacactt caaaaatgag ccgccaaaag actctctttt					40

<210> SEQ ID NO 66
<211> LENGTH: 40
<212> TYPE: DNA
<213> ORGANISM: Artificial sequence
<220> FEATURE:
<223> OTHER INFORMATION: Primer No. 66

<400> SEQUENCE: 66
aaactctctt ccaaactact tcttattgat gacgtcgatg					40

<210> SEQ ID NO 67
<211> LENGTH: 38
<212> TYPE: DNA
<213> ORGANISM: Artificial sequence
<220> FEATURE:
<223> OTHER INFORMATION: Primer No. 67

<400> SEQUENCE: 67
gaccaccccc taaaaatgac gccgcaagcc gacatcac					38

<210> SEQ ID NO 68
<211> LENGTH: 35
<212> TYPE: DNA
<213> ORGANISM: Artificial sequence
<220> FEATURE:
<223> OTHER INFORMATION: Primer No. 68

<400> SEQUENCE: 68
tctcttggat ctttcttact caatggacaa cgggc						35

<210> SEQ ID NO 69

-continued

<210> SEQ ID NO 69
<211> LENGTH: 38
<212> TYPE: DNA
<213> ORGANISM: Artificial sequence
<220> FEATURE:
<223> OTHER INFORMATION: Primer No. 69

<400> SEQUENCE: 69
cagcccgcat caacaatgcc cgcctacacg acgacatc        38

<210> SEQ ID NO 70
<211> LENGTH: 37
<212> TYPE: DNA
<213> ORGANISM: Artificial sequence
<220> FEATURE:
<223> OTHER INFORMATION: Primer No. 70

<400> SEQUENCE: 70
ctcttccaca gaagcctact tgtagagatt ggcgatg        37

<210> SEQ ID NO 71
<211> LENGTH: 37
<212> TYPE: DNA
<213> ORGANISM: Artificial sequence
<220> FEATURE:
<223> OTHER INFORMATION: Primer No. 71

<400> SEQUENCE: 71
cagcccgcat caacaatgag aataccttcc cttatcc        37

<210> SEQ ID NO 72
<211> LENGTH: 35
<212> TYPE: DNA
<213> ORGANISM: Artificial sequence
<220> FEATURE:
<223> OTHER INFORMATION: Primer No. 72

<400> SEQUENCE: 72
ctcttccaca gaagcctacg tcgtgcccat gttca        35

<210> SEQ ID NO 73
<211> LENGTH: 453
<212> TYPE: PRT
<213> ORGANISM: Nannochloropsis oceanica

<400> SEQUENCE: 73

Met Lys Phe Thr Gly Leu Val Thr Leu Leu Ser Val Ala Ser Ala Gln
1               5                   10                  15

Ala Phe Val Ala Pro Ala Met Phe Lys Ala Ala Ser Ala Gly Ser Leu
            20                  25                  30

Thr Thr Ala Thr Ser Ala Val Thr Ala Ala Pro Val Cys Pro Ser Asn
        35                  40                  45

Arg Gln Gly Val Val Thr Met Ala Lys Lys Ser Val Ser Ser Leu Ser
    50                  55                  60

Asp Ala Glu Leu Lys Gly Lys Arg Val Phe Val Arg Cys Asp Leu Asn
65                  70                  75                  80

Val Pro Leu Asp Gly Lys Lys Ile Thr Asp Thr Arg Ile Arg Ala
                85                  90                  95

Ser Val Pro Thr Ile Glu Tyr Leu Ala Ser Lys Gly Ala Lys Val Leu
                100                 105                 110

Leu Thr Ser His Leu Gly Arg Pro Lys Gly Lys Glu Asp Lys Tyr Ser
            115                 120                 125

Leu Ala Pro Val Ala Asp Arg Leu Thr Glu Leu Leu Gly Lys Lys Val

```
                        130             135             140
Thr Phe Val Pro Asp Cys Ile Gly Glu Thr Val Thr Ser Ala Val Ala
145                 150                 155                 160

Gly Leu Ala Glu Gly Asp Val Ala Leu Leu Glu Asn Val Arg Phe Tyr
                165                 170                 175

Pro Glu Glu Lys Asn Val Pro Ala Phe Ala Glu Lys Leu Ala Ala
            180                 185                 190

Asn Ala Asp Leu Tyr Val Asn Asp Ala Phe Gly Thr Ala His Arg Ala
                195                 200                 205

His Gly Ser Thr Glu Gly Val Ser Lys Phe Leu Lys Pro Ala Val Ala
            210                 215                 220

Gly Phe Leu Leu Gln Lys Glu Leu Asp Tyr Leu Asp Gly Ala Val Ser
225                 230                 235                 240

Gln Pro Lys Arg Pro Phe Ala Ala Ile Val Gly Gly Ser Lys Val Ser
                245                 250                 255

Thr Lys Ile Thr Val Ile Glu Thr Leu Ile Asn Lys Val Asp Lys Ile
                260                 265                 270

Val Ile Gly Gly Gly Met Val Phe Thr Phe Leu Lys Ala Arg Gly His
                275                 280                 285

Asn Val Gly Gly Ser Leu Val Glu Glu Asp Lys Leu Asp Leu Ala Arg
290                 295                 300

Glu Leu Glu Ala Leu Ala Ala Lys Lys Gly Val Lys Phe Ile Leu Pro
305                 310                 315                 320

Thr Asp Val Val Ile Ala Asp Lys Phe Ala Pro Asp Ala Asn Ser Lys
                325                 330                 335

Val Val Ala Ala Thr Ala Ile Pro Glu Gly Trp Met Gly Leu Asp Asn
                340                 345                 350

Gly Pro Glu Ser Thr Lys Met Ile Gln Ala Glu Leu Ala Asp Cys Lys
                355                 360                 365

Thr Ile Ile Trp Asn Gly Pro Met Gly Val Phe Glu Phe Asp Lys Phe
            370                 375                 380

Ala Ala Gly Thr Ser Ala Ile Ala Gln Thr Met Ala Glu Leu Thr Ala
385                 390                 395                 400

Lys Gly Ala Thr Thr Ile Val Gly Gly Gly Asp Ser Val Ala Ala Val
                405                 410                 415

Glu Lys Ala Gly Leu Ala Asp Lys Leu Ser His Val Ser Thr Gly Gly
            420                 425                 430

Gly Ala Ser Leu Glu Leu Leu Glu Gly Lys Val Leu Pro Gly Val Ala
                435                 440                 445

Ala Leu Asn Glu Ser
450

<210> SEQ ID NO 74
<211> LENGTH: 1362
<212> TYPE: DNA
<213> ORGANISM: Nannochloropsis oceanica

<400> SEQUENCE: 74
atgaagttca ccggcctcgt cacgctcctg agcgtcgcct ctgcgcaagc ctttgtggcc      60
cccgccatgt tcaaggccgc ctccgcgggc tctctgacca cggccacctc cgccgtgacg     120
gctgccccgg tctgtccttc caaccgacaa ggcgttgtga ccatggctaa gaagagcgtg     180
tcctccctga cgacgcgga gctcaagggc aagcgtgtgt ttgtgcgttg cgacttgaac     240
gtgccccttg acggaaagaa gatcacggac gacacccgta tccgtgcgtc ggtgcccacc     300
```

```
atcgagtacc tggcctccaa gggcgccaag gtcctcctca cctcccactt gggccgaccc    360
aagggcaagg aggacaagta ctccctggcc ccgtggctg atcgcctgac cgagctcttg    420
ggcaagaagg tgactttcgt cccggactgc atcggcgaga ctgtcaccag cgccgtcgct    480
ggccttgcgg aaggagatgt cgctctcctg gagaacgtcc gcttctaccc cgaggaggag    540
aagaatgtgc ctgccttcgc tgagaagctg gctgccaacg ctgacttgta cgtgaacgat    600
gccttcggca cggcccaccg cgctcacggc tccactgagg gtgtctccaa gttcctcaag    660
cccgctgtcg ccggtttcct tctccagaag gagctcgact accttgacgg cgccgtctcc    720
cagcccaagc gccccttcgc cgccatcgtt ggcgggtcta aggtctccac caagatcact    780
gtgattgaga cgctcatcaa caaggtcgac aagatcgtca tcggcggcgg catggtcttt    840
accttcctga aggcccgtgg acacaacgtc ggcggctccc tcgtcgagga ggacaagctc    900
gacttggccc gtgagttgga ggccctcgcc gcgaagaaag gcgtcaaatt cattctgccc    960
acggacgtgg tcatcgccga caaatttgct ccggacgcca acagcaaggt ggtggctgcc   1020
actgccatcc ggaggggtg gatgggcctt gacaacggcc ccgagtcgac caagatgatc   1080
caggcggagc tcgcggactg caagaccatc atctggaacg gtcccatggg cgtgtttgag   1140
ttcgacaaat cgccgcagg caccagcgcg atcgcccaga ctatggcgga gctcactgcc   1200
aagggcgcta ccaccatcgt cggcggcggt gactcggtgg ctgctgtcga aaaggccggc   1260
ctggccgaca agctctccca cgtctccacc ggcggggtg cttccttgga gctgctcgag   1320
ggcaaggtgc tccccggtgt ggcggccctc aacgagtctt aa                     1362
```

<210> SEQ ID NO 75
<211> LENGTH: 403
<212> TYPE: PRT
<213> ORGANISM: Nannochloropsis oceanica

<400> SEQUENCE: 75

```
Met Ser Gly Lys Glu Thr Leu Lys Ser Leu Ala Ser Asn Thr Glu Leu
1               5                   10                  15

Lys Gly Glu Arg Val Phe Val Arg Val Asp Phe Asn Val Pro Leu Asp
            20                  25                  30

Lys Glu Ser Lys Val Thr Asp Asp Thr Arg Ile Arg Ala Ala Leu Pro
        35                  40                  45

Thr Ile Lys Phe Leu Val Glu Lys Ala Arg Val Ile Leu Cys Ser
    50                  55                  60

His Leu Gly Arg Pro Lys Gly Val Thr Glu Ser Leu Arg Leu Gly Pro
65                  70                  75                  80

Val Ala Ala Arg Leu Ser Glu Leu Leu Gly Thr Asp Val Val Tyr Leu
                85                  90                  95

Lys Asp Cys Val Gly Asp Glu Ile Glu Ser Ser Val Ala Ala Leu Thr
            100                 105                 110

Pro Gly Gln Val Ala Leu Leu Glu Asn Val Arg Phe Tyr Pro Glu Glu
        115                 120                 125

Glu Lys Asn Ala Pro Asp Phe Ala Lys Lys Leu Ala Arg Leu Ala Asp
    130                 135                 140

Val Tyr Val Asn Asp Ala Phe Gly Thr Ala His Arg Ala His Ala Ser
145                 150                 155                 160

Thr Glu Gly Val Ala Lys Leu Val Lys Ala Thr Cys Ala Gly Phe Leu
                165                 170                 175

Met Glu Lys Glu Leu Asp Tyr Leu Asp Gly Ala Val Lys Asn Pro Lys
```

|     | 180 |     |     | 185 |     |     | 190 |     |
|---|---|---|---|---|---|---|---|---|

Arg Pro Phe Ala Ala Ile Val Gly Gly Ser Lys Val Ser Thr Lys Ile
            195                 200                 205

Thr Val Glu Ala Leu Ile Asn Lys Val Asp Lys Leu Ile Ile Gly
        210                 215                 220

Gly Gly Met Val Phe Thr Phe Leu Lys Ala Gln Gly His Gly Val Gly
225                 230                 235                 240

Ser Ser Leu Val Glu Glu Asp Phe Leu Glu Leu Ala Lys Lys Leu Glu
                245                 250                 255

Ile Ile Ala Lys Glu Lys Gly Val Lys Leu Val Leu Pro Thr Asp Val
            260                 265                 270

Val Ile Ala Asp Lys Phe Ser Ala Asp Ala Glu Ser Lys Val Val Pro
        275                 280                 285

Ala Thr Glu Ile Pro Asp Gly Trp Met Gly Leu Asp Asn Gly Pro Glu
    290                 295                 300

Thr Thr Lys Met Ile Gln Ala Glu Leu Ala Asp Cys Lys Thr Ile Ile
305                 310                 315                 320

Trp Asn Gly Pro Met Gly Val Phe Glu Phe Asp Lys Phe Ala Thr Gly
                325                 330                 335

Thr Ser Ala Ile Ala Gln Thr Met Ala Glu Leu Thr Ser Lys Gly Ala
            340                 345                 350

Thr Thr Ile Val Gly Gly Asp Ser Val Ala Ala Val Glu Lys Ala
        355                 360                 365

Gly Leu Gly Glu Lys Leu Ser His Val Ser Thr Gly Gly Ala Ser
    370                 375                 380

Leu Glu Met Leu Glu Gly Lys Val Leu Pro Gly Val Ala Ala Ile Gln
385                 390                 395                 400

Asp Ala Lys

<210> SEQ ID NO 76
<211> LENGTH: 1212
<212> TYPE: DNA
<213> ORGANISM: Nannochloropsis oceanica

<400> SEQUENCE: 76

```
atgtctggaa aggagacgct caagagcctg gccagtaata ctgagcttaa gggcgaacga      60
gttttcgtcc gcgttgattt caatgtccct cttgataagg agtccaaggt cacgacgac     120
actcgcatcc gcgccgctct ccccaccatc aagttcctgg tggaaaaaga ggcccgcgtc     180
atcctctgta gtcacctcgg ccgtccaaag ggcgtgactg aatccctgcg cctgggtcct     240
gtcgctgccc gcctctccga gctcttaggc acagacgttg tgtacctcaa agactgtgtg     300
ggcgacgaaa tcgagtcgtc tgtcgctgcc ctcactccgg acaagttgcc ctgttggag     360
aacgtgcgtt tctatccgga ggaggagaag aatgcgccgg actttgctaa gaagctcgcg     420
aggcttgccg atgtgtatgt caatgacgcg ttcgggacgg cgcaccgtgc gcatgcgagt     480
accgaggggg ttgccaagct cgtgaaggcg acgtgtgccg gttttttgat ggaaaggag     540
ttggactatc tggatggggc ggtcaagaac ccgaagagac cttttgcagc aattgtgggg     600
ggatccaagg tctcgaccaa aatcacggtg gtggaggccc tcatcaacaa ggttgacaag     660
ctcatcatcg gcggggcat ggtcttcacc ttcctcaagg cccagggcca cggggtcggt     720
tcatccctcg tggaagagga tttccttgag ctcgcaaaga aattggaaat catcgccaag     780
gagaaaggag tcaagctcgt tcttcccacc gacgtggtga ttgctgataa attttctgcc     840
```

-continued

```
gatgcggaaa gcaaagtggt gcccgcgact gagatccccg acgggtggat gggcctcgac    900
aacggcccgg agacgaccaa gatgatccag gcggagctcg cggactgcaa gaccatcatc    960
tggaatggtc ccatgggcgt gtttgagttc gacaaattcg ccacaggcac cagcgcgatt   1020
gcccagacta tggcggaatt gacgtccaag ggcgctacta ctattgtggg tggaggggat   1080
tcagtggctg ctgtggagaa ggcaggactg ggggaaaagt tgtcgcatgt ctcgacgggg   1140
ggtggggcct cgttggagat gctggaaggg aaggtgttgc cgggtgtggc ggcgatccag   1200
gatgcgaagt ga                                                       1212
```

<210> SEQ ID NO 77
<211> LENGTH: 424
<212> TYPE: PRT
<213> ORGANISM: Nannochloropsis oceanica
<400> SEQUENCE: 77

| Met | Leu | Arg | Leu | Leu | Pro | Asn | Arg | Pro | Leu | Cys | Arg | Gly | Phe | Ala | Val |
|---|---|---|---|---|---|---|---|---|---|---|---|---|---|---|---|
| 1 | | | | 5 | | | | | 10 | | | | | 15 | |

| Ala | Ala | Ala | Gln | Lys | Lys | Thr | Ile | Ala | Asp | Leu | Ser | Lys | Glu | Val |
|---|---|---|---|---|---|---|---|---|---|---|---|---|---|---|
| | | 20 | | | | 25 | | | | | 30 | | | |

| Ser | Leu | Lys | Gly | Lys | Asn | Val | Phe | Val | Arg | Ala | Asp | Leu | Asn | Val | Pro |
|---|---|---|---|---|---|---|---|---|---|---|---|---|---|---|---|
| | 35 | | | | | 40 | | | | | 45 | | | | |

| Val | Lys | Gly | Gly | Ala | Val | Lys | Asp | Lys | Thr | Arg | Ile | Asn | Leu | Ser | Ala |
|---|---|---|---|---|---|---|---|---|---|---|---|---|---|---|---|
| 50 | | | | | 55 | | | | | 60 | | | | | |

| Pro | Thr | Ile | Arg | Tyr | Leu | Leu | Asp | Gln | Gly | Ala | Lys | Val | Val | Val | Ser |
|---|---|---|---|---|---|---|---|---|---|---|---|---|---|---|---|
| 65 | | | | | 70 | | | | | 75 | | | | | 80 |

| Ser | His | Leu | Gly | Arg | Pro | Lys | Gly | Gln | Val | Met | Glu | Asp | Lys | Arg | Leu |
|---|---|---|---|---|---|---|---|---|---|---|---|---|---|---|---|
| | | | | 85 | | | | | 90 | | | | | 95 | |

| Thr | Pro | Val | Ala | Ala | Val | Leu | Glu | Ala | Ala | Ile | Arg | Ala | Pro | Val | Arg |
|---|---|---|---|---|---|---|---|---|---|---|---|---|---|---|---|
| | | | 100 | | | | | 105 | | | | | 110 | | |

| Leu | Ala | Pro | Asp | Ser | Ala | Gly | Pro | Glu | Ala | Ala | Ala | Phe | Val | Lys | Asn |
|---|---|---|---|---|---|---|---|---|---|---|---|---|---|---|---|
| | | 115 | | | | | 120 | | | | | 125 | | | |

| Thr | Ser | Ala | Gly | Glu | Val | Val | Leu | Leu | Glu | Asn | Thr | Arg | Phe | His | Ala |
|---|---|---|---|---|---|---|---|---|---|---|---|---|---|---|---|
| 130 | | | | | 135 | | | | | 140 | | | | | |

| Gly | Glu | Thr | Lys | Asn | Asp | Glu | Ala | Tyr | Ala | Lys | Gln | Leu | His | Glu | Val |
|---|---|---|---|---|---|---|---|---|---|---|---|---|---|---|---|
| 145 | | | | | 150 | | | | | 155 | | | | | 160 |

| Ser | Gly | Ala | Asp | Ile | Tyr | Val | Asn | Asp | Ala | Phe | Gly | Ala | Ala | His | Arg |
|---|---|---|---|---|---|---|---|---|---|---|---|---|---|---|---|
| | | | | 165 | | | | | 170 | | | | | 175 | |

| Ala | His | Ala | Ser | Thr | His | Gly | Ile | Thr | Lys | Phe | Val | Ser | His | Lys | Val |
|---|---|---|---|---|---|---|---|---|---|---|---|---|---|---|---|
| | | | 180 | | | | | 185 | | | | | 190 | | |

| Ala | Gly | Leu | Leu | Leu | Asp | Lys | Glu | Leu | Thr | Ala | Leu | Gly | Thr | Ile | Met |
|---|---|---|---|---|---|---|---|---|---|---|---|---|---|---|---|
| | | 195 | | | | | 200 | | | | | 205 | | | |

| Thr | Ser | Pro | Glu | His | Pro | Val | Val | Ala | Cys | Ile | Gly | Gly | Ser | Lys | Val |
|---|---|---|---|---|---|---|---|---|---|---|---|---|---|---|---|
| 210 | | | | | 215 | | | | | 220 | | | | | |

| Ser | Thr | Lys | Leu | Pro | Val | Leu | Glu | Ser | Leu | Leu | Ala | Lys | Cys | Asp | Thr |
|---|---|---|---|---|---|---|---|---|---|---|---|---|---|---|---|
| 225 | | | | | 230 | | | | | 235 | | | | | 240 |

| Ile | Leu | Ile | Gly | Gly | Gly | Met | Met | Phe | Thr | Phe | Ser | Lys | Ala | Gln | Gly |
|---|---|---|---|---|---|---|---|---|---|---|---|---|---|---|---|
| | | | | 245 | | | | | 250 | | | | | 255 | |

| Tyr | His | Ile | Gly | Arg | Ser | Leu | Val | Glu | Glu | Asp | Leu | Val | Pro | Met | Ala |
|---|---|---|---|---|---|---|---|---|---|---|---|---|---|---|---|
| | | | 260 | | | | | 265 | | | | | 270 | | |

| Lys | Glu | Phe | Leu | Ala | Lys | Ala | Lys | Ala | Lys | Gly | Val | Lys | Val | Val | Leu |
|---|---|---|---|---|---|---|---|---|---|---|---|---|---|---|---|
| | | 275 | | | | | 280 | | | | | 285 | | | |

| Pro | Arg | Asp | Phe | Val | Val | Ala | Pro | Asp | Leu | Glu | Glu | Ala | Ser | Ser | Ser |
|---|---|---|---|---|---|---|---|---|---|---|---|---|---|---|---|
| | 290 | | | | | 295 | | | | | 300 | | | | |

```
Lys Ala Leu His Ala Asp Val Ala Ser Tyr Lys Gly Asp Gly Ile Gly
305                 310                 315                 320

Val Asp Ile Gly Pro Leu Thr Val Gly Asp Phe His Asn Glu Ile Lys
            325                 330                 335

Asp Ala Lys Thr Phe Phe Trp Asn Gly Pro Met Gly Val Ile Glu Val
                340                 345                 350

Pro Arg Tyr Ala Leu Gly Thr Asp Ala Val Thr Arg Met Ala Ala Phe
            355                 360                 365

Leu Ser Gln Lys Gly Gly Leu Ala Val Val Gly Gly Asp Ser Leu
    370                 375                 380

Val Thr Val Gln Lys Leu Gly Leu Phe Asp Lys Ile Thr His Val Ser
385                 390                 395                 400

Thr Gly Gly Gly Ala Met Leu Glu Phe Val Glu Gly Lys Val Leu Pro
                405                 410                 415

Gly Val Glu Val Leu Asp Asn Lys
            420
```

<210> SEQ ID NO 78
<211> LENGTH: 1275
<212> TYPE: DNA
<213> ORGANISM: Nannochloropsis oceanica

<400> SEQUENCE: 78

```
atgctccgtc tcctcccaaa caggcccctg tgccgtggct tgcggtcgc tgccgcccag        60
aagaagaaga ccatcgcaga tctcagcaag gaggtgtcgc ttaaggggaa gaatgtcttt      120
gtccgcgccg atctgaacgt gcctgttaag gcggcgctg tgaaggacaa gacccgcatc       180
aacctctcgg cgcccaccat tcgataccttc tcgaccaag gcgctaaggt ggtggtcagc      240
agtcacttgg gacgaccgaa ggggcaagtg atggaggata gcgtttgac acctgttgct      300
gcggtgctgg aggcggccat aagggcccct gtccgcttgg cgccggactc ggccgggccc     360
gaggcagctg cctttgtcaa gaacacttca gctggagagg tagtgctcct agaaaacact     420
cgtttccacg cggggagac gaagaacgac gaggcatatg cgaagcaatt gcacgaggta      480
tccggcgctg atatttacgt aaatgacgcg tttgggcgg cgcatcgggc gcacgcgtcc      540
acgcatggga tcacgaagtt tgtgtctcac aaggtggcag gattactgct tgacaaggag    600
ttgacggcct tgggcacgat catgacgagc ccagagcacc cggtggtggc gtgcattggg    660
gggtcgaagg tatcgacgaa gctgccggtg ctggagagct tgcttgccaa gtgcgacacg     720
attctgattg gtggggggat gatgtttacg ttttccaaag cccagggata tcacatcgga    780
cggagtttgg tggaggagga tttggtgccg atggcgaaag agtttctggc taaggccaag    840
gcgaagggtg tgaaggtggt gttgccgcgt gattttgtgg tggccccgga cctgaggag    900
gcgagcagta gcaaagcgct gcatgcggat gtggcgagct acaaggggga tgggatagga   960
gtggatatcg gccgttgac ggtgggcgac ttccataatg agatcaagga cgccaagacg     1020
ttcttttgga atgcccgat gggagttatc gaggtgccac gttacgcgct gggcacggat    1080
gccgtgacaa ggatggcggc tttcttgagc caaaaggag gtttggcggt ggtgggagga    1140
ggggactctc tggtgacggt gcagaagttg ggcttgtttg acaagatcac gcatgtttcc    1200
acgggcggcg gggccatgtt ggagttcgtg gagggcaagg tgctgccagg agtggaggtg    1260
ttggacaata agtaa                                                     1275
```

<210> SEQ ID NO 79
<211> LENGTH: 377

<212> TYPE: PRT
<213> ORGANISM: Nannochloropsis oceanica

<400> SEQUENCE: 79

Met Ala Pro Val Gln Ser Thr Leu Ile Gly Ala Leu Ala Leu Ala Gly
1               5                   10                  15

Ser Val Ser Ala Phe Val Thr Pro Ser Phe Lys Leu Asn Ala Val Gln
            20                  25                  30

His Ala Arg Ala Asn Asp Val His Met Ala Val Pro Ile Gly Ile Asn
        35                  40                  45

Gly Phe Gly Arg Ile Gly Arg Leu Val Ala Arg Ile Ala Val Lys Asp
    50                  55                  60

Pro Gln Cys Asn Leu Val Ala Ile Asn Thr Gly Ala Asp Ala Glu Tyr
65                  70                  75                  80

Met Ala Tyr Gln Phe Lys Tyr Asp Ser Val His Gly Arg Phe Asp Gly
                85                  90                  95

Lys Val Asp Val Glu Gly Asp Thr Ile Ile Asp Gly Gln Arg Val
            100                 105                 110

Met Thr Thr His Thr Arg Lys Pro Glu Glu Ile Gly Trp Gly Lys Leu
            115                 120                 125

Gly Ala Thr Tyr Leu Cys Glu Ser Thr Gly Ala Phe Leu Thr Lys Glu
    130                 135                 140

Thr Cys Gln Val His Ile Asp Gly Gly Ala Lys Lys Val Val Met Ser
145                 150                 155                 160

Ala Pro Ala Lys Asp Asp Ser Gln Val Ile Val Met Gly Val Asn Glu
                165                 170                 175

Glu Asp Tyr Val Gly Ala Asn Ile Leu Ser Cys Ala Ser Cys Thr Thr
            180                 185                 190

Asn Gly Leu Ala Pro Ile Val Lys Ile Ile Asn Asp Glu Phe Gly Ile
        195                 200                 205

Glu Glu Ala Leu Met Thr Thr Val His Ala Phe Thr Ala Thr Gln Met
    210                 215                 220

Val Val Asp Gly Ser Ser Lys Lys Asp Trp Arg Gly Gly Arg Ser Ala
225                 230                 235                 240

Ser Val Asn Ile Ile Pro Ser Ser Thr Gly Ala Ala Lys Ala Val Thr
                245                 250                 255

Lys Val Ile Pro Ser Leu Lys Gly Lys Leu Thr Gly Met Ala Phe Arg
            260                 265                 270

Val Pro Val Pro Asp Val Ser Val Val Asp Leu Thr Ala Arg Leu Ser
        275                 280                 285

Lys Pro Thr Thr Tyr Glu Ala Ile Cys Ala Ala Val Lys Lys Ala Ser
    290                 295                 300

Glu Thr Thr His Lys Gly Val Val Gly Tyr Thr Glu Leu Pro Met Val
305                 310                 315                 320

Ser Gln Asp Phe Val Ser Asp Ser Arg Ser Thr Ile Phe Asp Ala Gly
                325                 330                 335

Ala Gly Ile Ala Leu Asn Pro Gln Phe Val Lys Leu Val Ala Trp Tyr
            340                 345                 350

Asp Asn Glu Trp Gly Tyr Ser Cys Arg Val Val Asp Leu Ile Lys Lys
        355                 360                 365

Val Ala Lys His Asp Gly Val Gln Leu
    370                 375

<210> SEQ ID NO 80

<211> LENGTH: 1134
<212> TYPE: DNA
<213> ORGANISM: Nannochloropsis oceanica

<400> SEQUENCE: 80

```
atggctcccg tgcaatccac cctcatcggt gccttggccc tggccggctc cgtctctgcc      60
tttgtgaccc cttcctttaa gctgaacgcc gtccagcacg cgcgtgccaa cgacgtgcac     120
atggccgtgc ccatcgggat caacggcttc ggccgcatcg tcgccttgt tgcccgtatc     180
gccgtcaagg accccagtg caacctcgtc gctatcaaca ccggtgctga tgccgagtac     240
atggcgtacc agttcaaata cgactctgtg cacggccgtt cgacggcaa ggtagacgtg     300
gagggtgaca ccatcatcat cgacggccag cgtgtcatga ccacccacac ccgcaagccc     360
gaggagatcg gctggggcaa gctcggggcg acctacctgt gcgagtccac gggcgctttc     420
ttgaccaagg agacctgcca ggtgcacatt gacggtggcg ccaagaaggt ggtcatgtcc     480
gcccccgcga aggacgactc ccaggtcatc gtcatgggtg tcaacgagga ggactacgtc     540
ggcgccaaca tcctctcttg cgcgtcctgc accaccaacg gcctggcccc catcgtcaag     600
atcatcaacg acgagttcgg cattgaggag gcgctcatga ccacggtgca cgccttcacc     660
gccacccaga tggtggtcga cgggtcctcc aagaaggatt ggcgaggtgg ccgatcggcc     720
tccgtgaaca tcatcccttc ctccaccggt gccgccaagg ctgtaaccaa ggtgatcccc     780
tcccttaagg gcaagctcac cggcatggcc ttccgtgtcc ccgtcccga cgtttcggtc      840
gtggacctga ctgcccgtct ctctaagccc accacctatg aggccatctg cgctgctgtc     900
aagaaggctt ccgagaccac tcacaagggc gtggtcggct acactgagct tcccatggtc     960
agccaggact tgtttctga ctcccgctcc actatcttcg atgccggtgc cggtattgcg    1020
ctcaaccccc agttcgtgaa gctcgtggct tggtacgaca acgagtgggg atactcttgc    1080
cgtgtggttg accttatcaa gaaggtcgcc aagcacgacg tgttcagct ctaa          1134
```

<210> SEQ ID NO 81
<211> LENGTH: 575
<212> TYPE: PRT
<213> ORGANISM: Nannochloropsis oceanica

<400> SEQUENCE: 81

```
Met Arg Val Asn Thr Leu Leu Leu Ser Phe Leu Ser Leu Gly Leu
1               5                   10                  15

Pro Ser Ser Thr Ser Thr Ser Lys Ser Ser Pro Pro Ser Phe Phe
                20                  25                  30

Thr Pro Gly Ser Thr Met Ala Ala Val Pro Ser Lys Asn Gln Ala Glu
            35                  40                  45

Leu Leu Leu Lys Val Gln Glu Ala Ile Lys Ala Ser Leu Pro Asp Lys
    50                  55                  60

Ala Leu Ala Asp Thr Val Lys Ser Glu Val Asn His Ala Met Gly Ala
65                  70                  75                  80

Asp Ser Glu Pro Asp Ser Leu Lys Glu Met His Asp Gly Ile Val Tyr
                85                  90                  95

Lys Phe Leu Val Asn Gly Glu Trp Arg Val Ser Thr Ser Gly Arg Thr
            100                 105                 110

Ile Gln Asn Leu Thr Pro Tyr Asp Glu Thr Val Cys Tyr Glu Val Gln
        115                 120                 125

Ala Cys Thr Arg Glu Glu Ile Asp Glu Ala Tyr Thr Ser Ala His Ala
    130                 135                 140
```

```
Ala Gln Arg Val Trp Ala Lys Thr Pro Leu Trp Lys Arg Ala Glu Leu
145                 150                 155                 160

Leu His Lys Ala Ala Thr Val Leu Arg Gln Tyr Ala Ser Leu Ile Ala
            165                 170                 175

Thr Pro Val Leu Arg Glu Val Gly Lys Asn Arg Lys Ala Ala Arg Asp
            180                 185                 190

Glu Val Val Arg Thr Ala Glu Leu Leu Asp Tyr Ala Glu Glu Gly
            195                 200                 205

Leu Arg Ile Asn Gly Glu Val Leu Ala Ser Asp Ala Trp Val Gly Gln
    210                 215                 220

Lys Arg Asn Lys Leu Ala Ile Val Glu Arg Val Pro Val Gly Val Val
225                 230                 235                 240

Leu Cys Ile Pro Pro Phe Asn Tyr Pro Ile Asn Leu Cys Gly Ser Lys
            245                 250                 255

Ile Gly Pro Ala Leu Ile Ala Gly Asn Ala Val Val Lys Thr Pro
            260                 265                 270

Thr Gln Gly Ala Val Ser Thr Leu His Leu Gly Ala Ala Phe Lys Ile
        275                 280                 285

Ala Gly Ala Pro Pro Gly Leu Val Asn Val Val Thr Gly Lys Gly Ser
    290                 295                 300

Glu Ile Gly Asp Tyr Leu Val Gln His Pro Gly Ala Asn Leu Ile Ser
305                 310                 315                 320

Phe Thr Gly Gly Ser Thr Gly Ile Asp Val Ser Lys Lys Ala Gly Met
                325                 330                 335

Val Pro Leu Gln Met Glu Leu Gly Gly Lys Asp Ala Cys Ile Val Leu
            340                 345                 350

Pro Asp Ala Asp Leu Asp Leu Ala Ser Ser Ala Ile Val Lys Gly Gly
            355                 360                 365

Phe Ser Tyr Ser Gly Gln Arg Cys Thr Ala Val Lys Ile Val Phe Ala
    370                 375                 380

Thr Ala Glu Ile Ala Asp Ala Leu Leu Glu Lys Val Leu Ala Lys Met
385                 390                 395                 400

Ala Lys Leu Thr Val Gly His Pro Glu Asp Asn Val Asp Ile Thr Ala
            405                 410                 415

Val Ile Asn Arg Lys Ser Ala Asp Tyr Ile Glu Ser Leu Val Lys Asp
            420                 425                 430

Ala Glu Lys Lys Gly Ala Val Leu Thr Thr Pro Tyr Thr Arg Val Gly
        435                 440                 445

Asn Leu Ile His Pro Leu Ile Ile Asp His Val Lys Glu Asp Met Lys
    450                 455                 460

Ile His Trp Glu Glu Pro Phe Gly Pro Val Leu Pro Phe Val Arg Val
465                 470                 475                 480

Ala Asp Ala Thr Asp Ala Val Ala Leu Ala Asn Lys Ser Ser Met Gly
            485                 490                 495

Leu Gln Gly Cys Val Phe Thr Gln Asp Ile Asn Arg Ala Ile Leu Val
        500                 505                 510

Ala Asn Glu Leu Ala Ala Gly Thr Val Gln Ile Asn Gly Pro Pro Ala
    515                 520                 525

Arg Gly Pro Asp His Phe Pro Phe Thr Gly Phe Lys Asp Ser Gly Ile
        530                 535                 540

Gly Ala Gln Gly Ile Lys Tyr Ser Ile Glu Ser Met Ser Lys Val Lys
545                 550                 555                 560

Ser Phe Val Ile Asn Leu Pro Glu Ala Ala His Pro Gln Gly His
```

<210> SEQ ID NO 82
<211> LENGTH: 1728
<212> TYPE: DNA
<213> ORGANISM: Nannochloropsis oceanica

<400> SEQUENCE: 82

```
atgcgtgtga acaccctgct tctgctgtct tttctcagcc tcggcttgcc cagcagcact    60
agcacttcca agtcgtcgtc accgccatcc ttctttacgc ccggcagcac catggccgcc   120
gtcccttcga agaatcaggc cgagctcctg ctcaaggtcc aagaagccat caaggccagc   180
ctcccggaca aggccctcgc cgacacggtc aagtccgagg tcaaccacgc catgggcgcc   240
gattccgagc ccgactctct caaggagatg acgacggta tcgtctacaa attcctcgtc    300
aacggcgaat ggcgtgtctc cacctccggc cgcaccatcc aaaaccttac ccctacgat    360
gagactgtct gctatgaagt ccaagcctgc actcgcgagg agatcgacga agcctacact   420
tctgcccacg ctgcgcaacg cgtatgggcc aagaccccc tttggaagcg cgccgagctc    480
ctccacaaag ctgccacggt cctccgtcaa tacgcctccc taatcgccac tcctgtcctc   540
cgagaggtgg gaaagaaccg caaggccgcc cgtgatgagg tggtgcgcac cgcggagctg   600
cttgactatg cggctgagga gggtctgcgt attaatggcg aggtgcttgc gtccgatgcg   660
tgggtggggc aaaaacgaaa caagcttgcc atcgtcgaac gtgtaccgt cggcgtcgtc    720
ctttgcattc ccccttcaa ctaccccatt aatctctgtg gctcgaagat cggccctgcc    780
cttattgccg gtaacgccgt cgtcgtcaag accccacgc aaggcgccgt ctccaccctc    840
cacctcggcg cggccttcaa gatcgcaggt gcccccccg gcttgtcaa tgtggtgacg     900
ggcaagggat cggagattgg ggattacctg gtgcaacatc ccggagccaa cctgatttcc    960
ttcacggggg gttccactgg gattgatgtg tcgaagaagg caggcatggt gccgttgcag  1020
atggaactcg gcggcaagga cgcctgcatc gtcctccctg atgccgacct cgatctggct  1080
tcctctgcca ttgtaaaggg tgggttctcc tattccggac agaggtgcac ggctgtcaaa  1140
attgtcttcg ccaccgctga gattgccgat gcgttgctcg agaaggtcct ggcgaagatg  1200
gccaagctca cggtgggaca cccggaggac aatgtggaca tcacagccgt catcaaccgc  1260
aagtcagccg attacatcga gagcttggtg aaggatgcgg agaagaaggg ggcggtcctc  1320
accaccccctt acacccgcgt gggcaatctg attcaccccc tcatcatcga ccacgtcaag  1380
gaggacatga agatccactg ggaggagccg ttcgggcccg tcctgccctt cgtccgcgtc  1440
gccgatgcca cggacgcagt tgcactggcg aacaagtcca gcatgggctt gcagggctgt  1500
gtctttacgc aagacatcaa ccgtgccatt ctggtggcga atgagttggc ggcaggaacg  1560
gtgcagatta atggccccc ggcccgtgga cccgaccact tcccgtttac gggtttcaag  1620
gattcgggga ttggagcaca ggggattaag tactcgatcg agagtatgag caaggtgaag  1680
agctttgtta tcaacctgcc ggaggcggcg catccccagg gccattaa               1728
```

<210> SEQ ID NO 83
<211> LENGTH: 361
<212> TYPE: PRT
<213> ORGANISM: Nannochloropsis oceanica

<400> SEQUENCE: 83

```
Met Phe Arg Ala Thr Ser Ala Thr Ala Arg Thr Leu Ala Thr Asn Ser
1               5                   10                  15
```

```
Lys Lys Ala Thr Phe Thr Thr Ser Thr Ile Arg Asn Ala Pro Leu Arg
                20                  25                  30

Val Gly Ile Asn Gly Phe Gly Arg Ile Gly Arg Leu Val Leu Arg Ala
            35                  40                  45

Ala Gln Asn His Pro Glu Ile Glu Val Ala Val Asn Asp Pro Phe
        50                  55                  60

Ile Asp Thr Asn Tyr Ile Glu Tyr Met Phe Lys Tyr Asp Thr Val His
 65                  70                  75                  80

Gly Arg Tyr Lys Gly Val Val Ser His Asp Glu His Asn Leu Ile Ile
                85                  90                  95

Asp Gly Lys Lys Val Arg Cys Phe Gln Asp Met Lys Ala Gly Asp Ile
               100                 105                 110

Lys Trp Asp Ser Val Gly Ala Asp Tyr Ile Val Asp Ala Thr Gly Ile
           115                 120                 125

Asn Leu Thr Lys Gly Thr Ala Glu Ala His Phe Lys His Gly Ala Lys
       130                 135                 140

Lys Val Val Met Ser Ala Pro Ser Lys Asp Asp Thr Pro Met Phe Val
145                 150                 155                 160

Cys Gly Val Asn Leu Asp Ala Tyr Lys Gly Glu Lys Ile Val Ser Asn
               165                 170                 175

Ala Ser Cys Thr Thr Asn Cys Leu Ala Pro Leu Ala Lys Val Ile Asn
           180                 185                 190

Asp Thr Phe Gly Leu Asp Glu Gly Leu Met Thr Thr Val His Ala Val
       195                 200                 205

Thr Ala Thr Gln Lys Thr Val Asp Gly Pro Ser Lys Lys Asp Trp Arg
210                 215                 220

Gly Gly Arg Gly Ala Gly Phe Asn Ile Ile Pro Ser Gly Thr Gly Ala
225                 230                 235                 240

Ala Lys Ala Val Gly Lys Val Ile Pro Ala Leu Asn Gly Lys Leu Thr
               245                 250                 255

Gly Met Ala Phe Arg Val Pro Thr Ala Asp Val Ser Val Val Asp Leu
           260                 265                 270

Thr Cys Arg Leu Lys Lys Gly Ala Ser Tyr Asp Glu Ile Lys Ala Val
       275                 280                 285

Leu Lys Ala Ala Ser Glu Gly Pro Leu Ala Gly Ile Leu Gly Tyr Thr
290                 295                 300

Glu Asp Glu Val Val Ser Thr Asp Phe Tyr Gly Asp Thr His Ser Ser
305                 310                 315                 320

Ile Phe Asp Ala Lys Ala Gly Ile Ala Leu Ser Pro Asn Phe Val Lys
               325                 330                 335

Leu Val Ser Trp Tyr Asp Asn Glu Ala Gly Tyr Ser Asn Arg Val Leu
           340                 345                 350

Asp Leu Ile Lys His Ile Ala Lys His
       355                 360
```

<210> SEQ ID NO 84
<211> LENGTH: 1086
<212> TYPE: DNA
<213> ORGANISM: Nannochloropsis oceanica

<400> SEQUENCE: 84

| | | |
|---|---|---|
| atgttccgcg cgacttctgc cactgcccgc accctcgcga ctaactcaaa aaaggccacc | 60 |
| tttaccacct ccaccatccg taatgccccg cttcgcgtgg ggatcaatgg cttcggccgc | 120 |
| atcgggcgcc ttgtgcttcg cgctgcccag aaccacccgg agatcgaggt cgtggccgtc | 180 |

```
aacgacccgt tcattgacac caattacatc gagtacatgt tcaagtatga cactgtccat    240
ggtcgctaca agggcgtcgt ctcccacgac gaacataatc tcatcattga cgggaagaag    300
gtgcgatgtt tccaggacat gaaggctggg gatatcaagt gggactccgt cggcgccgac    360
tatatcgtgg atgccactgg catcaacctg accaagggca cggccgaggc gcactttaag    420
cacggggcca agaaggtggt catgtccgcc ccttccaagg acgacacccc catgtttgtc    480
tgcggtgtga acctggacgc atacaagggc gagaagatcg tctccaatgc ctcctgtacc    540
actaactgcc tggcccctct ggccaaggtt atcaacgata ccttcggcct cgacgaaggc    600
ctcatgacga ccgtgcacgc cgtgactgcc acccaaaaga ctgtggatgg cccgtccaag    660
aaggactggc gtggaggccg aggcgcgggc tttaacatca ttccctcggg cacggggggcg   720 gccaaggcgt tgggaaaagt gatcccggcg ctaaacggga agttgacggg catggccttc    780
cgtgtcccga cagctgacgt gtccgtggtg gacctgacgt gccgcttgaa gaagggtgcg    840
agctacgatg aaatcaaggc ggtgctcaag gcagccagcg aggggcccct ggccggtatc    900
ttggggtaca cggaagatga agtggtctcg actgatttct acggcgacac ccactcttcc    960
atctttgacg ccaaggccgg gattgccctg agcccgaact tcgtcaagct tgtgtcttgg   1020
tacgacaacg aggctggcta ctccaaccgt gtgctcgacc tgatcaagca catcgccaag   1080
cattaa                                                              1086
```

<210> SEQ ID NO 85
<211> LENGTH: 608
<212> TYPE: PRT
<213> ORGANISM: Nannochloropsis oceanica

<400> SEQUENCE: 85

```
Met Ser Phe Ser Thr Ala Ser Arg Arg Asn Leu Ile Gln Leu Val Gln
1               5                   10                  15

Thr Arg Gly Met Ala Ser Ala Gly Arg Lys Phe Phe Val Gly Gly Asn
            20                  25                  30

Trp Lys Cys Asn Gly Ser Val Ala Gln Val Asp Thr Leu Val Asn Met
        35                  40                  45

Leu Asn Glu Ser Lys Leu Ala Lys Thr Thr Glu Val Val Ile Ala Pro
    50                  55                  60

Ser Ser Val His Leu His Lys Ala Leu Ser Lys Val Arg Pro Asp Ile
65                  70                  75                  80

Ala Val Ala Ala Gln Asp Val Trp Thr Gln Gly Gly Ala Phe Thr
                85                  90                  95

Gly Glu Thr Ser Ala Glu Met Leu Lys Asp Leu Gly Ala Lys Trp Thr
            100                 105                 110

Leu Thr Gly His Ser Glu Arg Arg Phe Lys Gly Glu Gly Asp Glu Val
        115                 120                 125

Val Ala Lys Lys Ala Ala Tyr Ala Leu Asn Lys Gly Leu Gly Val Ile
    130                 135                 140

Ala Cys Ile Gly Glu Thr Lys Asp Glu Arg Glu Gly Gly Lys Thr Ile
145                 150                 155                 160

Glu Val Val Glu Arg Gln Val Ala Ala Tyr Ala Ala His Ile Lys Asp
                165                 170                 175

Trp Ser Asn Val Val Leu Ala Tyr Glu Pro Val Trp Ala Ile Gly Thr
            180                 185                 190

Gly Leu Thr Ala Thr Pro Asp Gln Ala Gln Glu Val His Ala Ala Leu
        195                 200                 205
```

Arg Lys Trp Phe Gly Lys Asn Val Ser Ala Ser Val Ala Asp Asn Leu
210                 215                 220

Arg Ile Ile Tyr Gly Gly Ser Val Thr Ala Lys Asn Ala Asn Glu Leu
225                 230                 235                 240

Ala Gly Lys Ser Asp Ile Asp Gly Phe Leu Val Gly Gly Ala Ser Leu
                245                 250                 255

Lys Pro Glu Phe Ile Asn Ile Val Asn Ala Ser Asp Ala Lys Ala Ser
                260                 265                 270

Thr Ala Gly Pro Ile Asn Val Gly Ile Asn Gly Phe Gly Arg Ile Gly
                275                 280                 285

Arg Leu Val Thr Arg Ala Ala Gln Gly Lys Ala Leu Thr Ser Ile Lys
290                 295                 300

Ala Ile Asn Asp Pro Phe Ile Thr Pro Asp Tyr Phe Lys Tyr Met Phe
305                 310                 315                 320

Glu Phe Asp Thr Val His Gly Pro Phe Lys Gly Ser Val Glu His Asp
                325                 330                 335

Asp Lys His Leu Ile Ile Asn Gly His Lys Ile Arg Val Phe His Glu
                340                 345                 350

Thr Asp Pro Ser Lys Ile Ala Trp Gly Asp Ala Gly Val Asp Tyr Val
                355                 360                 365

Val Glu Ser Thr Gly Ala Phe Leu Ser Lys Glu Lys Ala Gly Leu His
370                 375                 380

Leu Lys Gly Gly Ala Lys Lys Val Val Ser Ala Pro Ser Pro Asp
385                 390                 395                 400

Ala Pro Met Phe Val Cys Gly Val Asn Thr Asp Ala Tyr Ala Gly Glu
                405                 410                 415

Ala Ile Phe Ser Asn Ala Ser Cys Thr Thr Asn Cys Leu Ala Pro Leu
                420                 425                 430

Ala Lys Val Val His Asp Thr Phe Gly Ile Glu Glu Gly Leu Met Thr
                435                 440                 445

Thr Val His Ala Val Thr Ala Thr Gln Lys Thr Val Asp Gly Pro Ser
450                 455                 460

Lys Lys Asp Trp Arg Gly Gly Arg Gly Ala Gly Phe Asn Ile Ile Pro
465                 470                 475                 480

Ser Gly Thr Gly Ala Ala Lys Ala Val Gly Lys Val Ile Pro Ser Leu
                485                 490                 495

Asn Gly Lys Leu Thr Gly Met Ala Phe Arg Val Pro Thr Ala Asp Val
                500                 505                 510

Ser Val Val Asp Leu Thr Val Arg Leu Lys Lys Gly Ala Ser Tyr Glu
                515                 520                 525

Glu Ile Lys Gln Val Ile Lys Ala Ala Ser Glu Gly Gln Met Lys Gly
530                 535                 540

Val Leu Gly Tyr Thr Glu Gln Glu Val Val Ser Ser Asp Phe Ile Ser
545                 550                 555                 560

Ser Pro Leu Ser Ser Ile Phe Asp Ala Lys Ala Gly Ile Ala Leu Gly
                565                 570                 575

Pro Asn Phe Val Lys Leu Val Ser Trp Tyr Asp Asn Glu Met Gly Tyr
                580                 585                 590

Ser Thr Arg Val Leu Asp Leu Leu Lys Ile Val His Asp Lys Ser Ala
                595                 600                 605

<210> SEQ ID NO 86
<211> LENGTH: 1827

```
<212> TYPE: DNA
<213> ORGANISM: Nannochloropsis oceanica

<400> SEQUENCE: 86
atgagcttca gcacggccag ccgtaggaac cttatccagc tcgtgcaaac ccgaggcatg     60
gcctctgcag gccgcaagtt ctttgtgggc ggaaactgga agtgcaatgg ctcggtcgcc    120
caggtcgata ccttggtgaa catgctcaac gagtccaagc tcgccaagac caccgaggtc    180
gtcatcgccc cctcctccgt gcacctccac aaggccctgt ccaaggtccg ccccgatatc    240
gctgtggctg cgcaggacgt ctggactcag ggcgggggtg ccttcaccgg cgagacctcc    300
gcggagatgt tgaaggactt gggggccaag tggacgttga ctggccattc ggagcgccgc    360
ttcaagggg agggcgacga ggtggtggcg aagaaggctg cttatgccct caacaagggt    420
ctgggcgtga ttgcctgcat cggcgagact aaagacgagc gggagggtgg aagaccatc    480
gaggtggtgg agcgacaggt ggctgcttat gccgcccaca tcaaagactg gtccaacgtg    540
gtgctggcct acgaaccggt atgggccatc ggcactggcc tgaccgccac ccccgaccag    600
gcgcaagagg tgcacgcggc gctccgaaag tggttcggaa aaacgtgtc ggcctccgtg     660
gccgacaacc tgcgcatcat ctacggtggc tccgtcacgg ccaagaacgc caacgagctg    720
gccggcaaga gcgacatcga cggcttcttg gtcggcggtg cctctctcaa acctgagttt    780
attaacatcg tcaatgcctc cgacgccaag gccagcaccg ctggcccat caacgttggg     840
attaacggtt ttggccgcat cggccgtttg gtgacccgtg ccgcccaggg caaggctctg    900
accagcatta aggctatcaa cgatcccttt attacccccg attacttcaa atacatgttt    960
gagtttgaca ctgtccatgg cccccttcaag ggctctgtcg agcacgacga caagcacctg   1020
atcatcaacg gtcacaaaat ccgggtcttc cacgagacgg acccgtccaa gatcgcctgg   1080
ggagatgccg gggtggacta cgtggtggag tctacgggag ccttcctgtc caaggagaag   1140
gccggcctgc acttgaaagg tggcgcgaaa aaggtcgtcg tctcggcgcc ttctcccgat   1200
gcgcctatgt ttgtgtgtgg ggtcaacacg gacgcctatg ctggggaggc catcttctcc   1260
aatgcctcgt gcaccaccaa ctgcttggca cccctggcca aggtggtgca cgacaccttt   1320
gggattgagg agggcctcat gacaacggtc catgccgtaa cggccaccca gaaaacggtc   1380
gacggcccat ccaagaagga ctggcgtgga ggccgaggcg cgggtttcaa tatcatcccg   1440
tcgggcacgg gggcggccaa ggccgtgggg aaggtgattc cgtccttgaa tggcaaattg   1500
acgggcatgg cgttcagggt gcccacggcg gatgtgtcgg tggtggacct gacggtgcgc   1560
ctgaagaagg gagcaagcta cgaagagatc aagcaggtga tcaaggcagc gagcgagggc   1620
cagatgaagg gcgtgttggg gtacacggag caggaggtgg tgtcctccga ctttatctcc   1680
tccccctct cctccatctt tgacgccaag gccggcattg ccctgggacc aaacttcgtt   1740
aagctcgtgt cgtggtacga caacgagatg ggctactcca cgcgtgtgct ggacttgctg   1800
aaaatcgtgc atgacaagtc agcctaa                                       1827

<210> SEQ ID NO 87
<211> LENGTH: 342
<212> TYPE: PRT
<213> ORGANISM: Nannochloropsis oceanica

<400> SEQUENCE: 87

Met Ala Asp Thr Arg Val Arg Ile Gly Ile Asn Gly Phe Gly Arg Ile
1               5                   10                  15

Gly Arg Leu Val Cys Arg Ala Ala Val Gln Asn Pro Lys Thr Val Val
```

```
                  20                  25                  30
Thr Ala Ile Asn Asp Pro Phe Met Asp Val Glu Tyr Met Val Tyr Gln
             35                  40                  45
Phe Lys Tyr Asp Ser Val His Gly Arg Phe Asn Gly Thr Val Glu Ala
         50                  55                  60
Lys Asp Gly Asn Leu Val Ile Asn Gly Glu Val Ile Lys Val Tyr Lys
 65                  70                  75                  80
Ala Lys Asp Pro Ala Glu Ile Gly Trp Gly Glu Ala Gly Ala Asp Tyr
                 85                  90                  95
Val Cys Glu Ser Thr Gly Val Phe Thr Ser Thr Glu Lys Gly Gly Ser
            100                 105                 110
His Leu Lys Gly Gly Ala Lys Lys Val Ile Ile Ser Ala Pro Pro Lys
        115                 120                 125
Asp Ser Thr Pro Met Phe Val Met Gly Val Asn His Thr Asp Tyr Lys
    130                 135                 140
Ala Gly Thr Asp Val Val Ser Asn Ala Ser Cys Thr Thr Asn Cys Leu
145                 150                 155                 160
Ala Pro Val Ala Lys Val Leu Asn Asp Asn Phe Gly Ile Val Glu Gly
                165                 170                 175
Leu Met Thr Thr Val His Ala Met Thr Ala Asn Gln Leu Thr Val Asp
            180                 185                 190
Gly Pro Ser Lys Gly Lys Asp Trp Arg Ala Gly Arg Cys Ala Gly
        195                 200                 205
Tyr Asn Ile Ile Pro Ala Ser Thr Gly Ala Ala Lys Ala Val Gly Lys
    210                 215                 220
Val Ile Pro Glu Leu Asn Gly Lys Leu Thr Gly Met Ala Phe Arg Val
225                 230                 235                 240
Pro Thr Ala Asp Val Ser Val Val Asp Leu Thr Val Lys Leu Ala Lys
                245                 250                 255
Glu Thr Ser Leu Asp Glu Ile Lys Lys Leu Ile Lys Ala Ala Ser Glu
            260                 265                 270
Gly Ser Met Lys Gly Val Leu Gly Tyr Thr Glu Glu Asp Val Val Ser
        275                 280                 285
Cys Asp Phe Ile Thr Asp Ser Arg Ser Ser Ile Phe Asp Ala Gly Ala
    290                 295                 300
Cys Ile Gly Leu Ser Pro Thr Phe Phe Lys Leu Val Ser Trp Tyr Asp
305                 310                 315                 320
Asn Glu Trp Gly Tyr Ser Asn Arg Leu Val Asp Leu Ile Val His Met
                325                 330                 335
Ser Thr Val Asp Asn Lys
            340
```

<210> SEQ ID NO 88
<211> LENGTH: 1029
<212> TYPE: DNA
<213> ORGANISM: Nannochloropsis oceanica

<400> SEQUENCE: 88

| | | | | | |
|---|---|---|---|---|---|
| atggcagaca | cccgtgtccg | aattggaatc | aacggcttcg | gtcgcatcgg | ccgccttgtc | 60 |
| tgccgtgccg | ccgtgcaaaa | ccccaagacc | gtcgtcacag | ctatcaatga | cccgttcatg | 120 |
| gacgttgagt | acatggtgta | ccagtttaag | tacgactctg | tccacggccg | cttcaatggg | 180 |
| acggtagagg | ccaaggacgg | taacctcgtg | ataaatggtg | aagtgatcaa | ggtgtacaag | 240 |
| gccaaggacc | ccgcagagat | cggtgggggg | gaggcaggtg | ctgactatgt | gtgcgagtcc | 300 |

```
acgggcgtct tcacctccac tgagaagggc gggagccact tgaagggagg cgccaagaag    360
gtgatcatct cggccccgcc gaaggatagc acgcccatgt tcgtcatggg agtcaaccac    420
acagactata aggccggcac ggacgtggtc tccaatgcgt cgtgcaccac caattgcctg    480
gcccctgtgg ccaaggtcct gaacgataat ttcgggattg tggagggggct catgacgacg    540 gtgcatgcca tgactgccaa ccagctgacg gtcgatggcc cgagcaaggg aggcaaggac    600
tggcgggcgg ggcgttgcgc cggctacaac atcatccccg cctccactgg tgcagccaag    660
gccgtaggga aggtcatccc ggagctgaac gggaagttga ctggcatggc ttttcgtgtc    720
cctaccgccg atgtctctgt ggtggacctg acggtgaagc tcgcgaagga gacgagcttg    780
gacgagatca aaaagctgat caaggcggcg agtgaagggt ccatgaaagg cgtgttggga    840
tacacggagg aggatgtggt gagctgtgac ttcatcacgg actcccggtc gtccattttc    900
gatgcggggg cttgcatcgg cctgagcccg acgtttttca agctggtgtc gtggtatgac    960
aatgagtggg gctactccaa caggctggtg gacctgatcg tgcacatgtc gaccgtcgat   1020
aacaagtaa                                                         1029
```

<210> SEQ ID NO 89
<211> LENGTH: 272
<212> TYPE: PRT
<213> ORGANISM: Nannochloropsis oceanica

<400> SEQUENCE: 89

Met Ser Ser Ser Gln Gly Trp Ala Gln Tyr Leu Ala Arg Gly Val Pro
1               5                   10                  15

Pro Gln Lys Arg Tyr Leu Ile Gly Gly Asn Trp Lys Ala Asn Gly Thr
            20                  25                  30

Leu Ala Gln Ala Ala Gly Ile Val Lys Thr Leu Asn Gly Gly Pro
        35                  40                  45

Phe Pro Leu Glu Ala Glu Val Val Ile Ala Pro Ala His Leu Leu
    50                  55                  60

Gly Phe Val Lys Asp Asn Val Arg Pro Asp Val Ala Val Ser Ala Gln
65                  70                  75                  80

Asn Ser Ala Leu Thr Thr Lys Ala Gly Ala Phe Thr Gly Glu Leu Pro
                85                  90                  95

Ala Ala Leu Leu Lys Asp Phe Gly Leu Asn Trp Ala Ile Ile Gly His
            100                 105                 110

Ser Glu Arg Arg Glu Gly Phe Gly Gly Pro Gly Glu Thr Asp Glu Val
        115                 120                 125

Val Ala Thr Lys Thr Lys Val Ala Val Asp Ala Gly Leu His Val Met
    130                 135                 140

Ala Cys Val Gly Glu Lys Leu Glu Gln Arg Glu Ala Gly Gln Thr Thr
145                 150                 155                 160

Glu Val Val Leu Lys Gln Leu Ser Ala Ile Ala Ser Lys Leu Thr Lys
                165                 170                 175

Ser Asp Trp Ser Lys Val Val Ala Tyr Glu Pro Val Trp Ala Ile
            180                 185                 190

Gly Thr Gly Lys Val Ala Thr Pro Glu Gln Ala Gln Asp Val His Ala
        195                 200                 205

Ser Ile Arg Ala Phe Leu Thr Glu Lys Ile Gly Ala Ser Ala Ala Ser
    210                 215                 220

Leu Val Arg Ile Ile Tyr Gly Gly Ser Val Lys Gly Ser Ser Ala Pro
225                 230                 235                 240

Gly Leu Ile Leu Lys Pro Asp Ile Asp Gly Phe Leu Val Gly Gly Ala
                245                 250                 255

Ser Leu Thr Ser Asp Phe Ile Thr Ile Ile Gln Ala Ala Lys Ser Ser
            260                 265                 270

<210> SEQ ID NO 90
<211> LENGTH: 819
<212> TYPE: DNA
<213> ORGANISM: Nannochloropsis oceanica

<400> SEQUENCE: 90

```
atgtcctcat cgcaaggatg ggcgcagtac ctggctcgtg gcgtgccccc ccagaagcgg    60
tacctgatcg gcggcaactg gaaggctaat gggaccctgg cccaagccgc tggcattgtg   120
aagaccctga atggcggcgg gccttttcca ttggaagccg aggtggtgat agcgcccccc   180
gcgcacctgt tgggattcgt caaggacaac gtacgccccg atgtggctgt tcggctcag   240
aactcggcct tgaccactaa agccggggct tttacgggcg agctgcccgc ggcgctcttg   300
aaggacttcg ggttgaactg gccattatc ggacactcag agcgtaggga gggttttggt   360
gggccggggg agacggacga agtggtggcg accaagacca aggtgccgt ggacgcgggt   420
ttacacgtca tggcatgtgt gggggagaaa ttggagcagc gggaggcagg gcaaacgacc   480
gaggtagtgt tgaagcagct gccgcgatt gcctccaagt tgaccaagtc ggactggtcc   540
aaggtggtgg tggcgtacga gccggtgtgg gccattggca cggcaaggt ggcaacaccg   600
gaacaggccc aggatgtgca tgcgtccatt cgcgcgttct tgaccgagaa gattggggcg   660
agcgcggcgt cgttagttcg gattatttat gggggtccg tgaagggctc gtcagccccg   720
ggactgattt tgaagccgga catcgacggg tttctggtgg gggggcgtc gttgacgagt   780
gactttatca cgattatcca ggcagccaaa agctcataa                         819
```

<210> SEQ ID NO 91
<211> LENGTH: 298
<212> TYPE: PRT
<213> ORGANISM: Nannochloropsis oceanica

<400> SEQUENCE: 91

Met Met Arg Thr Phe Cys Leu Leu Ala Val Ala Met Leu Ala Ala Pro
1               5                   10                  15

Ala Ser Ala Phe Ile Pro Gln Thr Ser Phe Arg Ser Ser Ser Pro Val
            20                  25                  30

Val Ser Arg Ser Ala Ser Arg Arg Thr Ala Pro Ser Met Met Ala Ala
        35                  40                  45

Arg Arg Pro Phe Ile Ala Gly Asn Trp Lys Glu Asn Pro Asp Thr Leu
    50                  55                  60

Glu Ala Ala Leu Asp Leu Ala Lys Ala Val Ala Ala Ser Thr Ser
65              70                  75                  80

Ala Ser Asn Val Asp Val Ala Val Val Pro Phe Pro Phe Leu Val
                85                  90                  95

Pro Val Lys Asp Ala Leu Lys Gly Ser Asn Val Phe Leu Gly Ala Gln
            100                 105                 110

Asp Leu Tyr Thr Glu Asp Lys Gly Ala Tyr Thr Gly Ala Thr Ser Leu
        115                 120                 125

Pro Met Ile Lys Ser Val Gly Ala Gln Trp Val Leu Cys Gly His Ser
    130                 135                 140

Glu Arg Arg Ala Leu Phe Gly Asp Thr Asp Glu Thr Val Asn Ala Lys

```
            145                 150                 155                 160
Leu His Lys Val Leu Gly Ala Gly Leu Lys Ala Ile Leu Cys Ile Gly
                165                 170                 175

Glu Thr Lys Asp Glu Tyr Glu Leu Gly Val Asn Lys Leu Ile Cys Gly
            180                 185                 190

Leu Gln Leu Ala Lys Gly Leu Lys Gly Val Thr Lys Glu Gln Met Asp
        195                 200                 205

Asn Val Ala Ile Ala Tyr Glu Pro Val Trp Ala Ile Gly Thr Gly Leu
    210                 215                 220

Thr Ala Thr Pro Glu Ile Ala Gln Asp Val His Ala Asn Ile Arg Lys
225                 230                 235                 240

Ile Leu Ser Glu Ala Tyr Gly Lys Asp Val Ser Asp Lys Val Val Ile
                245                 250                 255

Gln Tyr Gly Gly Ser Val Thr Pro Glu Thr Val Asp Glu Leu Met Ala
            260                 265                 270

Met Pro Asp Ile Asp Gly Ala Leu Val Gly Gly Ala Ser Leu Val Gly
        275                 280                 285

Glu Lys Phe Ala Arg Ile Ile Asn His Lys
    290                 295
```

<210> SEQ ID NO 92
<211> LENGTH: 897
<212> TYPE: DNA
<213> ORGANISM: Nannochloropsis oceanica

<400> SEQUENCE: 92

```
atgatgagga ctttctgcct tcttgcggtg gccatgctgg ccgcgcccgc atccgccttc     60
atccctcaga cctccttccg ctccagcagc cccgtcgtca gcagatccgc gagtcgtcgt    120
actgcccccc tccatgatgg ccgcacgccg tccgttcatc gcaggcaactg gaaggagaac   180
cccgataccc tcgaggcagc cctggacctg gccaaggcgg tcgcagctgc ctcaactagc    240
gcctccaacg tggacgttgc cgtcgtcgtg ccctttccct tcttgttcc  tgtcaaggat    300
gccctcaaag gaagcaacgt tttcctcggc gcgcaagact tgtatacgga ggataaaggt    360
gcctacacgg gcgcgaccct ctcttccgatg atcaagtcag tgggggcgca gtgggtgctg    420
tgtggccact cggagcgacg ggccttgttc ggagataccg acgagacggt gaatgccaag    480
ctgcacaaag tgttgggcgc ggggttaaag gctatcctct gcattggcga gaccaaggac    540
gagtacgagc tgggcgtgaa caagctcatc tgcggcctgc aactcgccaa gggccttaag    600
ggcgtcacca aggaacaaat ggacaacgtg gccattgcct acgagccggt atgggccatc    660
ggcacgggcc taaccgccac ccccgagatc gcccaagacg tgcatgcgaa catccggaag    720
atcctgtccg aggcctacgg gaaggacgtg agcgacaagg tggtgatcca gtacggaggg    780
agcgtgacgc ccgagacggt ggacgagttg atggccatgc ccgacatcga cggcgccttg    840
gtgggcggcg cgtccttggt aggagagaaa tttgcgcgaa taatcaacca caagtga       897
```

<210> SEQ ID NO 93
<211> LENGTH: 358
<212> TYPE: PRT
<213> ORGANISM: Nannochloropsis oceanica

<400> SEQUENCE: 93

```
Met Thr Thr Pro Tyr Ala Ala Glu Leu Ile Ala Thr Ala His Ala Ile
1               5                   10                  15

Val Ala Thr Gly Lys Gly Ile Leu Ala Ala Asp Glu Ser Thr Gly Thr
```

20                  25                  30
Ile Gly Lys Arg Phe Ala Pro Ile Asn Val Glu Asn Ile Glu Glu Asn
            35                  40                  45

Arg Arg Lys Tyr Arg Gln Leu Leu Phe Thr Thr Lys Gly Leu Asn Glu
    50                  55                  60

Tyr Ile Ser Gly Val Ile Leu Phe Glu Glu Thr Leu Tyr Gln Lys Gly
65                  70                  75                  80

Asp Asp Gly Thr Ser Phe Val Asp Met Leu Asn Ala Gln Asn Ile Ile
                85                  90                  95

Pro Gly Ile Lys Val Asp Lys Gly Val Val Ala Leu Pro Gly Thr Asp
            100                 105                 110

Gly Glu Thr Val Thr Gln Gly Ile Asp Asp Leu Ala Lys Arg Ala Ala
        115                 120                 125

Glu Tyr Tyr Lys Ala Gly Ala Arg Phe Ala Lys Trp Arg Gly Val Leu
    130                 135                 140

Asn Ile Asn Asp Ser Thr Gly Ala Thr Pro Ser Gln Leu Ala Ile Asp
145                 150                 155                 160

Gln Asn Ala Gln Ala Leu Ala Arg Tyr Ala Gln Leu Cys Gln Gln Ser
                165                 170                 175

Gly Leu Val Pro Ile Val Glu Pro Glu Val Leu Met Asp Gly Thr His
            180                 185                 190

Ser Ile Glu His Ala Ala Ala Ile Thr Glu Lys Val Leu Ala Ala Thr
        195                 200                 205

Tyr Lys Ala Leu Ser Asp His His Val Leu Leu Glu Gly Thr Leu Leu
    210                 215                 220

Lys Pro Asn Met Val Arg Ser Gly Glu Ala Ala Val Gln Ala Ser
225                 230                 235                 240

Ala Glu Glu Ile Gly Ile Ala Thr Val Arg Val Leu Gln His Thr Val
                245                 250                 255

Pro Val Ala Val Pro Gly Ile Thr Phe Leu Ser Gly Gly Leu Ser Glu
            260                 265                 270

Glu Asn Ala Ser Leu Ala Leu Asp Ala Leu Asn Lys Ala Pro Gly Lys
        275                 280                 285

Lys Pro Trp Ala Leu Thr Phe Ser Tyr Gly Arg Ala Leu Gln Thr Ser
    290                 295                 300

Cys Leu Arg Ala Trp Gly Gly His Asp Ala Asn Ile Pro Ala Ala Lys
305                 310                 315                 320

Glu Thr Leu Leu Val Arg Ala Lys Ala Asn Ser Glu Ala Ser Lys Gly
                325                 330                 335

Val Tyr Ser Gly Gly Ala Gly Gly Ala Ala Lys Glu Ser Thr Phe
            340                 345                 350

Val Ala Asn Tyr Ser Tyr
        355

<210> SEQ ID NO 94
<211> LENGTH: 1077
<212> TYPE: DNA
<213> ORGANISM: Nannochloropsis oceanica

<400> SEQUENCE: 94
atgaccactc cttacgccgc tgagctcatt gcgaccgccc atgccatcgt ggcaacgggc    60
aaaggcatcc ttgctgctga cgagtccacg ggcactatcg gcaagcgctt cgcccccatt   120
aatgtggaga catcgagga gaaccgccgc aagtaccgcc agctcctctt cacgaccaag   180

-continued

```
ggcctgaacg agtacatcag cggggtgatt ctattcgagg agaccctcta tcagaaggga    240
gacgatggca ctagcttcgt cgatatgctt aatgcacaga acatcatccc cgggatcaaa    300
gtcgacaagg gtgtagttgc cttgcccggg accgacggtg agaccgtcac ccaaggaata    360
gacgatctgg ccaaacgcgc ggccgagtac tacaaggccg gggcccgctt cgccaagtgg    420
cgtggagtgc tcaacattaa tgacagcacc ggcgcgaccc cctcgcagct ggcgattgac    480
cagaacgcgc aggccctcgc ccggtatgcc cagctctgcc agcagtctgg cttggtccca    540
attgtcgagc ccgaggtgct catggacggg acgcactcca tcgagcacgc cgcagccatc    600
accgagaagg ttctggccgc tacttacaag gcgctgtctg accaccacgt tctcttggaa    660
ggcaccctgc tcaagcccaa catggtgcgc tccggcgagg ctgctgccgt gcaggcctcc    720
gctgaggaga ttggcattgc cacggtgcgc gtgctccagc acacggtccc agtggctgtg    780
cctggcataa ctttcctttc tggagggttg tcggaggaga atgcctccct tgctttggat    840
gccctaaaca aggcgccggg aaagaagcct tgggcgttga ccttctctta tggccgtgct    900
ctgcagacgt cgtgtctcag ggcctgggga gggcatgatg cgaacatccc cgcggcgaaa    960
gagacgctgt tggtccgtgc caaggccaat tcggaggcga gcaagggcgt gtacagcggg   1020
ggggctggag gggccgcggc gaaggagtcg acgtttgtgg ctaactactc ttattaa      1077
```

<210> SEQ ID NO 95
<211> LENGTH: 481
<212> TYPE: PRT
<213> ORGANISM: Nannochloropsis oceanica

<400> SEQUENCE: 95

```
Met Ser Ser Ser Glu Ser Asp Ser Asn Ser Ala Thr Ala Pro Ser
1               5                   10                  15

Pro Pro Val Thr Ala Pro Ala Pro Val Ser Ile Ser Ser His Gly Leu
            20                  25                  30

Glu Ala Tyr His Thr His Leu Val Glu Ala Ala Lys Leu Ala Thr Gln
        35                  40                  45

Leu Thr Gln Glu Gln Lys Asp Ala Leu Glu Thr Ile Ala Asn Gln Met
    50                  55                  60

Ala Arg Pro Gly Arg Gly Leu Leu Ala Ala Asp Glu Ser Val Pro Thr
65                  70                  75                  80

Leu Gly Lys Arg Leu Val Ala Ala Gly Leu Val Asn Asp Glu Thr
                85                  90                  95

Arg Arg Ala Tyr Arg Glu Val Leu Phe Gly His Pro Glu Met Gly Glu
            100                 105                 110

Tyr Leu Ser Gly Ala Ile Leu Phe Ser Glu Thr Leu Gly Gln Lys Ala
        115                 120                 125

Ile Lys Asp Pro Glu Gly Arg Leu Phe Pro Ala Leu Leu Gln Ser Lys
    130                 135                 140

Gly Val Leu Pro Gly Val Lys Val Asp Thr Gly Leu Glu Pro Leu Gly
145                 150                 155                 160

Tyr Ser Pro Arg Glu Thr His Thr Thr Gly Met Asp Asp Leu Met Lys
                165                 170                 175

Arg Cys Gln Gly Phe Tyr Ala Gln Gly Ala Arg Phe Ala Lys Trp Arg
            180                 185                 190

Ala Val Ile Arg Ile Asp Glu Thr Ala Gln Leu Pro Thr Arg Ala Cys
        195                 200                 205

Met Gln Ile Asn Ser Ala Glu Leu Ala Arg Tyr Ala Ala Val Cys Gln
    210                 215                 220
```

```
Ala Cys Gly Leu Val Pro Ile Val Glu Pro Glu Ile Leu Ile Glu Gly
225                 230                 235                 240

Ser His Thr Ala Glu Thr Phe Ala Arg Val Thr Glu Ala Ala Leu Ser
                245                 250                 255

Glu Val Tyr Tyr Thr Met Ala Gln Ala Lys Val Phe Leu Glu Gly Thr
            260                 265                 270

Leu Leu Lys Pro Gln Met Val Met Pro Gly Val Asp Ser Thr Pro Glu
        275                 280                 285

Glu Arg Pro Thr Pro Glu Glu Ala Ala Arg Arg Thr Leu Glu Val Leu
    290                 295                 300

Arg Arg Arg Val Pro Pro Ala Val Pro Gly Ile Met Phe Leu Ser Gly
305                 310                 315                 320

Gly Gln Thr Glu Glu Gln Ala Thr Gln Asn Leu Thr Leu Ile Asn Gln
                325                 330                 335

Leu Ala Lys Arg Ala Pro Ser Ser Phe Arg Pro Ser Leu Thr Thr Cys
            340                 345                 350

Pro Trp Ile Leu Ser Phe Ser Phe Gly Arg Ser Leu Gln Ala Ser Val
        355                 360                 365

Leu Ala Ala Trp Met Gly Lys Glu Glu Asn Tyr Thr Ala Ala Val Ala
    370                 375                 380

Ile Ala Gly Glu Leu Ala Lys Ala Asn Ala Gln Ala Gln Leu Gly Glu
385                 390                 395                 400

Tyr Val Gly Pro His Pro Ser Leu Leu Lys Asp Lys Ser Leu His Glu
                405                 410                 415

Thr Asn Arg Gly Phe Tyr Gly Gln Val Ala Gly Val Ala Gly Ala
            420                 425                 430

Ala Ala Ser Gly Glu Lys Glu Lys Thr Ala Glu Ala Pro Thr Glu Gly
        435                 440                 445

Leu Ala Glu Lys Pro Gly Glu Glu Val Gly Lys Ala Asp Ile Gln
    450                 455                 460

Ala Ala Val Ser Ala Asp Ala Thr Glu Arg Glu Ser Ser Arg Ser Thr
465                 470                 475                 480

Leu

<210> SEQ ID NO 96
<211> LENGTH: 1446
<212> TYPE: DNA
<213> ORGANISM: Nannochloropsis oceanica

<400> SEQUENCE: 96
atgtcctcct cctccgagtc cgattccaat tcggccacag ctccctctcc tcctgtgacg      60
gctcccgctc cggtatccat ctcctcgcat ggccttgagg cctatcacac gcacctcgtg     120
gaggccgcca agctggctac acaattgaca caggagcaaa aggacgccct cgagacaatc     180
gcgaatcaaa tggcccgtcc cgggcggggt ctgctggccg ccgacgaaag cgtgcccact     240
ctgggcaagc gcctagtggc cgccgggttg gtcaatgatg aagagacgag acgggcttac     300
cgtgaggtgt tgtttggtca ccctgaaatg ggggagtacc tgagtggtgc catcctcttc     360
tccgagacac ttgacagaa agcaatcaag gacccagaag gccgtctctt cccgcattg     420 ttgcaaagca agggcgtcct gccgggcgtt aaggttgaca ccggcttgga acccttgggg     480
tactctccgc gggagacgca taccacaggc atggacgacc tgatgaaacg ttgccaaggg     540
ttttatgcgc aaggcgcgcg ctttgcgaaa tggcgggctg tcatccgaat cgatgagacg     600
```

-continued

```
gcacagttgc ccacccgcgc atgcatgcag atcaacagtg cagagctcgc gaggtacgcg    660
gcagtgtgcc aggcgtgtgg gcttgtgccc attgtggagc cggaaatttt gattgaggga    720
agccatactg cggagacgtt tgcgagggtg accgaggcgg cgttgagcga ggtttattac    780
accatggcgc aagcaaaggt gttttggaa ggcacgttgc tcaagcccca aatggtcatg     840
ccaggagtcg atagcacccc agaagagcgg cctaccccag aagaggcagc gcggcgaacg    900
ctggaagtcc tgcggagacg cgtcccacct gctgtccccg cattatgtt tttgtcaggg     960 ggacaaactg aagaacaagc cacgcaaaat ctgaccctaa tcaaccagct cgccaagcga   1020
gctccctcct ccttccgtcc ctccctcacg acttgtccct ggatcttaag cttctccttt   1080
ggtcggtcgt tgcaagcctc agtgctggct gcgtggatgg gaaaggaaga aaactacacc   1140
gcagcagtgg caatagcagg cgagttggca aaggcaaatg ctcaagcaca actaggggag   1200
tatgtcggtc cacatccttc tctgctgaaa gacaagagcc tccatgaaac aaacagggt    1260 ttctacggcc agggcgtcgc aggagtagct ggggcagcag cgtcaggaga aaggagaag    1320 actgctgagg ctcctacaga ggggttggcc gagaagccgg gcgaggaaga ggtagggaag   1380
gcggacatac aagcggcagt ttctgctgat gcgacagaac gagaaagcag caggagcacg   1440
ttgtag                                                              1446
```

<210> SEQ ID NO 97
<211> LENGTH: 359
<212> TYPE: PRT
<213> ORGANISM: Nannochloropsis oceanica

<400> SEQUENCE: 97

```
Met Ala Thr Asn Asp Ile Asp Asn Val Gly Gly Asp Thr Asp Thr Lys
1               5                   10                  15

Thr Leu Gln Arg Phe Ile Ile Ser Ala Thr Lys Asp Ile Gln Leu Thr
            20                  25                  30

Leu Leu Met Thr Ser Ile Gln Met Gly Cys Lys Ala Ile Ala Arg Ala
        35                  40                  45

Val Arg Lys Ala Gly Ile Ala Gly Leu Tyr Gly Leu His Gly Ser Glu
    50                  55                  60

Asn Ile Ser Gly Asp Gln Val Lys Lys Leu Asp Val Leu Ser Asp Glu
65                  70                  75                  80

Ile Phe Val Asn Cys Leu Lys Glu Ser His Cys Cys Ala Val Leu Val
                85                  90                  95

Ser Glu Glu Arg Asp Glu Pro Ile Ile Val Glu Ala Thr Lys Ala Gly
            100                 105                 110

Lys Tyr Cys Val Ala Phe Asp Pro Leu Asp Gly Ser Ser Asn Ile Asp
        115                 120                 125

Cys Asn Val Ser Thr Gly Thr Ile Phe Ala Val Tyr Glu Arg Val Ser
    130                 135                 140

Pro Ser Asp Gln Thr Ala Thr Val Asp Asp Ile Leu Arg Ala Gly Thr
145                 150                 155                 160

Ala Ile Val Ala Ala Gly Tyr Cys Met Tyr Gly Ser Ala Thr Asp Met
                165                 170                 175

Val Leu Thr Phe Gly Leu Gly Val His Arg Phe Thr Leu Asp Pro Thr
            180                 185                 190

Leu Gly Glu Phe Ile His Thr Gln Gly Pro Val Gln Phe Pro Ala Val
        195                 200                 205

Ala Lys Arg Ile Tyr Ser Cys Asn Glu Gly Asn Tyr Ala Leu Trp Asp
    210                 215                 220
```

```
Glu Ala Met Arg Ala Ala Val Asp Gly Phe Lys Gln Gln Asp Pro Pro
225                 230                 235                 240

Tyr Ala Ala Arg Tyr Val Gly Ser Met Val Ser Asp Val His Arg Thr
            245                 250                 255

Leu Leu Tyr Gly Gly Ile Phe Leu Tyr Pro Ala Asp Arg Lys Ser Lys
        260                 265                 270

Ile Gly Lys Leu Arg Val Leu Tyr Glu Gly Phe Pro Met Ala Lys Ile
    275                 280                 285

Val Glu Asp Ala Gly Gly Ile Ala Thr Thr Gly Leu Phe Gln Gly Lys
290                 295                 300

Ile Gln Arg Val Leu Asn Leu His Pro Thr Gly Val His Asp Arg Cys
305                 310                 315                 320

Pro Ile Ile Leu Gly Thr Pro Ser Asp Val Gln Thr Val Leu Asp Ile
                325                 330                 335

Tyr Ala Gln Val Ser Ala Glu Thr Ala Lys Arg Glu Ala Ala Ala Lys
            340                 345                 350

Ser Lys Glu Leu Ala Leu Ser
        355
```

```
<210> SEQ ID NO 98
<211> LENGTH: 1080
<212> TYPE: DNA
<213> ORGANISM: Nannochloropsis oceanica

<400> SEQUENCE: 98
atggcgacca atgatattga caatgtgggc ggggatacag acacgaagac tttgcagcgt      60
ttcatcatct ccgccaccaa ggacatccag ttgactttgc tcatgacctc catccagatg     120
ggctgcaagg ctattgcccg tgccgtgcgc aaggccggca ttgcgggctt gtacgggttg     180
cacggatcgg agaacatctc cggagaccag gtcaaaaagc tagacgtgct ctcagatgag     240
atctttgtca actgtctcaa ggaatcacac tgttgcgcgg tactcgtgtc ggaggagaga     300
gatgaaccta tcatcgtgga ggccacaaag gctggcaagt attgtgtggc attcgatccc     360
ctagacgggt cgtccaatat cgattgcaat gtctccacgg gcactatttt cgccgtctac     420
gagcgcgtct cccccctccga tcagacagcc accgtggacg acatcctgcg ggcgggcacg     480
gcgatcgtag cggcgggata ctgcatgtac gggtcggcga cagacatggt gctgacgttc     540
gggctcggcg tgcaccgttt cacgctggac cccacgctgg gcgaattcat ccacacgcag     600
ggtcctgttc aatttccagc cgtggccaag cgtatctact cctgcaacga gggcaactac     660
gcgctgtggg acgaggccat gcgcgccgcc gtggacggct tcaagcagca ggacccacct     720
tatgcagcgc ggtacgtcgg ctccatggtc tcagacgtac accgcactct gctctacgga     780
ggtatctttc tttacccggc cgaccgcaag agcaagatcg gcaagctgcg cgtgctgtac     840
gagggcttcc ccatggccaa gatcgtggag gacgcgggcg gaatcgccac tacgggcctc     900
tttcagggga aaatacagcg cgtactcaat ctgcacccca ccggcgtgca tgatcgctgc     960
cccatcatcc tcggtacgcc ctccgacgta cagaccgtgc tagacatcta tgcccaggtg    1020
tccgccgaga ccgccaagag ggaggcggcg gccaagtcga agagctggcc cctgtcctag    1080
```

```
<210> SEQ ID NO 99
<211> LENGTH: 453
<212> TYPE: PRT
<213> ORGANISM: Nannochloropsis oceanica

<400> SEQUENCE: 99
```

```
Met Arg Ser Tyr Ala Val Leu Ser Leu Thr Met Met Pro Phe Ala Thr
1               5                   10                  15

Thr Arg Ala Phe Val Leu Pro Arg Tyr Ser Pro Arg Leu Glu Gln Leu
            20                  25                  30

Leu Val Arg Ser Ala Thr Thr Ile Pro Gln Thr Pro Ala Ala Pro Ser
        35                  40                  45

Ser Thr Thr Asn Ser Arg Gly Gln Phe Pro Leu Ile Glu Pro Val Phe
    50                  55                  60

Asp Glu Val Cys Glu Met Ser Gly Val Thr Leu Thr Arg Tyr Met Met
65                  70                  75                  80

Glu Val Ser Arg Ala Asn Pro His Leu Lys Glu Val Glu Ser Leu Met
                85                  90                  95

Asn Ser Ile Gln Thr Ala Cys Lys Thr Ile Ser Ser Leu Val Asn Arg
            100                 105                 110

Ala Cys Ile Thr Lys Met Thr Gly Tyr Gln Asp Asp Gly Cys Ser Ile
        115                 120                 125

Asn Val Gln Gly Glu Gln Gln Lys Lys Leu Asp Val Leu Thr Asn Asp
    130                 135                 140

Val Leu Lys Lys Ala Leu Arg Phe Thr Gly Arg Leu Thr Val Leu Ala
145                 150                 155                 160

Ser Glu Glu Asp Ala Pro Val Thr Met Glu Asp Arg Glu Arg Ile
                165                 170                 175

Tyr Ala Asp Lys Arg Asp Ser Asp Val Val Glu Glu Gly Asn Lys
            180                 185                 190

Tyr Val Ala Cys Phe Asp Pro Leu Asp Gly Ser Ser Asn Val Asp Ala
        195                 200                 205

Ser Ile Pro Val Gly Thr Ile Phe Gly Ile Phe Ala Asn Gly Asp Glu
    210                 215                 220

Lys Glu Cys Leu Leu Asp Asp Glu Asp Leu Glu Gly Ala Met Asp
225                 230                 235                 240

Pro Glu Ser Arg Ala Ala Lys Cys Leu Met Ser Thr Leu Gln Pro Gly
                245                 250                 255

Thr Asn Leu Val Ala Ala Gly Tyr Cys Leu Tyr Ser Ser Thr His
            260                 265                 270

Leu Val Phe Thr Leu Gly Lys Gly Val Asn Gly Phe Thr Tyr Asp Thr
        275                 280                 285

His Ile Gly Glu Phe Val Leu Thr His Pro Asn Ile Arg Ile Pro Glu
    290                 295                 300

Arg Gly Gln Ile Tyr Ser Phe Asn Glu Ala Asn Arg Trp Asp Trp Asp
305                 310                 315                 320

Lys Pro Met Gln Glu Tyr Val Thr Ala Leu Gln Met Gly Gln Gly Glu
                325                 330                 335

Ser Gly Lys Arg Tyr Ser Arg Tyr Ile Gly Ser Met Val Gly Asp
            340                 345                 350

Val His Arg Thr Leu Leu Tyr Gly Ile Phe Gly Tyr Pro Ala Asp
        355                 360                 365

Ala Asn Asn Lys Asp Gly Lys Leu Arg Leu Tyr Glu Ala Ala Pro
    370                 375                 380

Met Ala Phe Leu Val Glu Gln Ala Gly Gly Leu Ala Leu Thr Gly Lys
385                 390                 395                 400

Asn Arg Ile Met Glu Ile Arg Pro Arg Gly Val His Gln Arg Val Pro
                405                 410                 415
```

```
Cys Ile Leu Gly Ser Arg Glu Asp Val Glu Leu Arg Ser Phe Tyr
            420                 425                 430

Asn Ala Ser Lys Asp Pro Asp Leu Ile Arg Arg Cys Ile Glu Arg Leu
            435                 440                 445

Asn Ser Ala Ser Ser
    450

<210> SEQ ID NO 100
<211> LENGTH: 1362
<212> TYPE: DNA
<213> ORGANISM: Nannochloropsis oceanica

<400> SEQUENCE: 100
atgcgaagct acgcggtgct ttccctcacc atgatgccct cgccacgac aagggcattt      60 gttttacctc gatacagccc tcgtctcgag cagctgttgg tccgcagtgc caccaccatt     120
ccgcaaacgc cagccgctcc ttcctcgacg acaaactcac gtggtcaatt cccttttgatc    180 gaaccagttt tgacgaagt ctgcgagatg agcggcgtga ctcttactcg atatatgatg     240
gaagtaagcc gcgccaatcc ccacctcaag gaggttgagt ccttgatgaa cagcatccaa    300
acggcttgta agaccatttc cagcctggtc aaccgcgcat gcatcactaa atgaccggg    360 taccaagacg atggctgctc catcaacgtt caaggcgagc aacagaagaa gctcgatgtc    420
ctgacgaatg atgtgctcaa gaaagcactc cggttcacag gcaggctcac cgtgctcgcc    480
tccgaagagg aagatgcgcc tgtcaccatg gaggaccgcg agcggatcta tgcggacaag    540
cgcgattctg acgtggtggt ggaggagggc aataaatacg tcgcctgctt cgatcccttg    600
gatggcagct cgaacgttga cgcctcaatc ccggtcggga caatctttgg catcttcgcc    660
aatggcgatg agaaggagtg tttgctcgat gatgaagact tggaaggagg tgccatggat    720
cctgaatccc gtgcggccaa gtgtctgatg agcacgcttc agccgggaac gaatctagtg    780
gcggcaggct attgcctata cagttcctcg acccatttgg tgtttaccct cgggaaaggc    840
gtgaatggtt ttacctacga cacgcacatt ggcgagttcg ttttgacgca ccccaatatt    900
cggattcccg aacgagggca gatatacagc tttaatgaag cgaatcgatg ggattgggat    960
aagcccatgc aggaatacgt caccgccctc caaatgggcc agggcgaatc gggcaaacgc   1020
tattcctcgc gttacatcgg ttccatggtc ggggacgtcc accgcaccct cctctacggc   1080
ggcattttgg ataccccgc tgacgcgaac aacaaagacg gaaactccg tctgctctac    1140 gaggcagcac caatggcctt cctggtcgag caagcaggag gtttggcatt gacggggaag   1200
aaccgaatca tggaaatcag gccaagagga gtccatcagc gggtgccgtg tattttgggg   1260
tcaagggagg atgtagagga attgcgaagt ttttacaacg cgagcaagga cccggatctc   1320
atccgtcggt gcattgagcg tttgaattcg gcgtcttcat aa                      1362

<210> SEQ ID NO 101
<211> LENGTH: 405
<212> TYPE: PRT
<213> ORGANISM: Nannochloropsis oceanica

<400> SEQUENCE: 101

Met Leu Ser Glu Lys Asp Gln Ser Gln Leu Ser Thr Ser Ser Pro Pro
1               5                   10                  15

Ser Ile Gln Thr Arg Phe Leu Leu Leu Leu Leu Leu Leu Ala Ala
            20                  25                  30

Ile Ser Thr His Val Asp Ser Phe Trp His Ala Ala Pro Ser Leu
            35                  40                  45
```

```
Ser Gln Arg Val Ile Ala Lys Arg Met Ala Ile Pro Pro Thr Met Ser
 50                  55                  60

Ser Gly Arg Arg Thr Leu Leu Ser Phe Leu Gln Glu Arg Ala Ala
 65                  70                  75                  80

Gln Pro Thr Leu Val Asp Glu Asp Leu His Leu Val Leu Ala Ala Ile
                 85                  90                  95

Ala Ser Ala Val Lys Arg Ile Ser Tyr Met Val Arg Arg Ala Gly Ile
                100                 105                 110

Val Asp Leu Thr Gly Leu Tyr Thr Thr Glu His Gly Gly Glu Val Thr
                115                 120                 125

Leu Asn Lys Gly Gly Glu Lys Gln Lys Lys Leu Asp Val Leu Ala Asn
            130                 135                 140

Asp Ile Leu Lys Glu His Leu Gln Asp Cys Gly Tyr Val Ala Ala Phe
145                 150                 155                 160

Ala Ser Glu Glu Glu Asp Gly Val Ile Pro Leu Arg Thr Gly Gly Lys
                165                 170                 175

Phe Val Val Val Leu Asp Pro Leu Asp Gly Ser Ser Asn Val Asp Ala
                180                 185                 190

Ser Ile Pro Thr Gly Thr Ile Phe Gly Val Tyr Arg Ser Leu Gly Asp
            195                 200                 205

Ser Pro Ala Gln Leu Gln Ala Gly Ala Leu Gln Ala Gly Lys His Gln
210                 215                 220

Val Ala Ala Gly Tyr Cys Leu Phe Ser Ala Ala Thr Leu Leu Val Leu
225                 230                 235                 240

Thr Met Gly Arg Gly Thr Gly Thr His Val Leu Thr Leu Asp His His
                245                 250                 255

Ile Gly Asp Phe Val Leu Thr Thr Arg Arg Leu Arg Leu Pro Leu Arg
            260                 265                 270

Gly Ser Thr Tyr Ser Leu Asn Glu Ala Arg Phe Gly Asp Trp Pro Glu
        275                 280                 285

Gly Leu Gln Arg Tyr Val Thr Asp Met Lys Leu Gly Arg Asn Gln Lys
    290                 295                 300

Gln Thr Pro Tyr Asp Leu Val Tyr Val Cys Ser Leu Val Ala Asp Ala
305                 310                 315                 320

His Trp Val Leu Ile Arg Gly Gly Met Ala Cys Asn Pro Arg Ser His
                325                 330                 335

Leu Arg Leu Cys Phe Glu Gly Asn Pro Met Ser Leu Val Thr Glu Glu
            340                 345                 350

Ala Gly Gly Leu Ala Ser Ser Gly Asp Gly Pro Arg Ile Leu Asn Ile
                355                 360                 365

Val Pro Asp Ala Ile His Gln Arg Thr Pro Val Phe Leu Gly Ser Arg
370                 375                 380

Asp Asp Ile Leu Glu Leu Glu Ser Tyr Gly Asp Val Ala Gln Lys His
385                 390                 395                 400

Asn Pro Gly Tyr Ala
                405
```

<210> SEQ ID NO 102
<211> LENGTH: 1218
<212> TYPE: DNA
<213> ORGANISM: Nannochloropsis oceanica

<400> SEQUENCE: 102
atgctatccg aaaaagacca gtcccagctc tcgacctcct ccccccccctc gatccaaaca    60

```
cgatttctgc tcctcctact cctcctgtta gccgccatat ccacacacgt cgactcttt    120 tggcatgccg cagcgccgtc actatcccaa cgcgtgatag caaaaaggat ggcaattcct    180
ccgacaatgt cctcgggtcg acgaacactt ctctccttcc tgcaagagga gcgtgctgcc    240
caacccacgt tggtagacga ggacctgcac ctggtgctgg ccgcgattgc gtcggcggtg    300
aagcgcatca gctacatggt tcgacgagca ggcattgtgg acctgaccgg cttgtacacc    360
acggagcacg tggagaagt caccttaac aagggcgggg agaagcaaaa gaagcttgac    420
gtcttggcga acgacattct taaggagcat ttgcaagatt gcgggtatgt cgctgccttt    480
gcctcagagg aagaagatgg agtgattcct ttgcggaccg tggcaagtt tgtggtggtg    540 cttgacccttt tagatggctc gtcgaacgta gacgcatcca ttcccaccgg caccatcttt    600
ggagtctatc gcagcctagg cgacagcccc gcccaactcc aagccggggc gcttcaagct    660
ggcaaacatc aagttgctgc tgggtattgc ctctttcgg cggccacgct gctcgtgctg    720
acaatgggta gaggcacagg cacgcatgtt ttgacccttg atcatcacat tggggacttc    780
gtcttgacta cccgccgtct ccgactccct ttgcggggtt ctacttattc attaaatgag    840
gctcgattcg gtgattggcc cgagggctta cagcgttatg tcacggacat gaagctgggc    900
aggaatcaaa aacagacgcc gtatgatttg gtgtatgttt gttccttagt ggcagacgcg    960
cattgggttt tgattcgagg gggcatggca tgtaacccta ggagtcattt gcggttgtgc   1020 tttgaggggta acctatgag cttggtgacc gaagaagcag gcggcctggc aagctcaggt   1080
gacgggcctc gcatcttgaa cattgtacct gatgccattc accacgcac gcctgtcttc   1140 ttgggtagtc gggacgatat cttggaattg gagtcctatg gcgatgttgc tcagaaacat   1200
aacccgggtt acgcataa                                                 1218
```

<210> SEQ ID NO 103
<211> LENGTH: 455
<212> TYPE: PRT
<213> ORGANISM: Nannochloropsis oceanica

<400> SEQUENCE: 103

```
Met Gln Tyr Ala Ala His Pro Leu Phe Asp His Arg Asn His Leu Pro
1               5                   10                  15

Arg Leu Arg Met Thr Thr Thr Thr Ile Met Pro Ala Ala Val Ala Ala
            20                  25                  30

Thr Pro Ala Arg Lys Arg Arg Lys Leu His Gln Asn Pro Leu Ala Ala
        35                  40                  45

Leu Ser Ser Leu His Ala Leu Leu Leu Gly Leu Ala Trp Leu Glu
    50                  55                  60

Cys Arg Ala Phe Val Ile Pro Arg Pro Thr Ser Ser Pro Ser Leu Val
65                  70                  75                  80

Leu Ser Leu Thr Leu Pro Arg Gln His Arg Pro Arg Gln Leu Arg Met
                85                  90                  95

Ile Met Asp Glu Pro Lys Val Gly Glu Pro Ser Val Met Ser Gln
            100                 105                 110

Ala Leu Ser Lys Gln Lys Thr Leu Ser Arg Tyr Val Glu Val Glu Thr
        115                 120                 125

Trp Lys His Arg Glu Leu Thr Asp Leu Gln Pro Val Met Arg Gly Ile
    130                 135                 140

Glu Ser Ala Cys Arg Gly Ile Ala Thr Leu Val Arg Arg Ala Gln Cys
145                 150                 155                 160
```

```
Asp Glu Ile Ala Gly Leu His Gly Asn Asp Gly Asp Met Asn Val Gln
                165                 170                 175
Gly Glu Val Gln Lys Val Met Asp Val Leu Ala Asn Asn Ile Leu Ala
            180                 185                 190
Ala Ser Met Cys Ala Pro Gly Lys Met Asp Tyr Val Ala Ser Glu Glu
        195                 200                 205
Glu Glu Glu Pro Thr Tyr Cys Ser Ala Val Leu Gln Asn Ala Ala Phe
    210                 215                 220
Gln Gly Glu Tyr Ala Gly Val Phe Asp Pro Leu Asp Gly Ser Ser Asn
225                 230                 235                 240
Ile Glu Ala Gly Leu Pro Val Gly Thr Ile Phe Gly Ile Tyr Arg Arg
                245                 250                 255
Pro Gln Leu Asn Leu Ser Pro Glu Arg Glu Arg Asp Pro Leu Glu Ala
            260                 265                 270
Ile Met Gln Pro Gly Ser Lys Leu Leu Ala Ser Gly Tyr Cys Leu Tyr
        275                 280                 285
Gly Gly Gln Thr Ile Leu Val Leu Thr Leu Gly Gln Gly Val His Gly
    290                 295                 300
Phe Thr Leu Asn Lys Pro Gly Gly Asp Phe Ile Leu Thr Gln Pro Asn
305                 310                 315                 320
Met Arg Ile Pro Ala Arg Gly Gln Leu Tyr Ala Ile Asn Glu Gly Ser
                325                 330                 335
Ser His Leu Trp Glu Pro Lys Val Thr Glu Tyr Val Arg Arg Leu Lys
            340                 345                 350
Leu Gly Glu Gly Glu Gly Asn Val Pro His Arg Thr Ala Tyr Val Gly
        355                 360                 365
Ala Met Val Ala Asp Val His Arg Val Leu Val Glu Gly Gly Val Tyr
    370                 375                 380
Ala Tyr Pro Gly Thr Val Asp Ala Pro Asn Gly Lys Ile Arg Leu Leu
385                 390                 395                 400
Tyr Glu Ala Asn Pro Met Ser Met Leu Val Glu Gln Ala Gly Gly Leu
                405                 410                 415
Ser Thr Thr Gly Arg Gln Arg Ile Leu Asp Leu Lys Pro Thr Gly Ile
            420                 425                 430
His Gln Arg Val Pro Ile Phe Ile Gly Ser Lys Glu Asp Ile Lys Asp
        435                 440                 445
Leu Gln Ala Leu Leu Lys Asp
    450                 455

<210> SEQ ID NO 104
<211> LENGTH: 1368
<212> TYPE: DNA
<213> ORGANISM: Nannochloropsis oceanica

<400> SEQUENCE: 104
atgcaatacg ccgcccatcc cctctttgat caccgcaacc atctcccgcg cctccgcatg      60
acgactacta cgatcatgcc agcagccgta gctgctacac cagccagaaa gcgaaggaaa     120
ctacatcaga acccactcgc agccttgtca tccctccatg ccctcctctt gcttggtctc     180
gcgtggcttg agtgccgagc cttcgttatc cctcgaccca cgtcctcgcc ttcgctcgtc     240
ttaagcttga ccctaccacg gcagcaccgg ccacgacagc ttcggatgat tatggacgaa     300
ccaaaagttg gtgaagagcc ctcggtcatg tcacaagctt tgagcaagca aaagaccttg     360
tcgcgctacg tggaagtcga gacgtggaag caccgggagc taacagacct gcaacccgtc     420
```

```
atgcgcggca ttgagtccgc ctgtcggggc atcgccacct tagtccgccg cgcgcaatgt    480
gacgaaattg cgggtctaca tggtaatgac ggagatatga atgtacaggg ggaggtgcaa    540
aaagttatgg atgtcctcgc gaacaatatc ctggccgctt caatgtgtgc ccccggtaaa    600
atggactacg tcgcctcaga ggaagaagaa gagcccactt actgctctgc ggtcctgcaa    660
aatgctgcat tccaagggga gtatgccggg gtttttgatc cattagatgg tagctctaac    720
attgaggcag gtctgcccgt gggtaccatc tttggaatct accgacgccc ccaactcaac    780
ctctctccgg aacgagaacg agatcctctc gaggccatca tgcaaccagg cagcaaatta    840
ttagcctcag gatactgcct gtatggagga cagaccattc tcgtcctcac cctcgggcag    900
ggtgtgcacg gcttcacgtt gaacaagccc ggtggggact ttattttaac ccagcccaac    960
atgcgcattc cagcccgagg acagctttat gccatcaatg agggatcctc ccacctctgg    1020
gaaccgaagg tgaccgagta cgtacgtcga ctgaaattag gcgaggggga ggggaatgtg    1080 cccacagaa cggcatacgt gggagcgatg gtcgcagacg tgcatagggt gctggtagag    1140
ggaggggtgt acgcttaccc tggtacggtg gatgcgccga atgaaaaat tcggttgttg    1200 tacgaggcaa atcccatgag catgttggtg gagcaggcgg gcggattgag caccacgggt    1260
aggcaaagga tcttggactt gaagccgacg gggattcacc agcgggtgcc gatattcatt    1320
ggtagcaagg aggatatcaa ggacctgcag gcattgttga aggattga                 1368
```

<210> SEQ ID NO 105
<211> LENGTH: 379
<212> TYPE: PRT
<213> ORGANISM: Nannochloropsis oceanica

<400> SEQUENCE: 105

Met Ala Arg Leu Ser Ala Leu Ser Gly Leu Val Leu Phe Leu Ala Ser
1               5                   10                  15

Gly Ala Gln Ala Phe Val Pro Ser Pro Leu Ala Arg Met Asn Thr Ala
                20                  25                  30

Ala Lys Val Ala Pro Arg Ser Lys Gly Thr Met Ser Met Val Gln Thr
            35                  40                  45

Asp Val Met Thr Leu Thr Arg Tyr Met Ile Glu Asn Thr Lys Gln Phe
        50                  55                  60

Pro Asp Ala Gln Asp Leu Glu Val Leu Met Ser Ser Ile Gln Val Ala
65                  70                  75                  80

Cys Lys Thr Ile Ser Asn Leu Val Cys Arg Ala Gly Ile Asn Asp Leu
                85                  90                  95

Thr Gly Leu Gln Gly Gly Ile Asn Val Gln Gly Glu Gln Lys Lys
                100                 105                 110

Leu Asp Val Ile Ser Asn Asp Val Leu Lys Asn Ala Leu Arg Phe Thr
            115                 120                 125

Gly Lys Leu Gly Val Val Ala Ser Glu Glu Asp His Pro Val Leu
        130                 135                 140

Val Glu Glu Ala Phe Asn Ser Lys Tyr Val Ala Val Phe Asp Pro Leu
145                 150                 155                 160

Asp Gly Ser Ser Asn Ile Asp Ala Ala Ile Ser Thr Gly Thr Ile Phe
                165                 170                 175

Gly Ile Phe Leu Glu Asn Asp Ala Cys Leu Ile Asp Pro Glu Gly Asp
            180                 185                 190

Ile Ser Glu Gln Gln Met Ala Cys Leu Leu Asn Thr Leu Gln Pro Gly
        195                 200                 205

```
Ser Asn Leu Val Ala Ser Gly Tyr Val Met Tyr Ser Ser Thr Ile
    210                 215                 220
Phe Val Leu Thr Leu Gly Asn Gly Val Asn Gly Phe Thr Leu Asp Pro
225                 230                 235                 240
Gln Ile Gly Glu Phe Val Leu Thr His Pro Asn Ile Lys Ile Pro Lys
                245                 250                 255
Arg Gly Lys Ile Tyr Ser Phe Asn Glu Ala Asn Tyr Phe Asp Trp Asp
            260                 265                 270
Pro Lys Leu Gln Asp Tyr Val Asn Gly Leu Lys Lys Lys Gly Tyr Ser
        275                 280                 285
Ser Arg Tyr Ile Gly Ser Met Val Gly Asp Ile His Arg Thr Leu Leu
    290                 295                 300
Tyr Gly Gly Val Phe Gly Tyr Pro Ser Asp Lys Lys Asn Val Asn Gly
305                 310                 315                 320
Lys Leu Arg Leu Leu Tyr Glu Ala Ala Pro Met Gly Phe Ile Met Glu
                325                 330                 335
Gln Ala Gly Gly Lys Ala Thr Thr Gly Thr Glu Pro Ile His Asp Leu
            340                 345                 350
Gln Pro Lys Ser Val His Gln Arg Val Pro Thr Tyr Leu Gly Ser Pro
        355                 360                 365
Glu Asp Val Asp Glu Leu Val Ala Met Leu Lys
370                 375

<210> SEQ ID NO 106
<211> LENGTH: 1140
<212> TYPE: DNA
<213> ORGANISM: Nannochloropsis oceanica

<400> SEQUENCE: 106
atggcccgtc tctctgcttt gagcggcctt gtcctcttcc ttgcctctgg cgcccaagcc      60
ttcgttccct cccctttggc caggatgaac accgccgcta aggtcgcccc ccgcagcaag     120
ggcactatga gcatggtcca gaccgacgtc atgacgctga cccgctatat gattgagaac     180
accaagcagt tccccgatgc ccaggacctc gaggtgctca tgtcttccat ccaggtggcc     240
tgcaagacca tctctaacct ggtctgccgc gcgggcatca cgacttgac gggtcttcag      300
ggcggtatta acgtgcaagg ggaggagcag aagaagctgg atgtcatctc caacgatgtc     360
ctcaaaaacg ccctccgctt cacgggcaaa ctcggtgtgg tggcttcgga ggaggaggat     420
catcccgtcc ttgtcgagga ggccttcaac agcaagtacg tggccgtttt cgaccccctc     480
gacgggagca gcaacatcga cgccgctatc tccacgggca ccattttggg aatcttttg     540
gagaacgacg cctgcttgat cgacccggag ggcgacatct ctgagcaaca atggcgtgc     600
ctcctcaaca cccttcagcc cgggagcaac ctggtggcat ccgggtatgt tatgtactcc     660
tcctccacca tcttcgtcct gaccctcggc aacggcgtca acggcttcac cctcgatcct     720
cagatcggcg agttcgtcct caccccccc aacatcaaga tcccaaagcg cggcaagatc     780
tactccttca cgaggcaaa ttacttcgac tgggatccca agctccaaga ttacgtcaac     840
ggcctcaaga gaaaggata ctcttcccgc tacatcggct ccatggtcgg agacatccac     900
cgcaccctcc tatacggcgg ggtgttcggc taccttcgg acaagaagaa cgtgaatggc     960
aagctccgtc tgctttatga ggcggcgccc atgggcttca tcatggagca ggccggcggg    1020
aaggccacca ccggcacgga gcccatccac gatctgcagc caagagcgt ccaccagcgg     1080
gtgcctacct accttggatc ccctgaggat gtagacgagc tcgtggccat gctcaagtaa    1140
```

<210> SEQ ID NO 107
<211> LENGTH: 375
<212> TYPE: PRT
<213> ORGANISM: Nannochloropsis oceanica

<400> SEQUENCE: 107

| | | | | | | | | | | | | | | | |
|---|---|---|---|---|---|---|---|---|---|---|---|---|---|---|---|
| Met | Lys | Gly | Ala | Ile | Leu | Leu | Ala | Leu | Val | Ala | Pro | Thr | Leu | Ala | Phe |
| 1 | | | | 5 | | | | | 10 | | | | | 15 | |
| Val | Pro | Val | Lys | Pro | Val | Val | Pro | Met | Ala | Lys | Thr | Gln | Ser | Arg | Ser |
| | | | 20 | | | | | 25 | | | | | 30 | | |
| Arg | Ala | Gln | Thr | Ile | Met | Gln | Met | Asp | Pro | Ser | Val | Met | Pro | Gly | Leu |
| | | 35 | | | | | 40 | | | | | 45 | | | |
| Ala | Ser | Thr | Pro | Gly | Gln | Pro | Thr | Val | Glu | Ser | Trp | Leu | Met | Asp | Asn |
| | 50 | | | | | 55 | | | | | 60 | | | | |
| Ala | Asp | Lys | Lys | Leu | Ser | Lys | Ala | Val | Met | Gly | Ile | Phe | Ser | Ala | Cys |
| 65 | | | | | 70 | | | | | 75 | | | | | 80 |
| Lys | Glu | Ile | Ala | Tyr | Lys | Ile | Arg | Thr | Ala | Ser | Cys | Asp | Lys | Met | Ala |
| | | | | 85 | | | | | 90 | | | | | 95 | |
| Cys | Phe | Asn | Glu | Phe | Gly | Asp | Glu | Gln | Leu | Ala | Ile | Asp | Ile | Leu | Ala |
| | | | 100 | | | | | 105 | | | | | 110 | | |
| Asn | Asn | Val | Leu | Phe | Gln | Asn | Leu | Lys | Asp | Ser | Gly | Val | Val | Ala | Thr |
| | | | 115 | | | | | 120 | | | | | 125 | | |
| Ala | Ser | Ser | Glu | Glu | Thr | Pro | Thr | Glu | Asp | Pro | Met | Gly | Gly | Glu | Gly |
| | 130 | | | | | 135 | | | | | 140 | | | | |
| Phe | Ser | Val | Ala | Phe | Asp | Pro | Leu | Asp | Gly | Ser | Ser | Ile | Ile | Asp | Thr |
| 145 | | | | | 150 | | | | | 155 | | | | | 160 |
| Asn | Phe | Ala | Val | Gly | Thr | Ile | Phe | Gly | Val | Trp | Pro | Gly | Ser | Arg | Leu |
| | | | | 165 | | | | | 170 | | | | | 175 | |
| Thr | Gly | Ile | Thr | Gly | Arg | Gln | Leu | Ala | Ala | Ser | Gly | Ile | Ala | Val | Tyr |
| | | | 180 | | | | | 185 | | | | | 190 | | |
| Gly | Pro | Arg | Thr | Thr | Ile | Thr | Phe | Ala | Ile | Asp | Gly | Val | Asp | Gly | Ala |
| | | | 195 | | | | | 200 | | | | | 205 | | |
| His | Glu | Phe | Leu | Leu | Val | Asp | Asp | Phe | Thr | Ala | Arg | His | Gly | Gln | Trp |
| | 210 | | | | | 215 | | | | | 220 | | | | |
| Ile | Lys | Thr | Asn | Thr | Phe | Thr | Ser | Ile | Gly | Glu | Gly | Lys | Leu | Phe | Ala |
| 225 | | | | | 230 | | | | | 235 | | | | | 240 |
| Pro | Gly | Asn | Leu | Arg | Ala | Ile | Ala | Asp | Asn | Pro | Gly | Tyr | Asn | Ala | Met |
| | | | | 245 | | | | | 250 | | | | | 255 | |
| His | Ser | Tyr | Trp | Leu | Glu | Asn | Lys | Tyr | Gln | Leu | Arg | Tyr | Thr | Gly | Gly |
| | | | 260 | | | | | 265 | | | | | 270 | | |
| Met | Val | Pro | Asp | Val | Asn | Gln | Ile | Met | Val | Lys | Gly | Lys | Gly | Val | Phe |
| | | | 275 | | | | | 280 | | | | | 285 | | |
| Val | Asn | Pro | Glu | Ser | Pro | Ser | Ala | Lys | Ala | Lys | Leu | Arg | Leu | Leu | Tyr |
| | 290 | | | | | 295 | | | | | 300 | | | | |
| Glu | Val | Ala | Pro | Ile | Gly | Tyr | Met | Ile | Glu | Lys | Ala | Gly | Gly | Ala | Ser |
| 305 | | | | | 310 | | | | | 315 | | | | | 320 |
| Ser | Tyr | Gly | Ala | Gly | Ser | Val | Leu | Asp | Leu | Asn | Ile | Tyr | Lys | Thr | Glu |
| | | | | 325 | | | | | 330 | | | | | 335 | |
| Asp | Arg | Thr | Gln | Val | Ala | Tyr | Gly | Ser | Lys | Asp | Glu | Val | Lys | Arg | Phe |
| | | | 340 | | | | | 345 | | | | | 350 | | |
| Glu | Asp | Met | Val | Gly | Ile | Lys | Tyr | Ala | Ser | Ser | His | Pro | Asp | Ile | Val |
| | | | 355 | | | | | 360 | | | | | 365 | | |
| Ser | Gln | Asn | Ala | Ala | His | Ala | | | | | | | | | |
| | 370 | | | | | 375 | | | | | | | | | |

<210> SEQ ID NO 108
<211> LENGTH: 1128
<212> TYPE: DNA
<213> ORGANISM: Nannochloropsis oceanica

<400> SEQUENCE: 108

```
atgaagggtg ctatcctcct cgccttggtc gctccgacct tggctttcgt ccccgtcaag      60
cctgttgtgc ccatggccaa gacccagtcc cgtagcaggg cgcagaccat catgcagatg     120
gatccctcgg tcatgcccgg ccttgcctcc accccgggtc aacccacagt tgagagctgg     180
ttgatggaca acgccgacaa gaagctttcc aaggccgtga tgggcatctt ctccgcctgc     240
aaagagatcg cctacaagat ccgcacggcg tcttgtgaca aaatggcgtg cttcaacgag     300
ttcggtgacg agcagcttgc cattgacatc ctggccaaca acgtcctctt ccaaaacctc     360
aaggactccg gggtggtcgc cacggcctcc tcggaggaaa ccccctacgga ggatccgatg     420
gggggtgagg gcttctctgt ggcttttgat cccctcgatg gctcttccat tatcgacact     480
aactttgccg tgggcaccat tttcggcgtg tggcccggct cccgcctgac tggtatcact     540
ggacgacagc tcgctgcatc cgggattgct gtctatggac cccgtacgac catcaccttt     600
gcgattgatg gcgtggatgg tgcgcacgag tttttgctgg tggatgactt cactgcccgc     660
cacgggcagt ggatcaagac caacacattt accagcattg ggagggcaa gcttttcgcc     720
cccgggaact tgcgggccat tgccgataac cccggctaca acgccatgca ctcgtactgg     780
ttggagaaca ataccagct tcgctacacg ggcggcatgg tgcccgacgt gaaccagatc     840
atggtcaagg gcaagggcgt gttcgtcaac cccgagtcgc cctctgccaa ggccaagctc     900
cgcttgctgt acgaggtggc acccattgga tacatgattg agaaggccgg cggtgcatct     960
tcttatggcg cgggttcggt gctggacttg aacatttaca gacggagga ccgcacccag    1020
gtggcatacg gaagcaagga tgaggtgaag cgctttgagg acatggtggg gattaagtat    1080
gcctcctccc acccggacat cgtttcccag aatgcggcgc acgcgtaa               1128
```

<210> SEQ ID NO 109
<211> LENGTH: 341
<212> TYPE: PRT
<213> ORGANISM: Nannochloropsis oceanica

<400> SEQUENCE: 109

```
Met Ala Ala Ala Thr Leu Ser Ser Pro Thr Leu Thr Thr Asn Ala Ser
1               5                  10                  15

Ser Leu Asp Leu Pro Met Leu Arg Lys Ile Val Pro Glu Leu Pro Glu
            20                  25                  30

Asp Leu Glu Gln Leu Leu Gly Ala Ile Ala Gln Ala Ser His Arg Ile
        35                  40                  45

Ala Asp Thr Leu Arg Thr Gly Asp Ser His Thr Lys Ser Gly Ile Glu
    50                  55                  60

Asn Thr Phe Gly Asp Glu Gln Leu His Leu Asp Val Val Thr Asn Glu
65                  70                  75                  80

Ile Cys Phe Glu Glu Leu Arg Ala Cys Gly Leu Val His Ile Ala Ser
                85                  90                  95

Ser Glu Glu Thr Pro Thr Glu Glu Asp Leu Gly Gly Ala Asn Ser Gly
            100                 105                 110

Ala Gly Asp Gly Phe Ser Val Ser Phe Asp Pro Leu Asp Gly Ser Ser
        115                 120                 125
```

```
Ile Ile Asp Thr Asn Phe Ser Val Gly Ser Ile Phe Gly Ile Trp Pro
    130                 135                 140

Gly Arg Gly Leu Leu Gly Arg Thr Gly Arg Glu Gln Cys Ser Ser Val
145                 150                 155                 160

Leu Thr Ile Tyr Gly Pro Arg Val Thr Leu Val Ile Ala Leu Pro His
                165                 170                 175

Ala Ala Gly Gly Pro Arg Ser Val Gln Leu Met Leu Gln His Asp Arg
            180                 185                 190

Thr Trp Glu Val Val His Glu Thr Leu Thr Val Ala Pro Ala Gly Lys
        195                 200                 205

Val Phe Ala Pro Gly Asn Leu Arg Ala Thr Ala Asp Asn Ala Ala Tyr
    210                 215                 220

Lys Arg Leu Val Asp Tyr Trp Ile Ser Glu Arg Tyr Thr Leu Arg Tyr
225                 230                 235                 240

Thr Gly Gly Leu Val Pro Asp Val Tyr His Ile Leu Ile Lys Gly Lys
                245                 250                 255

Gly Val Val Thr Asn Val Ser Ala Ala Lys Ala Lys Leu Arg
            260                 265                 270

Leu Leu Tyr Glu Ala Ala Pro Ile Ala Leu Val Met Glu Cys Ala Gly
        275                 280                 285

Ala Ala Ser Cys Thr Ala Pro Gly Pro Asn Gly Glu His Pro Glu Pro
    290                 295                 300

Ile Ser Ile Leu Asp Leu Val Val Thr Gly Leu Glu Phe Lys Cys Gly
305                 310                 315                 320

Val Ala Tyr Gly Gly Val Glu Glu Val Glu Thr Phe Lys Lys Phe Leu
                325                 330                 335

Tyr Pro Ala Lys Glu
            340

<210> SEQ ID NO 110
<211> LENGTH: 1026
<212> TYPE: DNA
<213> ORGANISM: Nannochloropsis oceanica

<400> SEQUENCE: 110
atggcggccg caaccttgag cagtcccacc cttactacca atgcttcctc tttggacctt      60
cccatgctgc gcaaaatcgt gccagaactg ccggaagact ggagcagct ccttggggcc     120 attgcccagg cctcccaccg tattgcagac acgctgagaa ctggcgactc ccacaccaag     180
agcggcattg aaaacacttt tggggatgaa caattgcatt tggacgtggt taccaacgag     240
atttgtttcg aagagcttcg ggcgtgtggc ctcgtgcaca ttgccagtag cgaggagaca     300
ccgacggagg aggacttggg cggggccaac tcagggcag gggacggt ttccgttcc       360 tttgatccgc tggatgggag tagcatcatc gataccaatt tctcggttgg ttctattttt     420
gggatctggc ctggaagagg actgttggga cggacggggc gagagcaatg ctcttccgtg     480
ttgacgatct acggcccgcg tgtcacgttg gtcattgccc tgcctcacgc tgctggggg     540 cctcgctcgg tgcaactcat gcttcaacat gatcgtactt gggaggtagt ccacgaaacc     600
ctgacagtgg caccagcagg gaaagtcttc gcgccaggca atttaagggc gacgcggat      660 aatgcagctt acaagcggtt ggttgattat tggatttcgg aacgatacac cttgcgctac     720
actggtggcc tagtcccgga cgtctatcac attttaatca aggaaaagg ggttgtgact      780 aacgtggtgt cagctgccgc caaggccaag cttcgtttgc tctacgaggc agcacccatt     840
gccctggtga tggagtgtgc cggggctgcc tcttgcacgg ctcccgggcc gaatggggag     900
```

-continued

```
caccctgaac cgatttcaat attggacttg gtcgtcacgg ggttggagtt taagtgtggt        960
gtggcgtatg gagggtgga ggaggtggaa accttcaaga gtttctcta cccggcgaag         1020 gaatag                                                                   1026
```

<210> SEQ ID NO 111
<211> LENGTH: 742
<212> TYPE: PRT
<213> ORGANISM: Nannochloropsis oceanica

<400> SEQUENCE: 111

```
Met Ser Thr Lys Arg Pro Ser Glu Glu Thr Thr Asn Gly Ser Ala Ser
1               5                   10                  15

Lys Lys Gly Lys Glu Ser Leu Val Ser Ala Leu Ser Thr Lys Ala Val
            20                  25                  30

Asp Thr Val Arg Val Leu Ser Asp Ile Val Gln Lys Ala Asn Ser
        35                  40                  45

Gly His Pro Gly Ala Pro Met Ser Leu Ala Pro Leu Ala Tyr Leu Leu
    50                  55                  60

Trp Thr Lys Val Met Lys Tyr Asn Pro Gln Asp Pro Glu Trp Leu Ala
65                  70                  75                  80

Arg Asp Arg Phe Val Leu Ser Asn Gly His Ala Cys Ala Leu Leu Tyr
                85                  90                  95

Gly Met Leu His Leu Thr Gly Tyr Pro Gln Val Thr Met Asp Asp Leu
            100                 105                 110

Lys Asn Phe Arg Gln Ile Asp Ser Ile Thr Ala Gly His Pro Glu Asn
        115                 120                 125

Thr Leu Ile Lys Gly Ile Glu Val Ser Thr Gly Pro Leu Gly Gln Gly
    130                 135                 140

Ile Ser Asn Ala Val Gly Leu Ala Ile Ala Glu Ser His Leu Ala Ala
145                 150                 155                 160

Val Phe Asn Lys Glu Gly His Ala Lys Val Ile Asp Asn Tyr Thr Tyr
                165                 170                 175

Val Ile Cys Gly Asp Gly Cys Leu Gln Glu Gly Val Ser Ser Glu Ala
            180                 185                 190

Ser Ser Leu Ala Gly His Leu Gly Leu Gly Lys Leu Ile Val Tyr Gln
        195                 200                 205

Glu Gly Val Ser Ser Glu Ala Ser Ser Leu Ala Gly His Leu Gly Leu
    210                 215                 220

Gly Lys Leu Ile Val Tyr Tyr Asp Asp Asn Arg Ile Thr Ile Asp Gly
225                 230                 235                 240

Asp Thr Gly Leu Ser Phe Thr Glu Asp Val Glu Lys Arg Tyr Glu Ala
                245                 250                 255

Tyr Gly Trp His Val Gln Thr Val Asp Asp Val Gln Asp Leu Asp Ser
            260                 265                 270

Leu Met Ala Ala Thr Glu Ala Ala Lys Ala Val Thr Asp Lys Pro Ser
        275                 280                 285

Met Ile Lys Val Lys Thr Glu Ile Gly Phe Gly Ser Lys Lys Gln Gly
    290                 295                 300

Ser His Ser Val His Gly Ser Pro Leu Gly Ala Glu Asp Leu Lys Gln
305                 310                 315                 320

Leu Lys Glu Lys Phe Gly Phe Asn Pro Glu Glu Thr Phe Leu Val Ala
                325                 330                 335

Pro Glu Val Ser Glu Leu Phe Leu Ala Ala Gly Ala Arg Gly Ala Ala
```

```
                340                 345                 350
Ala Gln Ala Ala Trp Gln Met Gly Leu Asp Gly Tyr Lys Gly Ala Tyr
            355                 360                 365

Pro Lys Glu Thr Ala Glu Leu Val Arg Gln Cys Glu His Lys Met Pro
            370                 375             380

Asp Gly Trp Lys Glu Ala Leu Pro Arg Tyr Ser Ala Thr Asp Lys Ala
385                 390                 395                 400

Met Ala Thr Arg Lys Phe Ser Glu Ile Ala Leu Asn Ala Leu Ala Pro
                405                 410                 415

Ile Met Pro Glu Leu Val Gly Gly Ser Ala Asp Leu Thr Pro Ser Thr
            420                 425                 430

Leu Thr Ala Leu Ala Cys Ser Gly Asp Tyr Gln Lys Glu Thr Pro Ala
            435                 440                 445

Gly Arg Tyr Phe Arg Phe Gly Val Arg Glu His Gly Met Thr Ala Val
            450                 455                 460

Ala Asn Gly Ile Phe Ala Tyr Gly Ala Leu Arg Pro Phe Val Ala Thr
465                 470                 475                 480

Phe Leu Asn Phe Ile Gly Tyr Ala Trp Gly Ser Val Arg Leu Thr Ala
                485                 490                 495

Leu Ser His Leu Gly Val Ile Phe Val Met Thr His Asp Ser Ile Gly
            500                 505                 510

Leu Gly Glu Asp Gly Pro Thr His Gln Pro Val Glu Ile Leu Glu Gln
            515                 520                 525

Cys Arg Val Met Pro Asn Leu Asn Leu Ile Arg Pro Ala Asp Gly Asn
            530                 535                 540

Glu Val Ser Gly Ala Tyr Ile Ser Ala Val Asp His Pro Phe Thr Pro
545                 550                 555                 560

Thr Val Leu Ala Leu Ser Arg Gln Asn Leu Pro Asn Leu Glu Gly Ser
                565                 570                 575

Ser Val Glu Lys Thr Leu Leu Gly Ala Tyr Val Leu Ser Glu Ala Gly
            580                 585                 590

Gly Asn Glu Glu Glu Gly Gly Pro Glu Leu Ile Leu Thr Gly Ser Gly
            595                 600                 605

Ser Glu Val Ala Ile Ala Val Glu Ala Ala Lys Lys Leu Val Ala Glu
            610                 615                 620

Gly Val Arg Val Arg Val Val Ser Phe Pro Ser Trp Glu Leu Phe Glu
625                 630                 635                 640

Gln Gln Glu Lys Asp Tyr Arg Leu Glu Val Phe Pro Val Gly Val Pro
                645                 650                 655

Val Val Ser Val Glu Ala Ser Ser Ile His Gly Trp Ala Lys Tyr Ser
            660                 665                 670

His Ala Ala Leu Gly Leu Thr Trp Phe Gly Ala Ser Gly Pro Tyr Thr
            675                 680                 685

Lys Val Tyr Glu Lys Phe Gly Leu Thr Val Glu Asn Leu Ala Glu Lys
            690                 695             700

Ala Lys Glu Val Met Ser Phe Tyr Lys Asp Gly Gly Lys Pro Val Pro
705                 710                 715                 720

Ser Leu Ile Asp Val Pro Val Ile Ser Gly His Tyr Glu His Lys Pro
                725                 730                 735

Val Ala Thr Ser Gln Ala
            740

<210> SEQ ID NO 112
```

<211> LENGTH: 2229
<212> TYPE: DNA
<213> ORGANISM: Nannochloropsis oceanica

<400> SEQUENCE: 112

```
atgtcgacca agcgcccctc cgaagagacc accaatgggt ccgcgtccaa gaaagggaag        60
gaatccctcg tcagcgccct ctccaccaag gccgtcgaca ctgtccgcgt cctctccgcc       120
gacatcgtgc aaaaagccaa cagcgggcac cctggtgcac ccatgagctt ggccccgctt       180
gcttatctgc tgtgtgaccaa agtcatgaag tacaaccccc aggaccctga atggctggcg       240
cgcgatcgtt tcgtcttgtc caacggccac gcttgtgcct tgctttatgg aatgttgcat       300
ctcacgggct accctcaggt gacgatggac gatttgaaga acttcaggca gattgattcg       360
atcacgcgg ggcatccgga gaacactcta atcaagggga ttgaggtctc aacggggcca       420
ttggggcagg ggatctcgaa cgcagtgggt ttagcgattg ctgagagcca cttggcagct       480
gtgtttaaca aggagggcca cgctaaggtg attgacaact ataccatgt gatttgtggg        540
gacgggtgct gcaggaggg ggtgtcgagc gaggccagtt ctctggcggg gcatttggga        600
ctggggaaat taattgttta ccaggagggg gtgtcgagcg aggccagttc tctggcgggg       660
catttgggac tggggaaatt aattgtttac tatgacgaca accggatcac gattgatggg       720
gatacgggat tgtcgttcac ggaggatgtg gagaagaggt acgaggctta tgggtggcat       780
gtgcagaccg tggatgacgt ccaggacctt gattcgttga tggcagcgac ggaggcagcc       840
aaggccgtga cggacaagcc gagcatgatc aaagtgaaga cggagatcgg gtttgggagc       900
aagaagcagg ggtcgcattc tgtccacggg tcgccgttgg gggcggagga tctgaagcag       960
ttgaaggaaa aatttggatt caacccggag gagacgttcc tggtagcccc tgaggtgagt      1020
gagttgtttt tggcggcggg cgcgaggggg gcggcggcgc aggcggcttg gcagatgggg      1080
ttggacggat ataagggagc ttaccccaag gagactgcgg agttggtgcg acagtgtgag      1140
cacaagatgc cggatgggtg gaaggaggcg ttgccgcgt atagcgcgac ggacaaggcc      1200
atggcgacga ggaagttctc ggagattgcg ctgaacgcat ggcgcccat catgccggag      1260
ttggttgggg ggtcggcgga tctgacgcct tcgacgctga cagcttttggc atgttcgggc      1320
gattatcaga aggagactcc cgcggggagg tatttcaggt ttggagtgag ggagcatggg      1380
atgacggcgg tggcaaacgg gatattcgcc tacggggcgt tgagacccett tgtcgcgacg      1440
tttttgaatt tcattggtta tgcctggggt tctgtgaggt tgactgcatt gtctcacttg      1500
ggggtaattt ttgtgatgac gcacgattca atcggattgg gggaggacgg acccacgcac      1560
cagccggtgg agatcctgga gcagtgtcgg gtgatgccta atttgaactt aatcagacct      1620
gcagatggga acgaggtgtc gggtgcttac atatcggcag tcgaccatcc cttcacgccc      1680
acggtgttgg ccttgagtcg acagaacctg ccgaatctgg aggggagcag cgtggagaaa      1740
actctgttag gcgcttatgt cctgtcggag gcgggagga atgaagagga gggggggcca      1800
gaactcattt taacgggttc gggttcggag gtagcgattg cggtcgaggc agccaagaag      1860
ctggtggcgg agggggttag ggtgcgtgtg gtgagtttcc ctagttggga gctgttcgag      1920
cagcaggaga aggattacag gttggaagtt ttcccggtgg gagtgccggt tgtgagtgtt      1980
gaggcatctt cgatccatgg ctgggcgaag tactcgcatg cagctctggg cttgacctgg      2040
tttggggcct cggggcctta tacaaaggtg tatgagaaat ttgggttgac ggtcgaaaat      2100
ctggcggaga aggcgaagga ggtgatgtct ttctataagg atggggggtaa gccggtaccg      2160
agtttgattg acgtgcccgt gatttcgggt cactatgagc acaaaccggt ggccacctca      2220
``` caggcataa 2229

<210> SEQ ID NO 113
<211> LENGTH: 266
<212> TYPE: PRT
<213> ORGANISM: Nannochloropsis oceanica

<400> SEQUENCE: 113

Met Ala Arg Leu Ser Leu Val Ala Cys Gly Val Val Met Ala Thr
1               5                   10                  15

Val Thr His Gly Phe Val Val Pro Ala Pro Arg Thr Tyr Ser Arg Gly
            20                  25                  30

Arg Ile Ala Met Ala Ala Lys Lys Asp Phe Trp Ile Ala Pro Ser Ile
        35                  40                  45

Leu Ser Ala Asp Phe Ala Lys Leu Gly Gln Glu Val Asp Asn Val Leu
    50                  55                  60

Ala Ala Gly Ala Asp Ile Val His Phe Asp Val Met Asp Asn His Tyr
65                  70                  75                  80

Val Pro Asn Leu Thr Ile Gly Pro Met Val Cys Lys Ala Leu Arg Asp
                85                  90                  95

His Gly Val Thr Ala Pro Ile Asp Val His Leu Met Val Ser Pro Val
            100                 105                 110

Asp Arg Ile Ile Pro Asp Phe Ala Asp Ala Gly Ala Ser Phe Ile Thr
        115                 120                 125

Phe His Pro Glu Ala Thr Asn His Ile Asp Arg Thr Leu Gln Leu Ile
    130                 135                 140

Lys Ser Lys Gly Cys Lys Ala Gly Leu Val Phe Asn Pro Ala Thr Pro
145                 150                 155                 160

Leu Thr Met Ala Lys His Val Leu Asp Lys Ile Asp Ile Leu Leu
                165                 170                 175

Met Ser Val Asn Pro Gly Phe Gly Gly Gln Ser Phe Ile Pro Glu Thr
            180                 185                 190

Leu Val Lys Leu Arg Glu Ala Arg Lys Met Ile Asp Glu Ser Gly Tyr
        195                 200                 205

Asp Ile Arg Leu Glu Val Asp Gly Gly Val Gly Val Ala Asn Ile Lys
    210                 215                 220

Glu Ile Ala Glu Ala Gly Ala Asp Phe Phe Val Ala Gly Ser Ala Ile
225                 230                 235                 240

Leu Lys Asn Pro Arg Thr Gln Asp Ala Tyr Lys Gly Thr Ile Asp Gln
                245                 250                 255

Met Arg Ala Glu Leu Ala Lys Val Ser Lys
            260                 265

<210> SEQ ID NO 114
<211> LENGTH: 801
<212> TYPE: DNA
<213> ORGANISM: Nannochloropsis oceanica

<400> SEQUENCE: 114
atggctcgcc tttcgcttgt tgcctgtggc gtagttgtca tggccacggt cactcacggc    60
tttgttgtcc cggctccccg cacttactcc cgcggccgca tcgccatggc tgccaagaag   120
gacttctgga ttcgccctc catcctctct gctgactttg ccaagcttgg caagaagtg   180 gacaacgtcc tggccgctgg tgctgacatc gtgcacttcg atgtgatgga caaccactac   240
gtccccaact tgacgatcgg ccccatggtc tgcaaggccc tgcgcgacca cggcgtcacc   300

```
gcccccattg acgtgcactt gatggtttcc cccgttgacc gtatcatccc tgattttgct    360
gatgccggcg cttccttcat caccttccac ccggaagcta ccaaccacat tgaccgaacc    420
ctgcaactta tcaagagcaa agggtgcaag gctggcttgg tcttcaaccc cgctaccccc    480
ctcaccatgg ccaagcacgt cctggacaaa atcgacatca ttcttctcat gtctgtgaac    540
cccggttttg gtgggcaatc cttcattccc gaaaccctgg tcaagctgcg tgaggcccgt    600
aaaatgatcg acgagtccgg gtatgatatc cgcctggagg tcgatggtgg ggttggcgtg    660
gccaacatca aggagattgc cgaagctggc gctgatttct ttgtggcggg gagtgctatc    720
ttgaagaacc cccgcaccca ggatgcctac aagggaacga ttgaccagat gcgtgccgag    780
ctggcgaagg tgagcaagta g                                              801
```

<210> SEQ ID NO 115
<211> LENGTH: 236
<212> TYPE: PRT
<213> ORGANISM: Nannochloropsis oceanica

<400> SEQUENCE: 115

Met Cys His Ser Cys Lys Cys Leu Ile Gly Pro Ser Met Leu Ala Ser
1               5                   10                  15

Asp Leu Ser Cys Met Ala Ala Glu Ala Gln Lys Val Val Ala Gly Gly
            20                  25                  30

Ala Asp Tyr Leu His Leu Asp Val Met Asp Gly His Phe Val Pro Asn
        35                  40                  45

Ile Thr Trp Gly Ala Pro Val Ile Lys His Leu Arg Lys His Cys Pro
50                  55                  60

Gly Val Phe Phe Asp Cys His Met Met Val Ser Asn Pro Glu Gln Trp
65                  70                  75                  80

Val Glu Glu Ile Lys Asp Ala Gly Gly Asp Gln Tyr Thr Phe His Leu
                85                  90                  95

Glu Ser Thr Lys Asp Pro Ala Ala Leu Ile Lys Gln Ile Leu Ala Ser
            100                 105                 110

Gly Met Lys Val Gly Ile Ala Leu Arg Pro Gly Thr Pro Val Lys Asp
        115                 120                 125

Val Leu Pro Trp Val Asp Leu Val Asp Met Val Leu Ile Met Thr Val
130                 135                 140

Glu Pro Gly Phe Gly Gly Gln Lys Phe Lys Ala Asp Met Met Pro Lys
145                 150                 155                 160

Val Ala Leu Leu Arg Glu Lys Tyr Pro Glu Lys Asp Ile Gly Val Asp
                165                 170                 175

Gly Gly Leu Gly Pro Ser Thr Ile Glu Ala Ala Ala Asp Ala Gly Ala
            180                 185                 190

Asn Met Ile Val Ala Gly Ser Ser Val Phe Lys Ser Pro Ala Pro Ala
        195                 200                 205

Gln Val Ile Ala Thr Leu Arg Arg Ala Val Glu Arg Leu Gly Asn Gly
    210                 215                 220

Lys Lys Glu Glu Glu Leu Thr Pro Leu Pro Pro Ala
225                 230                 235

<210> SEQ ID NO 116
<211> LENGTH: 711
<212> TYPE: DNA
<213> ORGANISM: Nannochloropsis oceanica

<400> SEQUENCE: 116

-continued

```
atgtgccata gctgcaagtg cctcattggc ccctccatgc tagccagcga cttgtcgtgc    60
atggccgctg aggcgcaaaa ggtggtggcg ggtggcgcag actacctgca cttagacgtg   120
atggacggtc atttcgtgcc aacattaca tgggggccc cagtaatcaa gcacttaaga   180
aagcactgtc ctggcgtttt ttttgactgt cacatgatgg tgagcaaccc cgagcaatgg   240
gtggaggaaa tcaaggatgc cggtggagat cagtacacat ccacctcga atctaccaag   300
gaccccgctg ccctaatcaa gcaaattctg gcctcaggga tgaaggtcgg tattgccctt   360
cgccctggca cgcctgtgaa agatgtattg ccctgggttg atcttgtgga catggtttta   420
atcatgacgg tggaaccggg ctttgggggg cagaaattta aggcggacat gatgcccaag   480
gtggcgcttc tccgggaaaa atacccagaa aaagacattg gagtcgatgg agggctcgga   540
ccttcgacta tcgaagcagc ggccgacgcg ggagctaata tgatagtggc tgggagctcc   600
gttttcaaga gtccggcgcc tgcccaggtg atcgaacgt tgcgaagggc tgtggagagg   660
cttgggaatg ggaaaaagga ggaggagctg acgcccttgc ctccggcata a            711
```

```
<210> SEQ ID NO 117
<211> LENGTH: 307
<212> TYPE: PRT
<213> ORGANISM: Nannochloropsis oceanica

<400> SEQUENCE: 117
```

```
Met Pro Pro Thr Pro Thr Pro Asn Ala Pro Ser Thr Leu Ala Ala Ala
1               5                   10                  15

Thr Ser Ala Val Ala Pro Ser Ser Val Asn Ala Ser Ser Ser Pro Pro
            20                  25                  30

Glu Pro Ser Leu Arg Ala Ser Leu Pro Ser Thr Leu Pro Thr Glu Leu
        35                  40                  45

Phe Phe Asp Arg Asp Leu Glu Ala Thr Ile Pro Ala Gly Met Ala Leu
    50                  55                  60

Ser Glu Trp Lys Ala Arg Val Glu Leu Ala Cys Met Tyr Arg Val Phe
65                  70                  75                  80

Phe Ala Arg Gly Trp Asp Glu Glu Val Ile Asn His Ile Thr Leu Arg
                85                  90                  95

Val Pro Gly Pro Asp Ala His Phe Leu Ile Asn Pro Phe Gly Leu Tyr
            100                 105                 110

Tyr Gly Glu Val Thr Ala Leu Asn Leu Val Lys Ile Asp Leu Ser Gly
        115                 120                 125

Arg Glu Val Asp Pro Ser Pro Tyr Thr Val Asn Arg Ala Gly Phe Val
    130                 135                 140

Ile His Ser Ala Ile His Gly Ala Arg Pro Asp Asp Ala His Cys Val
145                 150                 155                 160

Ile His Thr His Ser Thr Pro Gly Val Ala Val Ala Cys Lys Glu Glu
                165                 170                 175

Gly Leu Arg Met Asp Asn Phe Tyr Ser Ile Phe Leu His Gly Gln Val
            180                 185                 190

Ala Tyr His Pro Phe Glu Gly Val Thr Val Arg Met Gly Glu Gln Glu
        195                 200                 205

Arg Leu Val Ala Asn Met Gly His Lys Ser Val Leu Ile Leu Gln Asn
    210                 215                 220

His Gly Leu Leu Val Ala Gly Pro Ser Thr Ala Arg Ala Phe Phe Thr
225                 230                 235                 240

Tyr Tyr Ala Leu His Arg Ala Cys Glu Ile Gln Cys Ala Thr Gln Ser
```

-continued

```
                    245                 250                 255
Met Pro Gly Arg Asn Val Pro Ile Ser Glu Ala Val Ala Val Gly Gly
            260                 265                 270

Leu Gln Gly Ala Glu Asp Ala Asp Pro Glu Gly Val Leu His Trp Lys
        275                 280                 285

Ile Phe Ala Gly Ala Val Arg Arg Ala Gly Ile Arg Arg Val Glu Asp
    290                 295                 300

Val Thr Gly
305

<210> SEQ ID NO 118
<211> LENGTH: 924
<212> TYPE: DNA
<213> ORGANISM: Nannochloropsis oceanica

<400> SEQUENCE: 118
atgcctccca ccccaacccc caatgcacct tccaccctcg ccgccgcgac ctctgctgtc      60
gccccctctt cggtcaatgc ctcatcttcc cctcccgaac catccctccg tgcttcactg     120
ccctccacct tgccgactga gctcttttc gacagagacc tcgaagcaac catccccgcc     180
ggcatggcct tgagtgaatg gaaagctcgc gtggaacttg cctgcatgta ccgtgtcttt     240
tttgcacgtg gctgggacga ggaggtgata aatcatatta cgttgcgcgt gcccggtcca     300
gacgcacact ttctcatcaa tccttcggg ctctactacg gcgaagtcac ggcgttgaat     360
ctggtgaaga ttgacttgag cggacgagag gtcgacccga gtccatacac tgtcaaccgg     420
gcaggctttg tgatccactc ggccatccac ggtgccaggc ccgacgacgc ccactgcgtg     480
attcacacac acagtactcc cggggtcgcc gtcgcatgca aggaagaagg cctgcggatg     540
gacaactttt actccatttt cctccacggc caggtggcct accacccctt tgaaggtgtg     600
accgtgcgca tgggcgagca ggaacgcctc gtggccaaca tgggccacaa gtccgtcctc     660
atcctccaga accacggcct gctcgtcgcg gggccctcca ccgctcgagc attcttcacc     720
tattacgccc tccaccgtgc ctgtgagatt cagtgcgcca cccaatccat gcccgggcgg     780
aacgtcccca tctccgaagc cgtggccgtg ggcggacttc aaggcgcgga ggacgctgat     840
ccggaaggtg tattgcactg gaaaatcttc gcggggggcgg tcagaagggc gggcattcgg     900
cgggtggagg acgtgacggg gtga                                           924

<210> SEQ ID NO 119
<211> LENGTH: 405
<212> TYPE: PRT
<213> ORGANISM: Nannochloropsis oceanica

<400> SEQUENCE: 119

Met Val Lys Thr Ala Ala Val Gly Leu Leu Ala Leu Ala Gly Leu Thr
1               5                   10                  15

Ser Ala Phe Val Pro Thr Asn Thr Asn Leu Arg Met Ser Asn Lys Trp
            20                  25                  30

Val Thr Lys Ala Lys Asp Ala Ser Phe Thr Arg Asn Leu Met Met Lys
        35                  40                  45

Leu Gly Ala Gly Glu Lys Val Ile Leu Ile Gly Val Ala Ala Asp Ser
    50                  55                  60

Gly Cys Gly Lys Ser Thr Phe Met Arg Arg Leu Thr Asn Ile Phe Gly
65                  70                  75                  80

Gly Ser Asn Val Gly Pro Leu Gly Gly Gly Phe Asp Asn Gly Gly Trp
                85                  90                  95
```

```
Glu Thr Asn Thr Leu Val Ser Asp Thr Thr Val Ile Cys Leu Asp
            100                 105                 110

Asp Tyr His Ala Asn Asp Arg Gly Gly Arg Lys Ile Thr Gly Arg Thr
        115                 120                 125

Ala Leu Glu Ala Ala Glu Gln Asn Phe Asp Leu Met Tyr Glu Gln Leu
    130                 135                 140

Lys Ala Leu Lys Glu Gly Lys Thr Val Ala Lys Pro Ile Tyr Asn His
145                 150                 155                 160

Val Asn Gly Thr Leu Asp Lys Pro Glu Asp Val Val Pro Thr Pro Ile
                165                 170                 175

Val Ile Val Glu Gly Leu His Pro Trp Tyr Asp Ala Arg Val Lys Asp
            180                 185                 190

Leu Leu Asp Tyr Thr Ile Tyr Leu Asp Ile Ser Asp Glu Ile Lys Arg
        195                 200                 205

Ala Trp Lys Ile Gln Arg Asp Met Ala Glu Arg Gly Trp Thr Leu Asp
    210                 215                 220

Gln Val Glu Ala Glu Ile Glu Lys Arg Lys Pro Asp Phe Asn Lys Phe
225                 230                 235                 240

Val Gly Pro Gln Lys Glu Val Ala Asp Ala Val Ile Gln Val Leu Pro
                245                 250                 255

Thr Glu Leu Thr Asn Asp Pro Glu Gly Lys Ile Leu Arg Val Arg Leu
            260                 265                 270

Ile Gln Lys Asp Asp Gly Lys Tyr Glu Pro Val Tyr Leu Phe Asp Gln
        275                 280                 285

Gly Ser Thr Val Ser Trp Val Pro Cys Gly Lys Gln Leu Thr Cys Ser
    290                 295                 300

Tyr Pro Gly Ile Lys Phe Gly Ser Gly Pro Asp Gln Trp Phe Asn Asn
305                 310                 315                 320

Ala Val Asn Ile Val Glu Met Asp Gly Gln Phe Asp Asn Leu Glu Glu
                325                 330                 335

Leu Ser Tyr Val Glu Lys His Leu Gly Asn Thr Ala Ser Lys Tyr Ala
            340                 345                 350

Gly Glu Ile Thr Ala Gln Met Leu Lys Asn Lys Gly Ala Pro Gly Ser
        355                 360                 365

Leu Asn Gly Ser Gly Leu Phe Gln Thr Ile Val Ser Leu Lys Ile Arg
    370                 375                 380

Glu Val Tyr Glu Lys Leu Ser Gly Lys Lys Val Asp Ala Ser Val Lys
385                 390                 395                 400

Ala Pro Val Ala Ala
            405

<210> SEQ ID NO 120
<211> LENGTH: 1218
<212> TYPE: DNA
<213> ORGANISM: Nannochloropsis oceanica

<400> SEQUENCE: 120
atggtcaaga ctgctgccgt cggcctcctg gccttggccg ggctcacctc tgcctttgtg      60
cccaccaaca cgaacctccg catgtctaac aagtgggtga ccaaggccaa ggacgcctcc     120
ttcacccgca acctgatgat gaagctgggc gcgggtgaaa aggtcatcct cattggtgtg     180
gccgctgact ccgggtgcgg caagtccacc ttcatgcgac gcctgaccaa catattcggc     240
ggaagcaacg ttgggccctt gggtggtggc ttcgacaacg gcggatggga aactaatacg     300
```

```
cttgtgtccg acaccaccac tgttatttgc ctggatgact accatgccaa tgaccgtggg    360
ggccgcaaga tcacgggccg cactgcccct gaggcggcgg agcagaactt cgacctcatg    420
tacgagcagc ttaaggcctt gaaggagggc aagacggtgg ccaagcccat ctacaatcac    480
gtcaacggca ccttggacaa gccagaggat gtagtgccca ctcctattgt catcgtcgag    540
gggctgcacc cttggtatga tgcccgtgtg aaggacctct ggactacac tatctacctg     600
gacatctccg acgagattaa gcgtgcctgg aaaatccagc gtgatatggc tgagcgtggc    660
tggactctgg accaggtgga ggccgagatt gagaagcgca agcccgactt caacaagttc    720
gtgggccccc agaaggaggt cgccgatgcc gtcatccagg tcctccccac cgagctgacc    780
aacgacccgg aaggcaagat cctccgtgtg cgtctcatcc agaaggatga cgggaaatac    840
gagcccgtct acctgttcga tcagggctcc acagtctcgt gggtgccctg cgggaagcag    900
ctcacctgct cttaccccgg catcaagttc ggctccggcc ctgaccagtg gttcaacaac    960
gccgtgaaca tcgtggagat ggacggccag ttcgacaact tggaagaact gtcttacgtg    1020
gagaagcacc tcgggaacac ggcctccaag tacgcaggag agatcaccgg cagatgttg    1080
aaaaacaagg gggctccggg tagcttgaac ggctcgggct tgttccagac aatcgtgagc    1140
ttgaagatta gggaggtcta cgagaagctg agcggaaaga aggtggatgc ctcggtgaag    1200
gcgccggtgg cggcttaa                                                  1218

<210> SEQ ID NO 121
<211> LENGTH: 345
<212> TYPE: PRT
<213> ORGANISM: Synechococcus elongatus

<400> SEQUENCE: 121

Val Glu Lys Thr Ile Gly Leu Glu Ile Ile Glu Val Val Glu Gln Ala
1               5                   10                  15

Ala Ile Ala Ser Ala Arg Leu Met Gly Lys Gly Glu Lys Asn Glu Ala
            20                  25                  30

Asp Arg Val Ala Val Glu Ala Met Arg Val Arg Met Asn Gln Val Glu
        35                  40                  45

Met Leu Gly Arg Ile Val Ile Gly Glu Gly Glu Arg Asp Glu Ala Pro
    50                  55                  60

Met Leu Tyr Ile Gly Glu Glu Val Gly Ile Tyr Arg Asp Ala Asp Lys
65                  70                  75                  80

Arg Ala Gly Val Pro Ala Gly Lys Leu Val Glu Ile Asp Ile Ala Val
                85                  90                  95

Asp Pro Cys Glu Gly Thr Asn Leu Cys Ala Tyr Gly Gln Pro Gly Ser
            100                 105                 110

Met Ala Val Leu Ala Ile Ser Glu Lys Gly Gly Leu Phe Ala Ala Pro
        115                 120                 125

Asp Phe Tyr Met Lys Lys Leu Ala Ala Pro Ala Ala Lys Gly Lys
    130                 135                 140

Val Asp Ile Asn Lys Ser Ala Thr Glu Asn Leu Lys Ile Leu Ser Glu
145                 150                 155                 160

Cys Leu Asp Arg Ala Ile Asp Glu Leu Val Val Val Met Asp Arg
                165                 170                 175

Pro Arg His Lys Glu Leu Ile Gln Glu Ile Arg Gln Ala Gly Ala Arg
            180                 185                 190

Val Arg Leu Ile Ser Asp Gly Asp Val Ser Ala Ala Ile Ser Cys Gly
        195                 200                 205
```

```
Phe Ala Gly Thr Asn Thr His Ala Leu Met Gly Ile Gly Ala Ala Pro
    210                 215                 220
Glu Gly Val Ile Ser Ala Ala Met Arg Cys Leu Gly Gly His Phe
225                 230                 235                 240
Gln Gly Gln Leu Ile Tyr Asp Pro Glu Val Val Lys Thr Gly Leu Ile
                245                 250                 255
Gly Glu Ser Arg Glu Ser Asn Ile Ala Arg Leu Gln Glu Met Gly Ile
                260                 265                 270
Thr Asp Pro Asp Arg Val Tyr Asp Ala Asn Glu Leu Ala Ser Gly Gln
            275                 280                 285
Glu Val Leu Phe Ala Ala Cys Gly Ile Thr Pro Gly Leu Leu Met Glu
    290                 295                 300
Gly Val Arg Phe Phe Lys Gly Gly Ala Arg Thr Gln Ser Leu Val Ile
305                 310                 315                 320
Ser Ser Gln Ser Arg Thr Ala Arg Phe Val Asp Thr Val His Met Phe
                325                 330                 335
Asp Asp Val Lys Thr Val Ser Leu Arg
                340                 345

<210> SEQ ID NO 122
<211> LENGTH: 1038
<212> TYPE: DNA
<213> ORGANISM: Synechococcus elongatus

<400> SEQUENCE: 122
gtggagaaga cgatcggtct cgagattatt gaagttgtcg agcaggcagc gatcgcctcg      60
gcccgcctga tgggcaaagg cgaaaagaat gaagccgatc gcgtcgcagt agaagcgatg     120
cgggtgcgga tgaaccaagt ggaaatgctg ggccgcatcg tcatcggtga aggcgagcgc     180
gacgaagcac cgatgctcta tatcggtgaa gaagtgggca tctaccgcga tgcagacaag     240
cgggctggcg taccggctgg caagctggtg gaaatcgaca tcgccgttga ccccctgcgaa    300 ggcaccaacc tctgcgccta cggtcagccc ggctcgatgg cagttttggc catctccgag     360
aaaggcggcc tgtttgcagc tcccgacttc tacatgaaga aactggctgc accccccagct   420 gccaaaggca aagtagacat caataagtcc gcgaccgaaa acctgaaaat tctctcggaa     480
tgtctcgatc gcgccatcga tgaattggtg gtcgtggtca tggatcgtcc ccgccacaaa    540
gagctaatcc aagagatccg ccaagcgggt gcccgcgtcc gtctgatcag cgatggtgac    600
gtttcggccg cgatctcctg cggttttgct ggcaccaaca cccacgccct gatgggcatc    660
ggtgcagctc ccgagggtgt gatttcggca gcagcaatgc gttgcctcgg cggtcacttc    720
caaggccagc tgatctacga cccagaagtg gtcaaaaccg gcctgatcgg tgaaagccgt   780
gagagcaaca tcgctcgcct gcaagaaatg ggcatcaccg atcccgatcg cgtctacgac   840
gccaacgaac tggcttcggg tcaagaagtg ctgtttgcgg cttgcggtat caccccgggc   900
ttgctgatgg aaggcgtgcg cttcttcaaa ggcggcgctc gcacccagag cttggtgatc    960
tccagccagt cacggacggc tcgcttcgtt gacaccgttc acatgttcga cgatgtcaaa  1020
acggttagcc tccgttaa                                                 1038

<210> SEQ ID NO 123
<211> LENGTH: 99
<212> TYPE: DNA
<213> ORGANISM: Nannochloropsis oceanica

<400> SEQUENCE: 123
```

```
atgaagaccg ccgctctcct cactgtctcc accctcatgg gcgcccaggc ctttatggcc    60
cccgccccca agttctcccg cacccgcggt gttgcgcgc                           99
```

<210> SEQ ID NO 124
<211> LENGTH: 36
<212> TYPE: DNA
<213> ORGANISM: Artificial sequence
<220> FEATURE:
<223> OTHER INFORMATION: Primer No. 124

<400> SEQUENCE: 124

```
cagcccgcat caacaatgaa gaccgccgct ctcctc                              36
```

<210> SEQ ID NO 125
<211> LENGTH: 28
<212> TYPE: DNA
<213> ORGANISM: Artificial sequence
<220> FEATURE:
<223> OTHER INFORMATION: Primer No. 125

<400> SEQUENCE: 125

```
gcgcgcaaca ccgcgggtgc gggagaac                                       28
```

<210> SEQ ID NO 126
<211> LENGTH: 36
<212> TYPE: DNA
<213> ORGANISM: Artificial sequence
<220> FEATURE:
<223> OTHER INFORMATION: Primer No. 126

<400> SEQUENCE: 126

```
cagcccgcat caacaatgaa gttcaccggc ctcgtc                              36
```

<210> SEQ ID NO 127
<211> LENGTH: 35
<212> TYPE: DNA
<213> ORGANISM: Artificial sequence
<220> FEATURE:
<223> OTHER INFORMATION: Primer No. 127

<400> SEQUENCE: 127

```
ctcttccaca gaagcttaag actcgttgag ggccg                               35
```

<210> SEQ ID NO 128
<211> LENGTH: 39
<212> TYPE: DNA
<213> ORGANISM: Artificial sequence
<220> FEATURE:
<223> OTHER INFORMATION: Primer No. 128

<400> SEQUENCE: 128

```
cagcccgcat caacaatgcg aagctacgcg gtgctttcc                           39
```

<210> SEQ ID NO 129
<211> LENGTH: 39
<212> TYPE: DNA
<213> ORGANISM: Artificial sequence
<220> FEATURE:
<223> OTHER INFORMATION: Primer No. 129

<400> SEQUENCE: 129

```
ctcttccaca gaagcttatg aagacgccga attcaaacg                           39
```

<210> SEQ ID NO 130
<211> LENGTH: 38

<212> TYPE: DNA
<213> ORGANISM: Artificial sequence
<220> FEATURE:
<223> OTHER INFORMATION: Primer No. 130

<400> SEQUENCE: 130
cagcccgcat caacaatggc ccgtctctct gctttgag       38

<210> SEQ ID NO 131
<211> LENGTH: 37
<212> TYPE: DNA
<213> ORGANISM: Artificial sequence
<220> FEATURE:
<223> OTHER INFORMATION: Primer No. 131

<400> SEQUENCE: 131
ctcttccaca gaagcttact tgagcatggc cacgagc        37

<210> SEQ ID NO 132
<211> LENGTH: 38
<212> TYPE: DNA
<213> ORGANISM: Artificial sequence
<220> FEATURE:
<223> OTHER INFORMATION: Primer No. 132

<400> SEQUENCE: 132
cagcccgcat caacaatgaa gggtgctatc ctcctcgc       38

<210> SEQ ID NO 133
<211> LENGTH: 37
<212> TYPE: DNA
<213> ORGANISM: Artificial sequence
<220> FEATURE:
<223> OTHER INFORMATION: Primer No. 133

<400> SEQUENCE: 133
ctcttccaca gaagcttacg cgtgcgccgc attctgg        37

<210> SEQ ID NO 134
<211> LENGTH: 36
<212> TYPE: DNA
<213> ORGANISM: Artificial sequence
<220> FEATURE:
<223> OTHER INFORMATION: Primer No. 134

<400> SEQUENCE: 134
cagcccgcat caacaatggt caagactgct gccgtc         36

<210> SEQ ID NO 135
<211> LENGTH: 37
<212> TYPE: DNA
<213> ORGANISM: Artificial sequence
<220> FEATURE:
<223> OTHER INFORMATION: Primer No. 135

<400> SEQUENCE: 135
ctcttccaca gaagcttaag ccgccaccgg cgccttc        37

<210> SEQ ID NO 136
<211> LENGTH: 36
<212> TYPE: DNA
<213> ORGANISM: Artificial sequence
<220> FEATURE:
<223> OTHER INFORMATION: Primer No. 136

<400> SEQUENCE: 136

```
cgcggtgttg cgcgcgagaa gacgatcggt ctcgag                                    36
```

```
<210> SEQ ID NO 137
<211> LENGTH: 37
<212> TYPE: DNA
<213> ORGANISM: Artificial sequence
<220> FEATURE:
<223> OTHER INFORMATION: Primer No. 137

<400> SEQUENCE: 137
ctcttccaca gaagcctacc gctccggccg ccatttg                                   37

<210> SEQ ID NO 138
<211> LENGTH: 437
<212> TYPE: PRT
<213> ORGANISM: Nannochloropsis oceanica

<400> SEQUENCE: 138

Met Ser Met His Lys Leu Thr Arg Pro Ser Val Leu Ser Ile Glu Tyr
1               5                   10                  15

Pro Ser Arg Asp Tyr Thr Gly Tyr Leu Asn Leu Ala Met Ile Ile Leu
            20                  25                  30

Gly Val His Phe Ser His Ala Val Val Asp Cys Val Ser Leu Val Trp
        35                  40                  45

Arg Tyr Gly Val Gln Leu Pro Lys His Ser Leu Val Glu Val Pro Cys
    50                  55                  60

Leu Met Cys Ala Leu Ser Leu Thr Ile Asn Ile Phe Leu Ala Trp Phe
65              70                  75                  80

Thr Glu Tyr Leu Ala Ser Arg Arg Phe Phe Pro Ser Ser Met Ala Val
                85                  90                  95

Gly Val Leu His Ser Leu Asn Cys Leu Trp Thr Leu Leu Tyr Pro Cys
            100                 105                 110

His Val Ala Trp Ser Arg Pro Asp Val Pro Leu His Thr Phe Leu Leu
        115                 120                 125

Leu Phe Trp Ser Val Ile Ala Phe Leu Lys Leu Val Ser Trp Ser His
    130                 135                 140

Thr Asn Trp Asp Leu Arg His Ala Phe Phe Ser Arg Arg Ala Arg Lys
145             150                 155                 160

Ser Gln Ala His Leu Pro Ala Ala Ala Leu His Glu Asp Gly Tyr Asn
                165                 170                 175

Asn Ala Lys Pro Leu Glu Ser Gly Ala Thr Arg Tyr Pro His Ser Val
            180                 185                 190

Ser Leu Ser Asn Ile Ser Phe Phe Phe Phe Cys Pro Thr Leu Cys Tyr
        195                 200                 205

Gln Pro Asp Tyr Pro Arg Ala Pro Thr Ile Arg Leu Arg Thr Leu Ala
    210                 215                 220

Ser Leu Thr Phe Arg Ile Ile Val Met Thr Ala Phe Ala Gly Phe Ile
225             230                 235                 240

Ile Asp Gln Gln Ile His Pro Ile Gln Asn Thr Met Ser His Val
                245                 250                 255

Asp Ser Leu Asp Leu Leu Lys Ala Leu Gly Glu Leu Leu Arg Leu Ala
            260                 265                 270

Ile Pro Ser Thr Phe Val Trp Leu Ile Phe Phe Tyr Val Tyr Phe His
        275                 280                 285

Cys Thr Leu Asn Leu Phe Ala Glu Leu Thr Arg Phe Gly Asp Arg Leu
    290                 295                 300
```

```
Phe Phe Lys Asp Trp Trp Asn Ser Thr Ser Phe Ser Arg Tyr Trp Arg
305                 310                 315                 320
Thr Trp Asn Leu Pro Val His Gln Phe Val Arg His Val Tyr Phe
                325                 330                 335
Pro Leu Leu Arg Ala Gly Ala Ser Lys Met Thr Ala Asn Val Ala Val
                340                 345                 350
Phe Ala Val Ser Ala Phe Phe His Glu Leu Leu Ile Ser Ile Pro Cys
                355                 360                 365
His Val Val Arg Leu Trp Ala Phe Leu Ala Met Met Gly Gln Ile Pro
                370                 375                 380
Leu Ile Tyr Leu Thr Asp Gln Leu Glu Lys Thr Leu Phe Lys Glu Thr
385                 390                 395                 400
Gln Ala Gly Asn Tyr Thr Phe Trp Leu Ile Phe Cys Ile Phe Gly Gln
                    405                 410                 415
Pro Met Ala Val Leu Leu Tyr Tyr Ala Asp Phe Ser Ala Arg Thr Thr
                420                 425                 430
Ser Glu Ser Ala Leu
            435
```

<210> SEQ ID NO 139
<211> LENGTH: 1314
<212> TYPE: DNA
<213> ORGANISM: Nannochloropsis oceanica

<400> SEQUENCE: 139

```
atgtctatgc acaaactgac tcgaccgagc gtgctgtcca ttgagtatcc ctcgcgggat      60
tatacgggtt atttgaacct ggcaatgatc atcctcggtg tccactttc ccacgccgta     120
gtcgactgcg tctcgctggt gtggcggtac ggagtgcagc tcccgaagca ttctctggtg    180
gaggtgccct gcctcatgtg cgcgctctcc ctcaccatca acatcttctt ggcttggttc    240
accgaatacc tcgcctcccg tgcttcttc ccctcctcga tggcggtagg tgtgctgcat     300
tccctgaact gcctatggac gctgctctac ccctgccacg tggcatggag ccggccggac    360
gtgcctctgc acacgttctt gttgctattt tggagtgtga tcgccttctt aaagctcgtc    420
tcctggtccc acactaattg ggatcttcga catgctttct tctcccggcg cgcccgcaag    480
tctcaggctc acctgccagc agcggcccct cacgaagacg gctacaacaa tgccaagccc    540
ctcgagagcg cgccacgcg gtacccgcac tcggtctcac taagcaacat aagcttcttc     600
ttcttctgtc ccactctctg ctaccagccc gactaccac gcgcgccaac gattcgattg      660
cggacactcg cctcgctcac ctttcgtatc atcgtcatga cggcctttgc gggcttcatc    720
atcgaccagc agatccaccc catcatccag aacaccatga ccacgtcga tagcctcgat     780
ctcctcaagg ccctgggtga gctgctccgc cttgccatcc cctccacctt cgtctggctc    840
attttcttct acgtctactt ccactgcacc ctcaatcttt tcgcggaatt aacgcgtttc    900
ggggatcgat tgttttcaa ggattggtgg aacagcacca gcttctcccg ctattggcga     960
acttggaatc ttcccgtcca tcagtttgtc gtccgtcatg tgtacttccc cttgctacgc   1020
gcgggggcgt ctaaaatgac ggccaacgtc gccgttttcg ctgtctcggc cttcttccac   1080
gagctgctga tctcgatacc ctgccacgtc gtgcggctgt gggcgttttt ggccatgatg   1140
ggccagatcc ctctcatcta ccttacggac cagctggaga aaaccttgtt caaggaaacg   1200
caggcaggga attacacctt ctggcttatc ttctgtatct tcggacagcc aatggcagtg   1260
ctcttgtact atgctgactt ctctgcccgc actaccagcg agagcgctct ttag          1314
```